US012402857B2

(12) United States Patent
Yamazaki et al.

(10) Patent No.: US 12,402,857 B2
(45) Date of Patent: Sep. 2, 2025

(54) ELECTRONIC DEVICE

(71) Applicant: Semiconductor Energy Laboratory Co., Ltd., Atsugi (JP)

(72) Inventors: Shunpei Yamazaki, Setagaya (JP); Koji Kusunoki, Isehara (JP); Kazunori Watanabe, Machida (JP); Tatsunori Inoue, Yamato (JP)

(73) Assignee: Semiconductor Energy Laboratory Co., Ltd., Atsugi (JP)

( * ) Notice: Subject to any disclaimer, the term of this patent is extended or adjusted under 35 U.S.C. 154(b) by 58 days.

(21) Appl. No.: 18/281,654

(22) PCT Filed: Mar. 28, 2022

(86) PCT No.: PCT/IB2022/052789
§ 371 (c)(1),
(2) Date: Sep. 12, 2023

(87) PCT Pub. No.: WO2022/214905
PCT Pub. Date: Oct. 13, 2022

(65) Prior Publication Data
US 2024/0173014 A1    May 30, 2024

(30) Foreign Application Priority Data
Apr. 8, 2021    (JP) .................. 2021-065754

(51) Int. Cl.
*A61B 8/10*    (2006.01)
*A61B 3/12*    (2006.01)
(Continued)

(52) U.S. Cl.
CPC .................. *A61B 8/10* (2013.01); *A61B 3/12* (2013.01); *A61B 8/06* (2013.01); *G02B 27/017* (2013.01); *G06T 19/006* (2013.01)

(58) Field of Classification Search
CPC .... A61B 8/10; A61B 3/12; A61B 8/06; A61B 3/10; A61B 8/4427; A61B 8/488;
(Continued)

(56) References Cited

U.S. PATENT DOCUMENTS 5,317,236 A * 5/1994 Zavracky ............. G02B 27/017
257/E29.295
6,421,031 B1 * 7/2002 Ronzani ............. G02B 27/0172
359/630
(Continued)

FOREIGN PATENT DOCUMENTS

CN    104252042 A    12/2014
CN    105359167 A    2/2016
(Continued)

OTHER PUBLICATIONS

International Search Report (Application No. PCT/IB2022/052789) Dated Jul. 5, 2022.
(Continued)

*Primary Examiner* — Bo Joseph Peng
(74) *Attorney, Agent, or Firm* — Eric J. Robinson; Robinson Intellectual Property Law Office, P.C.

(57) ABSTRACT

An electronic device capable of measuring the blood flow speed in a retina blood vessel or the like of an eye is provided. The electronic device includes a display portion, a sending portion, a receiving portion, and a control circuit. The sending portion has a function of generating a first ultrasonic wave with a first frequency and a function of sending a first electric signal corresponding to the first frequency to the control circuit. The receiving portion has a function of receiving a second ultrasonic wave, which is the first ultrasonic wave reflected by an object, with a second frequency, a function of generating a second electric signal corresponding to the second frequency, and a function of sending the second electric signal to the control circuit. Note
(Continued)

that the object is one or more selected from a retina blood vessel and a blood vessel included in a retina of a user's eye. The control circuit has a function of calculating the blood flow speed in one or more selected from the retina blood vessel and the blood vessel with the use of the first electric signal and the second electric signal and a function of sending a third electric signal corresponding to the blood flow speed to the display portion. The display portion has a function of receiving the third electric signal and displaying the blood flow speed.

7 Claims, 46 Drawing Sheets

(51) Int. Cl.
    *A61B 8/06* (2006.01)
    *G02B 27/01* (2006.01)
    *G06T 19/00* (2011.01)

(58) Field of Classification Search
    CPC .. A61B 8/5223; G02B 27/017; G06T 19/006; G06F 3/01
    See application file for complete search history.

(56) References Cited

U.S. PATENT DOCUMENTS

| | | | |
|---|---|---|---|
| 6,683,584 B2* | 1/2004 | Ronzani | G02B 27/0176 |
| | | | 359/630 |
| 8,899,752 B2 | 12/2014 | Kato et al. | |
| 8,922,366 B1 | 12/2014 | Honore et al. | |
| 9,097,890 B2* | 8/2015 | Miller | G02B 27/0093 |
| 9,128,305 B2 | 9/2015 | Honore et al. | |
| 9,557,582 B2 | 1/2017 | Honore et al. | |
| 10,302,944 B2 | 5/2019 | Kobayashi et al. | |
| 10,466,781 B2 | 11/2019 | Komaki | |
| 10,685,595 B2* | 6/2020 | Kunitomo | G02B 27/017 |
| 11,054,900 B2 | 7/2021 | Komaki | |
| 11,217,142 B1* | 1/2022 | Buckley | G06T 5/10 |
| 11,423,844 B2 | 8/2022 | Ikeda et al. | |
| 11,481,028 B2 | 10/2022 | Komaki | |
| 11,568,224 B2 | 1/2023 | Kurokawa et al. | |
| 11,790,817 B2 | 10/2023 | Yamazaki et al. | |
| 12,200,950 B2 | 1/2025 | Godo et al. | |
| 12,230,172 B2 | 2/2025 | Yamazaki et al. | |
| 2009/0099785 A1 | 4/2009 | Yamamoto et al. | |
| 2013/0214998 A1* | 8/2013 | Andes | G02B 27/0172 |
| | | | 345/8 |
| 2015/0002373 A1 | 1/2015 | Kobayashi et al. | |
| 2016/0035137 A1* | 2/2016 | Sendai | G02B 27/017 |
| | | | 345/633 |
| 2016/0091877 A1* | 3/2016 | Fullam | G06T 19/006 |
| | | | 700/275 |
| 2016/0165220 A1* | 6/2016 | Fujimaki | G09G 3/3406 |
| | | | 345/87 |
| 2017/0097524 A1 | 4/2017 | Honore et al. | |
| 2017/0289533 A1* | 10/2017 | Ono | G06F 3/04883 |
| 2019/0196771 A1* | 6/2019 | Kunitomo | G09G 5/003 |
| 2019/0286226 A1 | 9/2019 | Komaki | |
| 2019/0317608 A1* | 10/2019 | Ono | G06F 3/015 |
| 2019/0347977 A1* | 11/2019 | Kunitomo | G02B 27/0172 |
| 2020/0004334 A1 | 1/2020 | Komaki | |
| 2020/0329561 A1 | 10/2020 | Lee | |
| 2021/0110787 A1* | 4/2021 | Buckley | G06T 5/77 |
| 2021/0259565 A1 | 8/2021 | Ohno et al. | |
| 2021/0279449 A1 | 9/2021 | Yamazaki et al. | |
| 2021/0287561 A1 | 9/2021 | Udaka et al. | |
| 2022/0137409 A1 | 5/2022 | Yamazaki et al. | |
| 2023/0004221 A1 | 1/2023 | Komaki | |
| 2024/0169539 A1 | 5/2024 | Yamazaki et al. | |
| 2024/0179987 A1 | 5/2024 | Ito et al. | |

FOREIGN PATENT DOCUMENTS

| | | |
|---|---|---|
| JP | 2015-177403 A | 10/2015 |
| JP | 2015-188467 A | 11/2015 |
| JP | 2016-534767 | 11/2016 |
| JP | 2019-162251 A | 9/2019 |
| WO | WO-2012/160741 | 11/2012 |
| WO | WO-2014/209657 | 12/2014 |
| WO | WO-2019/220278 | 11/2019 |
| WO | WO-2022/162497 | 8/2022 |
| WO | WO-2022/185151 | 9/2022 |
| WO | WO-2022/200936 | 9/2022 |
| WO | WO-2022/208221 | 10/2022 |

OTHER PUBLICATIONS

Written Opinion (Application No. PCT/IB2022/052789) Dated Jul. 5, 2022.

\* cited by examiner

ANN

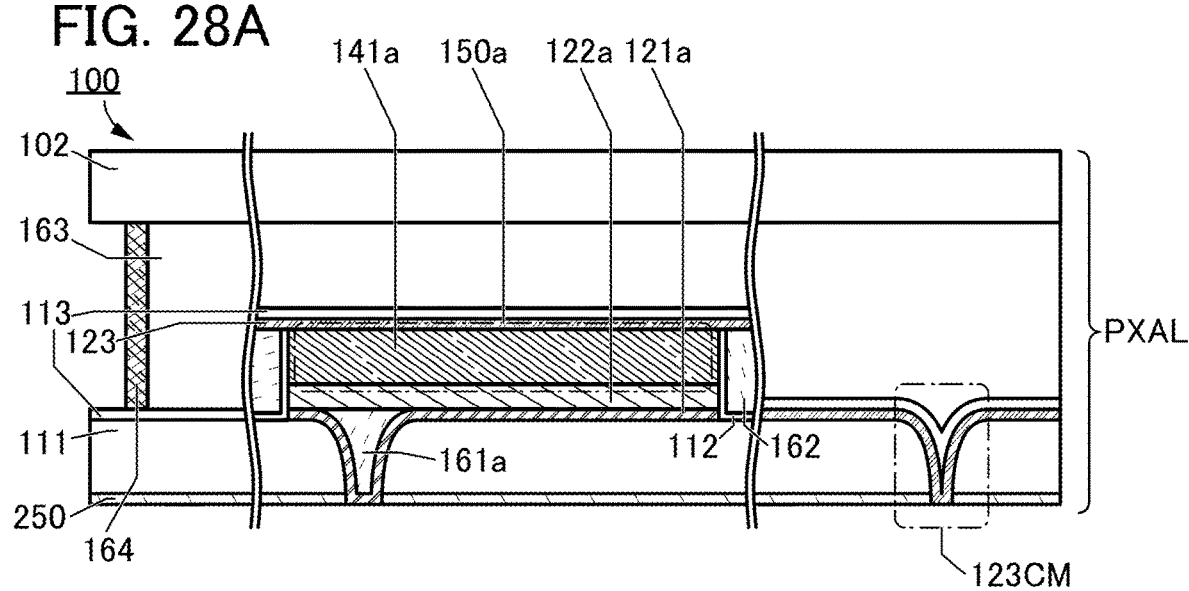
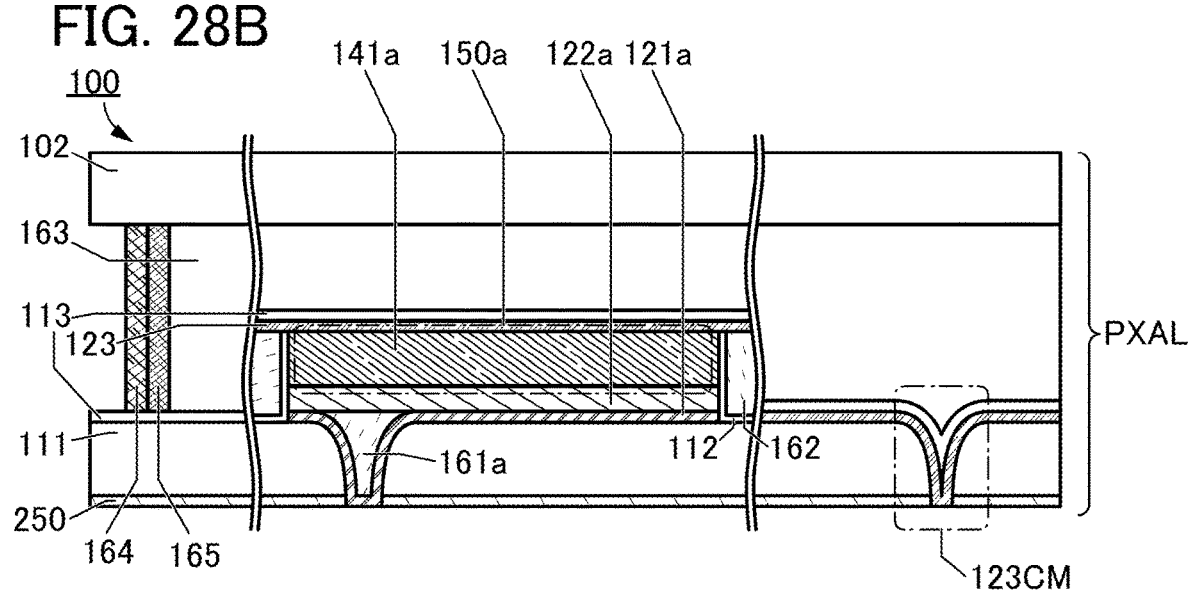

400A

400B

400C

400D

ELECTRONIC DEVICE

TECHNICAL FIELD

One embodiment of the present invention relates to an electronic device.

Note that one embodiment of the present invention is not limited to the above technical field. The technical field of the invention disclosed in this specification and the like relates to an object, a driving method, or a manufacturing method. Alternatively, one embodiment of the present invention relates to a process, a machine, manufacture, or a composition of matter. Therefore, specific examples of the technical field of one embodiment of the present invention disclosed in this specification include a semiconductor device, a display apparatus, a liquid crystal display apparatus, a light-emitting apparatus, a power storage device, an imaging device, a memory device, a signal processing device, a processor, an electronic device, a system, a driving method thereof, a manufacturing method thereof, and a testing method thereof.

BACKGROUND ART

Display apparatuses that can be used for XR (Cross Reality or Extended Reality) such as VR (Virtual Reality) or AR (Augmented Reality) have been required. Specifically, such display apparatuses have been desired to have a high resolution, high color reproducibility, and the like so as to offer enhanced realistic feeling and an enhanced sense of immersion, for example.

Examples of apparatuses that can be used as such display apparatuses include a liquid crystal display apparatus. Other examples of apparatuses that can be used as such display apparatuses include a light-emitting apparatus including a light-emitting device such as organic EL (Electro Luminescence) or a light-emitting diode (LED). Patent Document 1 discloses a display apparatus with a large number of pixels and a high resolution, which includes a light-emitting device containing organic EL.

An XR electronic device (e.g., a head-mounted display) is assumed to be worn on a head; thus, a distance between eyes of a user wearing the electronic device and a display portion is inevitably short. In addition, the user tends to directly view the display portion for a long time when wearing the XR electronic device. For these reasons, the XR electronic device worn on the user facilitates the eye fatigue and might cause drowsiness, lower concentration, or the like.

This raises attention to a method for measuring eye fatigue. Patent Document 2 discloses a visual fatigue level measuring apparatus that determines a user's visual fatigue level by comparing eye movement in two or more time intervals.

REFERENCES

Patent Document

[Patent Document 1] PCT International Publication No. 2019/220278
[Patent Document 2] PCT International Publication No. 2012/160741

SUMMARY OF THE INVENTION

Problems to be Solved by the Invention

An example of a method for measuring a user's eye fatigue level is capturing an image of an eye with the use of an imaging device. For example, with an imaging device for capturing an image of a user's eye provided around the display portion of the XR electronic device, the user's eye can be monitored while the user is using the XR electronic device. In addition, monitoring the user's eye enables the imaging device to measure the state of the fundus of the eye.

In the case where the user suffers from a disease such as a cataract, for example, it is difficult to capture an image of the fundus of the user's eye with the use of the imaging device. This is because the cataract makes the user's crystalline lens cloudy, and the cloudy region in the crystalline lens hinders image capturing of the fundus of the eye.

An object of one embodiment of the present invention is to provide an electronic device measuring the blood flow speed in a user's eye. Another object of one embodiment of the present invention is to provide an electronic device measuring a body temperature around a user's eye. Another object of one embodiment of the present invention is to provide an electronic device measuring a user's pulse. Another object of one embodiment of the present invention is to provide an electronic device measuring a user's blood oxygen saturation. Another object of one embodiment of the present invention is to provide any of the above electronic devices including a display apparatus. Another object of one embodiment of the present invention is to provide a novel electronic device.

Note that the objects of one embodiment of the present invention are not limited to the objects listed above. The objects listed above do not preclude the existence of other objects. Note that the other objects are objects that are not described in this section and will be described below. The objects that are not described in this section are derived from the description of the specification, the drawings, and the like and can be extracted as appropriate from the description by those skilled in the art. Note that one embodiment of the present invention is to achieve at least one of the objects listed above and the other objects. Note that one embodiment of the present invention does not necessarily achieve all the objects listed above and the other objects.

Means for Solving the Problems (1)

One embodiment of the present invention is an electronic device including a display portion, a sending portion, a receiving portion, and a control circuit. The sending portion has a function of generating a first ultrasonic wave with a first frequency and a function of sending a first electric signal corresponding to the first frequency to the control circuit. The receiving portion has a function of receiving a second ultrasonic wave, which is the first ultrasonic wave reflected by an object, with a second frequency, a function of generating a second electric signal corresponding to the second frequency, and a function of sending the second electric signal to the control circuit. Note that the object is one or more selected from a retina blood vessel and a blood vessel included in a fundus of an eye of a user. The control circuit has a function of calculating a blood flow speed in one or more selected from the retina blood vessel and the blood vessel with use of the first electric signal and the second electric signal, and a function of sending a third electric signal corresponding to the blood flow speed to the display portion. The display portion has a function of receiving the third electric signal and displaying the blood flow speed.

(2)

Another embodiment of the present invention may have a structure including a sound output portion in the above (1). The control circuit preferably has a function of sending a fourth electric signal corresponding to the blood flow speed to the sound output portion. The sound output portion preferably has a function of receiving the fourth electric signal and generating a sound corresponding to the fourth electric signal.

(3)

Another embodiment of the present invention may have a structure including a housing in the above (1) or (2). The housing preferably includes the display portion, the sending portion, the receiving portion, and the control circuit. It is also preferable that the housing include a structure body worn on a head of the user, the display portion be positioned in a region overlapping with the eye of the user when the housing is worn on the head of the user, and the sending portion and the receiving portion be positioned to be aligned with the eye of the user in one direction in a front view.

(4)

Another embodiment of the present invention is an electronic device including a display portion and a sensor portion. The display portion includes a first region and a second region. The first region and the second region each include a light-emitting device. The second region includes a light-receiving device. The sensor portion includes a diamond layer containing an NV center. The sensor portion is positioned in a region overlapping with the first region. A wall having a function of preventing entry of light between the first region and the second region from the light-emitting devices of the respective regions is provided between the first region and the second region. The sensor portion has a function of, when first light from the light-emitting device included in the second region enters the sensor portion, making second light enter the light-receiving device included in the second region. Thus, the electronic device measures a temperature from the intensity of the second light Note that in this specification and the like, a semiconductor device refers to a device that utilizes semiconductor characteristics, and means a circuit including a semiconductor element (e.g., a transistor, a diode, and a photodiode), a device including the circuit, and the like. The semiconductor device also means all devices that can function by utilizing semiconductor characteristics. For example, an integrated circuit, a chip including an integrated circuit, and an electronic component including a chip in a package are each an example of the semiconductor device. Moreover, a memory device, a display apparatus, a light-emitting apparatus, a lighting device, and an electronic device themselves are semiconductor devices or include semiconductor devices in some cases.

In the case where there is description "X and Y are connected" in this specification and the like, the case where X and Y are electrically connected, the case where X and Y are functionally connected, and the case where X and Y are directly connected are regarded as being disclosed in this specification and the like. Accordingly, without being limited to a predetermined connection relation, for example, a connection relation shown in drawings or texts, a connection relation other than one shown in drawings or texts is regarded as being disclosed in the drawings or the texts. Each of X and Y denotes an object (e.g., a device, an element, a circuit, a wiring, an electrode, a terminal, a conductive film, or a layer).

For example, in the case where X and Y are electrically connected, one or more elements that allow electrical connection between X and Y (e.g., a switch, a transistor, a capacitor, an inductor, a resistor, a diode, a display device, a light-emitting device, and a load) can be connected between X and Y. Note that a switch has a function of being controlled to be turned on or off. That is, the switch has a function of being in a conducting state (on state) or a non-conducting state (off state) to control whether current flows or not.

For example, in the case where X and Y are functionally connected, one or more circuits that allow functional connection between X and Y (e.g., a logic circuit (e.g., an inverter, a NAND circuit, or a NOR circuit); a signal converter circuit (e.g., a digital-analog converter circuit, an analog-digital converter circuit, or a gamma correction circuit); a potential level converter circuit (e.g., a power supply circuit such as a step-up circuit or a step-down circuit, or a level shifter circuit for changing the potential level of a signal); a voltage source; a current source; a switching circuit; an amplifier circuit (e.g., a circuit that can increase signal amplitude, the amount of current, or the like, an operational amplifier, a differential amplifier circuit, a source follower circuit, or a buffer circuit); a signal generation circuit; a memory circuit; or a control circuit) can be connected between X and Y. For example, even if another circuit is interposed between X and Y, X and Y are regarded as being functionally connected when a signal output from X is transmitted to Y.

Note that an explicit description "X and Y are electrically connected" includes the case where X and Y are electrically connected (i.e., the case where X and Y are connected with another element or another circuit interposed therebetween) and the case where X and Y are directly connected (i.e., the case where X and Y are connected without another element or another circuit interposed therebetween).

This specification and the like describes a circuit structure where a plurality of elements are electrically connected to a wiring (a wiring supplying a constant potential or a wiring transmitting a signal). For example, in the case where X is directly electrically connected to the wiring and Y is directly electrically connected to the wiring, this specification may describe that X and Y are directly electrically connected to each other.

It can be expressed as, for example, "X, Y, a source (sometimes called one of a first terminal and a second terminal) of a transistor, and a drain (sometimes called the other of the first terminal and the second terminal) of the transistor are electrically connected to each other, and X, the source of the transistor, the drain of the transistor, and Y are electrically connected to each other in this order". Alternatively, it can be expressed as "a source of a transistor is electrically connected to X; a drain of the transistor is electrically connected to Y; and X, the source of the transistor, the drain of the transistor, and Y are electrically connected to each other in this order". Alternatively, it can be expressed as "X is electrically connected to Y through a source and a drain of a transistor, and X, the source of the transistor, the drain of the transistor, and Y are provided in this connection order". When the connection order in a circuit structure is defined by an expression similar to the above examples, a source and a drain of a transistor can be distinguished from each other to specify the technical scope. Note that these expressions are examples and the expression is not limited to these expressions. Here, X and Y each denote an object (e.g., a device, an element, a circuit, a wiring, an electrode, a terminal, a conductive film, or a layer).

Even when independent components are electrically connected to each other in a circuit diagram, one component has functions of a plurality of components in some cases. For example, when part of a wiring also functions as an electrode, one conductive film has functions of both components: a function of the wiring and a function of the electrode. Thus, electrical connection in this specification includes, in its category, such a case where one conductive film has functions of a plurality of components.

In this specification and the like, a "resistor element" can be, for example, a circuit element having a resistance value higher than 0Ω or a wiring having a resistance value higher than 0Ω. Therefore, in this specification and the like, a "resistor element" sometimes includes a wiring having a resistance value, a transistor in which current flows between its source and drain, a diode, and a coil. Thus, the term "resistor element" can be sometimes replaced with the terms "resistor", "load", or "region having a resistance value". Conversely, the term "resistor", "load", or "region having a resistance value" can be sometimes replaced with the term "resistor element". The resistance value can be, for example, preferably higher than or equal to 1 mΩ and lower than or equal to 10Ω, further preferably higher than or equal to 5 mΩ and lower than or equal to 5Ω, still further preferably higher than or equal to 10 mΩ and lower than or equal to 1Ω. As another example, the resistance value may be higher than or equal to 1Ω and lower than or equal to $1 \times 10^9$Ω.

In this specification and the like, a "capacitor" can be, for example, a circuit element having an electrostatic capacitance value higher than 0 F, a region of a wiring having an electrostatic capacitance value higher than 0 F, parasitic capacitance, or gate capacitance of a transistor. The term "capacitor", "parasitic capacitance", or "gate capacitance" can be replaced with the term "capacitance" in some cases. Conversely, the term "capacitance" can be replaced with the term "capacitor", "parasitic capacitance", or "gate capacitance" in some cases. The term "pair of electrodes" of "capacitor" can be replaced with "pair of conductors", "pair of conductive regions", or "pair of regions". Note that the electrostatic capacitance value can be higher than or equal to 0.05 fF and lower than or equal to 10 pF, for example. As another example, the electrostatic capacitance value may be higher than or equal to 1 pF and lower than or equal to 10 μF.

In this specification and the like, a transistor includes three terminals called a gate, a source, and a drain. The gate is a control terminal for controlling the conducting state of the transistor. Two terminals functioning as the source and the drain are input/output terminals of the transistor. One of the two input/output terminals serves as the source and the other serves as the drain on the basis of the conductivity type (n-channel type or p-channel type) of the transistor and the levels of potentials supplied to the three terminals of the transistor. Thus, the terms "source" and "drain" can be sometimes replaced with each other in this specification and the like. In this specification and the like, expressions "one of a source and a drain" (or a first electrode or a first terminal) and "the other of the source and the drain" (or a second electrode or a second terminal) are used in description of the connection relation of a transistor. Depending on the transistor structure, a transistor sometimes includes a back gate in addition to the above three terminals. In this case, in this specification and the like, one of the gate and the back gate of the transistor is sometimes referred to as a first gate and the other of the gate and the back gate of the transistor is sometimes referred to as a second gate. Moreover, the terms "gate" and "back gate" can be replaced with each other in one transistor in some cases. In the case where a transistor includes three or more gates, the gates are sometimes referred to as a first gate, a second gate, and a third gate, for example, in this specification and the like.

In this specification and the like, for example, a transistor with a multi-gate structure having two or more gate electrodes can be used as the transistor. With the multi-gate structure, channel formation regions are connected in series; accordingly, a plurality of transistors are connected in series. Thus, with the multi-gate structure, the amount of off-state current can be reduced, and the withstand voltage of the transistor can be increased (the reliability can be improved). Alternatively, with the multi-gate structure, drain-source current does not change much even if drain-source voltage changes at the time of operation in a saturation region, and thus the voltage-current characteristics with a flat slope can be obtained. By utilizing the flat slope of the voltage-current characteristics, an ideal current source circuit or an active load having an extremely high resistance value can be achieved. Accordingly, a differential circuit, a current mirror circuit, and the like having excellent properties can be achieved.

The case where a single circuit element is illustrated in a circuit diagram sometimes indicates a case where the circuit element includes a plurality of circuit elements. For example, the case where a single resistor is illustrated in a circuit diagram sometimes indicates a case where two or more resistors are electrically connected to each other in series. As another example, the case where a single capacitor is illustrated in a circuit diagram sometimes indicates a case where two or more capacitors are electrically connected to each other in parallel. As another example, the case where a single transistor is illustrated in a circuit diagram sometimes indicates a case where two or more transistors are electrically connected to each other in series and their gates are electrically connected to each other. Similarly, as another example, the case where a single switch is illustrated in a circuit diagram sometimes indicates a case where the switch includes two or more transistors which are electrically connected to each other in series or in parallel and their gates are electrically connected to each other.

In this specification and the like, a node can be referred to as a terminal, a wiring, an electrode, a conductive layer, a conductor, an impurity region, or the like depending on the circuit structure and the device structure. Furthermore, a terminal, a wiring, or the like can be referred to as a node.

In this specification and the like, "voltage" and "potential" can be replaced with each other as appropriate. "Voltage" refers to a potential difference from a reference potential, and when the reference potential is a ground potential, for example, "voltage" can be replaced with "potential". Note that the ground potential does not necessarily mean 0 V. Moreover, potentials are relative values, and a potential supplied to a wiring, a potential applied to a circuit and the like, and a potential output from a circuit and the like, for example, change with a change of the reference potential.

In this specification and the like, the terms "high-level potential" and "low-level potential" each do not mean a particular potential. For example, in the case where two wirings are both described as "functioning as a wiring for supplying a high-level potential", the levels of the high-level potentials supplied from the wirings are not necessarily equal to each other. Similarly, in the case where two wirings are both described as "functioning as a wiring for supplying a low-level potential", the levels of the low-level potentials supplied from the wirings are not necessarily equal to each other.

"Current" means a charge transfer phenomenon (electrical conduction); for example, the description "electrical conduction of positively charged particles occurs" can be rephrased as "electrical conduction of negatively charged particles occurs in the opposite direction". Therefore, unless otherwise specified, "current" in this specification and the like refers to a charge transfer phenomenon (electrical conduction) accompanied by carrier movement. Examples of a carrier here include an electron, a hole, an anion, a cation, and a complex ion, and the type of carrier differs between current flow systems (e.g., a semiconductor, a metal, an electrolyte solution, and a vacuum). The "direction of current" in a wiring refers to the direction in which a carrier with a positive charge moves, and the amount of current is expressed as a positive value. In other words, the direction in which a carrier with a negative charge moves is opposite to the direction of current, and the amount of current is expressed as a negative value. Thus, in the case where the polarity of current (or the direction of current) is not specified in this specification and the like, the description "current flows from element A to element B" can be rephrased as "current flows from element B to element A". The description "current is input to element A" can be rephrased as "current is output from element A".

Ordinal numbers such as "first", "second", and "third" in this specification and the like are used to avoid confusion among components. Thus, the ordinal numbers do not limit the number of components. In addition, the ordinal numbers do not limit the order of components. In this specification and the like, for example, a "first" component in one embodiment can be referred to as a "second" component in other embodiments or the scope of claims. For another example, a "first" component in one embodiment in this specification and the like can be omitted in other embodiments or the scope of claims.

In this specification and the like, the terms for describing positioning, such as "over" and "under", are sometimes used for convenience to describe the positional relation between components with reference to drawings. The positional relation between components is changed as appropriate in accordance with the direction in which the components are described. Thus, the positional relation is not limited to the terms described in the specification and the like, and can be described with another term as appropriate depending on the situation. For example, the expression "an insulator positioned over (on) the top surface of a conductor" can be replaced with the expression "an insulator positioned under (on) a bottom surface of a conductor" when the direction of a drawing showing these components is rotated by 180°.

Furthermore, the term "over" or "under" does not necessarily mean that a component is placed directly over or directly under and in direct contact with another component. For example, the expression "electrode B over insulating layer A" does not necessarily mean that the electrode B is formed over and in direct contact with the insulating layer A, and does not exclude the case where another component is provided between the insulating layer A and the electrode B.

In this specification and the like, components arranged in a matrix and their positional relation are sometimes described using terms such as "row" and "column". The positional relation between components is changed as appropriate in accordance with the direction in which the components are described. Thus, the positional relationship is not limited to the terms described in the specification and the like, and can be described with another term as appropriate depending on the situation. For example, the term "row direction" can be replaced with the term "column direction" when the direction of the diagram is rotated by 90°.

In addition, in this specification and the like, the terms "film," "layer," and the like can be interchanged with each other depending on the situation. For example, the term "conductive layer" can be changed into the term "conductive film" in some cases. As another example, the term "insulating film" can be changed into the term "insulating layer" in some cases. Alternatively, the term "film", "layer", or the like is not used and can be interchanged with another term depending on the case or the situation. For example, the term "conductive layer" or "conductive film" can be changed into the term "conductor" in some cases. As another example, the term "insulating layer" or "insulating film" can be changed into the term "insulator" in some cases.

In this specification and the like, the terms such as "electrode", "wiring", and "terminal" do not limit the functions of such components. For example, an "electrode" is used as part of a wiring in some cases, and vice versa. Furthermore, the term "electrode" or "wiring" can also mean, for example, the case where a plurality of "electrodes" or "wirings" are formed in an integrated manner. For example, a "terminal" is used as part of a "wiring" or an "electrode" in some cases, and vice versa. Furthermore, the term "terminal" also includes the case where one or more selected from "electrodes", "wirings", and "terminals" are formed in an integrated manner. Therefore, for example, an "electrode" can be part of a "wiring" or a "terminal", and a "terminal" can be part of a "wiring" or an "electrode". Moreover, the term "electrode", "wiring", "terminal", or the like is sometimes replaced with the term "region" or the like depending on the case.

In this specification and the like, the term "wiring", "signal line", "power supply line", and the like can be interchanged with each other depending on the case or the situation. For example, the term "wiring" can be changed into the term "signal line" in some cases. As another example, the term "wiring" can be changed into the term "power supply line" or the like in some cases. Conversely, the term "signal line", "power supply line", or the like can be changed into the term "wiring" in some cases. The term "power source line" or the like can be changed into the term "signal line" or the like in some cases. Conversely, the term "signal line" or the like can be changed into the term "power source line" or the like in some cases. The term "potential" that is applied to a wiring can be changed into the term "signal" or the like depending on the case or the situation. Conversely, the term "signal" can be changed into the term "potential" in some cases.

In this specification and the like, an impurity in a semiconductor refers to, for example, an element other than a main component of a semiconductor layer. For example, an element with a concentration of lower than 0.1 atomic % is an impurity. When an impurity is contained, for example, the density of defect states in a semiconductor is increased, carrier mobility is decreased, or crystallinity is decreased in some cases. In the case where the semiconductor is an oxide semiconductor, examples of an impurity that changes characteristics of the semiconductor include Group 1 elements, Group 2 elements, Group 13 elements, Group 14 elements, Group 15 elements, and transition metals other than the main components; specific examples include hydrogen (contained also in water), lithium, sodium, silicon, boron, phosphorus, carbon, and nitrogen. Specifically, in the case where the semiconductor is a silicon layer, examples of an impurity that changes characteristics of the semiconductor include Group 1 elements, Group 2 elements, Group 13 elements, and Group 15 elements (except oxygen and hydrogen).

In this specification and the like, a switch has a function of being in a conducting state (on state) or a non-conducting state (off state) to determine whether current flows or not. Alternatively, a switch has a function of selecting and changing a current path. Thus, in some cases, a switch has two or more terminals through which current flows, in addition to a control terminal. For example, an electrical switch or a mechanical switch can be used. That is, a switch can be any element capable of controlling current, and is not limited to a particular element.

Examples of an electrical switch include a transistor (e.g., a bipolar transistor and a MOS transistor), a diode (e.g., a PN diode, a PIN diode, a Schottky diode, a MIM (Metal Insulator Metal) diode, a MIS (Metal Insulator Semiconductor) diode, and a diode-connected transistor), and a logic circuit in which such elements are combined. Note that in the case of using a transistor as a switch, a "conducting state" of the transistor refers to a state where a source electrode and a drain electrode of the transistor can be regarded as being electrically short-circuited or a state where current can be made to flow between the source electrode and the drain electrode. Furthermore, a "non-conducting state" of the transistor refers to a state where the source electrode and the drain electrode of the transistor can be regarded as being electrically disconnected. Note that in the case where a transistor operates just as a switch, there is no particular limitation on the polarity (conductivity type) of the transistor.

An example of a mechanical switch is a switch formed using a MEMS (micro electro mechanical systems) technology. Such a switch includes an electrode that can be moved mechanically, and operates by controlling conduction and non-conduction with movement of the electrode.

In this specification and the like, a device formed using a metal mask or an FMM (fine metal mask) is sometimes referred to as a device having an MM (metal mask) structure. In this specification and the like, a device formed without using a metal mask or an FMM is sometimes referred to as a device having an MML (metal maskless) structure.

In this specification and the like, a structure where light-emitting layers in light-emitting devices of different colors (here, blue (B), green (G), and red (R)) are separately formed or separately patterned is sometimes referred to as an SBS (Side By Side) structure. In this specification and the like, a light-emitting device capable of emitting white light is sometimes referred to as a white-light-emitting device. Note that a combination of white-light-emitting devices with coloring layers (e.g., color filters) enables a full-color display apparatus.

Structures of light-emitting devices can be classified roughly into a single structure and a tandem structure. A device having a single structure includes one light-emitting unit between a pair of electrodes, and the light-emitting unit preferably includes one or more light-emitting layers. To obtain white light emission, two or more light-emitting layers are selected such that emission colors of the light-emitting layers are complementary colors. For example, when an emission color of a first light-emitting layer and an emission color of a second light-emitting layer are complementary colors, the light-emitting device can be configured to emit white light as a whole. The same applies to a light-emitting device including three or more light-emitting layers.

A device having a tandem structure includes two or more light-emitting units between a pair of electrodes, and each light-emitting unit preferably includes one or more light-emitting layers. To obtain white light emission, the structure is made so that light from light-emitting layers of the light-emitting units can be combined to be white light. Note that a structure for obtaining white light emission is similar to a structure in the case of a single structure. In the device having a tandem structure, it is suitable that an intermediate layer such as a charge generation layer is provided between a plurality of light-emitting units.

When the white-light-emitting device (having a single structure or a tandem structure) and a light-emitting device having an SBS structure are compared to each other, the light-emitting device having an SBS structure can have lower power consumption than the white-light-emitting device. To reduce power consumption, a light-emitting device having an SBS structure is suitably used. Meanwhile, the white-light-emitting device is suitable in terms of lower manufacturing cost or higher manufacturing yield because the manufacturing process of the white-light-emitting device is simpler than that of a light-emitting device having an SBS structure.

In this specification, "parallel" indicates a state where two straight lines are placed at an angle greater than or equal to $-10°$ and less than or equal to $10°$. Thus, the case where the angle is greater than or equal to $-5°$ and less than or equal to $5°$ is also included. In addition, "approximately parallel" or "substantially parallel" indicates a state where two straight lines are placed at an angle greater than or equal to $-30°$ and less than or equal to $30°$. Moreover, "perpendicular" indicates a state where two straight lines are placed at an angle greater than or equal to 800 and less than or equal to $100°$. Thus, the case where the angle is greater than or equal to 850 and less than or equal to 950 is also included. Furthermore, "approximately perpendicular" or "substantially perpendicular" indicates a state where two straight lines are placed at an angle greater than or equal to 600 and less than or equal to $120°$.

Effect of the Invention

One embodiment of the present invention can provide an electronic device measuring the blood flow speed in a user's eye. Another embodiment of the present invention can provide an electronic device measuring a body temperature around a user's eye. Another embodiment of the present invention can provide an electronic device measuring a user's pulse. Another embodiment of the present invention can provide an electronic device measuring a user's blood oxygen saturation. Another embodiment of the present invention can provide any of the above electronic devices including a display apparatus. Another embodiment of the present invention can provide a novel electronic device.

Note that the effects of one embodiment of the present invention are not limited to the effects listed above. The effects listed above do not preclude the existence of other effects. Note that the other effects are effects that are not described in this section and will be described below. The effects that are not described in this section are derived from the description of the specification, the drawings, and the like and can be extracted as appropriate from the description by those skilled in the art. Note that one embodiment of the present invention has at least one of the effects listed above and the other effects. Accordingly, depending on the case, one embodiment of the present invention does not have the effects listed above in some cases.

BRIEF DESCRIPTION OF THE DRAWINGS

FIG. 28A and FIG. 28B are schematic cross-sectional views illustrating structure examples of a display apparatus.

MODE FOR CARRYING OUT THE INVENTION

Figure 1A:
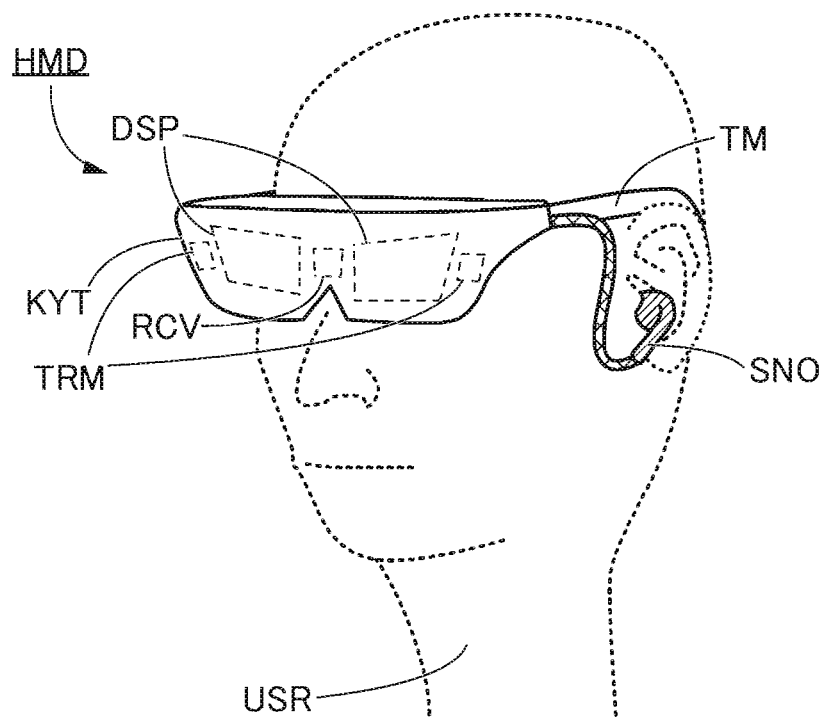
FIG. 1A is a perspective view illustrating a structure example of an electronic device.

In this specification and the like, a metal oxide is an oxide of a metal in a broad sense. Metal oxides are classified into an oxide insulator, an oxide conductor (including a transparent oxide conductor), an oxide semiconductor (also simply referred to as an OS), and the like. For example, in the case where a metal oxide is included in a channel formation region of a transistor, the metal oxide is referred to as an oxide semiconductor in some cases. That is, when a metal oxide can form a channel formation region of a transistor that has at least one of an amplifying function, a rectifying function, and a switching function, the metal oxide can be referred to as a metal oxide semiconductor. In the case where an OS transistor is mentioned, the OS transistor can also be referred to as a transistor including a metal oxide or an oxide semiconductor.

In this specification and the like, a metal oxide containing nitrogen is also collectively referred to as a metal oxide in some cases. A metal oxide containing nitrogen may be called a metal oxynitride.

In this specification and the like, one embodiment of the present invention can be constituted by appropriately combining a structure described in an embodiment with any of the structures described in the other embodiments. In addition, in the case where a plurality of structure examples are described in one embodiment, the structure examples can be combined as appropriate.

Note that a content (or part of the content) described in one embodiment can be applied to, combined with, or replaced with at least one of another content (or part of the content) in the embodiment and a content (or part of the content) described in one or a plurality of different embodiments.

Note that in each embodiment, a content described in the embodiment is a content described using a variety of diagrams or a content described with text disclosed in the specification.

Note that by combining a diagram (or part thereof) described in one embodiment with at least one of another part of the diagram, a different diagram (or part thereof) described in the embodiment, and a diagram (or part thereof) described in one or a plurality of different embodiments, much more diagrams can be formed.

Embodiments described in this specification are described with reference to the drawings. Note that the embodiments can be implemented in many different modes, and it will be readily appreciated by those skilled in the art that modes and details can be changed in various ways without departing from the spirit and scope thereof. Therefore, the present invention should not be interpreted as being limited to the description in the embodiments. Note that in the structures of the invention in the embodiments, the same portions or portions having similar functions are denoted by the same reference numerals in different drawings, and repeated description thereof is omitted in some cases. In perspective views and the like, some components are not illustrated for clarity of the drawings in some cases.

In this specification and the like, when a plurality of components are denoted with the same reference numerals, and in particular need to be distinguished from each other, an identification sign such as "_1", "[n]", or "[m,n]" is sometimes added to the reference numerals. Components denoted with identification signs such as "_1", "[n]", and "[m,n]" in the drawings and the like are sometimes denoted without such identification signs in this specification and the like when the components do not need to be distinguished from each other.

In the drawings in this specification, the size, the layer thickness, or the region is exaggerated for clarity in some cases. Therefore, they are not limited to the illustrated scale. The drawings are schematic views showing ideal examples, and embodiments of the present invention are not limited to shapes, values, or the like shown in the drawings. For example, variations in a signal, a voltage, or a current due to noise, variations in a signal, a voltage, or a current due to difference in timing, or the like can be included.

Embodiment 1

In this embodiment, an electronic device of one embodiment of the present invention is described.

FIG. 1A illustrates a state where a user USR wears an electronic device HMD that is an embodiment of a head-mounted display. The electronic device HMD has a function of sending an ultrasonic wave to the user USR and a function of receiving the ultrasonic wave reflected by the user USR.

In FIG. 1A, the electronic device HMD includes a housing KYT, a display portion DSP, a sending portion TRM, and a receiving portion RCV, for example. The electronic device HMD also includes a temple TM that is part of the housing.

In addition, the electronic device HMD in FIG. 1A includes a sound output portion SNO functioning as an earphone, for example. The sound output portion SNO is electrically connected to a circuit in the housing KYT through a wiring.

The housing KYT includes a structure body that can be worn on a head of the user USR, for example.

The housing KYT is provided with two display portions DSP for the right eye and the left eye, for example. Note that one of the display portions DSP is provided to be positioned in a region overlapping with one eye when the housing KYT is worn on the head of the user USR. Similarly, the other of the display portions DSP is provided to be positioned in a region overlapping with the other eye when the housing KYT is worn on the head of the user USR.

The sending portion TRM has a function of generating an ultrasonic wave and propagating it to the user USR, for example.

The receiving portion RCV has a function of receiving the ultrasonic wave reflected by the user USR, for example.

Figure 1B:
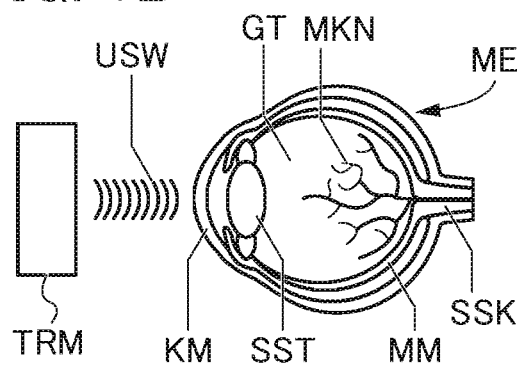
FIG. 1B and FIG. 1C are schematic views illustrating examples of circuits included in the electronic device and an eye.
Figure 1C:
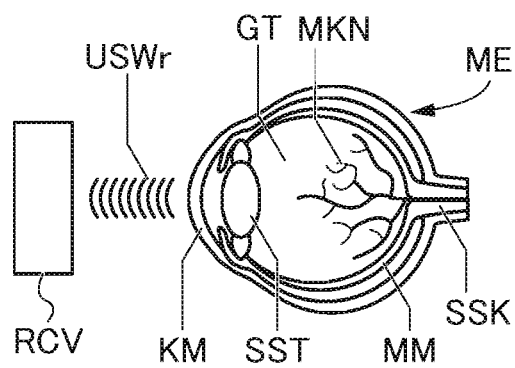

FIG. 1B illustrates a state where a ultrasonic wave USW is propagated from the sending portion TRM to an eye ME of the user USR, for example, and FIG. 1C illustrates a state where a ultrasonic wave USWr reflected by the eye ME of the user USR is obtained, for example.

In FIG. 1B and FIG. 1C, the eye ME of the user USR includes a cornea KM, a crystalline lens SST, a retina MM, an optic nerve SSK, a vitreous humor GT, and a retina blood vessel MKN.

As illustrated in FIG. 1B, the ultrasonic wave USW propagated from the sending portion TRM reaches the retina blood vessel MKN and the retina MM through the cornea KM, the crystalline lens SST, and the vitreous humor GT of the eye ME. Note that the ultrasonic wave USW propagated from the sending portion TRM may reach the retina blood vessel MKN and the retina MM by a route not passing through the crystalline lens SST.

As illustrated in FIG. 1C, the ultrasonic wave USWr obtained by the receiving portion RCV is the ultrasonic wave USW propagated from the sending portion TRM and reflected by one or both of the retina blood vessel MKN and a blood vessel included in the fundus of the eye ME.

As illustrated in FIG. 1B and FIG. 1C, the ultrasonic wave USWr, which is the ultrasonic wave USW propagated from the sending portion TRM and reflected by one or both of the retina blood vessel MKN and a blood vessel included in the fundus of the eye, is obtained by the receiving portion RCV.

A difference in frequency between the ultrasonic wave USW and the ultrasonic wave USWr is determined in accordance with the speed of blood cells flowing in a blood vessel. That is, obtaining the frequency of the ultrasonic wave USWr by the receiving portion RCV enables calculation of the blood flow speed in at least one of the retina blood vessel MKN and a blood vessel included in the fundus of the eye of the user USR.

Figure 2:
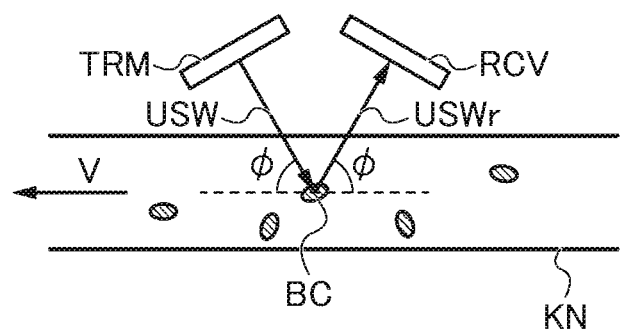
FIG. 2 is a schematic view illustrating examples of circuits included in an electronic device and a blood vessel.

As a specific example, a blood vessel KN and a blood cell BC flowing in the blood vessel KN illustrated in FIG. 2 are considered. In the case where the ultrasonic wave USW with a frequency $f_0$ is propagated from the sending portion TRM, the ultrasonic wave USW is reflected by the blood cell BC in the blood vessel KN, and the ultrasonic wave USWr with a frequency f is input to the receiving portion RCV, a blood flow speed V can be represented by $V=\{V_B\times(f-f_0)\}/\{(2\cos\phi)\times f_0\}$. Note that $V_B$ represents the sound velocity in blood, and $\phi$ represents an angle formed by the flowing direction of the blood cell and the propagating direction of the ultrasonic wave USW (the ultrasonic wave USWr).

In the case where the user USR has eye fatigue, the blood flow speed of the user USR is lower than usual. That is, measuring the blood flow speed of the user USR with the sending portion TRM, the receiving portion RCV, and the like of the electronic device HMD allows the eye fatigue level of the user USR to be checked successively.

In some cases, a blood pressure can also be measured by measurement of a pulse wave (a volume change in a blood vessel with heartbeat) from the ultrasonic wave USW and the ultrasonic wave USWr, which is reflected by at least one of the retina blood vessel MKN and a blood vessel included in the fundus of the eye. In some cases, a heart rate, blood oxygen saturation, or the like can also be measured in a similar manner.

Note that the electronic device HMD is illustrated as a goggles-type head-mounted display in FIG. 1A; however, the electronic device of one embodiment of the present invention may be a glasses-type head-mounted display.

Next, structure examples of the display portion DSP, the sending portion TRM, and the receiving portion RCV included in the electronic device HMD illustrated in FIG. 1A are described.

Figure 3A:
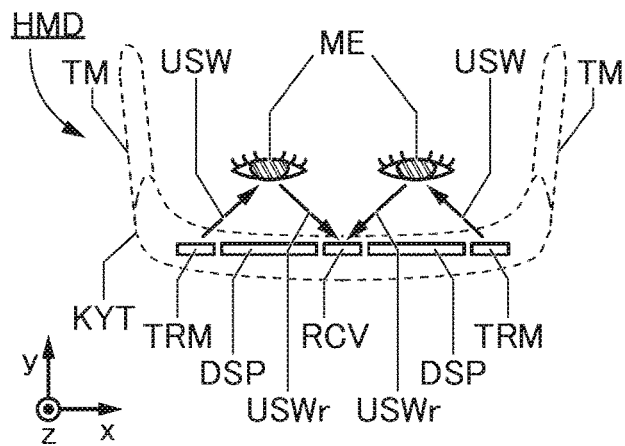
FIG. 3A, FIG. 3C, and FIG. 3E are top views illustrating structure examples of an electronic device.

FIG. 3A is a top view of a structure example of the electronic device HMD which can be employed for FIG. 1A. Note that FIG. 3A shows arrows indicating the x direction and the y direction; in this specification and the like, the top views illustrated in FIG. 3A and the like are sometimes referred to as xy plane views seen from the z direction, for example. In addition, a view seen in the z direction is sometimes referred to as a top view. FIG. 3A employs a right-handed coordinate, and thus the z direction in FIG. 3A is a direction toward the front of the diagram.

In this specification and the like, one of the x direction, the y direction, and the z direction is referred to as a "first direction" in some cases. Another one of the directions is referred to as a "second direction" in some cases. The remaining one of the directions is referred to as a "third direction" in some cases.

Figure 3B:
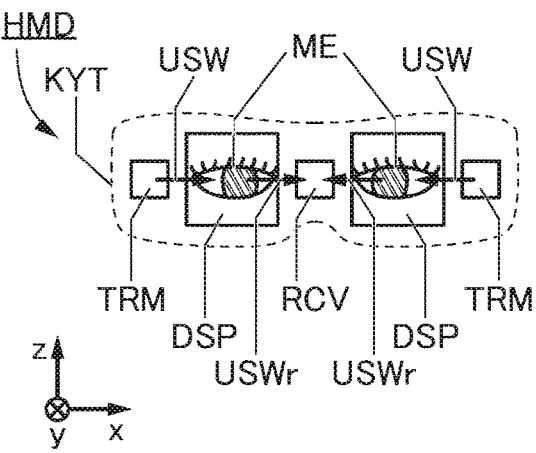
FIG. 3B, FIG. 3D, and FIG. 3F are front views illustrating the structure examples of the electronic device.

FIG. 3B is a front view illustrating the structure example of the electronic device HMD illustrated in FIG. 3A. Note that in this specification and the like, the front view illustrated in FIG. 3B is a zx plane view seen from the y direction. In addition, a view seen in the y direction is sometimes referred to as a front view.

The electronic device HMD illustrated in FIG. 3A and FIG. 3B has a structure where the receiving portion RCV is provided between the display portion DSP for the right eye and the display portion DSP for the left eye. In FIG. 3B (in the zx plane view seen from the y direction), the sending portion TRM is provided such that the receiving portion RCV, the eye ME of the user USR, and the sending portion TRM are aligned in the x direction. In particular, the sending portion TRM is provided to be aligned with the receiving portion RCV with the display portion DSP therebetween. Thus, in FIG. 3A and FIG. 3B, the sending portions TRM are provided next to the display portion DSP for the right eye and next to the display portion DSP for the left eye.

In order that the receiving portion RCV efficiently obtains the ultrasonic wave USWr, which is the ultrasonic wave USW propagated from the sending portion TRM and reflected by at least one of the retina blood vessel MKN and a blood vessel included in the fundus of the eye ME, the sending portion TRM and the receiving portion RCV are preferably placed in the electronic device HMD such that the sending portion TRM, the eye ME, and the receiving portion RCV are aligned in one direction in the zx plane view seen from the y direction, i.e., the front view, as illustrated in FIG. 3A and FIG. 3B.

The electronic device of one embodiment of the present invention is not limited to having the structure illustrated in FIG. 3A and FIG. 3B. The structure of the electronic device of one embodiment of the present invention may be changed as appropriate as long as an object is achieved.

Figure 3C:
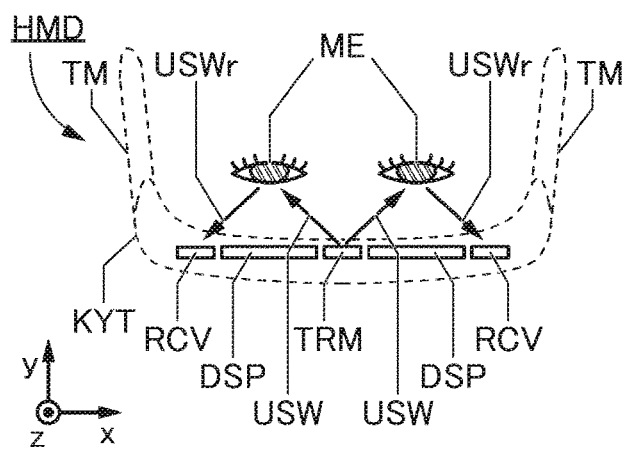
Figure 3D:
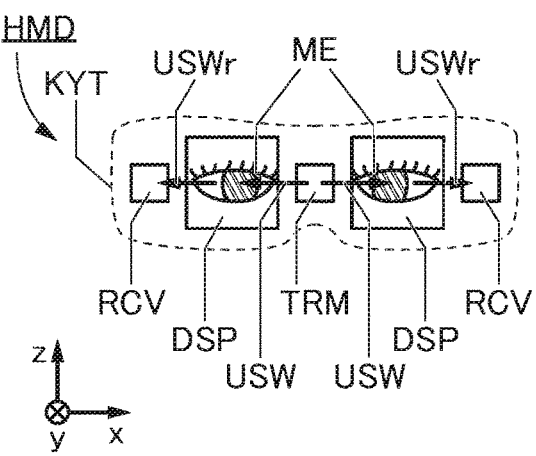

For example, the electronic device of one embodiment of the present invention may have a structure where the positions of the sending portion TRM and the receiving portion RCV are replaced with each other in the electronic device HMD in FIG. 3A and FIG. 3B. As an example, FIG. 3C and FIG. 3D illustrate a structure of the electronic device HMD where the positions of the sending portion TRM and the receiving portion RCV are replaced with each other in FIG. 3A and FIG. 3B.

Figure 3E:
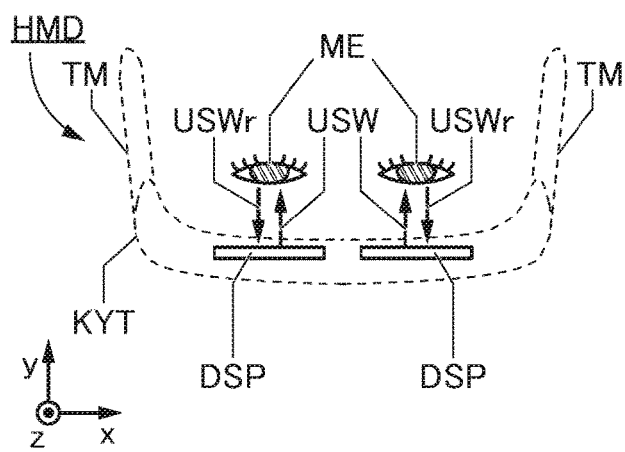
Figure 3F:
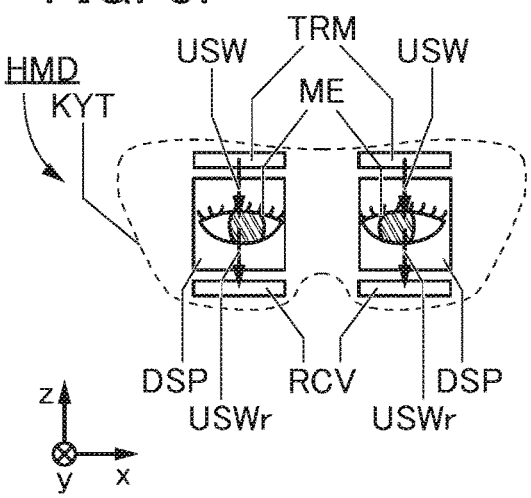

As another example, the electronic device of one embodiment of the present invention may have a structure where the receiving portion RCV, the eye ME of the user USR, and the sending portion TRM are provided to be aligned in the z direction. As a specific example, FIG. 3E and FIG. 3F illustrate a structure of the electronic device HMD where the sending portion TRM is provided above the display portion DSP and the receiving portion RCV is provided above the display portion DSP, in the zx plane view seen from the y direction. Thus, the electronic device HMD in FIG. 3E and FIG. 3F is different from the electronic device HMD in FIG. 3A to FIG. 3D in that two sending portions TRM and two receiving portions RCV are provided.

Figure 4A:
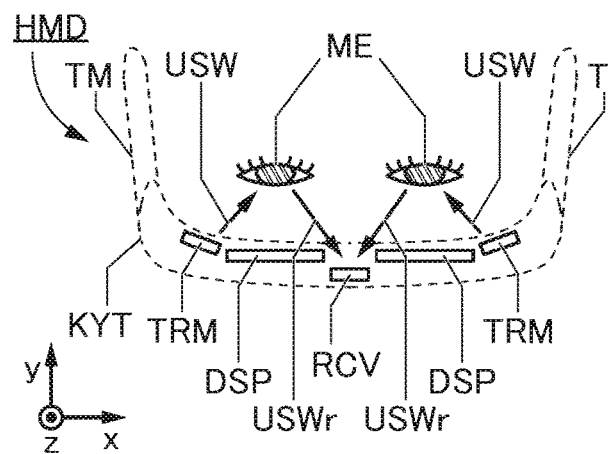
FIG. 4A and FIG. 4C are top views illustrating structure examples of an electronic device.
Figure 4B:
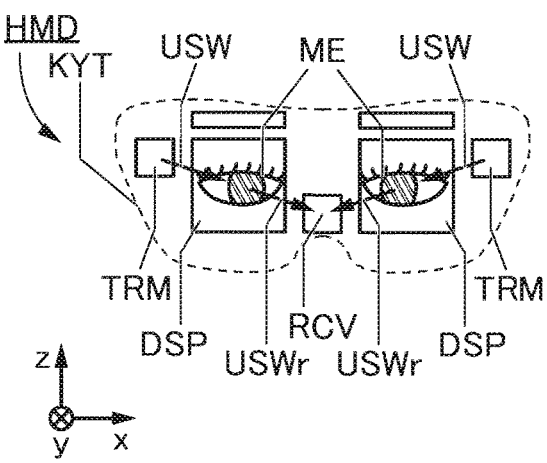
FIG. 4B is a front view illustrating a structure example of an electronic device.

In FIG. 3A to FIG. 3F, the sending portion TRM, the display portion DSP, and the receiving portion RCV are provided along the y direction or the z direction in the zx plane seen from the y direction; however, in the case where the ultrasonic wave USW propagated from the sending portion TRM is reflected by at least one of the retina blood vessel MKN and a blood vessel included in the fundus of the eye ME and the reflected ultrasonic wave USWr can be obtained by the receiving portion RCV, the positional relation of the sending portion TRM and the receiving portion RCV is not necessarily limited to that in the structure example of the electronic device HMD in any of FIG. 3A to FIG. 3F. For example, as illustrated in FIG. 4A, the electronic device HMD may have a structure where the sending portion TRM is provided such that its position in the y direction is higher than the position of the receiving portion RCV in the y direction, in the xy plane seen from the z direction. Although not illustrated, a structure may be employed where the sending portion TRM is provided such that its position in the y direction is lower than the position of the receiving portion RCV in the y direction. As another example, as illustrated in FIG. 4B, the electronic device HMD may have a structure where the sending portion TRM is provided such that its position in the z direction is higher than the position of the receiving portion RCV in the z direction in the zx plane seen from the y direction. Although not illustrated, a structure may be employed where the sending portion TRM is provided such that its position in the z direction is lower than the position of the receiving portion RCV in the z direction.

Figure 4C:
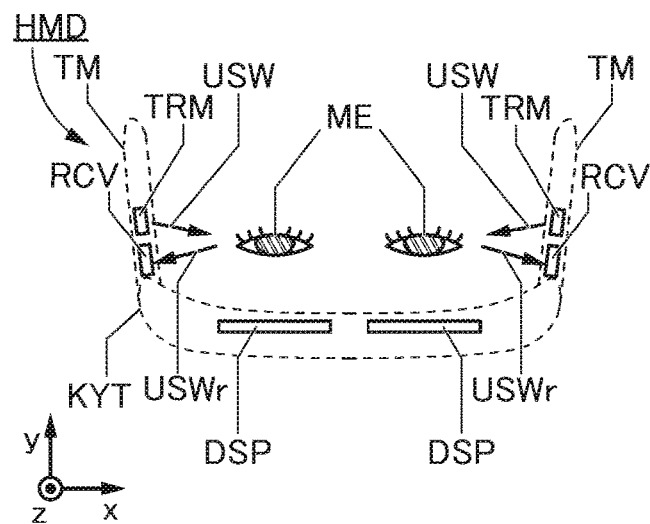

The sending portion TRM and the receiving portion RCV may be provided in the temple TM, not inside the housing KYT including the display portion DSP. Specifically, as illustrated in FIG. 4C, the sending portion TRM and the receiving portion RCV may be provided inside the temple TM that is part of the housing KYT. In this case, the electronic device HMD may be configured to measure the blood flow speed in a blood vessel around the eye ME.

In FIG. 3A to FIG. 4C and the like, the electronic device HMD obtains information on one or both of the blood flow speed and the pulse wave (blood pressure) from the retina blood vessel MKN and a blood vessel included in the fundus of the eye ME of the user USR; however, one embodiment of the present invention may have a structure where an ultrasonic wave is applied to a blood vessel around the eye ME of the user USR, not to the inside of the eye ME, so as to obtain information on one or both of the blood flow speed in the blood vessel and the pulse wave (blood pressure).

Although the display portion DSP has a quadrangular shape in FIG. 3A to FIG. 4C and the like, the shape of the display portion DSP included in the electronic device of one embodiment of the present invention may be a triangular shape, a shape with five or more vertices, a circular shape, an oval shape, or a shape with curve, for example.

In FIG. 3A to FIG. 4C, information on one or both of the blood flow speed and the pulse wave (blood pressure) is obtained with the sending portion TRM and the receiving portion RCV from a blood vessel around the eye ME, the retina blood vessel MKN, and a blood vessel included in the fundus of the eye of the user USR; however, in some cases, the electronic device of one embodiment of the present invention can obtain information on one or both of the blood flow speed and the pulse wave (blood pressure) from a blood vessel in a place other than the eye ME.

Figure 5:
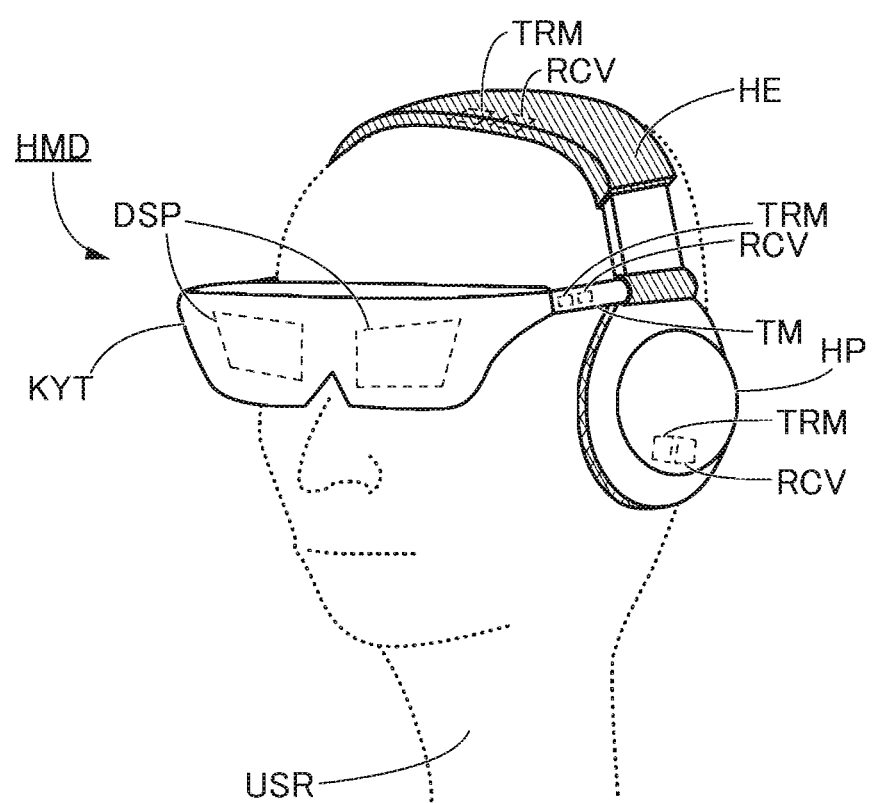
FIG. 5 is a perspective view illustrating a structure example of an electronic device.

For example, the electronic device HMD illustrated in FIG. 5 is considered. The electronic device HMD in FIG. 5 has a structure where the earphone of the electronic device HMD in FIG. 1A is changed into a headphone, and includes a wearing portion HP and a wearing portion HE. The wearing portion HP is a portion worn on an ear of the user USR, for example, and the wearing portion HP includes a sound output portion and an ear pad. The wearing portion HE is a portion worn on a head of the user USR, for example. The wearing portion HE may be provided with a wiring. The wearing portion HE may be provided with a circuit in addition to a wiring.

By providing the sending portion TRM and the receiving portion RCV in at least one of the temple TM, the wearing portion HP, and the wearing portion HE in the electronic device HMD in FIG. 5, information on one or both of the blood flow speed and the pulse wave (blood pressure) can be obtained from a blood vessel in a portion other than the eye ME of the user USR, in some cases.

For example, in the electronic device HMD in FIG. 5, the sending portion TRM and the receiving portion RCV can be provided in the temple TM. FIG. 4C illustrates a structure of the electronic device HMD that includes the sending portion TRM and the receiving portion RCV in the temple TM and obtains information on one or both of the blood flow speed and the pulse wave (blood pressure) from a blood vessel in a portion of the eye ME of the user USR; however, information on one or both of the blood flow speed and the pulse wave (blood pressure) of the user USR can be obtained from a blood vessel in a portion other than the eye ME, for example, a blood vessel included in a region of the user USR in contact with the temple TM or a region in close contact therewith.

In the electronic device HMD in FIG. 5, the sending portion TRM and the receiving portion RCV can be provided in the wearing portion HP, for example. Since the wearing portion HP is a portion worn on the ear of the user USR as described above, the wearing portion HP provided with the sending portion TRM and the receiving portion RCV can obtain information on one or both of the blood flow speed and the pulse wave (blood pressure) in a blood vessel in the ear or its periphery from the blood vessel.

As another example, in the electronic device HMD in FIG. 5, the sending portion TRM and the receiving portion RCV can be provided in the wearing portion HE. Since the wearing portion HE is a portion worn on the head of the user USR as described above, the wearing portion HE provided with the sending portion TRM and the receiving portion RCV can obtain information on one or both of the blood flow speed and the pulse wave (blood pressure) in a blood vessel in the head from the blood vessel.

Structure Example 1

Next, a structure example of the above-described electronic device HMD is described.

Figure 6:
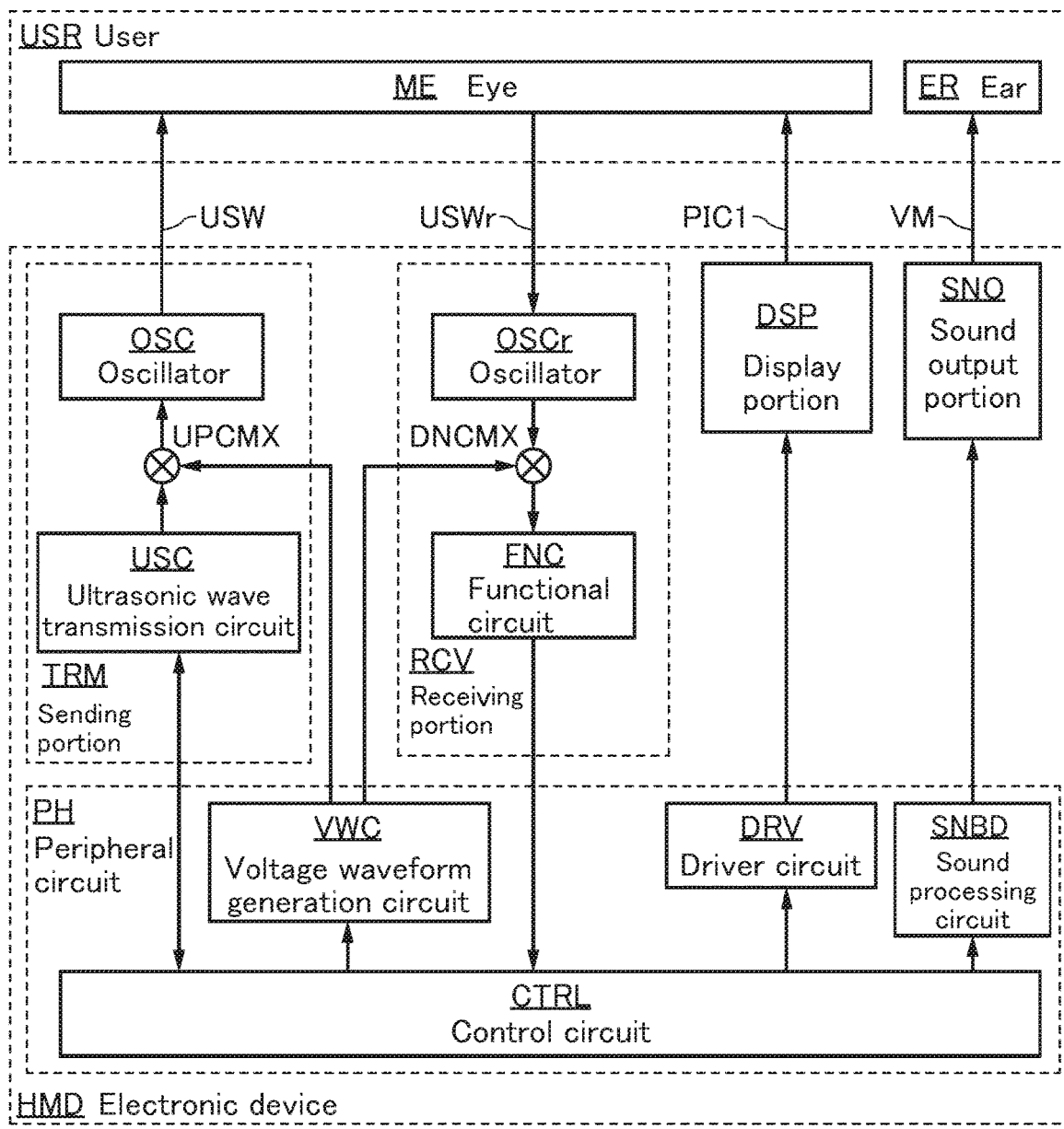
FIG. 6 is a block diagram illustrating a structure example of an electronic device.

FIG. 6 is a block diagram illustrating a structure example of the electronic device HMD of one embodiment of the present invention. The electronic device HMD includes the sending portion TRM, the receiving portion RCV, a peripheral circuit PH, the display portion DSP, and the sound output portion SNO, for example. Note that for description of the structure example, FIG. 6 also illustrates the user USR, and the eye ME and an ear ER of the user USR.

In the electronic device HMD, the sending portion TRM includes an oscillator OSC, a mixer UPCMX, and an ultrasonic wave transmission circuit USC. The receiving portion RCV includes an oscillator OSCr, a mixer DNCMX, and a functional circuit FNC. The peripheral circuit PH includes a voltage waveform generation circuit VWC, a driver circuit DRV, a sound processing circuit (sometimes referred to as a soundboard) SNBD, and a control circuit CTRL.

The control circuit CTRL has a function of controlling circuits included in the electronic device HMD, for example. Thus, the control circuit CTRL is electrically connected to the sending portion TRM, the receiving portion RCV, the voltage waveform generation circuit VWC, the sound processing circuit SNBD, and the like. The control circuit CTRL has a function of processing information sent from the circuits included in the electronic device HMD and sending the processing results to a predetermined circuit, for example.

The ultrasonic wave transmission circuit USC has a function of generating a high-frequency electric signal and sending the electric signal to the mixer UPCMX to be described later. The ultrasonic wave transmission circuit USC may have a function of sending the electric signal to the control circuit CTRL. The electric signal sent to the control circuit CTRL may be an analog signal or may be converted into a digital voltage (digital value). Note that the electric signal converted into a digital voltage can be, for example, a voltage corresponding to information on the frequency of an ultrasonic wave generated in the ultrasonic wave transmission circuit USC or the like. In this specification and the like, the electric signal sent from the ultrasonic wave transmission circuit USC to the control circuit CTRL is referred to as a first electric signal.

The voltage waveform generation circuit VWC has a function of generating a signal for converting a waveform of the electric signal generated in the ultrasonic wave transmission circuit USC. Note that the conversion is performed in the mixer UPCMX to be described later. Note that the voltage waveform generation circuit VWC can be a circuit generating a timing pulse or a local oscillator, for example.

The mixer UPCMX has a function of mixing a high-frequency electric signal generated in the ultrasonic wave transmission circuit USC and an electric signal generated in the voltage waveform generation circuit VWC, and sending the mixed electric signals to the oscillator OSC.

The oscillator OSC has a function of generating the ultrasonic wave USW based on the voltage waveform of the electric signals that are mixed in the mixer UPCMX and input to the oscillator OSC. Note that the ultrasonic wave USW is propagated to the eye of the user USR.

The oscillator OSCr has a function of receiving the ultrasonic wave USWr that is reflected by one or both of the retina blood vessel and a blood vessel included in the fundus of the eye ME of the user USR, and generating an electric signal corresponding to the ultrasonic wave USWr.

Like the mixer UPCMX, the mixer DNCMX has a function of mixing an electric signal generated in the oscillator OSCr and an electric signal generated in the voltage waveform generation circuit VWC, and sending the mixed electric signals to the functional circuit FNC.

Note that depending on the situation, the electronic device HMD may have a structure not including one or more selected from the voltage waveform generation circuit VWC, the mixer UPCMX, and the mixer DNCMX.

The functional circuit FNC can be a circuit including one or more selected from a band pass filter, an amplifier, and an analog-digital converter circuit, for example. The functional circuit FNC has a function of obtaining an electric signal from the mixer DNCMX, processing the electric signal with the above-described circuit, and sending the processed electric signal to the control circuit CTRL.

The band pass filter has a function of outputting an AC voltage in a particular frequency band to an output terminal of the band pass filter. In addition, the band pass filter has a function of attenuating an AC voltage that is not in the particular frequency band. That is, the band pass filter can select one or two or more channels from an electric signal with a plurality of channels by determining a particular frequency band to be output to the output terminal.

The amplifier has a function of amplifying the voltage amplitude of an electric signal, for example.

The analog-digital converter circuit has a function of converting an electric signal into a digital signal, for example.

Note that in this specification and the like, an electric signal sent from the oscillator OSCr to the mixer DNCMX, an electric signal sent from the mixer DNCMX to the functional circuit FNC, and an electric signal sent from the functional circuit FNC to the control circuit CTRL are collectively referred to as a second electric signal.

The second electric signal output from the functional circuit FNC is sent to the control circuit CTRL. The control circuit CTRL obtains information on the frequency or the like of the ultrasonic wave USW from the first electric signal, obtains information on the frequency or the like of the ultrasonic wave USWr from the second electric signal, and with the use of these information pieces, performs arithmetic operation of the blood flow speed measured in a blood vessel in a portion of the eye ME or the pulse wave (blood pressure) of the user USR. After that, the control circuit CTRL sends the arithmetic operation result as an electric signal to one or both of the display portion DSP and the sound output portion SNO.

As a specific example, in the case where the result of the processing performed in the control circuit CTRL (the blood flow speed or the pulse wave (blood pressure)) is displayed on the display portion DSP, the control circuit CTRL converts the result into a proper electric signal (referred to as a third electric signal in this specification and the like), and sends the third electric signal to the display portion DSP through the driver circuit DRV. Then, the display portion DSP displays an image PIC1 corresponding to the electric signal, for the eye ME of the user USR. As another example, in the case where the sound output portion SNO outputs the result of the processing performed in the control circuit CTRL as a sound, the control circuit CTRL converts the result (the blood flow speed or the pulse wave (blood pressure)) into a proper electric signal (referred to as a fourth electric signal in this specification and the like), and sends the fourth electric signal to the sound output portion SNO through the sound processing circuit SNBD to be described later. Then, the sound output portion SNO outputs a sound VM corresponding to the electric signal to the ear ER of the user USR.

When the electronic device HMD is configured in the above manner, the electronic device HMD can measure one or both of the blood flow speed and pulse wave (blood pressure) of the user USR. In addition, with the electronic device HMD, the user USR can find one or both of the blood flow speed and pulse wave of the user himself or herself.

Structure Example 2

Note that the structure of the electronic device of one embodiment of the present invention is not limited to the structure example of the electronic device HMD illustrated in FIG. 6. The structure of the electronic device of one embodiment of the present invention may be changed as appropriate as long as an object is achieved.

Figure 7:
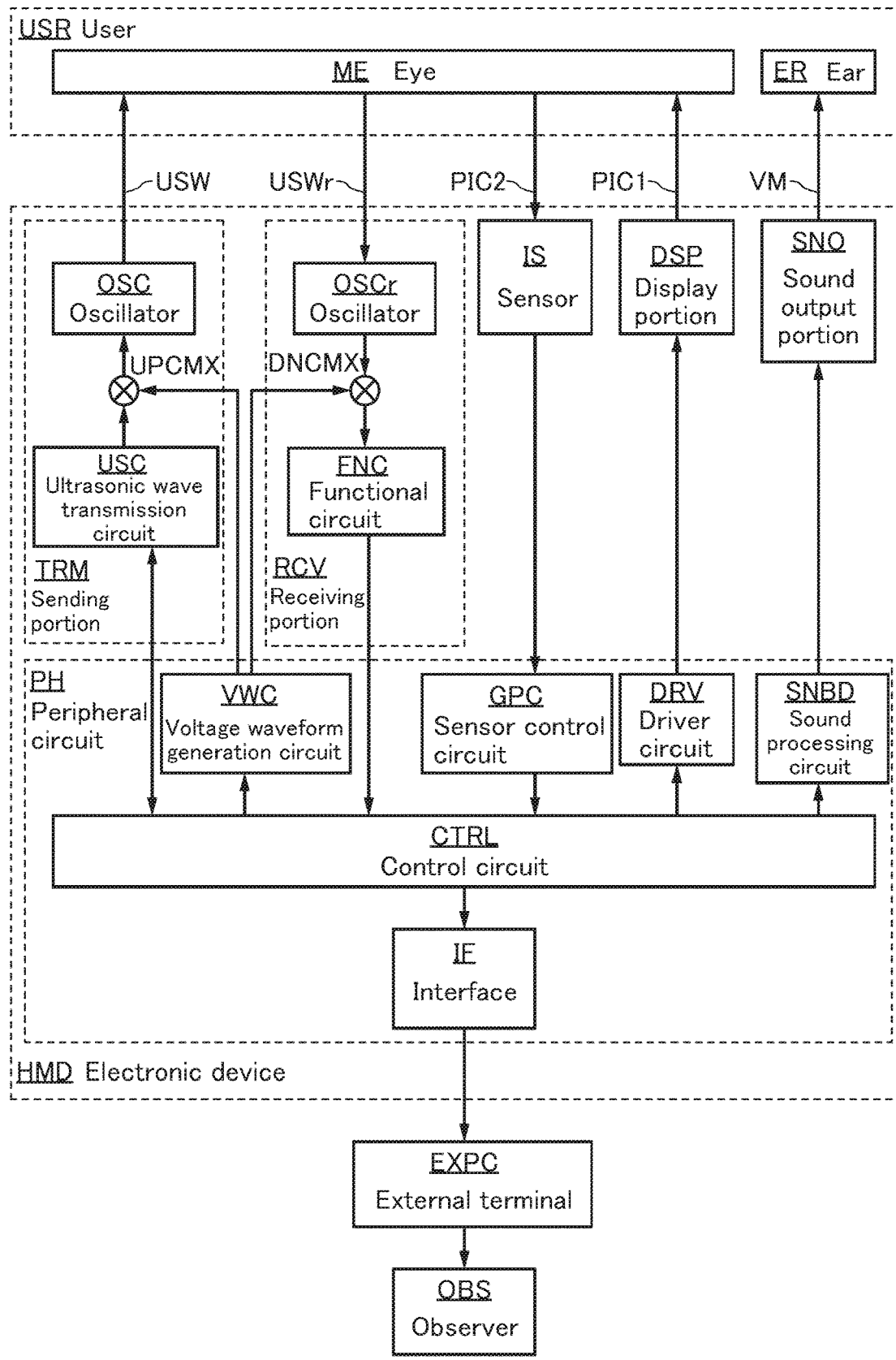
FIG. 7 is a block diagram illustrating a structure example of an electronic device.

The electronic device HMD illustrated in FIG. 7 has a structure where a sensor IS, a sensor control circuit GPC, and an interface IF are added to the electronic device HMD in FIG. 6, for example. FIG. 7 also illustrates an external terminal EXPC and an observer OBS.

The peripheral circuit PH includes the sensor control circuit GPC and the interface IF, for example.

The control circuit CTRL is electrically connected to the sensor control circuit GPC, and the sensor control circuit GPC is electrically connected to the sensor IS. The control circuit CTRL is electrically connected to the interface IF.

The sensor IS can be an imaging device (sometimes referred to as an image sensor), for example. In this case, the sensor IS has a function of capturing an image of the eye ME or the fundus of the eye of the user USR, and obtaining the imaging result as an image PIC2. In addition, the sensor IS has a function of sending the image PIC2 to the sensor control circuit GPC, for example. When the electronic device HMD includes the sensor IS including an imaging device, not only the blood flow speed in at least one of a blood vessel around the eye ME, the retina blood vessel MKN, and a blood vessel included in the fundus of the eye of the user USR, but also the state of the fundus of the eye ME of the user USR can be monitored.

Alternatively, the sensor IS can be a temperature sensor, for example. In this case, the sensor IS can measure the body temperature of the user USR, for example. Note that the electronic device HMD in FIG. 7 has a structure where the sensor IS obtains the body temperature of the user USR from the eye ME; however, in the case where the sensor IS a temperature sensor, the body temperature of the user USR may be obtained from not only the eye ME but also one or both of the ear ER and a skin.

The sensor control circuit GPC has a function of controlling the sensor IS. The sensor control circuit GPC has a function of receiving an instruction signal from the control circuit CTRL to drive the sensor IS. The sensor control circuit GPC may further include a current-voltage converter circuit, an analog-digital converter circuit, or the like. For example, in the case where information is obtained from the driven sensor IS and an analog current corresponding to the information is supplied to the sensor control circuit GPC, the sensor control circuit GPC can convert the analog current into an analog voltage with the current-voltage converter circuit, and can convert the analog voltage into a digital value with the analog-digital converter circuit.

The interface IF has a function of, for example, sending and receiving information to and from the external terminal EXPC positioned outside the electronic device HMD. The interface IF can be an input/output terminal, for example. The interface IF may perform wireless communication between the electronic device HMD and the external terminal EXPC with the use of a high frequency (RF) circuit, for example.

FIG. 7 illustrates a case where the observer OBS uses the external terminal EXPC, for example. In particular, information on one or more selected from the blood pressure, pulse, blood oxygen saturation, and body temperature of the user USR wearing the electronic device HMD are sent to the external terminal EXPC through the interface IF, whereby the observer OBS can find the information on the user USR. Accordingly, the observer OBS can find the physical condition of the user USR. That is, with a system constructed to include the electronic device HMD and the external terminal EXPC as illustrated in FIG. 7, the observer OBS can manage and grasp the physical condition of the user USR.

As an application example of the system illustrated in FIG. 7, when the user USR is a student and the observer OBS is a teacher in an educational site such as a school, the teacher can manage and grasp the physical condition of the student during a class. As another example, when the user USR is a subordinate and the observer OBS is a superior in a workplace, the superior can grasp and manage the physical condition of the subordinate at work.

Structure Example 3

Although the above structure example describes the electronic device HMD where the sensor IS an image sensor, a temperature sensor, or the like, the electronic device HMD can include a sensor using an NV (Nitrogen Vacancy) center.

An example of a sensor using an NV center is a sensor including a diamond layer containing an NV center. The diamond layer containing an NV center can be used as a composite sensor such as a magnetic sensor, an electric field sensor, and/or a temperature sensor, for example.

Figure 8:
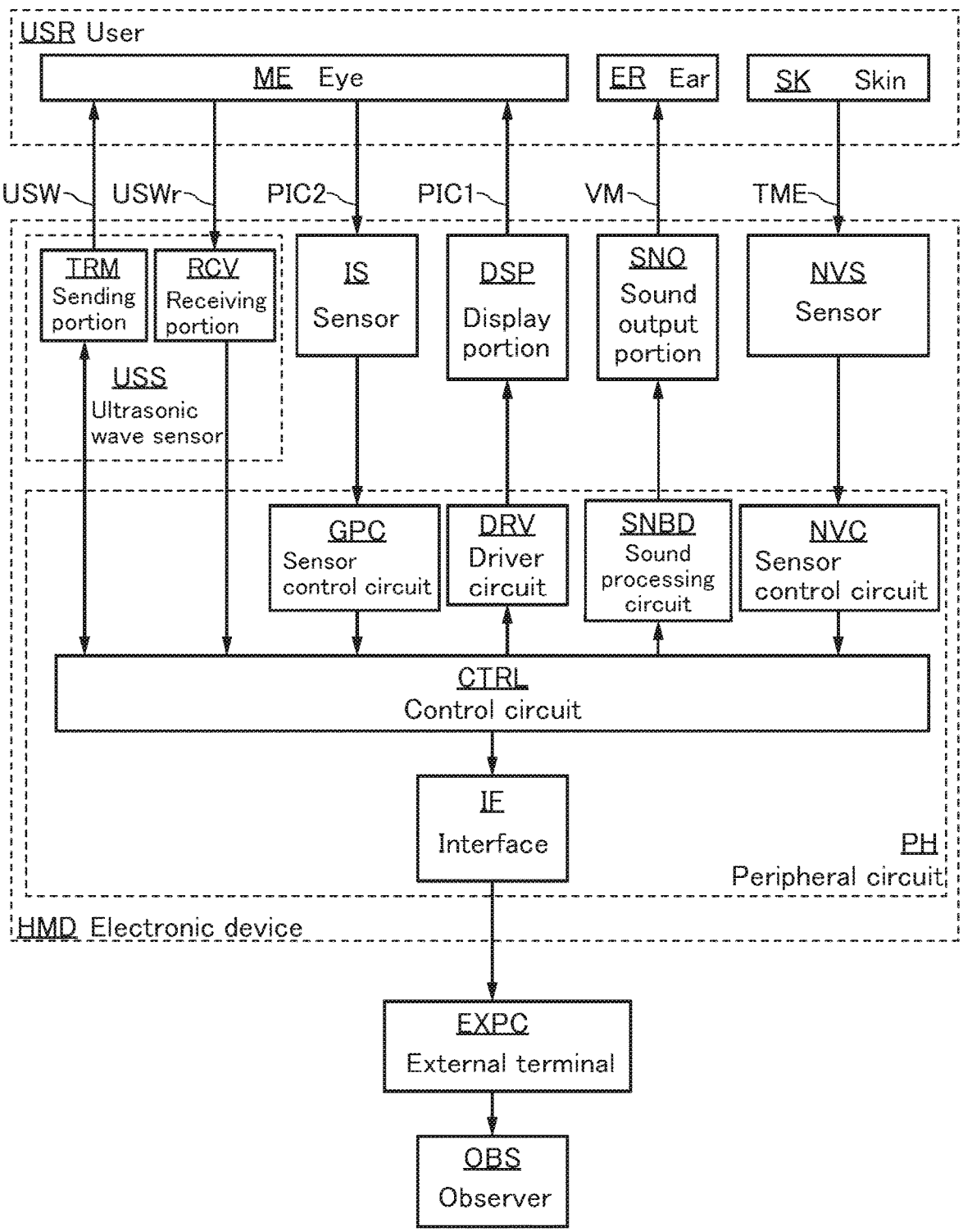
FIG. 8 is a block diagram illustrating a structure example of an electronic device.

FIG. 8 illustrates a structure example of the electronic device HMD including a sensor using an NV center. The electronic device HMD in FIG. 8 has a structure where a sensor NVS using an NV center is added to the electronic device HMD in FIG. 7. In the electronic device HMD in FIG. 8, the peripheral circuit PH includes a sensor control circuit NVC having a function of controlling the sensor NVS. Note that FIG. 8 collectively illustrates the sending portion TRM and the receiving portion RCV as an ultrasonic wave sensor USS.

The sensor NVS is described as a sensor including a diamond layer containing an NV center, for example. Thus, the sensor NVS functions as a sensor sensing one or more selected from magnetism, an electric field, and temperature.

The sensor NVS has a function of detecting information on the body temperature of a skin SK of the user USR, for example. The sensor NVS may have a function of detecting information of a magnetic field and an electric field output from cells included in the skin SK, for example. Note that in this specification and the like, the above-described information pieces are collectively referred to as information TME.

The information TME detected by the sensor NVS is sent to the sensor control circuit NVC. The sensor control circuit NVC has a function of converting information obtained by the sensor NVS into a proper electric signal and sending the electric signal to the control circuit CTRL, for example. The conversion into a proper electric signal here is, for example, an analog-digital conversion where an analog current or an analog voltage is converted into a digital voltage. Thus, the sensor control circuit NVC may include an analog-digital converter circuit.

<<Structure Example of Composite Sensor>>

Figure 9A:
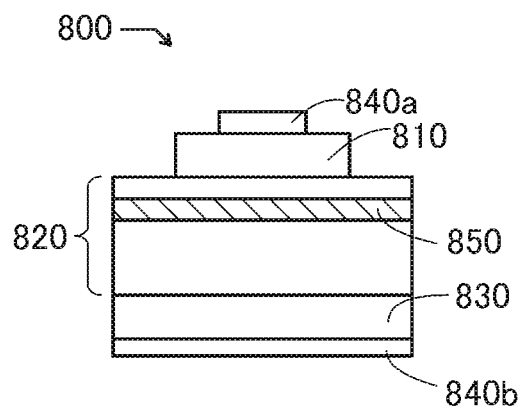
FIG. 9A is a cross-sectional view illustrating a structure example of a sensor.

FIG. 9A illustrates an embodiment of a semiconductor device functioning as a composite sensor including a diamond layer containing an NV center.

A semiconductor device 800 illustrated in FIG. 9 is a PIN (p-intrinsic-n) diode, for example, and includes an n-plus layer 810, a p-minus layer 820, a p-plus layer 830, an electrode 840a, and an electrode 840b. Note that the semiconductor device 800 contains at least carbon and nitrogen. Alternatively, a PN junction diode or a field-effect transistor may be used as the semiconductor device 800.

The n-plus layer 810 is a semiconductor such as a diamond doped with an impurity such as arsenic or phosphorus at a concentration higher than or equal to a predetermined value (e.g., $8 \times 10^{19}$ cm$^{-3}$). The thickness of the n-plus layer 810 is 500 nm, for example, and appropriately set depending on the electrical characteristics or the like required for the semiconductor device 800.

The p-minus layer 820 is a semiconductor such as a diamond doped with an impurity such as boron at a concentration lower than a predetermined value (e.g., $2 \times 10^{14}$ cm$^{-3}$). The thickness of the p-minus layer 820 is 5 µm, and appropriately set depending on the electrical characteristics or the like required for the semiconductor device 800. The p-minus layer 820 includes a sensor portion 850 that is formed into a diamond layer containing an NV center by ion implantation of nitrogen ions, for example. The sensor portion 850 is preferably positioned at a depth of 300 nm to 400 nm inclusive from a surface bonded to the n-plus layer 810, further preferably positioned at a depth of approximately 350 nm.

Note that a semiconductor such as a diamond can be synthesized by a high pressure and high temperature (HPHT) method, a CVD method, or a detonation method.

In the case where the sensor portion 850 containing an NV center is irradiated with a microwave, fluorescent light emitted by the NV center changes in accordance with one or more selected from an electric field, temperature, and a magnetic field. Thus, one or more selected from the electric field, temperature, and magnetic field in the semiconductor device 800 at a position where the sensor portion 850 is placed can be measured on the basis of the frequency of the microwave at which the intensity of fluorescent light emitted by the NV center decreases.

The p-plus layer 830 is a semiconductor such as a diamond doped with an impurity such as boron at a concentration higher than or equal to a predetermined value (e.g., $1 \times 10^{17}$ cm$^{-3}$). The thickness of the p-plus layer 830 is 500 μm, and appropriately set in accordance with the electrical characteristics or the like required for the semiconductor device 800.

The electrode 840a and the electrode 840b each apply a voltage supplied from an external power source of the semiconductor device 800 to the semiconductor device 800.

Figure 9B:
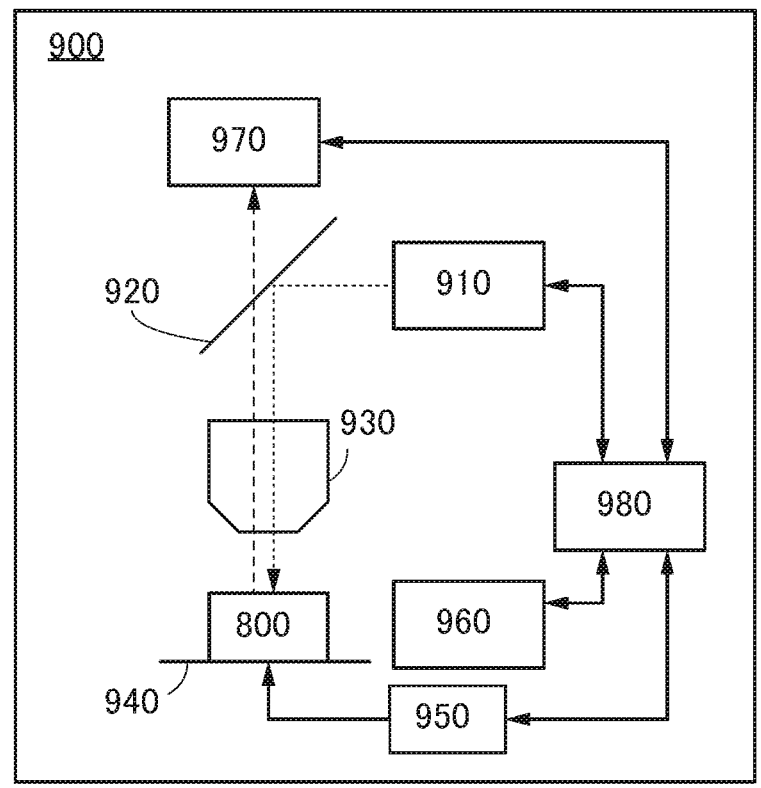
FIG. 9B is a block diagram illustrating a structure example of a measuring apparatus including the sensor.

FIG. 9B illustrates an example of a measurement apparatus for measuring a physical parameter in the semiconductor device 800 illustrated in FIG. 9A. A measurement apparatus 900 illustrated in FIG. 9B can be a confocal laser scanning microscope, for example, and includes the semiconductor device 800, a laser light source 910, a beam splitter 920, an objective lens 930, a slide glass 940, a power source 950, a microwave source 960, a detection device 970, and a control device 980. Note that the measurement apparatus 900 may include a digital camera or a spectrometer.

The laser light source 910 emits laser light with a wavelength of 532 nm, for example, which excites an NV center in the sensor portion 850 placed in the semiconductor device 800 illustrated in FIG. 9A.

The beam splitter 920 reflects the laser light emitted from the laser light source 910 toward the semiconductor device 800. In addition, the beam splitter 920 transmits a luminous flux of fluorescent light emitted by the sensor portion 850 of the semiconductor device 800 and emits the luminous flux toward the detection device 970.

The objective lens 930 adjusts the beam width of the laser light emitted from the laser light source 910 for irradiating the semiconductor device 800 with the laser light. In addition, the objective lens 930 collimates the fluorescent light emitted by the sensor portion 850 of the semiconductor device 800, and emits the collimated light to the detection device 970.

The slide glass 940 is a quartz glass or the like, where the semiconductor device 800 that is a measurement object is placed. Over a surface of the slide glass 940 on the side where the semiconductor device 800 is placed, an electrode is formed and a wiring for operating the semiconductor device 800 is formed. The slide glass 940 on the side where the semiconductor device 800 is placed is provided with a microwave wire including an antenna for irradiating the semiconductor device 800 with a microwave emitted from the microwave source 960.

The power source 950 supplies electric power of tens or hundreds of volts to the semiconductor device 800 placed over the slide glass 940 in accordance with a control instruction from the control device 980.

The microwave source 960 is a radio wave transmission device that emits a microwave in a certain frequency range around 2.87 GHz. In addition, the microwave source 960 irradiates the semiconductor device 800 with the emitted microwave through the antenna placed over the slide glass 940 to bring an NV center in the sensor portion 850 into an ESR (Electron Spin Resonance) state.

The laser light source 910 and the microwave source 960 operate as driver portions for driving the sensor portion 850.

The detection device 970 includes an APD (avalanche photodiode), receives fluorescent light emitted from the sensor portion 850, and detects the intensity of the received fluorescent light at each position on the XY plane, for example. The detection device 970 outputs the intensity of the fluorescent light detected at each position on the XY plane to the control device 980. Note that the spatial resolution of the detection device 970 is determined depending on the focus of laser light by the objective lens 930, the accuracy of a sample holder (piezoscanner) fixing the semiconductor device 800 over the slide glass 940, or the like, and is preferably within a range from 10 nm to 300 nm inclusive. An imaging device including one or both of a CCD (Charge Coupled Devices) image sensor and a CMOS (Complementary Metal Oxide Semiconductor) image sensor may be used as the detection device 970 to perform measurement by imaging.

The control device 980 is a computer device including an arithmetic processing device (e.g., a processor) and a memory device (e.g., a hard disk device), and controls operations of components of the measurement apparatus 900. For example, the control device 980 controls a voltage applied from the power source 950 to the semiconductor device 800, the frequency of microwave emitted by the microwave source 960, and the like. In addition, the control device 980 calculates the intensity distribution of fluorescent light at each position on the XY plane with use of the intensity of fluorescent light from the sensor portion 850 detected by the detection device 970. The control device 980 calculates the frequency where the intensity becomes the lowest at each position on the XY plane, on the basis of the calculated intensity distribution. Accordingly, the control device 980 can calculate one or more physical parameters selected from an electric field, a magnetic field, and temperature at each position on the XY plane on the basis of data on the frequency where the intensity becomes the lowest at each position on the XY plane.

From the above, the control device 980 can be, for example, the sensor control circuit NVC in the structure example of the electronic device HMD in FIG. 8. Alternatively, the control device 980 can be a circuit provided with a memory device or the like in addition to the sensor control circuit NVC in the structure example of the electronic device HMD in FIG. 8.

Structure Example 4

Figure 10:
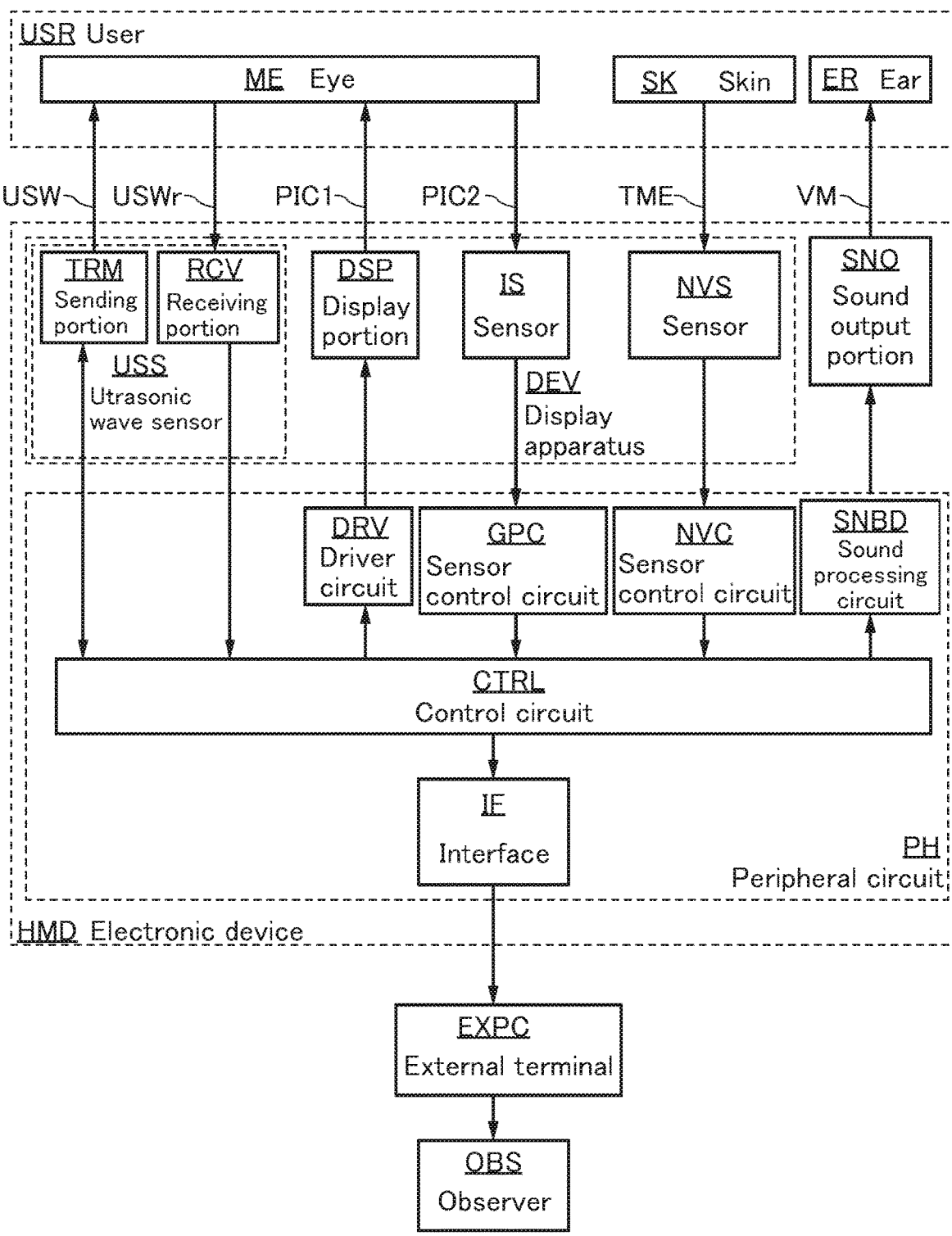
FIG. 10 is a block diagram illustrating a structure example of an electronic device.

The electronic device HMD illustrated in FIG. 10 is a variation example of the electronic device HMD in FIG. 8, and has a structure where the display portion DSP, the ultrasonic wave sensor USS, the sensor IS, and the sensor NVS are included in a display apparatus DEV. Although the electronic device HMD in FIG. 10 includes the display portion DSP, the ultrasonic wave sensor USS, the sensor IS, and the sensor NVS in the display apparatus DEV, the display apparatus DEV may include one or more selected from the ultrasonic wave sensor USS, the sensor IS, and the sensor NVS. As a specific example, the display apparatus DEV may include the display portion DSP and the sensor IS, or may include the display portion DSP and the sensor NVS.

Figure 11:
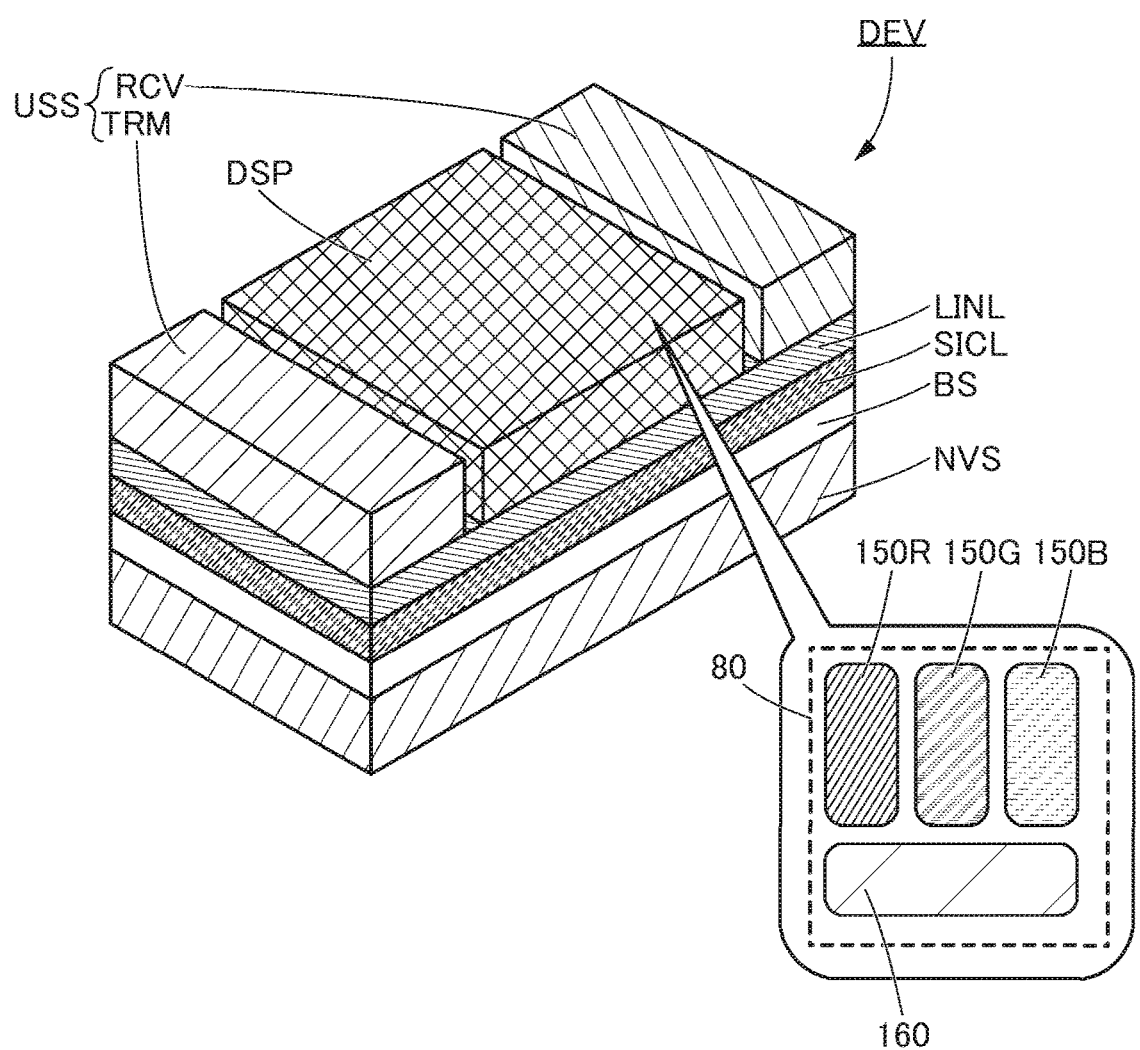
FIG. 11 is a schematic perspective view illustrating a structure example of a display apparatus.

Here, a structure example of the display apparatus DEV that can be provided in the electronic device HMD in FIG. 10 is described. The display apparatus DEV illustrated in FIG. 11 is an example of the display apparatus DEV that can be provided in the electronic device HMD in FIG. 10, and substrates each provided with a circuit are mounted above and below a substrate BS. The display apparatus DEV illustrated in FIG. 11 includes, for example, a circuit layer SICL, a wiring layer LINL, the display portion DSP, the sending portion TRM, and the receiving portion RCV above the substrate BS, and includes the sensor NVS below the substrate BS.

As the substrate BS, a single crystal substrate (e.g., a semiconductor substrate formed of silicon or germanium) can be used, for example. Besides the single crystal substrate, for example, an SOI (Silicon On Insulator) substrate, a glass substrate, a quartz substrate, a plastic substrate, a sapphire glass substrate, a metal substrate, a stainless steel substrate, a substrate including stainless steel foil, a tungsten substrate, a substrate including tungsten foil, a flexible substrate, a bonding film, or paper or a base material film containing a fibrous material can be used as the substrate BS. Note that examples of the glass substrate include barium borosilicate glass, aluminoborosilicate glass, and soda lime glass. As examples of the flexible substrate, the attachment film, the base material film, and the like, the following can be given. Examples include plastics typified by polyethylene terephthalate (PET), polyethylene naphthalate (PEN), polyether sulfone (PES), and polytetrafluoroethylene (PTFE). Another example is a synthetic resin such as an acrylic resin. Other examples include polypropylene, polyester, polyvinyl fluoride, and polyvinyl chloride. Other examples include polyamide, polyimide, aramid, an epoxy resin, an inorganic vapor deposition film, and paper. Note that in the case where the fabrication process of the display apparatus DEV involves heat treatment, a highly heat-resistant material is preferably selected for the substrate BS.

The circuit layer SICL is provided over the substrate BS. The circuit layer SICL includes, for example, the driver circuit DRV for driving the display portion DSP, the sensor control circuit GPC for controlling the sensor IS, the sensor control circuit NVC for controlling the sensor NVS, the control circuit CTRL, and the like.

In the description of this embodiment, the substrate BS is a semiconductor substrate containing silicon or the like as a material. Therefore, a transistor included in the circuit layer SICL can be a transistor containing silicon in a channel formation region (hereinafter referred to as a Si transistor).

The wiring layer LINL is provided over the circuit layer SICL, and the display portion DSP, the sending portion TRM, and the receiving portion RCV are provided over the wiring layer LINL. Note that the display portion DSP, the sending portion TRM, and the receiving portion RCV can be mounted on the wiring layer LINL over the substrate BS by a bonding step, for example. Note that the bonding step will be described in detail in Embodiment 3.

A wiring is provided in the wiring layer LINL, for example. The wiring included in the wiring layer LINL functions as a wiring electrically connecting the circuits included in the circuit layer SICL provided below and the display portion DSP, the sending portion TRM, and the receiving portion RCV provided above.

Note that in the structure of the display apparatus DEV in FIG. 11, the sending portion TRM, the display portion DSP, and the receiving portion RCV are placed to be aligned in this order.

In the display apparatus DEV in FIG. 11, the display portion DSP includes a pixel 80. The pixel 80 includes a light-emitting device 150R, a light-emitting device 150G, a light-emitting device 150B, and a light-receiving device 160, for example. In particular, the above-described sensor IS can be the light-receiving device 160 illustrated in FIG. 11.

Note that the structure of the pixel 80 will be described in detail in Embodiment 3.

The sensor NVS is provided below the substrate BS, for example. The sensor NVS can be mounted below the substrate BS by a bonding step, for example.

In the case where the sensor NVS is provided below the substrate BS, the sensor NVS may function as a temperature sensor that senses a temperature of the substrate BS. For example, when the display apparatus DEV is driven for a long time, heat generated during the driving of the display apparatus DEV might increase the temperature of the display apparatus DEV. In this case, the sensor NVS used as a temperature sensor can sense the increased temperature of the display apparatus DEV. Furthermore, when the display apparatus DEV is provided with a function of limiting the amount of power supply to the display apparatus DEV or temporarily stopping a circuit included in the display apparatus DEV in accordance with the increased temperature of the display apparatus DEV sensed by the sensor NVS, for example, malfunction of the electronic device HMD, especially the display device DEV, due to heat can be prevented.

Structure Example 5

Figure 12A:
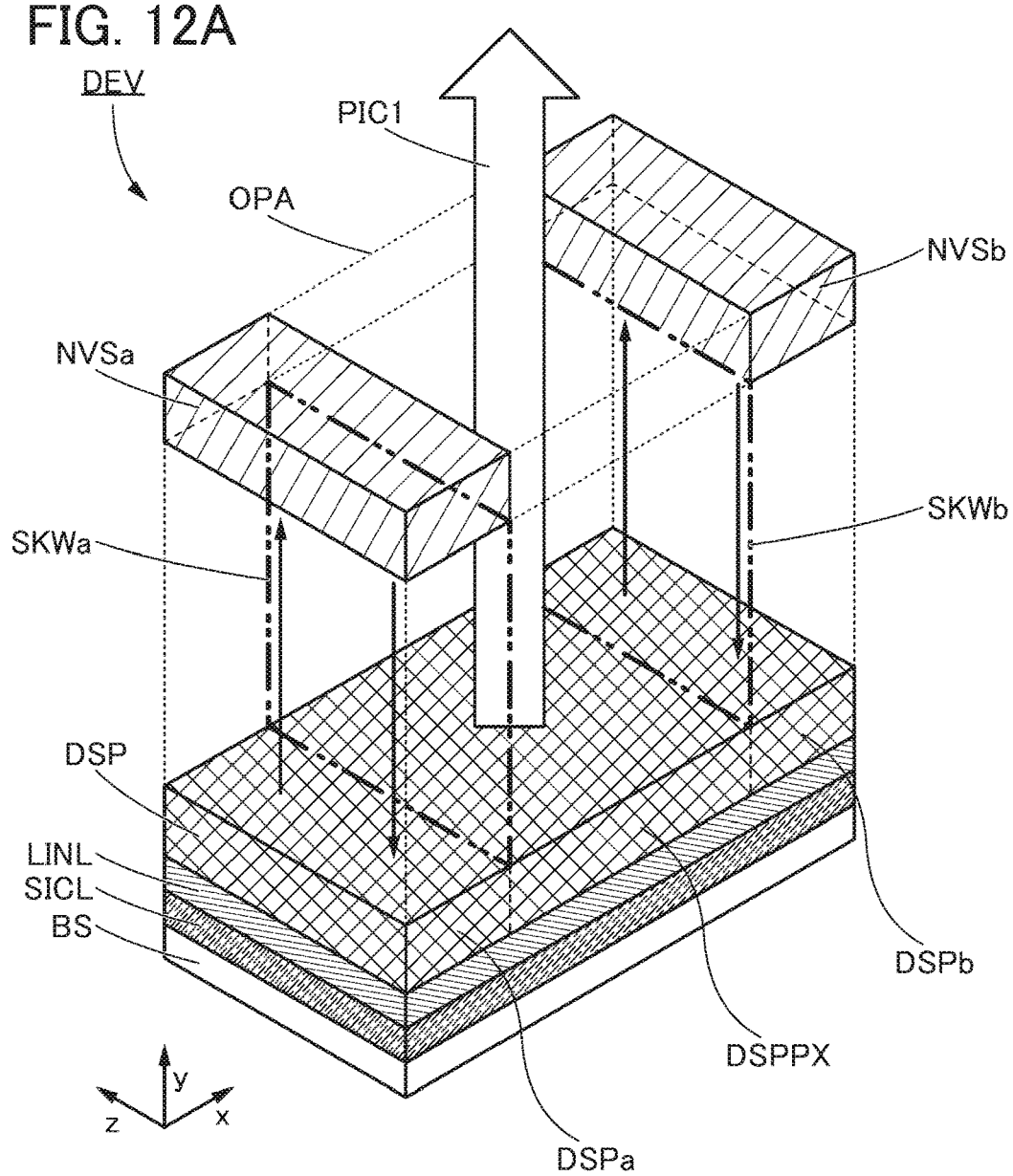
FIG. 12A is a schematic perspective view illustrating a structure example of a display apparatus.

FIG. 12A illustrates a structure example of a display apparatus that can be used for the electronic device of one embodiment of the present invention.

The display apparatus DEV in FIG. 12A includes the substrate BS, the circuit layer SICL provided over the substrate BS, the wiring layer LINL provided over the circuit layer SICL, and the display portion DSP provided over the wiring layer LINL. Refer to the description of the display apparatus DEV made with reference to FIG. 11 for the substrate BS, the circuit layer SICL, the wiring layer LINL, and the display portion DSP.

In the display apparatus DEV in FIG. 12A, the display portion DSP includes a region DSPPX, a region DSPa, and a region DSPb. Note that the display portion DSP includes a light-emitting device and a light-receiving device, as in the display apparatus DEV in FIG. 11.

A sensor NVSa is provided in a region overlapping with the region DSPa, and a sensor NVSb is provided in a region overlapping with the region DSPb. A region being positioned between the sensor NVSa and the sensor NVSb and overlapping with the region DSPPX is referred to as a region OPA. The region OPA functions as a region for emitting light from a light-emitting device included in the region DSPPX (illustrated as the image PIC1 in FIG. 12A) to the above.

The sensor NVSa and the sensor NVSb can be at least one of the sensor containing an NV center and a circuit included in the sensor containing an NV center, which are described in Structure example 3. For example, the sensor NVSa and the sensor NVSb can be the semiconductor device 800 and the slide glass 940 included in the measurement apparatus 900.

When the sensor NVSa and the sensor NVSb are driven, light emitted from the light-emitting devices included in the region DSPa and the region DSPb of the display portion DSP enters the sensor NVSa and the sensor NVSb. That is, in the display apparatus DEV illustrated in FIG. 12A, the light-emitting devices included in the region DSPa and the region DSPb each correspond to the laser light source 910 in the measurement apparatus 900.

At the time of driving the sensor NVSa and the sensor NVSb, fluorescent light emitted from the sensor NVSa and the sensor NVSb (specifically, the sensor portions 850 included in the sensor NVSa and the sensor NVSb) is received by the light-receiving devices included in the region DSPa and the region DSPb of the display portion DSP. That is, in the display apparatus DEV illustrated in FIG. 12A, the light-receiving devices included in the region DSPa and the region DSPb each correspond to the detection device 970 in the measurement apparatus 900.

Between the region DSPa and the region DSPPX and between the region DSPb and the region DSPPX, blocking walls for preventing entry of light between the regions are preferably provided so that light emitted from the light-emitting device included in the region DSPPX does not enter at least one of the sensor NVSa and the sensor NVSa and light emitted from the light-emitting devices included in the region DSPa and the region DSPb does not enter the region OPA. In the display apparatus DEV in FIG. 12A, for example, a wall SKWa and a wall SKWb that are for blocking light are provided between the region DSPa and the region DSPPX and between the region DSPb and the region DSPPX, respectively. Note that in FIG. 12A, the wall SKWa and the wall SKWb are indicated by thick dashed double-dotted lines.

In the display apparatus DEV in FIG. 12A, a light-emitting device and a light-receiving device are included in the same region (the region DSPa or the region DSPb); thus, the beam splitter 920 is not necessarily provided.

Although the objective lens 930 is not illustrated in the display apparatus DEV in FIG. 12A, the objective lens 930 may be provided in the display apparatus DEV in FIG. 12A, for example. The objective lens 930 can be provided between the region DSPa of the display portion DSP and the sensor NVSa, and between the region DSPb of the display portion DSP and the sensor NVSb.

In the display apparatus DEV in FIG. 12A, a lens may be provided for viewing the image PIC1 displayed on the display portion DSP. In addition, the lens can be provided in a region of the display portion DSP overlapping with the region DSPPX and the region OPA.

Figure 12B:
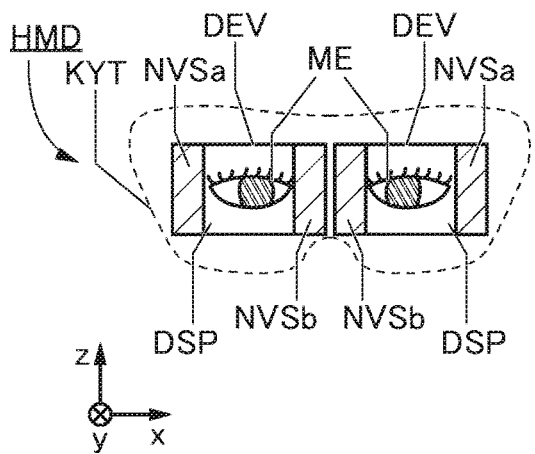
FIG. 12B and FIG. 12C are front views illustrating structure examples of an electronic device.

FIG. 12B illustrates an example of a front view (a zx plane view seen from the y direction) of a case where the display apparatus DEV in FIG. 12A is used in the electronic device HMD in FIG. 1, FIG. 5, and the like. The electronic device HMD illustrated in FIG. 12B is provided with the display apparatus DEV for the right eye and the display apparatus DEV for the left eye.

The display apparatus DEV for the right eye and that for the left eye each include the sensor NVSa and the sensor NVSb, and each of the sensors is preferably positioned to be in contact with the periphery of the eye ME of the USR, for example.

Figure 12C:
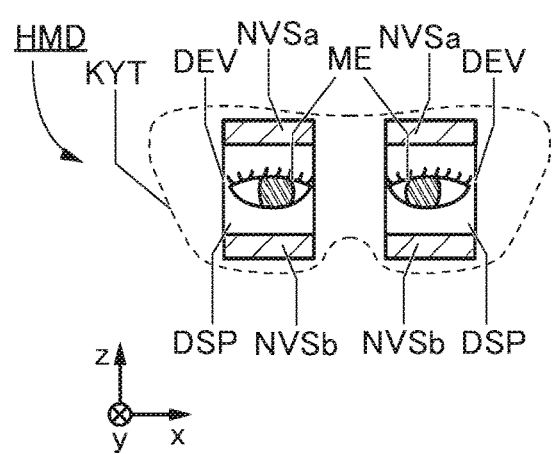

Note that the positions of the sensor NVSa and the sensor NVSb included in the display apparatus DEV for the right eye and that for the left eye are not limited to those in the electronic device HMD illustrated in FIG. 12B; for example, as in the electronic device HMD illustrated in FIG. 12C, the sensor NVSa, the display portion DSP, and the sensor NVSb may be placed to be aligned in the vertical direction of the eye ME (in the z direction). Alternatively, the positions of the sensor NVSa and the sensor NVSb included in the display apparatus DEV for the right eye and that for the left eye may be determined freely without being limited to the positions in FIG. 12B and FIG. 12C.

Although FIG. 12A to FIG. 12C each illustrate two sensors which are the sensor NVSa and the sensor NVSb in one display apparatus DEV, the number of sensors each containing an NV center in the display apparatus DEV may be one or three or more.

When the electronic device HMD illustrated in FIG. 12B and FIG. 12C is configured using the display apparatus DEV illustrated in FIG. 12A, the body temperature around the eye ME of the user USR wearing the electronic device HMD can be measured.

Although not illustrated, a combination of the display apparatus DEV illustrated in FIG. 12A to FIG. 12C and the ultrasonic wave sensor USS (the sending portion TRM and the receiving portion RCV), the sensor IS, or the like described in the above structure example enables measuring one or more selected from the blood flow speed, pulse, blood pressure, and blood oxygen saturation of the eye ME of the user USR, in addition to the body temperature around the eye ME of the user USR.

Although this embodiment describes the electronic device that obtains information on one or both of the blood flow speed and the pulse wave (blood pressure) using ultrasonic wave with the sending portion TRM and the receiving portion RCV, the electronic device of one embodiment of the present invention is not limited to this. For example, the electronic device of one embodiment of the present invention may use a light-emitting device such as an LED or organic EL and an imaging device instead of an ultrasonic wave. As a specific example, a capillary blood vessel that is to be measured with the light-emitting device is irradiated with light and then an image of the capillary blood vessel projected by the light is captured by the imaging device, so that information on one or both of the pulse wave (blood pressure) and the blood oxygen saturation can be obtained from the captured image.

Note that the structure examples described in this embodiment can be combined with each other as appropriate.

This embodiment can be combined with any of the other embodiments in this specification as appropriate.

Embodiment 2

In this embodiment, usage examples of electronic devices of one embodiment of the present invention are described with reference to FIG. 13 to FIG. 23.

Usage Example 1

Figure 13:
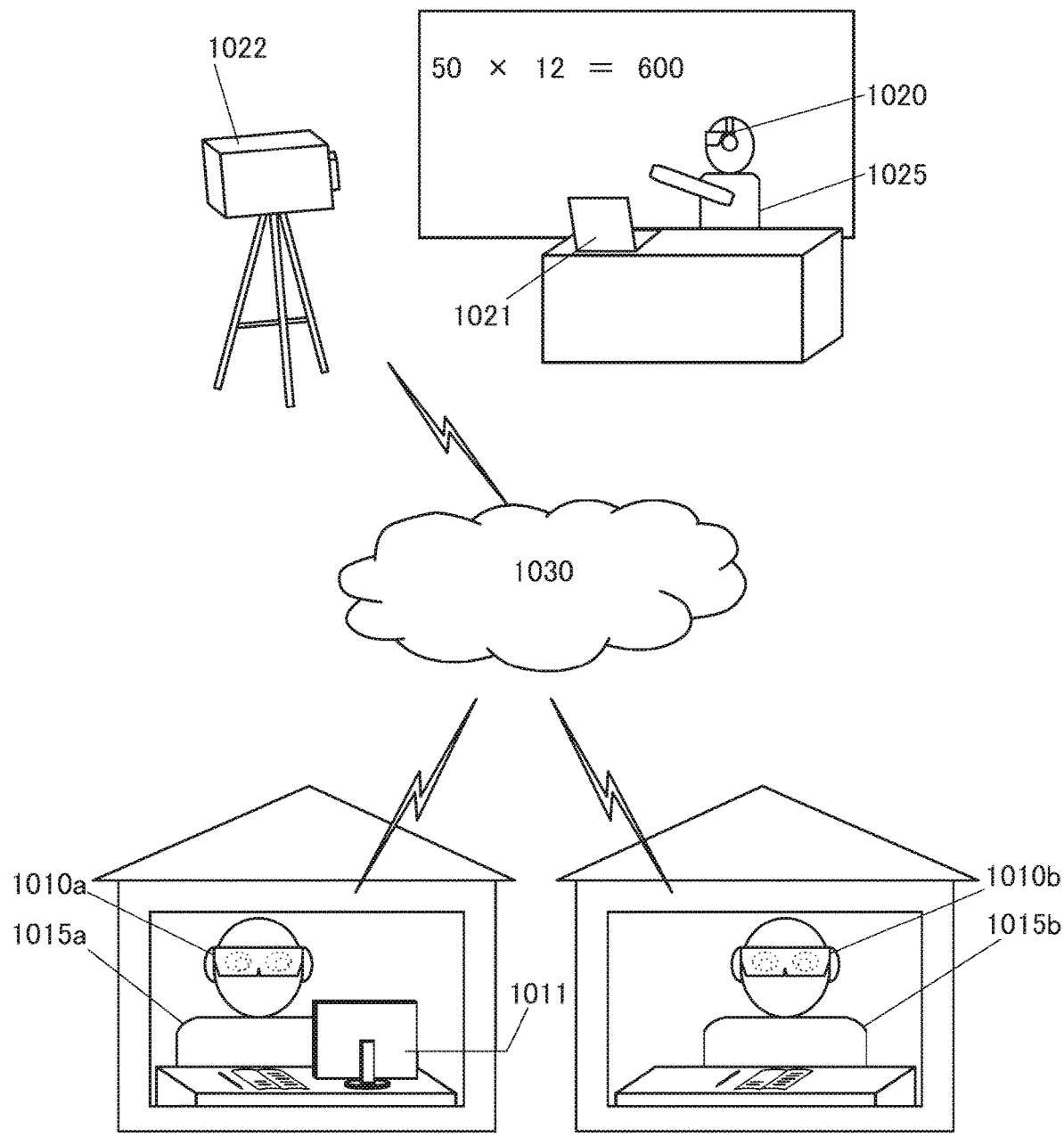
FIG. 13 is a diagram illustrating usage examples of electronic devices.

FIG. 13 illustrates an example where an online class is conducted using an electronic device 1010 (an electronic device 1010a and an electronic device 1010b) and one or both of an electronic device 1020 and an electronic device 1021. Although FIG. 13 illustrates a situation where a teacher 1025, a student 1015a, and a student 1015b join the online class, three or more students may join the online class. In this case, each student uses the electronic device 1010, and thus three or more electronic devices 1010 are used in the online class.

FIG. 13 illustrates a situation where the teacher 1025 conducts the class at a classroom or the like using the electronic device 1020, the electronic device 1021, and a camera 1022. Here, the electronic device 1020 corresponds to the electronic device HMD illustrated in FIG. 1A and the like. Although FIG. 13 illustrates a situation where the teacher 1025 uses the electronic device 1020 and the electronic device 1021, the electronic device used by the teacher 1025 may be one of the electronic device 1020 and the electronic device 1021.

A movie of the class is taken by the camera 1022 so that image data is generated. The image data includes the teacher 1025 and his or her surroundings. The surroundings of the teacher 1025 includes a blackboard, a whiteboard, or an electronic blackboard, for example. The image data is sent to one or more electronic devices (e.g., the electronic device 1010a and an electronic device including a display apparatus 1011 described later) used by the student 1015a and one or more electronic devices (e.g., the electronic device 1010b) used by the student 1015b via a network 1030.

Although the movie of the class is taken by the camera 1022 in FIG. 13, a camera provided in the electronic device 1021 may be used for taking the movie. In this case, the teacher 1025 needs to use at least the electronic device 1021.

FIG. 13 illustrates a situation where the student 1015a is taking a class at home or the like using the electronic device 1010a and an electronic device including the display apparatus 1011 (not illustrated in FIG. 13). Here, the electronic device 1010a corresponds to the electronic device HMD illustrated in FIG. 1A and the like. The electronic device including the display apparatus 1011 receives the image data via the network 1030, and the image data is displayed on the display apparatus 1011. The student 1015a can take the class by viewing the image data displayed on the display apparatus 1011 through the electronic device 1010a.

The electronic device 1010a can measure one or more selected from the blood pressure, pulse, oxygen saturation, and body temperature of the student 1015a. Information on one or more selected from the blood pressure, pulse, oxygen saturation, and body temperature of the student 1015a is sent to one or more electronic devices (e.g., the electronic device 1020 and the electronic device 1021) used by the teacher 1025, via the network 1030.

FIG. 13 illustrates a situation where the student 1015b is taking a class at home or the like using the electronic device 1010b. Here, the electronic device 1010b corresponds to the electronic device HMD illustrated in FIG. 1A and the like, and the display portion included in the electronic device 1010b corresponds to the display portion DSP illustrated in FIG. 1A and the like. The electronic device 1010b receives the image data via the network 1030. The student 1015b can take the class by viewing the image data displayed on the display portion included in the electronic device 1010b.

The electronic device 1010b can measure one or more selected from the blood pressure, pulse, oxygen saturation, and body temperature of the student 1015b. Information on one or more selected from the blood pressure, pulse, oxygen saturation, and body temperature of the student 1015b is sent to one or more electronic devices (e.g., the electronic device 1020 and the electronic device 1021) used by the teacher 1025, via the network 1030.

The electronic device 1020 receives information sent from the electronic device 1010a and the electronic device 1010b, and the information is displayed on the display portion included in the electronic device 1020. Alternatively, the electronic device 1021 receives information sent from the electronic device 1010a and the electronic device 1010b, and the information is displayed on the display portion included in the electronic device 1021. The teacher 1025 can check the states of the student 1015a and the student 1015b by viewing the information displayed on the display portion included in the electronic device 1020 and the display portion included in the electronic device 1021.

As described above, the online class can be conducted by data transmission and reception between the electronic device 1010 and the electronic device 1020. At this time, the student 1015a and the student 1015b can take the class while recognizing the health conditions of the student 1015a and the student 1015b themselves. Furthermore, the teacher 1025 can conduct the class while checking the states of the student 1015a and the student 1015b.

Next, FIG. 14A to FIG. 14C and FIG. 15 illustrate display examples of the display portion included in the electronic device used by the student.

Figure 14A:
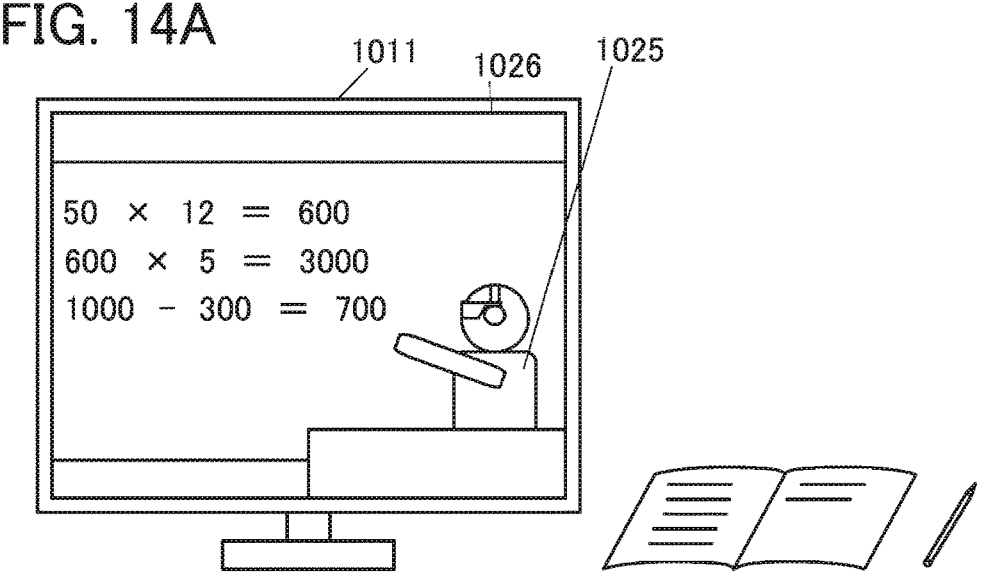
FIG. 14A to FIG. 14C are diagrams illustrating display examples of a display portion included in an electronic device.

FIG. 14A illustrates a real space viewed by the student 1015a. The student 1015a views the display apparatus 1011, a notebook, and a pencil. The student 1015a also views image data 1026 displayed on the display apparatus 1011. The image data 1026 is image data generated by image capturing by the camera 1022. The image data 1026 includes the teacher 1025 and his or her surroundings.

Figure 14B:
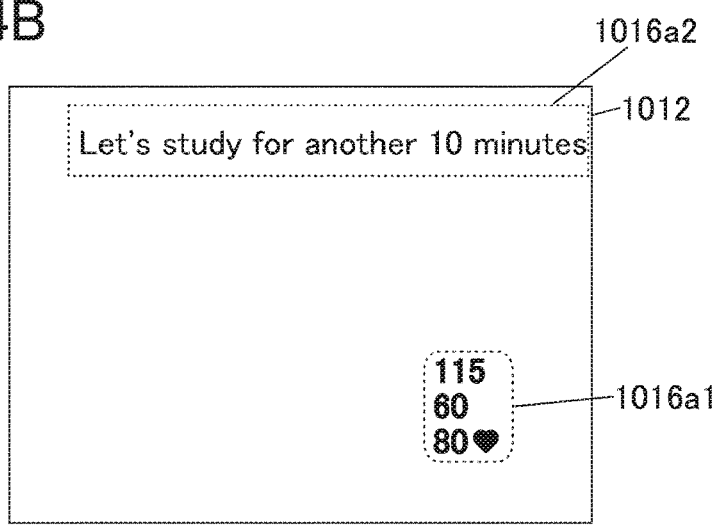

FIG. 14B shows image data displayed on a display portion 1012 of the electronic device 1010a used by the student 1015a. The display portion 1012 displays information on one or more selected from the blood pressure, pulse, oxygen saturation, and body temperature of the student 1015a which is measured by the electronic device 1010a. For example, as illustrated in FIG. 14B, the display portion 1012 displays an image 1016a1 including the systolic blood pressure, diastolic blood pressure, and pulse rate of the student 1015a.

Note that the display portion 1012 may display information other than information on the blood pressure, pulse, oxygen saturation, and body temperature of the student 1015a. For example, in the case where the eye fatigue level of the student 1015a is high, an image 1016a2 including character strings suitable for the student 1015a ("Let's study for another 10 minutes" in FIG. 14B) may be displayed on the display portion 1012 in accordance with judgment by the electronic device 1010.

Figure 14C:
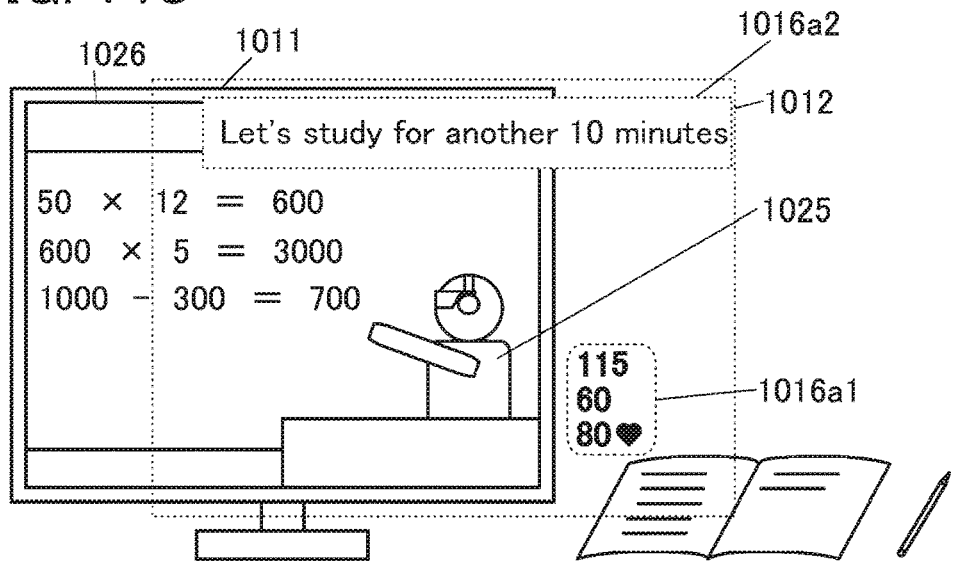

FIG. 14C shows a real space viewed by the student 1015a through the display portion 1012 of the electronic device 1010a. The student 1015a views the image 1016a1 and the image 1016a2 in addition to the display apparatus 1011, the notebook, and the pencil. With such a structure, the student 1015a can recognize the health condition of the student 1015a himself or herself in addition to the class conducted online. In addition, the student 1015a can recover his or her concentration on the online class, for example, by recognizing character strings included in the image 1016a2.

Note that the electronic device 1010a may have a function of estimating the direction of the gaze of the user (e.g., the student 1015a). When the electronic device 1010a has the function, the electronic device 1010a can place the image 1016a1 and the image 1016a2 in a space where the gaze of the student 1015a is not gathered, as illustrated in FIG. 14C. This can inhibit decrease in concentration of the student 1015a on the online class.

When the electronic device 1010a has the above function, a period during which the user looks away from the image data 1026 can be detected. For example, in the case where the period is long, concentration of the student 1015a on the online class can be recovered by outputting suitable character strings as a sound or outputting an alarm sound from the electronic device 1010a to the student 1015a.

The gaze of the user (e.g., the student 1015a) may be recognized using the electronic device 1010a provided with a plurality of electrodes capable of sensing current that flows in accordance with eye movement of the user. The direction of the gaze of the user (e.g., the student 1015a) may be estimated by a method utilizing one or both of a blink or eyelid movement, a method utilizing iris movement, or a scleral reflection method. Alternatively, the direction of the gaze of the user (e.g., the student 1015a) may be estimated using a trained model or an arithmetic circuit capable of arithmetic processing on the basis of an artificial neural network (ANN). Note that in this specification and the like, an artificial neural network is referred to as a neural network. As the trained model, preferably a neural network is used, and further preferably a convolutional neural network is used. As the arithmetic circuit, an arithmetic circuit having a function of performing a product-sum operation is preferably used.

Figure 15:
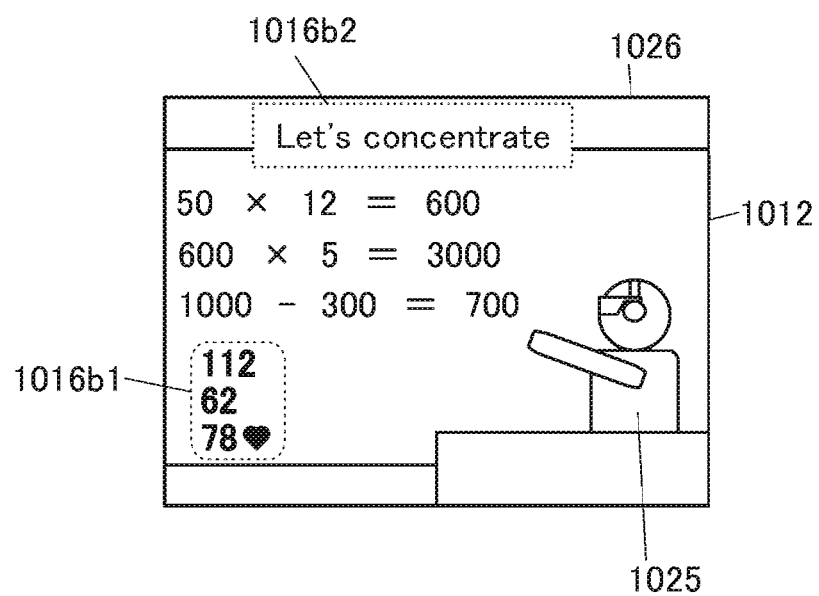
FIG. 15 is a diagram illustrating a display example of a display portion included in an electronic device.

FIG. 15 shows image data displayed on the display portion 1012 of the electronic device 1010b used by the student 1015b. The student 1015b is viewing the image data 1026 generated by image capturing by the camera 1022. The image data 1026 includes the teacher 1025 and his or her surroundings. In addition, an image 1016b1 and an image 1016b2 are superimposed on the image data 1026.

The image 1016b1 includes, for example, the systolic blood pressure, diastolic blood pressure, and pulse rate of the student 1015b. The image 1016b2 includes, for example, character strings suitable for the student 1015b ("Let's study for another 10 minutes" in FIG. 15).

With such a structure, the student 1015b can recognize the health condition of the student 1015b himself or herself in addition to the class conducted online. In addition, the student 1015b can recover his or her concentration on the online class, for example, by recognizing character strings included in the image 1016b2.

Note that the electronic device 1010b may have a function of estimating the direction of the gaze of the student 1015b. When the electronic device 1010b has the function, the electronic device 1010b can place the image 1016b1 and the image 1016b2 ("Let's concentrate" in FIG. 15) in the display portion 1012, as illustrated in FIG. 15, when the student 1015b is not concentrating on the class. When the student 1015b is not concentrating on the class, the gaze of the student 1015b tends to be gathered in a certain region in the display portion 1012 for a long time. By estimating the direction of the gaze of the student 1015b, the electronic device 1010b can judge whether or not the student 1015b is concentrating on the class. In the case where the student 1015b is not concentrating on the class, the image 1016b2 is placed as illustrated in FIG. 15, which can inhibit decrease in concentration of the student 1015b on the online class. In particular, the image 1016b2 is preferably displayed in a region of the display portion 1012 where the gaze of the student 1015b is gathered.

Next, FIG. 16A, FIG. 16B, and FIG. 17A to FIG. 17C illustrate display examples of the display portion included in the electronic device used by the teacher.

Figure 16A:
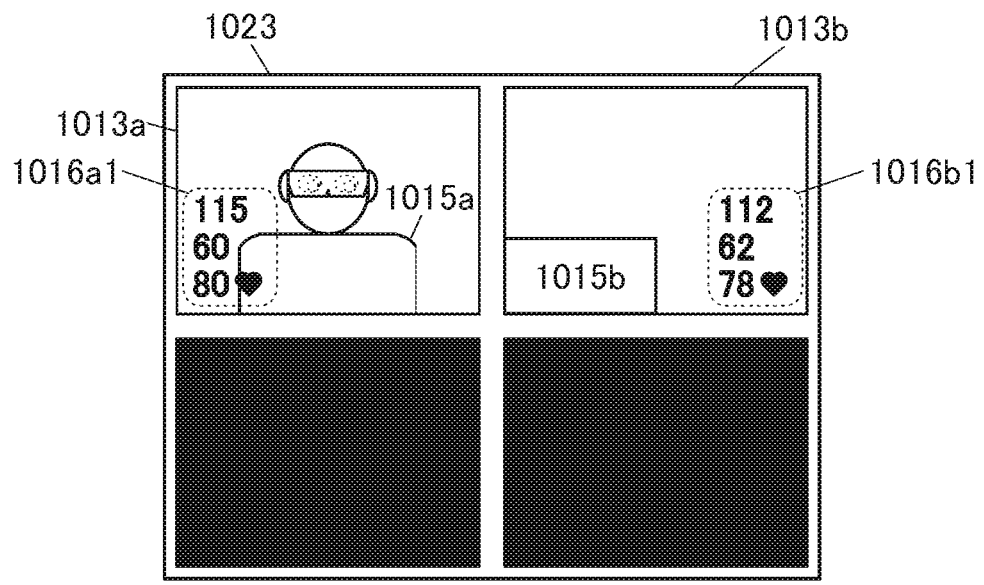
FIG. 16A and FIG. 16B are diagrams illustrating display examples of a display portion included in an electronic device.
Figure 16B:
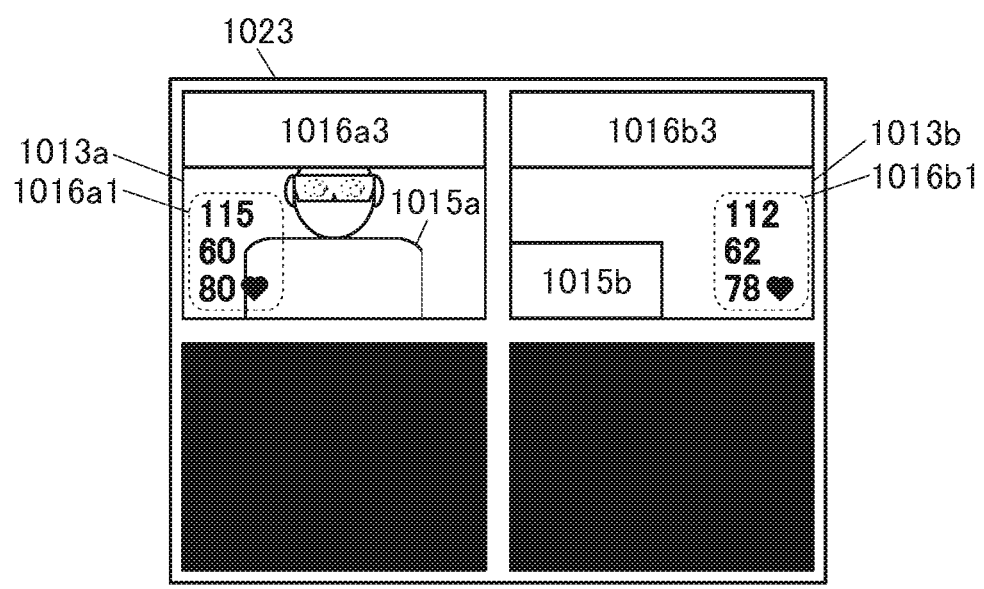

FIG. 16A and FIG. 16B illustrate display examples of the display portion included in the electronic device 1021 in the case where the electronic device 1021 receives information sent from the electronic device 1010a and the electronic device 1010b.

FIG. 16A illustrates a display example of a display portion 1023 included in the electronic device 1021 just after the online class started. FIG. 16B illustrates a display example of the display portion 1023 included in the electronic device 1021 after a certain period has passed since the online class started.

In FIG. 16A and FIG. 16B, the display portion 1023 includes a region 1013a and a region 1013b, and image data is displayed in each of the region 1013a and the region 1013b.

An image displayed in the region 1013a includes information on one or more selected from the blood pressure, pulse, oxygen saturation, and body temperature of the student 1015a which is measured by the electronic device 1010a. For example, as illustrated in FIG. 16A and FIG. 16B, the image 1016a1 including the systolic blood pressure, diastolic blood pressure, and pulse rate of the student 1015a is displayed in the region 1013a. Note that an image taken by a camera included in an electronic device including the display apparatus 1011 may be displayed in the region 1013a. That is, an image including the student 1015a and his or her surroundings may be displayed in the region 1013a.

The image displayed in the region 1013b shows information on one or more selected from the blood pressure, pulse, oxygen saturation, and body temperature of the student 1015b which is measured by the electronic device 1010b. For example, as illustrated in FIG. 16A and FIG. 16B, the image 1016b1 including the systolic blood pressure, diastolic blood pressure, and pulse rate of the student 1015b is displayed in the region 1013b. An image showing that the information displayed in the region 1013b is information on the student 1015b ("1015b" in FIG. 16A and FIG. 16B) is preferably displayed.

Just after the online class started, there is no change in the states of the student 1015a and the student 1015b. Thus, as illustrated in FIG. 16A, the image 1016a1 and the image 1016b1 are displayed in the region 1013a and the region 1013b, respectively.

After a certain period has passed since the online class started, the eye fatigue level is sometimes high depending on the user. For example, in the case where the eye fatigue level of the student 1015a is high, an image 1016a3 is displayed in the region 1013a as illustrated in FIG. 16B. The image 1016a3 includes character strings. Note that the character strings can be, for example, "The student might be sleepy" or "The student seems to have eye fatigue".

In addition, after a certain period has passed since the online class started, some users might look elsewhere. For example, in the case where the student 1015b is looking elsewhere, an image 1016b3 is displayed so as to overlap with the region 1013b as illustrated in FIG. 16B. The image 1016b3 includes character strings. Note that the character strings can be, for example, "The user tends to look elsewhere".

As described above, the use of one embodiment of the present invention enables the teacher 1025 to recognize the states of the student 1015a and the student 1015b from character string information. For example, the teacher 1025 can easily find a student with a high eye fatigue level, a student who is looking elsewhere, or the like among the students joining the online class, which allows close communication with the student. In the case where the online class is conducted for a large group, in particular, each image displayed on the display portion 1023 becomes small, which makes it difficult to grasp the states of the users displayed on the display portion 1023. Thus, one embodiment of the present invention can be suitably used for an online class for a large group. Furthermore, the teacher 1025 can recognize the health condition of a student even when the face of the student who is joining the class using only the electronic device 1010 cannot be seen.

Figure 17A:
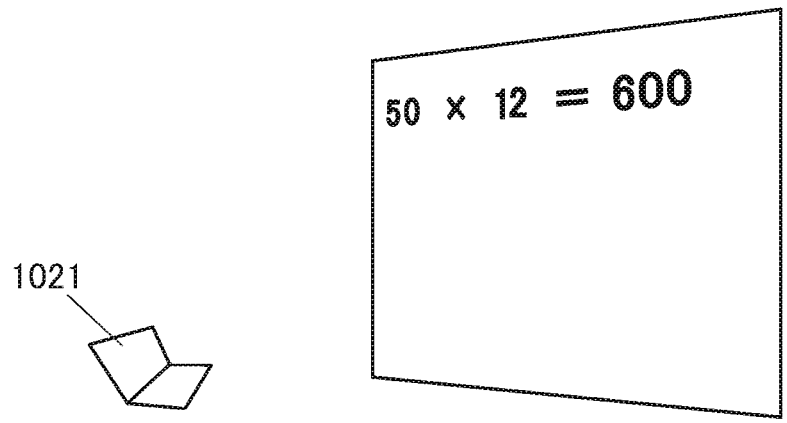
FIG. 17A to FIG. 17C are diagrams illustrating display examples of a display portion included in an electronic device.
Figure 17B:
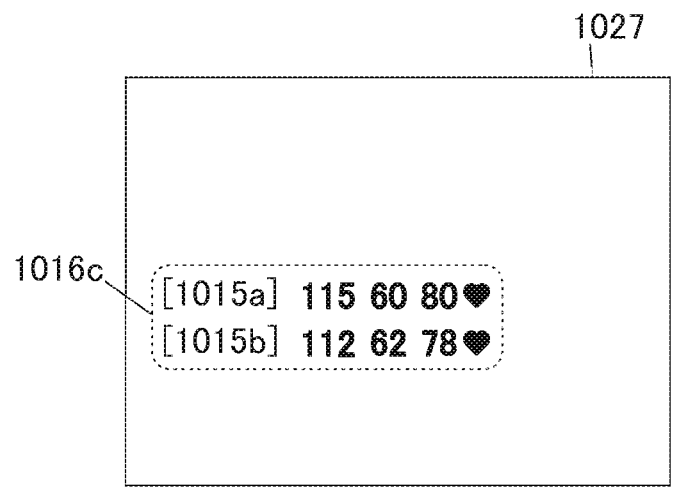
Figure 17C:
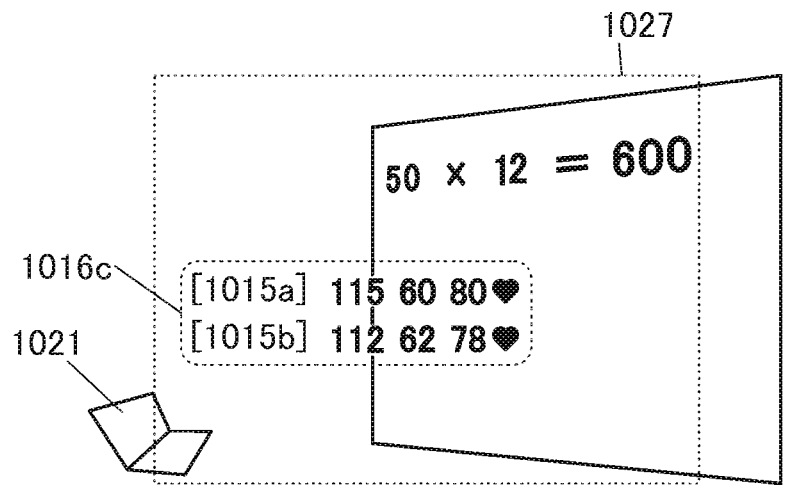

Next, FIG. 17A to FIG. 17C illustrate a display example of the display portion included in the electronic device 1020 in the case where the electronic device 1020 receives information sent from the electronic device 1010a and the electronic device 1010b.

FIG. 17A shows a real space viewed by the teacher 1025. The teacher 1025 is viewing a blackboard (this may be a whiteboard or an electronic blackboard instead, for example), the electronic device 1021, and the like.

FIG. 17B shows image data displayed on a display portion 1027 of the electronic device 1020 used by the teacher 1025. The display portion 1027 displays information on one or more selected from the blood pressure, pulse, oxygen saturation, and body temperature of the student 1015a which is measured by the electronic device 1010*a* and information on one or more selected from the blood pressure, pulse, oxygen saturation, and body temperature of the student 1015*b* which is measured by the electronic device 1010*b*. For example, an image 1016*c* including the systolic blood pressures, diastolic blood pressures, and pulse rates of the student 1015*a* and the student 1015*b* is displayed as illustrated in FIG. 17B.

Note that the display portion 1027 may display information other than information on the blood pressures, pulses, oxygen saturations, and body temperatures of the student 1015*a* and the student 1015*b*. For example, information showing a student with a high eye fatigue level may be displayed in the image 1016*c*. As another example, information showing a student who is looking elsewhere may be displayed.

FIG. 17C shows a real space viewed by the teacher 1025 through the display portion 1027 of the electronic device 1020. The teacher 1025 views the image 1016*c* in addition to a blackboard (this may be a whiteboard or an electronic blackboard instead, for example), the electronic device 1021, and the like. The structure enables the teacher 1025 to recognize the health conditions of the student 1015*a* and the student 1015*b*. This allows close communication with the students.

Note that the electronic device 1020 used by the teacher 1025 can measure one or more selected from the blood pressure, pulse, oxygen saturation, and body temperature of the teacher 1025. Information on one or more selected from the blood pressure, pulse, oxygen saturation, and body temperature of the teacher 1025 may be sent to an electronic device of a user who is not directly joining the online class, via the network 1030. Examples of the user include a superior or a colleague of the teacher 1025. The electronic device used by the user receives information on one or more selected from the blood pressure, pulse, oxygen saturation, and body temperature of the teacher 1025, and the information is displayed on the display portion included in the electronic device; accordingly, the superior of the teacher 1025 can recognize the tension or the like of the teacher 1025 and give guidance for the teacher 1025 in consideration of the tension or the like of the teacher 1025. In addition, the colleague of the teacher 1025 can advise the teacher 1025 on how to proceed the class in consideration of the tension or the like of the teacher 1025.

As described above, the use of the electronic device of one embodiment of the present invention allows close communication between the teacher and the students. In addition, close communication between teachers can also be achieved. Thus, the electronic device of one embodiment of the present invention can be suitably used in the field of educational technology (also referred to as EdTech, EduTech, or the like). Note that EdTech refers to a coined word combining Education and Technology in some cases.

Although an example where an online class is conducted between a teacher and students is described above, an online meeting may be held with the use of the electronic device 1010 (the electronic device 1010*a* and the electronic device 1010*b*) and one or both of the electronic device 1020 and the electronic device 1021.

Next, a method for estimating the eye fatigue level of the user and a method for estimating the direction of the user's gaze are described.

As described above, a method utilizing one or both of a blink and eyelid movement, a method utilizing iris movement, a scleral reflection method, and the like can be given as examples of the method for estimating the eye fatigue level of the user and the method for estimating the direction of the user's gaze.

A method for detecting one or both of a blink and eyelid movement of the user is described with reference to FIG. 18.

An electronic device is made to emit near-infrared light. The user's eye or the periphery of the user's eye is irradiated with the near-infrared light. The near-infrared light enters an electronic device after being reflected. In this manner, the state of an object can be detected.

Figure 18:
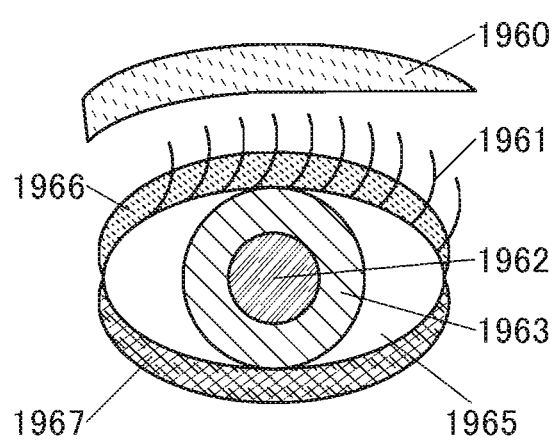
FIG. 18 is a schematic view illustrating a user's eye and surroundings of the user's eye.

Note that FIG. 18 is a schematic view illustrating the user's eye and the periphery of the user's eye. FIG. 18 illustrates a user's eyebrow 1960, user's eyelids (an upper eyelid 1966 and a lower eyelid 1967), user's eyelashes 1961, a user's pupil 1962, a user's cornea 1963, and a user's sclera 1965. The electronic device has a function of detecting one or more selected from the user's eyebrow 1960, the user's eyelids (the upper eyelid 1966 and the lower eyelid 1967), the user's eyelashes 1961, the user's pupil 1962, the user's cornea 1963, and the user's sclera 1965, which are illustrated in FIG. 18.

For example, the electronic device of one embodiment of the present invention can detect the state of the user's eye or the periphery of the user's eye illustrated in FIG. 18. For example, when the user closes the eyelids (the upper eyelid 1966 and the lower eyelid 1967), the surface of the eyelids, i.e., the skin is irradiated with the near-infrared light. When the user opens the eyelids, the surface of the user's eyeball is irradiated with the near-infrared light. Since the skin and the surface of the eyeball have different reflectances, the intensities of reflected near-infrared light are different from each other. By successive monitoring of the intensity of the reflected near-infrared light, the electronic device can detect one or both of the number of blinks and time taken for one blink.

While the user looks at a display for a long time, the number of blinks decreases in some cases. Furthermore, when the user feels fatigue, blink intervals might become longer and time taken for one blink might become longer.

The electronic device of one embodiment of the present invention can estimate the fatigue level of the user from one or both of the number of user's blinks and time taken for one blink. For example, a threshold value is preferably set such that the fatigue level of the user is determined to be high in the case where the number of blinks in a certain period becomes smaller than the threshold value. Alternatively, for example, the threshold value is preferably set such that the fatigue level of the user is determined to be high in the case where time taken for one blink of the user in a certain period becomes longer than the threshold value.

Next, a method for utilizing iris movement is described. When a boundary region between a cornea (e.g., the cornea 1963 illustrated in FIG. 18) and a sclera (e.g., the sclera 1965 illustrated in FIG. 18) is irradiated with an circular infrared spot, the ratio of a region including the cornea to a region including the sclera in a region irradiated with the infrared spot changes in accordance with the eyeball movement. The reflectance of the region including the sclera is much higher than that of the region including the cornea, and thus the amount of reflected light changes in accordance with the eyeball movement. By measuring this change, the direction of the user's view can be detected.

Next, a scleral reflection method is described. An electronic device is made to emit near-infrared light. The user's eye is irradiated with the near-infrared light through an optical system. The reflected light passes through the optical system again and enters the electronic device. In this manner, the state of the user can be detected. The user shifts his or her gaze when watching a fast-moving object in a displayed video. When the gaze is shifted, an eyeball moves. In the case where the eyeball moves, the ratio of the region including the cornea to the region including the sclera in the circular infrared spot changes; thus, by monitoring the reflected light component, the eyeball movement can be detected. That is, the electronic device of one embodiment of the present invention has an eye tracking function. A region the user watches carefully can be estimated by detecting the user's gaze by the eye tracking function.

In the above case, the electronic device preferably includes a light-emitting device emitting infrared light (including near-infrared light).

In addition, a model that has learned may be used for a method for estimating the eye fatigue level of the user and a method for estimating the direction of the user's gaze. A neural network is preferably used as the model that has learned. For the neural network, deep learning is particularly preferably used. For the deep learning, a convolutional neural network (CNN), a recurrent neural network (RNN), an autoencoder (AE), a variational autoencoder (VAE), random forest, a support vector machine, gradient boosting, a generative adversarial network (GAN), or the like is preferably used, for example.

For the method for estimating the eye fatigue level of the user or the direction of the user's gaze, an arithmetic circuit capable of arithmetic processing based on a neural network may be used. Note that the arithmetic circuit capable of arithmetic processing based on a neural network can be rephrased as an arithmetic circuit having a function of performing a product-sum operation. The use of the arithmetic circuit enables the image analysis to be performed with low power. That is, power consumption of the electronic device of one embodiment of the present invention can be reduced.

Here, an arithmetic circuit is described. The arithmetic circuit can be used as an arithmetic circuit having a function of performing a product-sum operation, for example. The arithmetic circuit can be used for arithmetic processing in the neural network. Note that an arithmetic circuit having a function of performing a product-sum operation can be rephrased as an arithmetic circuit of a neural network. As the neural network, a hierarchical neural network can be used, for example. The hierarchical neural network will be described later in this embodiment.

Usage Example 2

Figure 19:
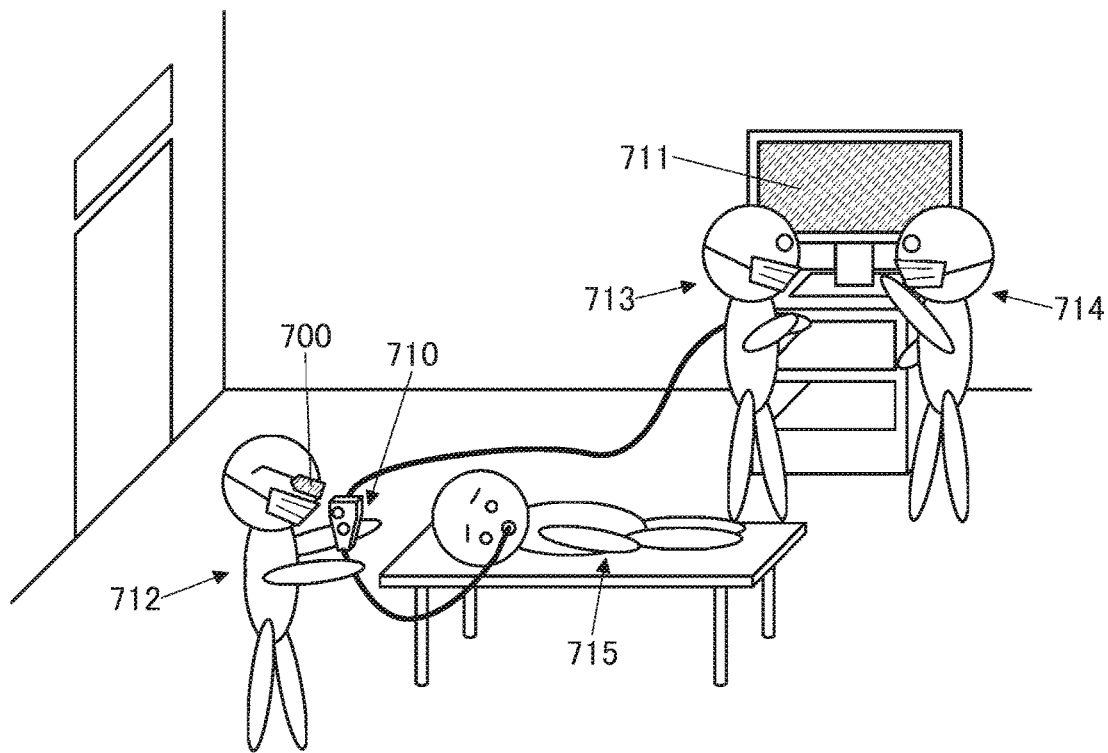
FIG. 19 is a diagram illustrating a usage example of an electronic device.

FIG. 19 illustrates an example of the case where an electronic device of one embodiment of the present invention is used in the medical field. Specifically, FIG. 19 illustrates a situation where a medical treatment is given with the use of an electronic device 700 of one embodiment of the present invention and an endoscope apparatus 710.

A doctor 712 operates the endoscope apparatus 710 to observe the inside of the body of a patient 715 and give a proper treatment. The doctor 712 wears the electronic device 700. A video taken by the endoscope apparatus 710 is displayed on a display portion of the electronic device 700 in real time, which allows the doctor 712 to give a treatment while looking at the video.

In addition, the video taken by the endoscope apparatus 710 can be displayed also on a monitor device 711 that is separately provided. This allows a doctor 713 and a doctor 714 to watch the treatment by the doctor 712 without interrupting the doctor 712. Although the monitor device 711 is placed in an operating room in the example illustrated here, the treatment can be watched in another room. For example, a resident can feel the real atmosphere of the treatment by watching the treatment by the doctor 712 through the monitor device placed in the operating room.

The display apparatus of one embodiment of the present invention can be used for not only the display portion of the electronic device 700 but also a display portion of the monitor device 711. Thus, the doctor 713 and the doctor 714 can make a highly accurate medical judgement with the use of an extremely-high-resolution image, and can share the judgement with the doctor 712 who is giving the treatment.

As described above, the use of the electronic device of one embodiment of the present invention can increase the quality of the medical practice of a doctor. Thus, the electronic device of one embodiment of the present invention can be suitably used in the field of medical technology (also referred to as MedTech, MediTech, or the like). Note that MedTech refers to a coined word combining Medical and Technology in some cases.

<<Hierarchical Neural Network>>

Figure 20A:
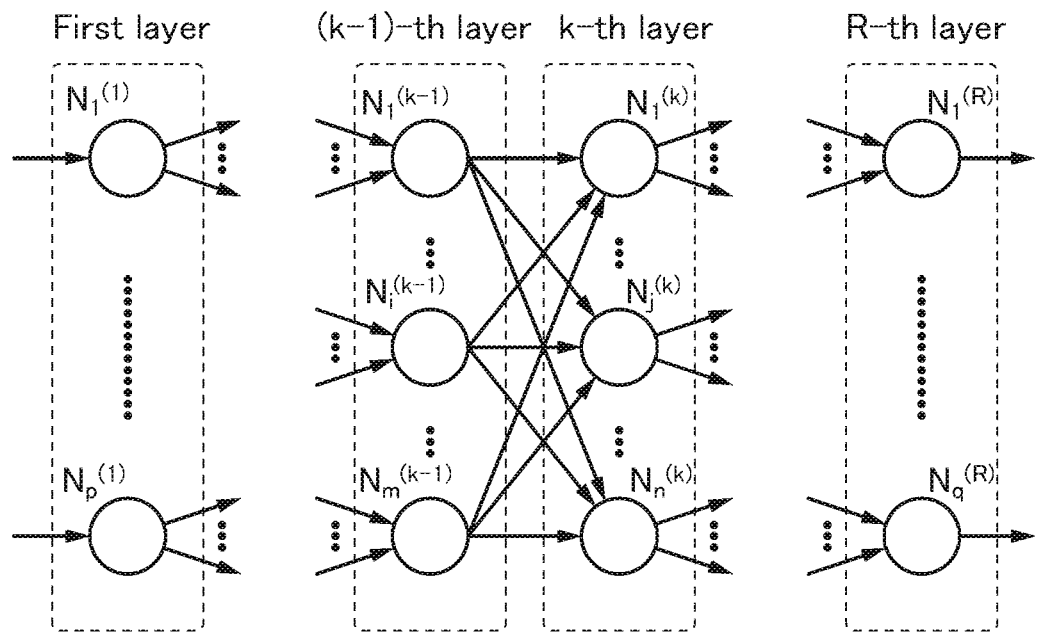
FIG. 20A and FIG. 20B are diagrams illustrating a structure example of a neural network.

A hierarchical neural network includes one input layer, one or a plurality of intermediate layers (hidden layers), and one output layer, for example, and is configured with a total of at least three layers. A hierarchical neural network ANN illustrated in FIG. 20A is one example, and the neural network ANN includes a first layer to an R-th layer (here, R can be an integer greater than or equal to 4). Specifically, the first layer corresponds to the input layer, the R-th layer corresponds to the output layer, and the other layers correspond to the intermediate layers. Note that FIG. 20A illustrates the (k−1)-th layer and the k-th layer (here, k is an integer greater than or equal to 3 and less than or equal to R−1) as the intermediate layers, and does not illustrate the other intermediate layers.

Each of the layers of the neural network ANN includes one or a plurality of neurons. In FIG. 20A, the first layer includes a neuron $N_1^{(1)}$ to a neuron $N_p^{(1)}$ (here, p is an integer greater than or equal to 1); the (k−1)-th layer includes a neuron $N_1^{(k-1)}$ to a neuron $N_m^{(k-1)}$ (here, m is an integer greater than or equal to 1); the k-th layer includes a neuron $N_1^{(k)}$ to a neuron $N_n^{(k)}$ (here, n is an integer greater than or equal to 1); and the R-th layer includes a neuron $N_1^{(R)}$ to a neuron $N_q^{(R)}$ (here, q is an integer greater than or equal to 1).

FIG. 20A illustrates a neuron $N_i^{(k-1)}$ (here, i is an integer greater than or equal to 1 and less than or equal to m) in the (k−1)-th layer and a neuron $N_j^{(k)}$ (here, j is an integer greater than or equal to 1 and less than or equal to n) in the k-th layer, in addition to the neuron $N_1^{(1)}$, the neuron $N_p^{(1)}$, the neuron $N_1^{(k-1)}$, the neuron $N_m^{(k-1)}$, the neuron $N_1^{(k)}$, the neuron $N_n^{(k)}$, the neuron $N_1^{(R)}$, and the neuron $N_q^{(R)}$; the other neurons are not illustrated.

Next, signal transmission from a neuron in one layer to a neuron in the subsequent layer and signals input to and output from the neurons are described. Note that description here is made focusing on the neuron $N_j^{(k)}$ in the k-th layer.

Figure 20B:
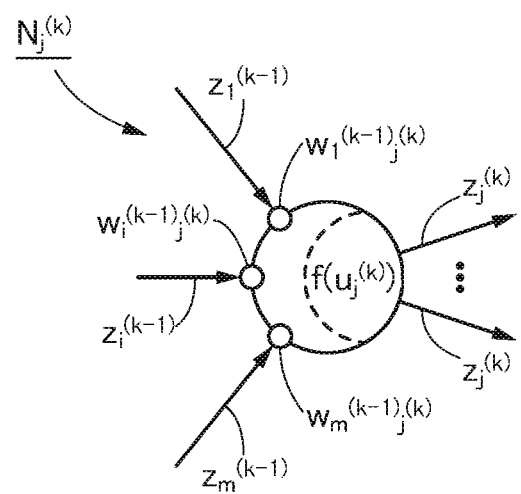

FIG. 20B illustrates the neuron $N_j^{(k)}$ in the k-th layer, signals input to the neuron $N_j^{(k)}$, and a signal output from the neuron $N_j^{(k)}$. FIG. 20B also illustrates weight data $w_{1\ j}^{(k-1)(k)}$, $w_{i\ j}^{(k-1)(k)}$, and $w_{m\ j}^{(k-1)(k)}$ between the (k−1)th layer and the k-th layer, and an activation function $f(u_j^{(k)})$.

Specifically, $z_1^{(k-1)}$ to $z_m^{(k-1)}$ that are output signals from the neuron $N_1^{(k-1)}$ to the neuron $N_m^{(k-1)}$ in the (k−1)-th layer are output to the neuron $N_j^{(k)}$. Then, the neuron $N_j^{(k)}$ generates $z_j^{(k)}$ in accordance with $z_1^{(k-1)}$ to $z_m^{(k-1)}$, and outputs $z_j^{(k)}$ as the output signal to the neurons in the (k+1)-th layer (not illustrated).

Structure Example 1 of Arithmetic Circuit

Next, a structure example of an arithmetic circuit of one embodiment of the present invention is described.

Figure 21:
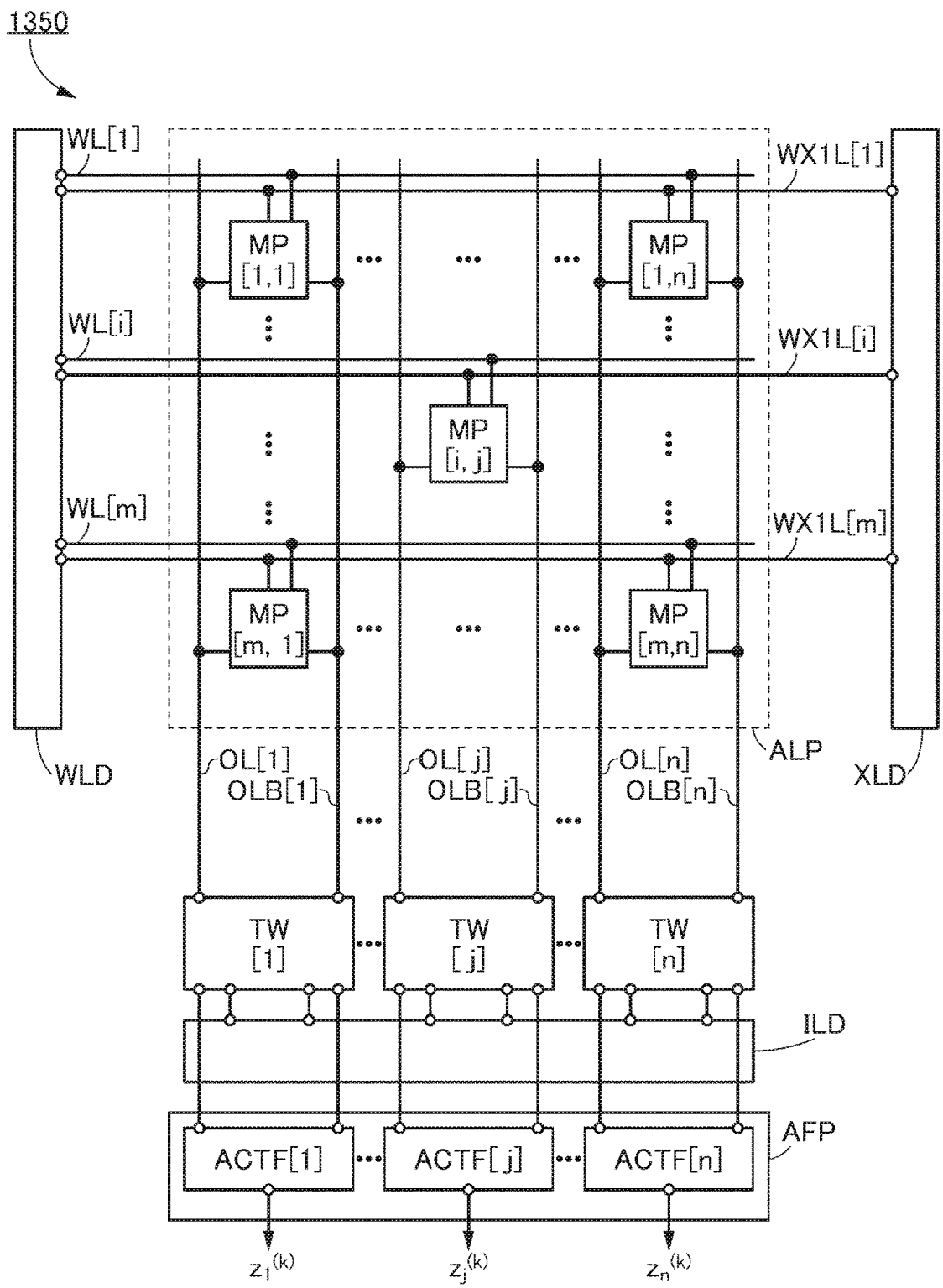
FIG. 21 is a diagram illustrating a structure example of an arithmetic circuit of a neural network.

An arithmetic circuit 1350 illustrated in FIG. 21 includes an array portion ALP, a circuit ILD, a circuit WLD, a circuit XLD, a circuit AFP, and a circuit TW[1] to a circuit TW[n], for example.

The circuit ILD and the circuit AFP are electrically connected to a wiring OL[1] to a wiring OL[n] and a wiring OLB[1] to a wiring OLB[n] through the circuit TW[1] to the circuit TW[n].

The circuit TW[1] to the circuit TW[n] function as switching circuits. In the circuit TW[1] to the circuit TW[n], switching between inputting output signals of the wiring OL[1] to the wiring OL[n] and the wiring OLB[1] to the wiring OLB[n] to the circuit AFP and inputting output signals of the circuit ILD to the wiring OL[1] to the wiring OL[n] and the wiring OLB[1] to the wiring OLB[n] can be performed.

The circuit WLD is electrically connected to a wiring WL[1] to a wiring WL[m] and a wiring WX1L[1] to a wiring WX1L[m]. The circuit XLD is electrically connected to the wiring WX1L[1] to the wiring X1WL[m].

The arithmetic circuit 1350 illustrated in FIG. 21 includes the array portion ALP in which circuits MP are arranged in a matrix of m×n. Note that in FIG. 21, the circuit MP positioned in the i-th row and the j-th column (here, i is an integer greater than or equal to 1 and less than or equal to m, and j is an integer greater than or equal to 1 and less than or equal to n) is denoted by a circuit MP[ij]. Note that FIG. 21 illustrates only the circuit MP[1,1], the circuit MP[1,n], the circuit MP[ij], the circuit MP[m,1], and the circuit MP[m,n] and does not illustrate the other circuits MP.

The circuit MP[ij] is electrically connected to the wiring WL[j], the wiring WX1L[j], the wiring OL[i], and the wiring OLB[j].

The circuit MP[ij] has a function of holding a weight coefficient (also referred to as first data), for example. The weight coefficient is also referred to as a weighted value. Specifically, the circuit MP[ij] holds information corresponding to a weight coefficient input from the wiring OL[j] and the wiring OLB[j].

The circuit ILD has a function of outputting information corresponding to the first data, which is a weight coefficient, to the wiring OL[1] to the wiring OL[n] and the wiring OLB[1] to the wiring OLB[n].

As the data corresponding to a weight coefficient, a potential, a resistance value, or a current amount can be used, for example. In the case where a current amount is used as information corresponding to a weight coefficient, a current to be input can be generated using a current output digital-analog converter (IDAC).

The circuit MP[ij] has a function of outputting the product of an input value input from the wiring WX1L[i] (also referred to as second data) and a weight coefficient (first data). As a specific example, when the second data is input from the wiring WX1L[i], the circuit MP[i,j] outputs, to the wiring OL[j] and the wiring OLB[j], a current corresponding to the product of the first data and the second data. Note that although FIG. 21 illustrates an example of the case where the wiring OL[j] and the wiring OLB[j] are provided, one embodiment of the present invention is not limited thereto. Only one of the wiring OL[j] and the wiring OLB[j] may be provided.

The circuit XLD has a function of supplying the second data, which is an input value, to the wiring WX1L[1] to the wiring WX1L[m].

Information corresponding to the input value can be, for example, a potential, a current amount, or the like. In the case where a current amount is used as information corresponding to an input value, a current to be input can be generated using a current output digital-analog converter.

Currents corresponding to the products of the first data and the second data output from the circuit MP[1,j] to the circuit MP[m,j] are added and the sum of the currents is output to the wiring OL[j] and the wiring OLB[j]. In this manner, the arithmetic circuit can perform a product-sum operation with the weight coefficients and the input values.

The circuit XLD and the circuit WLD each have a function of selecting the circuit MP to which information corresponding to the first data input from the circuit ILD is to be written. In the case where information (e.g., a potential, a resistance value, or a current value) is written to the circuit MP[i,1] to the circuit MP[i,n] positioned in the i-th row of the array portion ALP, for example, the circuit XLD supplies, to the wiring WX1L[i], a signal for turning on or off first writing switching elements included in the circuit MP[i,1] to the circuit MP[i,n], and supplies, to the other wirings WX1L, a potential for turning off first writing switching elements included in the circuits MP in rows other than the i-th row, for example. In addition, the circuit WLD supplies, to the wiring WL[i], a signal for turning on or off second writing switching elements included in the circuit MP[i,1] to the circuit MP[i,n], and supplies, to the other wirings WL, a potential for turning off second writing switching elements included in the circuits MP in rows other than the i-th row, for example.

The circuit AFP includes a circuit ACTF[1] to a circuit ACTF[n], for example. The circuit ACTF[j] is electrically connected to the wiring OL[j] and the wiring OLB[j] through the circuit TW[j] having a switching function. The circuit ACTF[j] can generate a signal that corresponds to information (e.g., a potential or a current amount) corresponding to the results of product-sum operations input from the wiring OL[j] and the wiring OLB[j], and can output the signal as $z_j^{(k)}$. The circuit AFP can compare information (e.g., a potential or a current amount) corresponding to the results of product-sum operations input from the wiring OL[1] to the wiring OL[n] and the wiring OLB[1] to the wiring OLB[n], generate signals corresponding to the comparison results, and output the signals as $z_1^{(k)}$ to $z_n^{(k)}$.

<<Circuit MP>>

Figure 22:
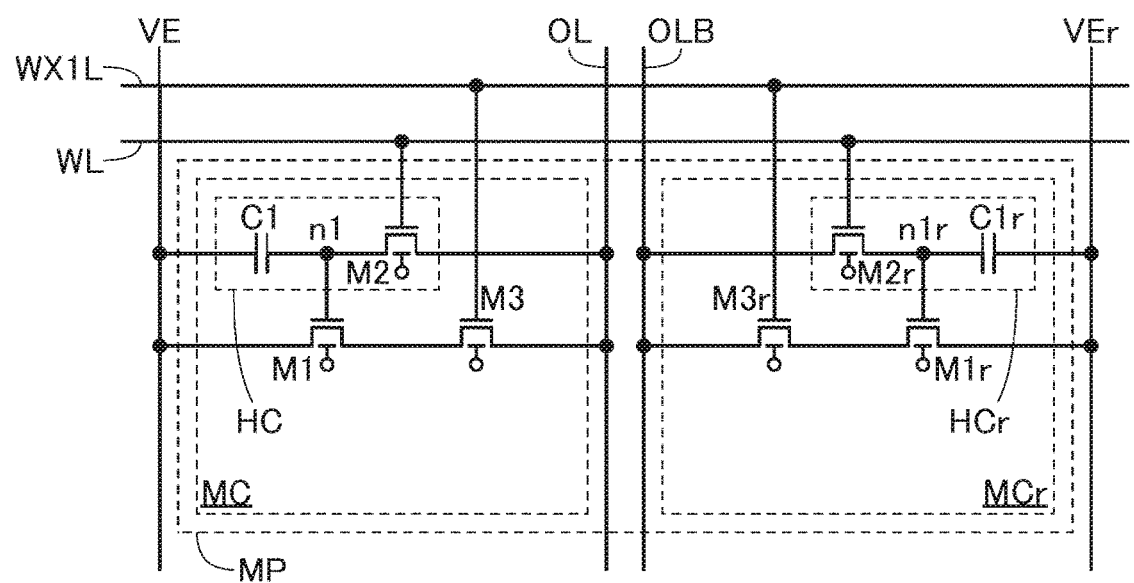
FIG. 22 is a diagram illustrating a structure example of an arithmetic circuit of a neural network.

Next, the circuit MP is described. FIG. 22 illustrates a circuit structure example that can be used for the circuit MP[i,j]. The circuit MP includes a circuit MC and a circuit MCr. The circuit MC includes a transistor M1 to a transistor M3 and a capacitor C1. Note that, for example, a holding portion HC includes the transistor M2 and the capacitor C1.

In the circuit MP in FIG. 22, the circuit MCr has substantially the same circuit structure as the circuit MC. Thus, "r" is added to the reference numerals of the circuit elements and the like included in the circuit MCr to differentiate them from the circuit elements and the like included in the circuit MC.

The transistor M1 to the transistor M3 illustrated in FIG. 22 are each an n-channel transistor having a multi-gate structure including gates over and under a channel, and the transistor M1 to the transistor M3 each include a first gate and a second gate.

The arithmetic circuit 1350 described in this section does not depend on the connection structure of the back gate of a transistor. In the transistor M1 to the transistor M3 illustrated in FIG. 22, the back gate is illustrated and the connection structure of the back gate is not illustrated; however, a target to which the back gate is electrically connected can be determined at the design stage. For example, in a transistor including a back gate, a gate and the back gate may be electrically connected to each other to increase the on-state current of the transistor. In other words, the gate and the back gate of the transistor M2 may be electrically connected to each other, for example. Alternatively, for example, in a transistor including a back gate, a wiring electrically connected to an external circuit or the like may be provided and a potential may be supplied to the back gate of the transistor by the external circuit or the like to change the threshold voltage of the transistor or to reduce the off-state current of the transistor. Note that the same applies to a transistor described in other parts of the specification and a transistor illustrated in other drawings, not only to the transistors in FIG. 22.

Note that unless otherwise specified, an off-state current in this specification and the like refers to a drain current of a transistor in an off state (also referred to as a non-conducting state or a cutoff state). Unless otherwise specified, an off state refers to, in an n-channel transistor, a state where voltage $V_{gs}$ between its gate and source is lower than the threshold voltage $V_{th}$ (in a p-channel transistor, higher than $V_{th}$).

The semiconductor device of one embodiment of the present invention does not depend on the structure of a transistor included in the semiconductor device. Transistors with a single gate structure may be used. It is also possible that some transistors have a structure including a back gate and the other transistors have a structure not including a back gate. Note that the same applies to a transistor described in other parts of the specification and a transistor illustrated in other drawings, not only to that in the circuit diagram illustrated in FIG. 22.

In this specification and the like, transistors with a variety of structures can be used as a transistor. Thus, there is no limitation on the type of transistors used. Examples of transistors include a transistor including single crystal silicon and a transistor including a non-single-crystal semiconductor film typified by amorphous silicon, polycrystalline silicon (including low-temperature polysilicon), microcrystalline (also referred to as microcrystal, nanocrystal, or semi-amorphous) silicon, or the like. Alternatively, a thin film transistor (TFT) including a thin film of any of these semiconductors can be used, for example. The use of the TFT has various advantages. For example, since the TFT can be manufactured at a lower temperature than the case of using single crystal silicon, manufacturing costs can be reduced or a larger manufacturing apparatus can be used.

Note that a transistor including a compound semiconductor (e.g., silicon germanium (SiGe) or gallium arsenide (GaAs)) or a transistor including an oxide semiconductor or the like (an OS transistor) can be used as the transistor. Alternatively, a thin film transistor including a thin film of such a compound semiconductor or oxide semiconductor can be used, for example. Note that such a compound semiconductor or oxide semiconductor can be used not only for a channel portion of the transistor but also for other applications. For example, such a compound semiconductor or oxide semiconductor can be used for a wiring, a resistor, a pixel electrode, or a light-transmitting electrode. Since such components can be deposited or formed at the same time as the transistor, the cost can be reduced.

As the oxide semiconductor, an oxide containing at least one of indium, an element M (as the element M, for example, one kind or a plurality of kinds selected from aluminum, gallium, yttrium, copper, vanadium, beryllium, boron, titanium, iron, nickel, germanium, zirconium, molybdenum, lanthanum, cerium, neodymium, hafnium, tantalum, tungsten, magnesium, and the like can be given), and zinc can be given.

As another example of the transistor, a transistor formed by an inkjet method or a printing method can be used, for example. The transistor can be manufactured at room temperature, manufactured at a low vacuum degree, or manufactured over a large substrate. Accordingly, the transistor can be manufactured without using a mask (reticle), so that the layout of the transistor can be easily changed. Alternatively, since the transistor can be manufactured without using a resist, the material cost is reduced, and the number of steps can be reduced. Alternatively, since a film can be formed only where needed, a material is not wasted as compared with a manufacturing method by which etching is performed after the film is formed over the entire surface; thus, the cost can be reduced.

As another example of the transistor, a transistor containing an organic semiconductor or a carbon nanotube can be used. Thus, a transistor can be formed over a bendable substrate. A device using a transistor containing an organic semiconductor or a carbon nanotube can be highly resistant to impact.

In the circuit MP in FIG. 22, a first terminal of the transistor M1 is electrically connected to a wiring VE. A second terminal of the transistor M1 is electrically connected to a first terminal of the transistor M3. A gate of the transistor M1 is electrically connected to a first terminal of the capacitor C1 and a first terminal of the transistor M2. A second terminal of the capacitor C1 is electrically connected to the wiring VE. A second terminal of the transistor M2 is electrically connected to the wiring OL. A gate of the transistor M2 is electrically connected to the wiring WL. A second terminal of the transistor M3 is electrically connected to the wiring OL, and a gate of the transistor M3 is electrically connected to the wiring WX1L.

The connection structure of the circuit MCr different from that of the circuit MC is described. A second terminal of a transistor M3r is electrically connected to not the wiring OL but the wiring OLB. A first terminal of a transistor M1r and a second terminal of a capacitor C1r are electrically connected to a wiring VEr.

Note that in the holding portion HC illustrated in FIG. 22, an electrical connection point of the gate of the transistor M1, the first terminal of the capacitor C1, and the first terminal of the transistor M2 is a node n1.

The holding portion HC has a function of holding a potential corresponding to a weight coefficient (the first data). The potential is held in the holding portion HC included in the circuit MC in FIG. 22 in the following manner: when the transistor M2 and the transistor M3 are brought into an on state, a current with a predetermined current amount is input from the wiring OL to write a potential corresponding to the current amount to the capacitor C1, and then the transistor M2 is brought into an off state. Thus, the potential of the node n1 can be held as the potential corresponding to the weight coefficient (the first data). At this time, a current is input from the wiring OL and a potential having a level corresponding to the amount of current can be held in the capacitor C1. Therefore, the input of the first data is less likely to be adversely affected by variations in current characteristics (e.g., threshold voltage) of the transistor M1.

The current input to the wiring OL can be input and generated using a current output digital-analog converter.

As the transistor M2, a transistor with a low off-state current is preferably used for a long-term holding of the potential of the node n1. As the transistor with a low off-state current, an OS transistor can be used, for example. Since an OS transistor includes an oxide semiconductor with a wide band gap in a channel formation region, the OS transistor can have a reduced off-state current.

Alternatively, a transistor including a back gate may be used as the transistor M2, and an off-state current may be reduced by applying a low-level potential to the back gate to shift the threshold voltage to the positive side.

Thus, an arithmetic circuit with high arithmetic operation accuracy is provided. Furthermore, an arithmetic circuit with high reliability is provided.

<<Structure Example 2 of Arithmetic Circuit>>

An arithmetic circuit MAC1 that performs a product-sum operation is described as another example.

Figure 23:
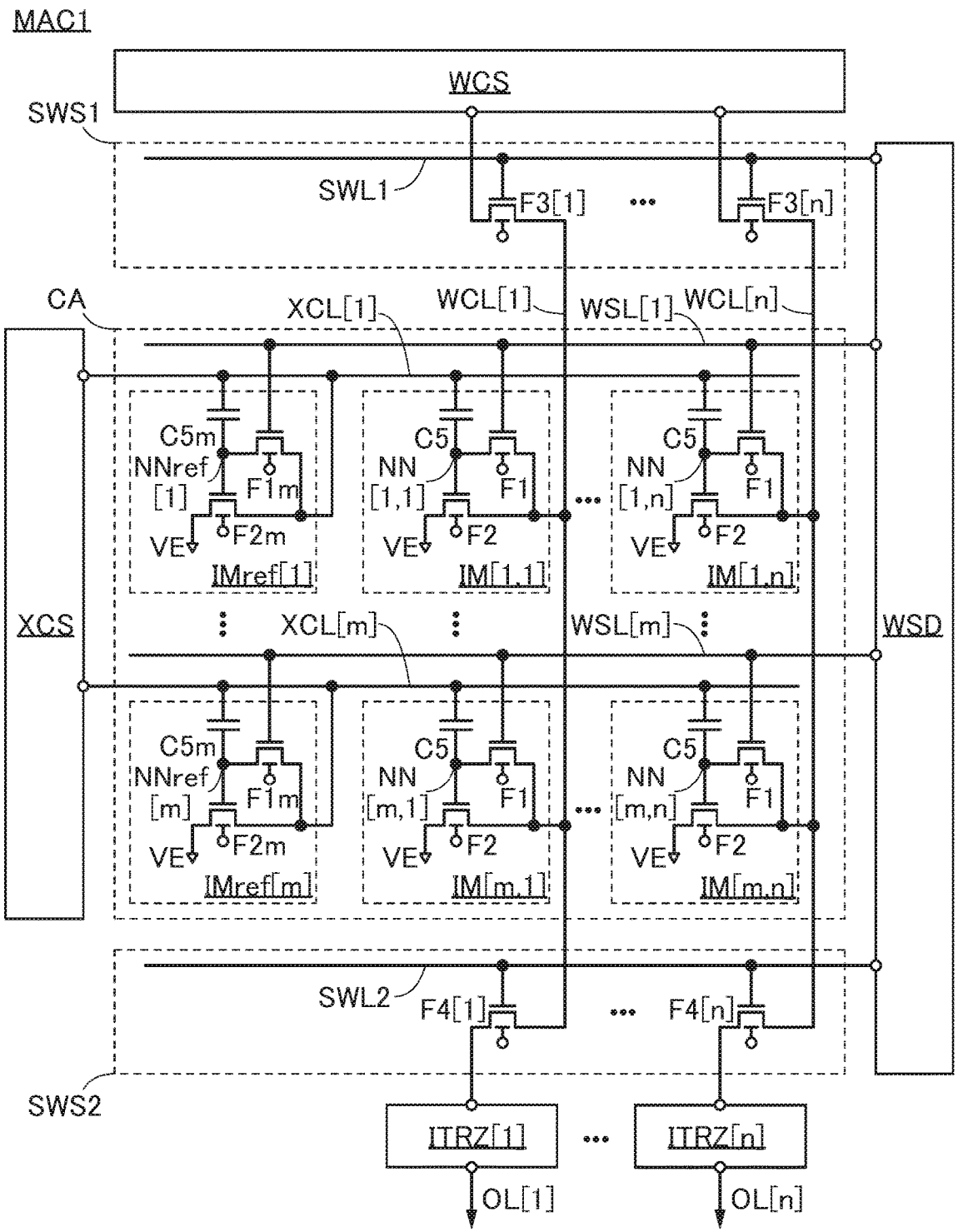
FIG. 23 is a diagram illustrating a structure example of an arithmetic circuit of a neural network.

FIG. 23 illustrates a structure example of an arithmetic circuit that performs a product-sum operation of positive or "0" first data and positive or "0" second data. The arithmetic circuit MAC1 illustrated in FIG. 23 is a circuit that performs a product-sum operation of the first data corresponding to a potential held in each cell and the input second data, and performs arithmetic operation of an activation function with the use of the product-sum operation result. Note that the first data and the second data can be analog data or multi-level data (discrete data), for example.

This arithmetic circuit, which also functions as a memory for holding the first data, can be referred to as a memory. In particular, in the case where analog data is used as the first data, the arithmetic circuit can be referred to as an analog memory.

The arithmetic circuit MAC1 includes a circuit WCS, a circuit XCS, a circuit WSD, a circuit SWS1, a circuit SWS2, a cell array CA, and a converter circuit ITRZ[1] to the converter circuit ITRZ[n].

The cell array CA includes a cell IM[1,1] to a cell IM[m,n] (here, m is an integer greater than or equal to 1 and n is an integer greater than or equal to 1) and a cell IMref[1] to a cell IMref[m]. The cell IM[1,1] to the cell IM[m,n] have a function of holding a potential corresponding to a current amount corresponding to the first data, and the cell IMref[1] to the cell IMref[m] have a function of supplying a potential corresponding to the second data necessary for performing a product-sum operation with the held potential to the wiring XCL[1] to the wiring XCL[m].

In the cell array CA in FIG. 23, cells are arranged in a matrix of n+1 rows and m columns; however, the cell array CA may have a structure where cells are arranged in a matrix of two or more rows and one or more columns.

The cell IM[1,1] to the cell IM[m,n] each include a transistor F1, a transistor F2, and a capacitor C5, and the cell IMref[1] to the cell IMref[m] each include a transistor F1m, a transistor F2m, and a capacitor C5m, for example.

It is particularly preferable that the sizes of the transistors F1 (e.g., the channel lengths, the channel widths, and the transistor structures) included in the cell IM[1,1] to the cell IM[m,n] be equal to each other, and the sizes of the transistors F2 included in the cell IM[1,1] to the cell IM[m,n] be equal to each other. It is preferable that the sizes of the transistors F1m included in the cell IMref[1] to the cell IMref[m] be equal to each other, and the sizes of the transistors F2m included in the cell IMref[1] to the cell IMref[m] be equal to each other. It is also preferable that the sizes of the transistor F1 and the transistor F1m be equal to each other, and the sizes of the transistor F2 and the transistor F2m be equal to each other.

Unless otherwise specified, the transistor F1 and the transistor F1m in an on state may operate in a linear region in the end. In other words, the gate voltage, the source voltage, and the drain voltage of each of the above transistors may be appropriately biased to voltages in the range where the transistor operates in the linear region. However, one embodiment of the present invention is not limited thereto. For example, the transistor F1 and the transistor F1m in an on state may operate in a saturation region or may operate both in a linear region and a saturation region.

Unless otherwise specified, the transistor F2 and the transistor F2m may operate in a subthreshold region (i.e., the gate-source voltage may be lower than the threshold voltage in the transistor F2 or the transistor F2m, further preferably, the drain current increases exponentially with respect to the gate-source voltage). In other words, the gate voltage, the source voltage, and the drain voltage of each of the above transistors may be appropriately biased to voltages in the range where the transistor operates in the subthreshold region. Thus, the transistor F2 and the transistor F2m may operate such that the off-state current flows between the source and the drain.

The transistor F1 and/or the transistor F1m are/is preferably the above-described OS transistor, for example. In addition, it is further preferable that channel formation regions of the transistor F1 and/or the transistor F1m be an oxide containing at least one of indium, the element M (as the element M, one or more kinds selected from aluminum, gallium, yttrium, copper, vanadium, beryllium, boron, titanium, iron, nickel, germanium, zirconium, molybdenum, lanthanum, cerium, neodymium, hafnium, tantalum, tungsten, magnesium, and the like can be given for example), and zinc.

With the use of an OS transistor as the transistor F1 and/or the transistor F1m, the leakage current of the transistor F1 and/or the transistor F1m can be inhibited, so that the power consumption of the arithmetic circuit can be reduced. Specifically, when the transistor F1 and/or the transistor F1m are/is in a non-conducting state, the amount of leakage current from a holding node to a write word line can be extremely small; thus, the frequency of refresh operation for the potential of the holding node can be reduced and power consumption of the arithmetic circuit can be reduced. An extremely low leakage current from the holding node to the write word line allows cells to hold the potential of the holding node for a long time, increasing the arithmetic operation accuracy of the arithmetic circuit.

The use of an OS transistor also as the transistor F2 and/or the transistor F2m enables operation with a wide range of current in the subthreshold region, leading to a reduction in the current consumption. With the use of an OS transistor also as the transistor F2 and/or the transistor F2m, the transistor F2 and/or the transistor F2m can be fabricated concurrently with the transistor F1 and the transistor F1m; thus, the fabrication process of the arithmetic circuit can sometimes be shortened. The transistor F2 and/or the transistor F2m can be, other than an OS transistor, a transistor containing silicon in its channel formation region (hereinafter, referred to as a Si transistor). As the silicon, amorphous silicon (referred to as hydrogenated amorphous silicon in some cases), microcrystalline silicon, polycrystalline silicon (including low-temperature polysilicon), single crystal silicon, or the like can be used, for example.

When an arithmetic circuit and the like are highly integrated into a chip or the like, heat may be generated in the chip by driving of the circuit. This heat increases the temperature of a transistor to change the characteristics of the transistor; thus, the field-effect mobility thereof might change or the operation frequency thereof might decrease, for example. Since an OS transistor has a higher heat resistance than a Si transistor, a change in field-effect mobility and a decrease in operation frequency due to a temperature change do not easily occur. Even when having a high temperature, an OS transistor is likely to keep a property of the drain current increasing exponentially with respect to the gate-source voltage. With the use of an OS transistor, a product-sum operation to be described later can thus be easily performed even in a high temperature environment. To form an arithmetic circuit highly resistant to heat due to driving, an OS transistor is preferably used as its transistor.

In each of the cell IM[1,1] to the cell IM[m,n], a first terminal of the transistor F1 is electrically connected to a gate of the transistor F2. A first terminal of the transistor F2 is electrically connected to the wiring VE. A first terminal of the capacitor C5 is electrically connected to the gate of the transistor F2.

In each of the cell IMref[1] to the cell IMref[m], a first terminal of the transistor F1m is electrically connected to a gate of the transistor F2m. A first terminal of the transistor F2m is electrically connected to the wiring VE. A first terminal of the capacitor C5m is electrically connected to the gate of the transistor F2m.

The arithmetic circuit described in this section does not depend on the polarity of transistors included in the arithmetic circuit. For example, the transistor F1 and the transistor F2 illustrated in FIG. 23 are n-channel transistors; however, some or all transistors may be replaced with p-channel transistors.

The above-described examples of changes in the structure and polarity of the transistor are not limited to the transistor F1 and the transistor F2. For example, the same applies to the transistor F1m, the transistor F2m, a transistor F3[1] to a transistor F3[n] and a transistor F4[1] to a transistor F4[n], which are described later, a transistor described in other parts of the specification, and a transistor illustrated in other drawings.

The wiring VE functions as a wiring for supplying a current between the first terminal and a second terminal of the transistor F2 of each of the cell IM[1,1], the cell IM[m,1], the cell IM[1,n], and the cell IM[m,n] and a wiring for supplying a current between the first terminal and a second terminal of the transistor F2m of each of the cell IMref[1] and the cell IMref[m]. The wiring VE functions as a wiring for supplying a constant voltage, for example. The constant voltage can be, for example, a low-level potential, a ground potential, or the like.

In the cell IM[1,1], a second terminal of the transistor F1 is electrically connected to a wiring WCL[1], and a gate of the transistor F1 is electrically connected to a wiring WSL[1]. The second terminal of the transistor F2 is electrically connected to the wiring WCL[1], and a second terminal of the capacitor C5 is electrically connected to the wiring XCL[1]. In the cell IM[1,1] in FIG. 23, a connection portion of the first terminal of the transistor F1, the gate of the transistor F2, and the first terminal of the capacitor C5 is a node NN[1,1].

In the cell IM[m,1], the second terminal of the transistor F1 is electrically connected to the wiring WCL[1], and the gate of the transistor F1 is electrically connected to the wiring WSL[m]. The second terminal of the transistor F2 is electrically connected to the wiring WCL[1], and the second terminal of the capacitor C5 is electrically connected to the wiring XCL[m]. In the cell IM[m,1] in FIG. 23, a connection portion of the first terminal of the transistor F1, the gate of the transistor F2, and the first terminal of the capacitor C5 is a node NN[m,1].

In the cell IM[1,n], the second terminal of the transistor F1 is electrically connected to the wiring WCL[n], and the gate of the transistor F1 is electrically connected to the wiring WSL[1]. The second terminal of the transistor F2 is electrically connected to the wiring WCL[n], and the second terminal of the capacitor C5 is electrically connected to the wiring XCL[1]. In the cell IM[1,n] in FIG. 23, a connection portion of the first terminal of the transistor F1, the gate of the transistor F2, and the first terminal of the capacitor C5 is a node NN[1,n].

In the cell IM[m,n], the second terminal of the transistor F1 is electrically connected to the wiring WCL[n], and the gate of the transistor F1 is electrically connected to the wiring WSL[m]. The second terminal of the transistor F2 is electrically connected to the wiring WCL[n], and the second terminal of the capacitor C5 is electrically connected to the wiring XCL[m]. In the cell IM[m,n] in FIG. 23, a connection portion of the first terminal of the transistor F1, the gate of the transistor F2, and the first terminal of the capacitor C5 is a node NN[m,n].

In the cell IMref[1], a second terminal of the transistor F1m is electrically connected to the wiring XCL[1], and the gate of the transistor F1m is electrically connected to the wiring WSL[1]. The second terminal of the transistor F2m is electrically connected to the wiring XCL[1], and the second terminal of the capacitor C5m is electrically connected to the wiring XCL[1]. In the cell IMref[1] in FIG. 23, a connection portion of the first terminal of the transistor F1m, the gate of the transistor F2m, and the first terminal of the capacitor C5m is a node NNref[1].

In the cell IMref[m], the second terminal of the transistor F1m is electrically connected to the wiring XCL[m], and the gate of the transistor F1m is electrically connected to the wiring WSL[m]. The second terminal of the transistor F2m is electrically connected to the wiring XCL[m], and the second terminal of the capacitor C5m is electrically connected to the wiring XCL[m]. In the cell IMref[m] in FIG. 23, a connection portion of the first terminal of the transistor F1m, the gate of the transistor F2m, and the first terminal of the capacitor C5m is a node NNref[m].

The node NN[1,1], the node NN[m,1], the node NN[1,n], the node NN[m,n], the node NNref[1], and the node NNref[m] described above function as holding nodes of the respective cells.

In the case where the transistor F1 is in an on state in each of the cell IM[1,1] to the cell IM[m,n], for example, the transistor F2 is a diode-connected transistor. When a constant voltage supplied from the wiring VE is a ground potential (GND), the transistor F1 is in an on state, and a current with a current amount I flows from the wiring WCL to the second terminal of the transistor F2, a potential of the gate of the transistor F2 (the node NN) is determined in accordance with the current amount I Since the transistor F1 is in an on state, a potential of the second terminal of the transistor F2 is ideally equal to that of the gate of the transistor F2 (the node NN). Here, by bringing the transistor F1 into an off state, the potential of the gate of the transistor F2 (the node NN) is held. Accordingly, the transistor F2 can make the current with the current amount I corresponding to a ground potential of the first terminal of the transistor F2 and the potential of the gate of the transistor F2 (the node NN) flow between the source and the drain of the transistor F2. In this specification and the like, such an operation is expressed as "the transistor F2 is programmed such that the amount of current flowing between the source and the drain of the transistor F2 is I".

The circuit SWS1 includes the transistor F3[1] to the transistor F3[n], for example. A first terminal of the transistor F3[1] is electrically connected to the wiring WCL[1], a second terminal of the transistor F3[1] is electrically connected to the circuit WCS, and a gate of the transistor F3[1] is electrically connected to a wiring SWL1. A first terminal of the transistor F3[n] is electrically connected to the wiring WCL[n], a second terminal of the transistor F3[n] is electrically connected to the circuit WCS, and a gate of the transistor F3[n] is electrically connected to the wiring SWL1.

Each of the transistor F3[1] to the transistor F3[n] is preferably an OS transistor that can be used as the transistor F1 and/or the transistor F2, for example.

The circuit SWS1 functions as a circuit that establishes or breaks electrical continuity between the circuit WCS and each of the wiring WCL[1] to the wiring WCL[n].

The circuit SWS2 includes the transistor F4[1] to the transistor F4[n], for example. A first terminal of the transistor F4[1] is electrically connected to the wiring WCL[1], a second terminal of the transistor F4[1] is electrically connected to an input terminal of the converter circuit ITRZ[1], and a gate of the transistor F4[1] is electrically connected to a wiring SWL2. A first terminal of the transistor F4[n] is electrically connected to the wiring WCL[n], a second terminal of the transistor F4[n] is electrically connected to an input terminal of the converter circuit ITRZ[n], and a gate of the transistor F4[n] is electrically connected to the wiring SWL2.

Each of the transistor F4[1] to the transistor F4[n] is preferably an OS transistor that can be used as the transistor F1 and/or the transistor F2, for example.

The circuit SWS2 functions as a circuit that establishes or breaks electrical continuity between the wiring WCL[1] and the converter circuit ITRZ[1] and between the wiring WCL[n] and the converter circuit ITRZ[n].

The circuit WCS has a function of supplying data that is to be stored in each cell included in the cell array CA.

The circuit XCS is electrically connected to the wiring XCL[1] to the wiring XCL[m]. The circuit XCS has a function of making a current corresponding to reference data or a current corresponding to the second data flow to each of the cell IMref[1] to the cell IMref[m] included in the cell array CA.

The circuit WSD is electrically connected to the wiring WSL[1] to the wiring WSL[m]. The circuit WSD has a function of selecting a row of the cell array CA to which the first data is written, by supplying a predetermined signal to the wiring WSL[1] to the wiring WSL[m] at the time of writing the first data to the cell IM[1,1] to the cell IM[m,n].

The circuit WSD is electrically connected to the wiring SWL1 and the wiring SWL2, for example. The circuit WSD has a function of establishing and breaking electrical continuity between the circuit WCS and the cell array CA by supplying a predetermined signal to the wiring SWL1, and a function of establishing and breaking electrical continuity between the cell array CA and each of the converter circuit ITRZ[1] to the converter circuit ITRZ[n] by supplying a predetermined signal to the wiring SWL2.

The converter circuit ITRZ[1] to the converter circuit ITRZ[n] each include an input terminal and an output terminal, for example. The output terminal of the converter circuit ITRZ[1] is electrically connected to the wiring OL[1], and the output terminal of the converter circuit ITRZ[n] is electrically connected to the wiring OL[n], for example.

The converter circuit ITRZ[1] to the converter circuit ITRZ[n] each have a function of converting a current input to the input terminal into a voltage corresponding to the amount of the current and outputting the voltage from the output terminal. The voltage can be, for example, an analog voltage or a digital voltage. The converter circuit ITRZ[1] to the converter circuit ITRZ[n] may each include an arithmetic circuit of a function system. In this case, for example, the arithmetic circuit may perform arithmetic operation of a function with the use of the converted voltage and may output the arithmetic operation results to the wiring OL[1] to the wiring OL[n].

In particular, in the case of performing arithmetic operation of a hierarchical neural network, a sigmoid function, a tanh function, a softmax function, a ReLU function, or a threshold function can be used as the above-described function.

As the circuit WCS illustrated in FIG. 23, a current output digital-analog converter can be used. As XCS illustrated in FIG. 23, a current output digital-analog converter can be used.

At least part of the structure examples, the drawings corresponding thereto, and the like described in this embodiment as an example can be combined with the other structure examples, the other drawings, and the like as appropriate.

At least part of this embodiment can be implemented in combination with the other embodiments described in this specification as appropriate.

Embodiment 3

In this embodiment, a display apparatus that can be provided in an electronic device of one embodiment of the present invention is described with reference to drawings. Note that the display apparatus described in this embodiment can be used in the display portion DSP described in the above embodiment.

<Structure Example of Display Apparatus>

Figure 24:
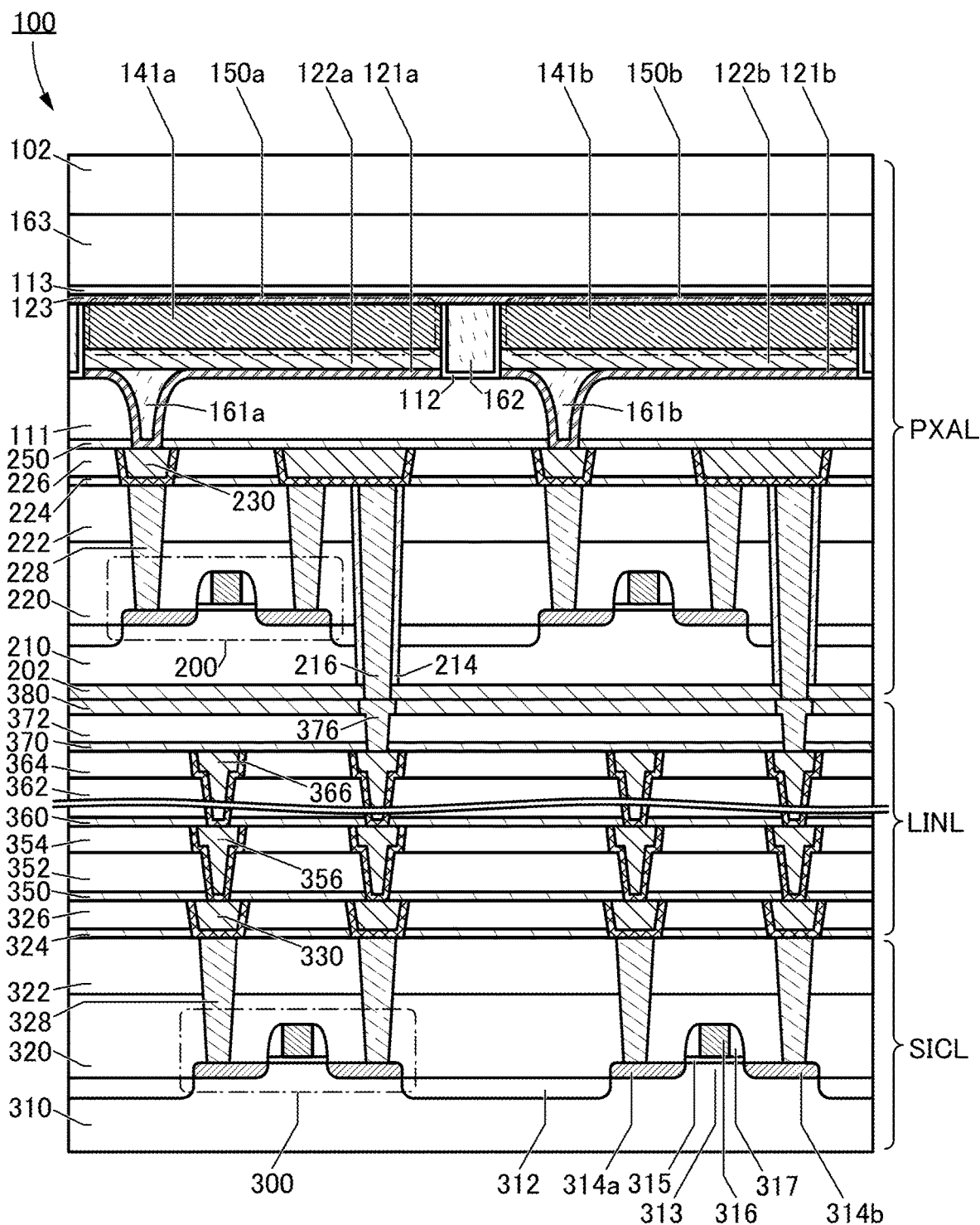
FIG. 24 is a schematic cross-sectional view illustrating a structure example of a display apparatus.

FIG. 24 is a cross-sectional view illustrating an example of a display apparatus that can be provided in the electronic device of one embodiment of the present invention. A display apparatus 100 illustrated in FIG. 24 has a structure where a pixel circuit and a driver circuit are provided over a substrate 310, for example.

Specifically, the display apparatus 100 includes, for example, the circuit layer SICL, the wiring layer LINL, and a pixel layer PXAL. The circuit layer SICL includes the substrate 310, for example, and a transistor 300 is formed on the substrate 310. The wiring layer LINL is provided above the transistor 300, and wirings that electrically connect the transistor 300, a transistor 200 to be described later, a light-emitting device 150a and a light-emitting device 150b that are to be described later, and the like are provided over the wiring layer LINL. The pixel layer PXAL is provided above the wiring layer LINL, and the pixel layer PXAL includes, for example, the transistor 200 and a light-emitting device 150 (the light-emitting device 150a and the light-emitting device 150b in FIG. 24).

As the substrate 310, a semiconductor substrate (e.g., a single crystal substrate) containing silicon or germanium as a material can be used, for example. Besides the semiconductor substrate, for example, an SOI (Silicon On Insulator) substrate, a glass substrate, a quartz substrate, a plastic substrate, a sapphire glass substrate, a metal substrate, a stainless steel substrate, a substrate including stainless steel foil, a tungsten substrate, a substrate including tungsten foil, a flexible substrate, an attachment film, or paper or a base material film containing a fibrous material can be used as the substrate 310. Examples of the glass substrate include barium borosilicate glass, aluminoborosilicate glass, and soda lime glass. Examples of the flexible substrate, the attachment film, the base material film, and the like include plastics typified by polyethylene terephthalate (PET), polyethylene naphthalate (PEN), polyether sulfone (PES), and polytetrafluoroethylene (PTFE). Another example of a flexible substrate, an attachment film, and a base material film is a synthetic resin such as an acrylic resin. Other examples of the flexible substrate, the attachment film, and the base material film are polypropylene, polyester, polyvinyl fluoride, and polyvinyl chloride. Other examples of the flexible substrate, the attachment film, and the base material film are polyamide, polyimide, aramid, an epoxy resin, an inorganic vapor deposition film, and paper. Note that in the case where the fabrication process of the display apparatus 100 involves heat treatment, a highly heat-resistant material is preferably selected for the substrate 310.

In the description of this embodiment, the substrate 310 is a semiconductor substrate containing silicon or the like as a material.

The transistor 300 is provided on the substrate 310 and includes an element isolation layer 312, a conductor 316, an insulator 315, an insulator 317, a semiconductor region 313 that is part of the substrate 310, and a low-resistance region 314a and a low-resistance region 314b that function as source region and a drain region. Thus, the transistor 300 is a Si transistor. Although FIG. 24 illustrates a structure where one of the source and the drain of the transistor 300 is electrically connected to a conductor 330, a conductor 356, and a conductor 366, which are described later, through a conductor 328 described later, the electrical connection in the semiconductor device of one embodiment of the present invention is not limited thereto. The semiconductor device of one embodiment of the present invention may have a structure where, for example, a gate of the transistor 300 is electrically connected to the conductor 330, the conductor 356, and the conductor 366 through the conductor 328.

The transistor 300 can be a fin type when, for example, the top surface of the semiconductor region 313 and the side surface thereof in the channel width direction are covered with the conductor 316 with the insulator 315 functioning as a gate insulating film therebetween. The effective channel width can be increased in the fin-type transistor 300, so that the on-state characteristics of the transistor 300 can be improved. In addition, contribution of the electric field of the gate electrode can be increased, so that the off-state characteristics of the transistor 300 can be improved.

Note that the transistor 300 may be either a p-channel transistor or an n-channel transistor. Alternatively, a plurality of transistors 300 may be provided and both the p-channel transistor and the n-channel transistor may be used.

A region of the semiconductor region 313 where a channel is formed, a region in the vicinity thereof, the low-resistance region 314a and the low-resistance region 314b functioning as the source region and the drain region, and the like preferably contain a silicon-based semiconductor, and further preferably contain single crystal silicon, in particular. Each of the above regions may be formed using a material containing germanium (Ge), silicon germanium (SiGe), gallium arsenide (GaAs), gallium aluminum arsenide (GaAlAs), or gallium nitride (GaN). Each of the above regions may employ a structure where silicon whose effective mass is controlled by applying stress to the crystal lattice and thereby changing the lattice spacing is used. Alternatively, the transistor 300 may be an HEMT (High Electron Mobility Transistor) containing gallium arsenide and aluminum gallium arsenide, for example.

For the conductor 316 functioning as a gate electrode, a semiconductor material such as silicon containing an element that imparts n-type conductivity, such as arsenic or phosphorus, or an element that imparts p-type conductivity, such as boron, or a conductive material such as a metal material, an alloy material, or a metal oxide material can be used.

Note that since the work function of a conductor is depends on the material of the conductor, the threshold voltage of the transistor can be adjusted by selecting the material of the conductor. Specifically, one or both of titanium nitride and tantalum nitride are preferably used as the material of the conductor. Moreover, in order to ensure both conductivity and embeddability, it is preferable to use stacked layers of metal materials of one or both of tungsten and aluminum for the conductor, and it is particularly preferable to use tungsten in terms of heat resistance.

The element isolation layer 312 is provided to separate a plurality of transistors formed on the substrate 310 from each other. The element isolation layer can be formed by, for example, a LOCOS (Local Oxidation of Silicon) method, an STI (Shallow Trench Isolation) method, or a mesa isolation method.

Note that the transistor 300 illustrated in FIG. 24 is an example and the structure is not limited thereto; an appropriate transistor is used in accordance with a circuit structure, a driving method, or the like. For example, the transistor 300 may have a planar structure instead of a fin-type structure.

Over the transistor 300 illustrated in FIG. 24, an insulator 320, an insulator 322, an insulator 324, and an insulator 326 are stacked in this order from the substrate 310 side.

For the insulator 320, the insulator 322, the insulator 324, and the insulator 326, one or more selected from silicon oxide, silicon oxynitride, silicon nitride oxide, silicon nitride, aluminum oxide, aluminum oxynitride, aluminum nitride oxide, and aluminum nitride can be used, for example.

The insulator 322 may have a function of a planarization film for eliminating a level difference caused by the transistor 300 or the like covered with the insulator 320 and the insulator 322. For example, the top surface of the insulator 322 may be planarized by planarization treatment using a chemical mechanical polishing (CMP) method or the like to have improved planarity.

For the insulator 324, it is preferable to use a barrier insulating film preventing diffusion of impurities such as water and hydrogen from the substrate 310 or the transistor 300 to a region above the insulator 324 (e.g., the region where the transistor 200, the light-emitting device 150a, the light-emitting device 150b, and the like are provided). Accordingly, for the insulator 324, it is preferable to use an insulating material that has a function of inhibiting diffusion of impurities such as a hydrogen atom, a hydrogen molecule, and a water molecule (through which the above impurities are less likely to pass). Furthermore, depending on the situation, for the insulator 324, it is preferable to use an insulating material having a function of inhibiting diffusion of impurities such as a nitrogen atom, a nitrogen molecule, a nitrogen oxide molecule ($N_2O$, NO, $NO_2$, or the like), and a copper atom (through which the above oxygen is less likely to pass). In addition, it is preferable that the insulator 324 have a function of inhibiting diffusion of oxygen (e.g., one or both of an oxygen atom and an oxygen molecule).

For the film having a barrier property against hydrogen, silicon nitride deposited by a CVD method can be used, for example.

The amount of released hydrogen can be analyzed by thermal desorption spectroscopy (TDS), for example. The amount of hydrogen released from the insulator 324 that is converted into hydrogen atoms per unit area of the insulator 324 is less than or equal to $10 \times 10^{15}$ atoms/$cm^2$, preferably less than or equal to $5 \times 10^{15}$ atoms/$cm^2$ in TDS analysis in a film-surface temperature range of 50° C. to 500° C., for example.

Note that the permittivity of the insulator 326 is preferably lower than that of the insulator 324. For example, the dielectric constant of the insulator 326 is preferably lower than 4, further preferably lower than 3. The dielectric constant of the insulator 326 is, for example, preferably 0.7 times or less, further preferably 0.6 times or less the dielectric constant of the insulator 324. When a material with a low permittivity is used for an interlayer film, the parasitic capacitance generated between wirings can be reduced.

In addition, the conductor 328, the conductor 330, and the like that are connected to the light-emitting devices and the like provided above the insulator 326 are embedded in the insulator 320, the insulator 322, the insulator 324, and the insulator 326. Note that the conductor 328, the conductor 330, and the like each function as a plug or a wiring. A plurality of conductors each functioning as a plug or a wiring are collectively denoted by the same reference numeral in some cases. Moreover, in this specification and the like, a wiring and a plug connected to the wiring may be a single component. That is, part of a conductor functions as a wiring in some cases and part of a conductor functions as a plug in other cases.

As a material for each of plugs and wirings (the conductor 328 and the conductor 330), a single layer or stacked layers of one or more conductive materials selected from a metal material, an alloy material, a metal nitride material, and a metal oxide material can be used. It is preferable to use a high-melting-point material having both heat resistance and conductivity, such as tungsten or molybdenum, and it is preferable to use tungsten. Alternatively, it is preferable to use a low-resistance conductive material such as aluminum or copper. The use of a low-resistance conductive material can reduce wiring resistance.

A wiring layer may be provided over the insulator 326 and the conductor 330. For example, in FIG. 24, an insulator 350, an insulator 352, and an insulator 354 are provided to be stacked in this order above the insulator 326 and the conductor 330. Furthermore, the conductor 356 is formed in the insulator 350, the insulator 352, and the insulator 354. The conductor 356 has a function of a plug or a wiring that is connected to the transistor 300. Note that the conductor 356 can be provided using a material similar to those for the conductor 328 and the conductor 330.

Note that for example, like the insulator 324, the insulator 350 is preferably formed using an insulator having a barrier property against hydrogen, oxygen, and water. Like the insulator 326, the insulator 352 and the insulator 354 are preferably formed using an insulator having a relatively low dielectric constant to reduce parasitic capacitance generated between wirings. The insulator 362 and the insulator 364 each have functions of an interlayer insulating film and a planarization film. Furthermore, the conductor 356 preferably includes a conductor having a barrier property against hydrogen, oxygen, and water.

For the conductor having a barrier property against hydrogen, tantalum nitride is preferably used, for example. The use of a stack including tantalum nitride and tungsten that has high conductivity can inhibit diffusion of hydrogen from the transistor 300 while the conductivity of a wiring is kept. In this case, a tantalum nitride layer having a barrier property against hydrogen is preferably in contact with the insulator 350 having a barrier property against hydrogen.

An insulator 360, an insulator 362, and an insulator 364 are stacked in this order over the insulator 354 and the conductor 356.

Like the insulator 324 or the like, the insulator 360 is preferably formed using an insulator having a barrier property against impurities such as water and hydrogen. Thus, the insulator 360 can be formed using any of the materials usable for the insulator 324 or the like, for example.

The insulator 362 and the insulator 364 each have functions of an interlayer insulating film and a planarization film. Like the insulator 324, the insulator 362 and the insulator 364 are preferably formed using an insulator having a barrier property against impurities such as water or hydrogen. Thus, one or both of the insulator 362 and the insulator 364 can be formed using any of the materials usable for the insulator 324.

An opening portion is provided in regions of the insulator 360, the insulator 362, and the insulator 364 that overlap with part of the conductor 356, and the conductor 366 is provided to fill the opening portion. The conductor 366 is also formed over the insulator 362. The conductor 366 has a function of a plug or a wiring connected to the transistor 300, for example. Note that the conductor 366 can be provided using a material similar to those for the conductor 328 and the conductor 330.

An insulator 370 and an insulator 372 are stacked in this order over the insulator 364 and the conductor 366.

Like the insulator 324 or the like, the insulator 370 is preferably formed using an insulator having a barrier property against impurities such as water and hydrogen. Thus, the insulator 370 can be formed using any of the materials usable for the insulator 324 or the like, for example.

The insulator 372 has functions of an interlayer insulating film and a planarization film. For example, like the insulator 324, the insulator 372 is preferably formed using an insulator having a barrier property against impurities such as water and hydrogen. Thus, the insulator 372 can be formed using any of the materials usable for the insulator 324.

An opening portion is formed in regions of the insulator 370 and the insulator 372 that overlap with part of the conductor 366, and a conductor 376 is provided to fill the opening portion. The conductor 376 is also formed over the insulator 372. After that, the conductor 376 is patterned into a form of a wiring, a terminal, or a pad by etching treatment or the like.

For example, copper, aluminum, tin, zinc, tungsten, silver, platinum, or gold can be used for the conductor 376. The material used for the conductor 376 preferably contains the same component as the material used for a later-described conductor 216 included in the pixel layer PXAL.

Then, the insulator 380 is formed to cover the insulator 372 and the conductor 376 and is subsequently subjected to planarization treatment by a chemical mechanical polishing (CMP) method or the like until the conductor 376 is exposed. In this manner, the conductor 376 serving as a wiring, a terminal, or a pad can be formed over the substrate 310.

Like the insulator 324, the insulator 380 is preferably formed using a film having a barrier property that prevents diffusion of impurities such as water and hydrogen, for example. In other words, the insulator 380 is preferably formed using any of the materials usable for the insulator 324. Like the insulator 326, the insulator 380 may be formed using an insulator having a relatively low dielectric constant to reduce the parasitic capacitance generated between wirings, for example. In other words, the insulator 380 may be formed using any of the materials usable for the insulator 326.

The pixel layer PXAL is provided with a substrate 210, the transistor 200, the light-emitting device 150 (the light-emitting device 150a and the light-emitting device 150b in FIG. 24), and a substrate 102. Moreover, the pixel layer PXAL is provided with an insulator 220, an insulator 222, an insulator 226, an insulator 250, an insulator 111, an insulator 112, an insulator 113, a layer 161 (a layer 161a and a layer 161b in FIG. 24), an insulator 162, and a resin layer 163, for example. Furthermore, the pixel layer PXAL is provided with the conductor 216, a conductor 228, a conductor 230, a conductor 121 (a conductor 121a and a conductor 121b in FIG. 24), a conductor 122, and a conductor 123, for example.

An insulator 202 in FIG. 24 functions as a bonding layer together with the insulator 380, for example. The insulator 202 preferably contains, for example, the same component as the material used for the insulator 380.

The substrate 210 is provided above the insulator 202. In other words, the insulator 202 is provided on the bottom surface of the substrate 210. The substrate 210 is preferably a substrate usable as the substrate 310, for example. Note that in the description of the display apparatus 100 in FIG. 24, the substrate 310 is a semiconductor substrate containing silicon as a material.

On the substrate 210, the transistor 200 is formed, for example. Being formed on the substrate 210 that is a semiconductor substrate containing silicon as a material, the transistor 200 functions as a Si transistor. Note that the description of the transistor 300 can be referred to for the structure of the transistor 200.

Above the transistor 200, the insulator 220 and the insulator 222 are provided. Like the insulator 320, the insulator 220 has functions of an interlayer insulating film and a planarization film, for example. Like the insulator 322, the insulator 222 has functions of an interlayer insulating film and a planarization film, for example.

A plurality of opening portions are provided in the insulator 220 and the insulator 222. The plurality of opening portions are formed in regions overlapping with a source and a drain of the transistor 200, a region overlapping with the conductor 376, and the like. The conductor 228 is formed in each of the opening portions formed in the regions overlapping with the source and the drain of the transistor 200, among the plurality of opening portions. An insulator 214 is formed on the side surface of the opening portion formed in the region overlapping with the conductor 376, among the other opening portions, and the conductor 216 is formed in the opening portion. The conductor 216 is sometimes particularly referred to as a through silicon via (TSV).

For the conductor 216 or the conductor 228, any of the materials usable for the conductor 328 can be used, for example. In particular, the conductor 216 is preferably formed using the same material as the conductor 376.

The insulator 214 has a function of electrically insulating the substrate 210 and the conductor 216 from each other, for example. Note that the insulator 214 is preferably formed using, for example, any of the materials usable for the insulator 320 and the insulator 324.

The insulator 380 and the conductor 376 that are formed over the substrate 310 are bonded to the insulator 202 and the conductor 216 that are formed on the substrate 210 by a bonding step, for example.

Before the bonding step, for example, planarization treatment is performed to make surfaces of the insulator 380 and the conductor 376 level with each other on the substrate 310 side. In a similar manner, planarization treatment is performed to make surfaces of the insulator 202 and the conductor 216 level with each other on the substrate 210 side.

In the case where bonding of the insulator 380 and the insulator 202, i.e., bonding of insulating layers, is performed in the bonding step, a hydrophilic bonding method or the like can be employed in which, after high planarity is obtained by polishing or the like, the surfaces subjected to hydrophilicity treatment with oxygen plasma or the like are brought into contact to be bonded to each other temporarily, and then dehydrated by heat treatment to perform final bonding. The hydrophilic bonding method can also cause bonding at an atomic level; thus, mechanically excellent bonding can be obtained.

When bonding of the conductor 376 and the conductor 216, i.e., bonding of the conductors, is performed, for example, a surface activated bonding method can be used in which an oxide film, a layer adsorbing impurities, and the like on the surface are removed by sputtering treatment or the like and the cleaned and activated surfaces are brought into contact to be bonded to each other. Alternatively, a diffusion bonding method in which the surfaces are bonded to each other by using temperature and pressure together can be used, for example. Both methods cause bonding at an atomic level, and therefore not only electrically but also mechanically excellent bonding can be obtained.

Through the above-described bonding step, the conductor 376 on the substrate 310 side can be electrically connected to the conductor 216 on the substrate 210 side. In addition, mechanically strong connection can be established between the insulator 380 on the substrate 310 side and the insulator 202 on the substrate 210 side.

In the case where the substrate 310 and the substrate 210 are bonded to each other, the insulating layers and the metal layers coexist on their bonding surfaces; therefore, the surface activated bonding method and the hydrophilic bonding method are performed in combination, for example. For example, it is possible to use a method in which the surfaces are made clean after polishing, the surfaces of the metal layers are subjected to antioxidant treatment and hydrophilicity treatment, and then bonding is performed. Furthermore, hydrophilicity treatment may be performed on the surfaces of the metal layers being hardly oxidizable metal such as gold.

Note that the substrate 310 and the substrate 210 may be bonded by a bonding method other than the above-described methods. For example, as the bonding method of the substrate 310 and the substrate 210, flip-chip bonding may be employed. In the case of employing flip-chip bonding, a connection terminal such as a bump may be provided above the conductor 376 on the substrate 310 side or below the conductor 216 on the substrate 210 side. Flip-chip bonding can be performed by, for example, injecting a resin containing anisotropic conductive particles between the insulator 380 and the insulator 202 and between the conductor 376 and the conductor 216, or by using a Sn—Ag solder. Alternatively, ultrasonic wave bonding can be employed in the case where the bump and a conductor connected to the bump are each gold. To reduce physical stress such as an impact and thermal stress, the above-described flip-chip bonding may be combined with injection of an underfill agent between the insulator 380 and the insulator 202 and between the conductor 376 and the conductor 216. Furthermore, a die bonding film may be used in bonding of the substrate 310 and the substrate 210, for example.

An insulator 224 and the insulator 226 are stacked in this order over the insulator 222, the insulator 214, the conductor 216, and the conductor 228.

Like the insulator 324, the insulator 224 is preferably a barrier insulating film inhibiting diffusion of impurities such as water and hydrogen to the region above the insulator 224. Thus, the insulator 224 is preferably formed using any of the materials usable for the insulator 324, for example.

Like the insulator 326, the insulator 226 is preferably an interlayer film with a low permittivity. Thus, the insulator 226 is preferably formed using any of the materials usable for the insulator 326, for example.

In the insulator 224 and the insulator 226, the conductor 230 electrically connected to the transistor 200, the light-emitting device 150, and the like is embedded. Note that the conductor 230 has a function of a plug or a wiring. Note that the conductor 230 can be formed using, any of the materials usable for the conductor 328, the conductor 330, and the like, for example.

Over the insulator 224 and the insulator 226, the insulator 250 and the insulator 111 are stacked in this order.

Like the insulator 324 or the like, the insulator 250 is preferably formed using an insulator having a barrier property against impurities such as water and hydrogen. Thus, the insulator 250 can be formed using any of the materials usable for the insulator 324 or the like, for example.

For example, an insulator having a function of inhibiting diffusion of oxygen and impurities such as water and hydrogen is preferably used as the insulator 111; for example, aluminum oxide, magnesium oxide, hafnium oxide, gallium oxide, indium gallium zinc oxide, silicon nitride, or silicon nitride oxide can be used. For example, silicon nitride, which has a high hydrogen barrier property, is preferably used for the insulator 111. For example, aluminum oxide or magnesium oxide, which has a function of trapping and fixing hydrogen well, is preferably used for the insulator 111.

The insulator 111 is preferably a film with high planarity. In this case, an organic material such as an acrylic resin or polyimide can be used for the insulator 111, for example.

Opening portions are formed in regions of the insulator 250 and the insulator 111 overlapping with part of the conductor 230, and the conductor 121 is provided to cover the region where the insulator 111 is formed. Note that in this specification and the like, the conductor 121a and the conductor 121b illustrated in FIG. 24 are collectively referred to as the conductor 121. The conductor 230 has a function of a plug or a wiring connected to the light-emitting device 150, for example. Note that the conductor 121 can be provided using a material similar to those for the conductor 328 and the conductor 330.

In the region where the conductor 121a is formed, the layer 161a is preferably embedded in a depressed portion of the opening portion. In addition, the conductor 122a is preferably formed over the conductor 121a and the layer 161a. In the region where the conductor 121b is formed, the layer 161b is preferably embedded in a depressed portion of the opening portion. In addition, the conductor 122b is preferably formed over the conductor 121b and the layer 161. Note that in this specification and the like, the layer 161a and the layer 161b illustrated in FIG. 24 are collectively referred to as the layer 161. The conductor 122a and the conductor 122b illustrated in FIG. 24 are collectively referred to as the conductor 122.

At least one of the conductor 121 and the conductor 122 is referred to as a pixel electrode in some cases.

The layer 161 has a planarization function for the depressed portion of the conductor 121. Providing the layer 161 can reduce the unevenness on a surface where the EL layer is to be formed, improving the coverage with the EL layer. Furthermore, providing the conductor 122 over the conductor 121 and the layer 161 enables the region overlapping with the depressed portion of the conductor 121 to be used as a light-emitting region in some cases. Thus, the aperture ratio of a pixel can be increased.

The layer 161 may be an insulating layer or a conductive layer. For example, the layer 161 can be formed using a material selected from a variety of inorganic insulating materials, organic insulating materials, and conductive materials. In particular, the layer 161 is preferably formed using an insulating material.

An insulating layer containing an organic material can be suitably used as the layer 161. For the insulating layer 161, an acrylic resin, a polyimide resin, an epoxy resin, a polyamide resin, a polyimide-amide resin, a siloxane resin, a benzocyclobutene-based resin, a phenol resin, a precursor of any of these resins, or the like can be used, for example. A photosensitive resin can also be used for the layer 161. As the photosensitive resin, a positive photosensitive material or a negative photosensitive material can be used.

When a photosensitive resin is used, the layer 161 can be formed through only light-exposure and development steps, reducing the influence of dry etching, wet etching, or the like on the surfaces of the conductor 121. When the layer 161 is formed using a negative photosensitive resin, the layer 161 can sometimes be formed using the same photomask (light-exposure mask) as the photomask used for forming the opening in the insulator 111.

The conductor 122 is provided over the conductor 121 and the layer 161. The conductor 122 includes a first region in contact with the top surface of the conductor 121 and a second region in contact with the top surface of the layer 161. The top surface level of the conductor 121 in contact with the first region and the top surface level of the layer 161 in contact with the second region are preferably equal to or substantially equal to each other.

A pixel electrode described in this embodiment contains a material that reflects visible light, and a counter electrode contains a material that transmits visible light, for example.

The display apparatus 100 has a top emission structure. Light from the light-emitting device is emitted toward the substrate 102. For the substrate 102, a material having a high visible-light-transmitting property is preferably used.

The light-emitting device 150a is provided above the conductor 121a, and the light-emitting device 150b is provided above the conductor 121b.

Here, the light-emitting device 150a and the light-emitting device 150b are described.

The light-emitting device described in this embodiment refers to a self-luminous light-emitting device such as an organic EL element (also referred to as an organic light-emitting diode (OLED)). The light-emitting device electrically connected to the pixel circuit can be a self-luminous light-emitting device such as an LED (Light Emitting Diode), a micro LED, a QLED (Quantum-dot Light-Emitting Diode), or a semiconductor laser.

The conductor 122a and the conductor 122b can be formed in such a manner that, for example, a conductive film is formed over the conductor 121a, the conductor 121b, the layer 161a, and the layer 161b, and then a photolithography method or an electron beam lithography method is used for the conductive film.

The conductor 122a to the conductor 122b function respectively as anodes of the light-emitting device 150a and the light-emitting device 150b included in the display apparatus 100, for example.

Indium tin oxide (sometimes referred to as ITO) or the like can be used for the conductor 122a and the conductor 122b, for example.

Each of the conductor 122a and the conductor 122b may have a stacked-layer structure of two or more layers instead of a single-layer structure. For example, a conductor having a high visible-light reflectance can be used for the first-layer conductor and a conductor having a high light-transmitting property can be used for the uppermost-layer conductor. Examples of a conductor having a high visible-light reflectance include silver, aluminum, and an alloy film of silver (Ag), palladium (Pd), and copper (Cu) (Ag—Pd—Cu (APC) film). Examples of a conductor having a high light-transmitting property include indium tin oxide described above. The conductor 122a and the conductor 122b can each be formed using a stacked-layer film in which a pair of titanium films sandwich aluminum (a film in which Ti, Al, and Ti are stacked in this order), or a stacked-layer film in which a pair of indium tin oxide films sandwich silver (a film in which ITO, Ag, and ITO are stacked in this order), for example.

An EL layer 141a is provided over the conductor 122a. An EL layer 141b is provided over the conductor 122b.

The EL layer 141a and the EL layer 141b preferably include light-emitting layers emitting light of different colors. For example, the EL layer 141a includes a light-emitting layer emitting light of any one of red (R), green (G), and blue (B), and the EL layer 141b includes a light-emitting layer emitting light of one of the other two colors. Although not illustrated in FIG. 24, in the case where an EL layer different from the EL layer 141a and the EL layer 141b is provided, the EL layer can include a light-emitting layer emitting light of the remaining one color. Thus, the display apparatus 100 may have a structure (an SBS structure) in which light-emitting layers for respective colors are provided over a plurality of pixel electrodes (the conductor 121a and the conductor 121b in FIG. 24).

Note that the combination of colors of light emitted by the light-emitting layers included in the EL layer 141a and the EL layer 141b is not limited to the above, and a color such as cyan, magenta, or yellow may also be used, for example. The number of colors of light emitted by the light-emitting devices 150 included in the display apparatus 100, which is three in the above example, may be two, three, or four or more.

The EL layer 141a and the EL layer 141b may each include one or more of an electron-injection layer, an electron-transport layer, a hole-injection layer, and a hole-transport layer in addition to the layer containing a light-emitting organic compound (the light-emitting layer).

Specifically, the EL layer 141a and the EL layer 141b can be formed, for example, by an evaporation method (a vacuum evaporation method or the like), a coating method (e.g., a dip coating method, a die coating method, a bar coating method, a spin coating method, or a spray coating method), or a printing method (e.g., an ink-jet method, a screen printing (stencil) method, an offset printing (planography) method, a flexography (relief printing) method, a gravure printing method, or a micro-contact printing method).

In the case where the coating method or the printing method is employed as the deposition method, a high molecular compound (e.g., an oligomer, a dendrimer, or a polymer), a middle molecular compound (a compound between a low molecular compound and a high molecular compound with a molecular weight of 400 to 4000), or an inorganic compound (e.g., a quantum dot material) can be used as the material to be deposited. As the quantum dot material, a colloidal quantum dot material, an alloyed quantum dot material, a core-shell quantum dot material, or a core quantum dot material can be used.

Figure 25A:
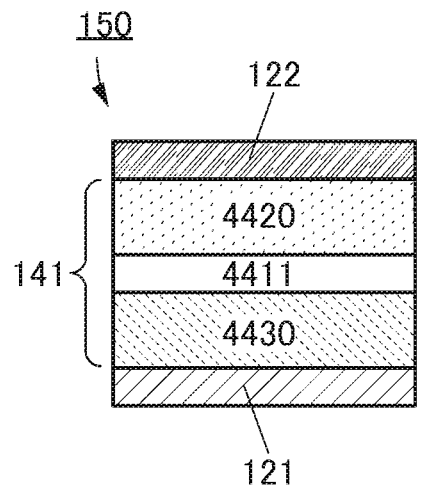
FIG. 25A to FIG. 25D are schematic views illustrating structure examples of a light-emitting device.

Like the light-emitting device 150 illustrated in FIG. 25A, the light-emitting device 150a and the light-emitting device 150b in FIG. 24 can be formed of a plurality of layers such as a light-emitting layer 4411 and a layer 4430.

A layer 4420 can include, for example, a layer containing a substance with a high electron-injection property (an electron-injection layer) and a layer containing a substance with a high electron-transport property (an electron-transport layer). The light-emitting layer 4411 contains a light-emitting compound, for example. The layer 4430 can include, for example, a layer containing a substance with a high hole-injection property (a hole-injection layer) and a layer containing a substance with a high hole-transport property (a hole-transport layer).

The structure including the layer 4420, the light-emitting layer 4411, and the layer 4430, which is provided between a pair of electrodes (the conductor 121 and the conductor 122 described later), can function as a single light-emitting unit, and the structure in FIG. 25A is referred to as a single structure in this specification and the like.

Figure 25B:
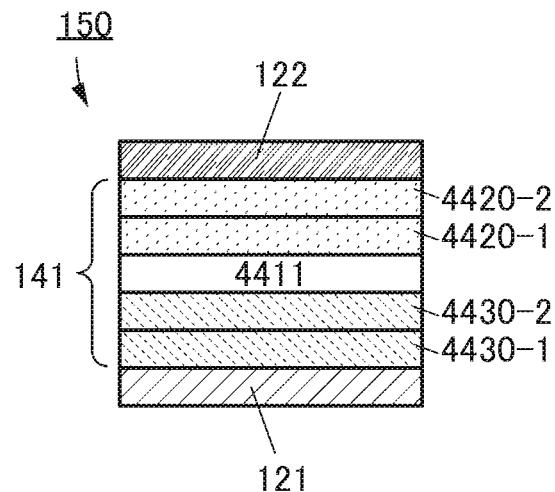

FIG. 25B is a variation example of the EL layer 141 included in the light-emitting device 150 illustrated in FIG. 25A. Specifically, the light-emitting device 150 illustrated in FIG. 25B includes a layer 4430-1 over the conductor 121, a layer 4430-2 over the layer 4430-1, the light-emitting layer 4411 over the layer 4430-2, a layer 4420-1 over the light-emitting layer 4411, a layer 4420-2 over the layer 4420-1, and the conductor 122 over the layer 4420-2. For example, when the conductor 121 functions as an anode and the conductor 122 functions as a cathode, the layer 4430-1 functions as a hole-injection layer, the layer 4430-2 functions as a hole-transport layer, the layer 4420-1 functions as an electron-transport layer, and the layer 4420-2 functions as an electron-injection layer. Alternatively, when the conductor 121 functions as a cathode and the conductor 122 functions as an anode, the layer 4430-1 functions as an electron-injection layer, the layer 4430-2 functions as an electron-transport layer, the layer 4420-1 functions as a hole-transport layer, and the layer 4420-2 functions as the hole-injection layer. With such a layered structure, carriers can be efficiently injected to the light-emitting layer 4411, and the efficiency of the recombination of carriers in the light-emitting layer 4411 can be enhanced.

Figure 25C:
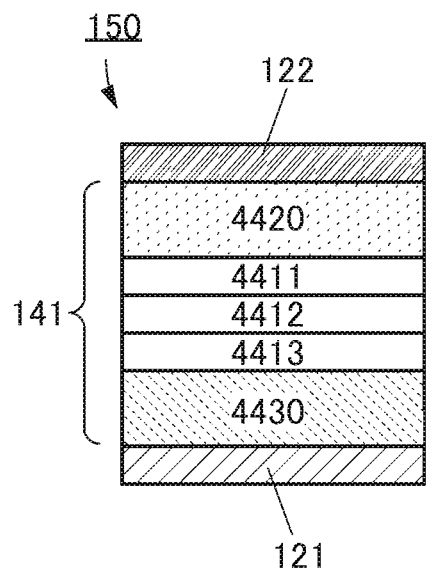

The structure where a plurality of light-emitting layers (the light-emitting layer 4411, a light-emitting layer 4412, and a light-emitting layer 4413) are provided between the layer 4420 and the layer 4430 as illustrated in FIG. 25C is another variation of the single structure.

Figure 25D:
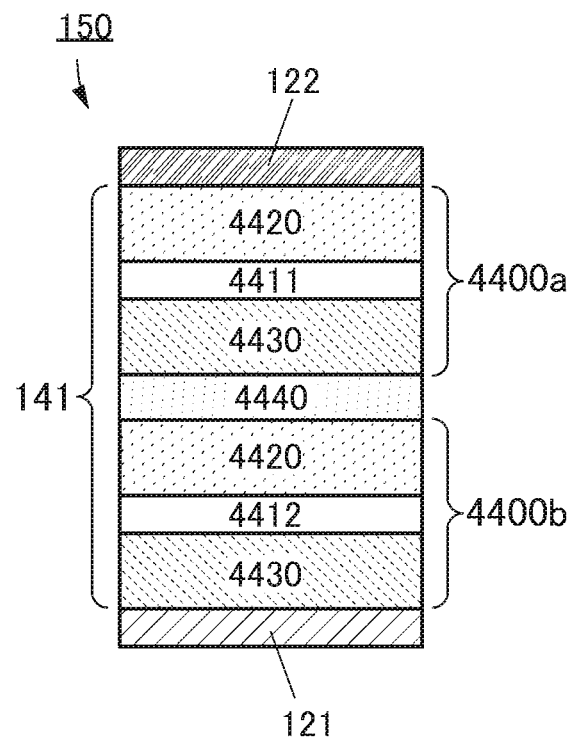

A stack including a plurality of layers such as the layer 4420, the light-emitting layer 4411, and the layer 4430 is sometimes referred to as a light-emitting unit. A plurality of light-emitting units can be connected in series with an intermediate layer (a charge generation layer) therebetween. Specifically, a light-emitting unit 4400a and a light-emitting unit 4400b, which are a plurality of light-emitting units, can be connected in series with an intermediate layer (a charge generation layer) 4440 therebetween as illustrated in FIG. 25D. Note that such a structure is referred to as a tandem structure in this specification. A tandem structure may be rephrased as, for example, a stack structure in this specification and the like. Note that a light-emitting device capable of high-luminance light emission can be obtained when the light-emitting device has a tandem structure. When a light-emitting device has a tandem structure, increased emission efficiency of the light-emitting device, an extended lifetime of the light-emitting device, and the like can be expected. In the case where the light-emitting device 150 of the display apparatus 100 in FIG. 24 has a tandem structure, the EL layer 141 can include, for example, the layer 4420, the light-emitting layer 4411, and the layer 4430 that are included in the light-emitting unit 4400a, the intermediate layer 4440, and the layer 4420, the light-emitting layer 4412, and the layer 4430 that are included in the light-emitting unit 4400b.

In displaying white, the aforementioned SBS structure consumes lower power than the aforementioned single structure and tandem structure. To reduce power consumption, the SBS structure is thus preferably used. Meanwhile, the single structure and the tandem structure are preferable in that the manufacturing cost is low or the manufacturing yield is high because the manufacturing processes of the single structure and the tandem structure are simpler than that of the SBS structure.

The emission color of the light-emitting device 150 can be red, green, blue, cyan, magenta, yellow, white, or the like depending on the material that constitutes the EL layer 141. Furthermore, the color purity can be further increased when the light-emitting device 150 has a microcavity structure.

The light-emitting device that emits white light preferably contains two or more kinds of light-emitting substances in the light-emitting layer. To obtain white light emission, for example, two or more kinds of light-emitting substances are selected such that their emission colors are complementary. To obtain white light emission, for example, light-emitting substances are selected such that an emission color of one light-emitting substance selected from three or more light-emitting substances and an emission color obtained by combining emissions of the other light-emitting substances are complementary.

The light-emitting layer preferably contains two or more light-emitting substances each of which emits light of R (red), G (green), B (blue), Y (yellow), O (orange), or the like. Alternatively, the light-emitting layer preferably contains two or more light-emitting substances that emit light containing two or more of spectral components of R, G, and B.

As illustrated in FIG. 24, there is a gap between two EL layers of adjacent light-emitting devices. Specifically, in FIG. 24, a depressed portion is formed between the adjacent light-emitting devices, and the insulator 112 is provided to cover the side surfaces (side surfaces of the conductor 121a, the conductor 122a, and the EL layer 141a and the side surfaces of the conductor 121b, the conductor 122b, and the EL layer 141b) and the bottom surface (a region in the insulator 111) of the depressed portion. The insulator 162 is formed over the insulator 112 to fill the depressed portion. In this manner, the EL layer 141a and the EL layer 141b are preferably provided so as not to be in contact with each other. This suitably prevents unintentional light emission (also referred to as crosstalk) from being caused by a current flowing through two adjacent EL layers (also referred to as a lateral leakage current or a side leakage current) As a result, the contrast can be increased to achieve a display apparatus with high display quality. Furthermore, with the structure with an extremely low lateral leakage current between light-emitting devices, the display apparatus can perform black display with as little light leakage or the like as possible (such display is also referred to as completely black display).

As the formation method of the EL layer 141a and the EL layer 141b, a method with photolithography can be given. For example, the EL layer 141a and the EL layer 141b can be formed in such a manner that an EL film to be the EL layer 141a and the EL layer 141b is formed over the conductor 122 and then subjected to patterning by a photolithography method. Accordingly, a gap can be provided between two EL layers of adjacent light-emitting devices.

The insulator 112 can be an insulating layer containing an inorganic material. As the insulator 112, an inorganic insulating film such as an oxide insulating film, a nitride insulating film, an oxynitride insulating film, or a nitride oxide insulating film can be used, for example. The insulator 112 may have a single-layer structure or a stacked-layer structure. Examples of the oxide insulating film include a silicon oxide film, an aluminum oxide film, a magnesium oxide film, an indium gallium zinc oxide film, a gallium oxide film, a germanium oxide film, an yttrium oxide film, a zirconium oxide film, a lanthanum oxide film, a neodymium oxide film, a hafnium oxide film, and a tantalum oxide film. Examples of the nitride insulating film include a silicon nitride film and an aluminum nitride film. Examples of the oxynitride insulating film include a silicon oxynitride film and an aluminum oxynitride film. Examples of the nitride oxide insulating film include a silicon nitride oxide film and an aluminum nitride oxide film. An aluminum oxide film is particularly preferable because it has high selectivity with respect to the EL layer in the etching step and has a function of protecting the EL layer during formation of the insulator 162 described later. In particular, when an inorganic insulating film such as an aluminum oxide film, a hafnium oxide film, or a silicon oxide film formed by an ALD method is used as the insulator 112, the insulator 112 having a small number of pin holes and an excellent function of protecting the EL layer can be formed.

Note that in this specification and the like, oxynitride refers to a material that contains more oxygen than nitrogen, and nitride oxide refers to a material that contains more nitrogen than oxygen. For example, in the case where silicon oxynitride is described, it refers to a material that contains more oxygen than nitrogen in its composition. In the case where silicon nitride oxide is described, it refers to a material that contains more nitrogen than oxygen in its composition.

The insulator 112 can be formed by a sputtering method, a CVD method, a PLD method, an ALD method, or the like. The insulator 112 is preferably formed by an ALD method achieving good coverage.

The insulator 162 provided over the insulator 112 has a planarization function for the depressed portion of the insulator 112, which is formed between the adjacent light-emitting devices. In other words, the insulator 162 has an effect of improving the planarity of the formation surface of the conductor 123 to be described later. As the insulator 162, an insulating layer containing an organic material can be favorably used. For example, the insulator 162 can be formed using an acrylic resin, a polyimide resin, an epoxy resin, an imide resin, a polyamide resin, a polyimide-amide resin, a silicone resin, a siloxane resin, a benzocyclobutene-based resin, a phenol resin, precursors of these resins, or the like. For example, the insulator 162 can be formed using an organic material such as polyvinyl alcohol (PVA), polyvinyl butyral, polyvinylpyrrolidone, polyethylene glycol, polyglycerin, pullulan, water-soluble cellulose, or an alcohol-soluble polyamide resin. Moreover, the insulator 162 can be formed using a photosensitive resin, for example. A photoresist may be used as the photosensitive resin, for example. As the photosensitive resin, a positive photosensitive material or a negative photosensitive material can be used.

A difference between the top surface level of the insulator 162 and the top surface level of the EL layer 141a or the EL layer 141b is preferably less than or equal to 0.5 times, further preferably less than or equal to 0.3 times the thickness of the insulator 162. The insulator 162 may be provided, for example, such that the top surface of the EL layer 141a or the EL layer 141b is at a higher level than the top surface of the insulator 162. Alternatively, the insulator 162 may be provided, for example, such that the top surface of the insulator 162 is at a higher level than the top surface of the light-emitting layer included in the EL layer 141a or the EL layer 141b.

The conductor 123 is provided over the EL layer 141a, the EL layer 141b, the insulator 112, and the insulator 162. The insulator 113 is provided over the light-emitting device 150a and the light-emitting device 150b.

The conductor 123 functions as, for example, a common electrode for the light-emitting device 150a and the light-emitting device 150b. The conductor 122 preferably contains a conductive material having a light-transmitting property so that light emitted by the light-emitting device 150 can be extracted to above the display apparatus 100.

The conductor 123 is preferably a light-transmitting and light-reflective material having high conductivity (sometimes referred to as a semi-transmissive and semi-reflective electrode). For example, an alloy of silver and magnesium, or indium tin oxide can be used as the conductor 122.

The insulator 113 is referred to as a protective layer in some cases, and the insulator 113 provided above the light-emitting device 150a and the light-emitting device 150b can increase the reliability of the light-emitting devices. That is, the insulator 113 functions as, for example, a passivation film that protects the light-emitting device 150a and the light-emitting device 150b. Thus, the insulator 113 is preferably formed using a material that prevents entry of water and the like. Any of the materials usable for the insulator 111 can be used as the insulator 113, for example. Specifically, aluminum oxide, silicon nitride, silicon nitride oxide, or the like can be used for the insulator 113.

The resin layer 163 is provided over the insulator 113. The substrate 102 is provided over the resin layer 163.

As the substrate 102, a substrate having a light-transmitting property is preferably used, for example. Using a substrate having a light-transmitting property as the substrate 102 enables extraction of light emitted from the light-emitting device 150a and the light-emitting device 150b to above the substrate 102.

Note that the structure of the display apparatus of one embodiment of the present invention is not limited to that of the display apparatus 100 illustrated in FIG. 24. The structure of the display apparatus of one embodiment of the present invention may be changed as appropriate as long as an object of one embodiment of the present invention is achieved.

For example, the transistor 200 included in the pixel layer PXAL in the display apparatus 100 in FIG. 24 may be a transistor including a metal oxide in a channel formation region (hereinafter referred to as an OS transistor). The display apparatus 100 illustrated in FIG. 26 has a structure where the light-emitting device 150 and a transistor 500 (an OS transistor), instead of the transistor 200 in the display apparatus 100 in FIG. 24, are provided above the circuit layer SICL and the wiring layer LINL.

Figure 26:
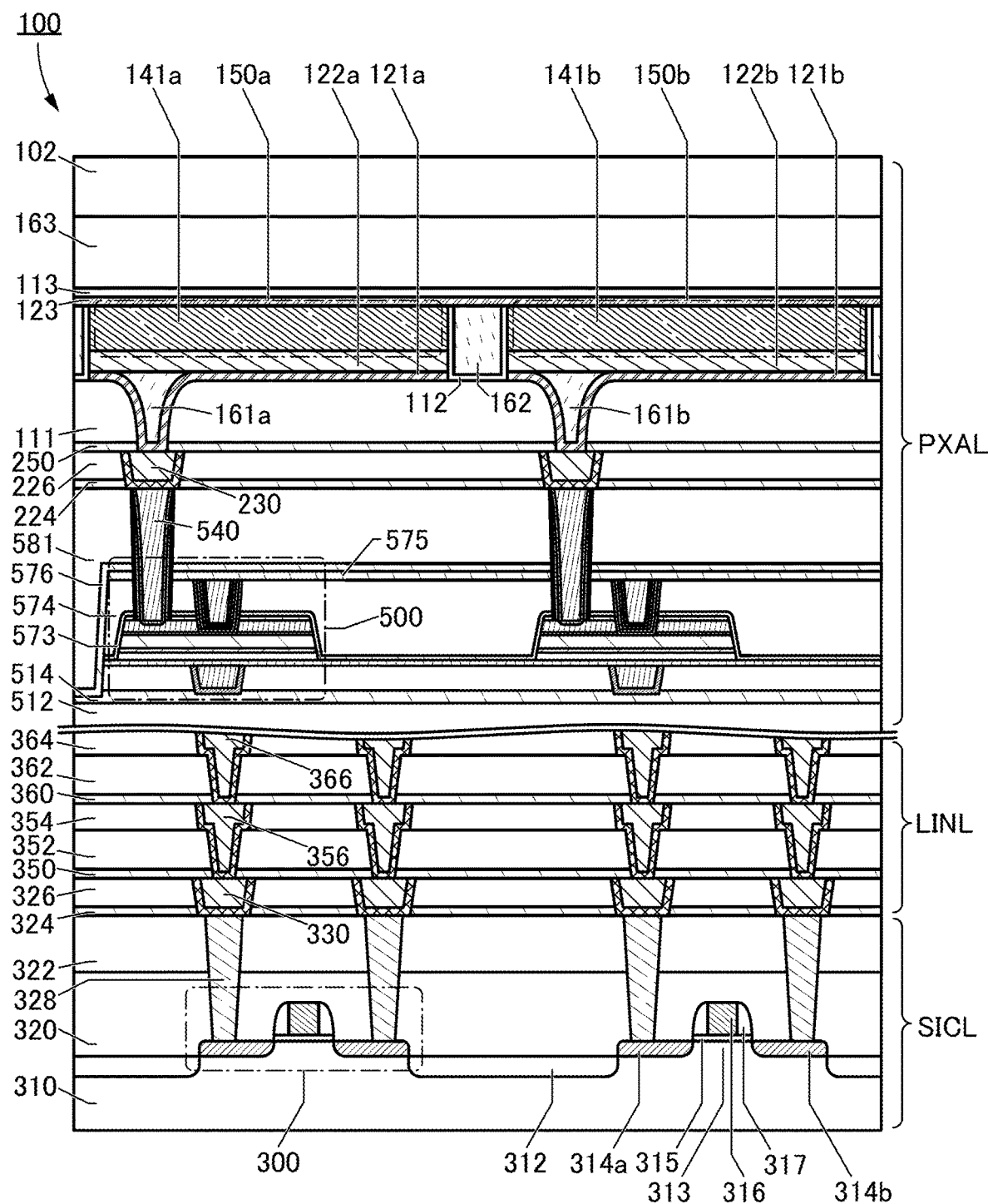
FIG. 26 is a schematic cross-sectional view illustrating a structure example of a display apparatus.

In FIG. 26, the transistor 500 is provided over an insulator 512. The insulator 512 is provided above the insulator 364 and the conductor 366, and the insulator 512 is preferably formed using a substance having a barrier property against oxygen and hydrogen, for example. Specifically, the insulator 512 is formed using, for example, silicon oxide, silicon oxynitride, silicon nitride oxide, silicon nitride, aluminum oxide, aluminum oxynitride, aluminum nitride oxide, or aluminum nitride.

For the film having a barrier property against hydrogen, silicon nitride deposited by a CVD method can be used, for example. Here, diffusion of hydrogen into a semiconductor element including an oxide semiconductor, such as the transistor 500, degrades the characteristics of the semiconductor element in some cases. Therefore, a film that inhibits hydrogen diffusion is preferably used between the transistor 500 and the transistor 300. The film that inhibits hydrogen diffusion is specifically a film from which a small amount of hydrogen is released.

A material similar to that for the insulator 320 can be used for the insulator 512, for example. When a material with a relatively low permittivity is used for these insulators, parasitic capacitance generated between wirings can be reduced. A silicon oxide film or a silicon oxynitride film can be used as the insulator 512, for example.

An insulator 514 is provided over the insulator 512, and the transistor 500 is provided over the insulator 514. An insulator 576 is formed over the insulator 512 so as to cover the transistor 500. An insulator 581 is formed over the insulator 576 to cover the insulator 576.

As the insulator 514, it is preferable to use a film having a barrier property that prevents diffusion of impurities such as water and hydrogen from the substrate 310, a region where the circuit element or the like below the insulator 512 is provided, or the like into a region where the transistor 500 is provided. Thus, silicon nitride deposited by a CVD method can be used for the insulator 514, for example.

The transistor 500 includes a first gate and a second gate. In addition, the transistor 500 includes a metal oxide in a channel formation region. Note that the metal oxide is positioned between the first gate and the second gate.

The transistor 500 includes a first gate insulating film over the first gate. Note that the first gate insulating film can be a single film or can have a stacked-layer structure where a plurality of films are stacked. Furthermore, the metal oxide is positioned over the first gate insulating film.

The transistor 500 illustrated in FIG. 26 is an OS transistor that includes a metal oxide in a channel formation region, as described above. As the metal oxide, it is possible to use, for example, a metal oxide such as an In-M-Zn oxide containing indium, the element M, and zinc (the element M is one or more kinds selected from aluminum, gallium, yttrium, tin, copper, vanadium, beryllium, boron, titanium, iron, nickel, germanium, zirconium, molybdenum, lanthanum, cerium, neodymium, hafnium, tantalum, tungsten, magnesium, and the like). Specifically, an oxide containing indium, gallium, and zinc (referred to as IGZO in some cases) may be used as the metal oxide, for example. Alternatively, an oxide containing indium, aluminum, and zinc (referred to as IAZO in some cases) may be used as the metal oxide, for example. Alternatively, an oxide containing indium, aluminum, gallium, and zinc (referred to as IAGZO in some cases) may be used as the metal oxide, for example. Alternatively, besides the above, an In—Ga oxide, an In—Zn oxide, or an indium oxide may be used as the metal oxide.

In particular, the metal oxide functioning as a semiconductor preferably has a band gap of 2 eV or more, preferably 2.5 eV or more. With the use of a metal oxide having such a wide band gap, the off-state current (sometimes also referred to as leakage current) of the transistor can be reduced.

In particular, as a driving transistor included in a pixel circuit, a transistor having a sufficiently low off-state current even when the source-drain voltage is high, for example, an OS transistor, is preferably used. With the use of an OS transistor as the driving transistor, the amount of off-state current flowing through the light-emitting device when the driving transistor is in an off state can be reduced, whereby the luminance of light emitted from the light-emitting device through which an off-state current flows can be sufficiently reduced. Thus, in the case where a driving transistor having a high off-state current and a driving transistor having a low off-state current are compared, a pixel circuit including the driving transistor having a low off-state current can have lower emission luminance than a pixel circuit including the driving transistor having a high off-state current when black display is performed by the pixel circuits. That is, the use of an OS transistor can inhibit black blurring when black display is performed by the pixel circuit.

The amount of off-state current per micrometer of channel width of the OS transistor at room temperature can be lower than or equal to 1 aA ($1 \times 10^{-18}$ A), lower than or equal to 1 zA ($1 \times 10^{-21}$ A), or lower than or equal to 1 yA ($1 \times 10^{-24}$ A). Note that the amount of off-state current per micrometer of channel width of a Si transistor at room temperature is higher than or equal to 1 fA ($1 \times 10^{-15}$ A) and lower than or equal to 1 pA ($1 \times 10^{-12}$ A). In other words, the off-state current of an OS transistor is lower than that of a Si transistor by approximately ten orders of magnitude.

To increase the emission luminance of the light-emitting device included in the pixel circuit, the amount of current fed through the light-emitting device needs to be increased. For this, it is necessary to increase the source-drain voltage of a driving transistor included in the pixel circuit. Since an OS transistor has a higher withstand voltage between the source and the drain than a Si transistor, a high voltage can be applied between the source and the drain of the OS transistor. Accordingly, when an OS transistor is used as the driving transistor included in the pixel circuit, a high voltage can be applied between the source and the drain of the OS transistor, so that the amount of current flowing through the light-emitting device can be increased and the emission luminance of the light-emitting device can be increased.

When transistors operate in a saturation region, a change in source-drain current relative to a change in gate-source voltage can be smaller in an OS transistor than in a Si transistor. Accordingly, when an OS transistor is used as the driving transistor included in the pixel circuit, the amount of current flowing between the source and the drain can be set minutely by a change in gate-source voltage; hence, the amount of current flowing through the light-emitting device can be controlled minutely. Therefore, the emission luminance of the light-emitting device can be controlled minutely (the number of gray levels in the pixel circuit can be increased).

Regarding saturation characteristics of current flowing when the transistor operates in a saturation region, the OS transistor can feed constant current (saturation current) more stably than the Si transistor even when the source-drain voltage gradually increases. Thus, by using an OS transistor as the driving transistor, a stable constant current can be fed through a light-emitting device that contains an EL material even when the current-voltage characteristics of the light-emitting device vary, for example. In other words, when the OS transistor operates in the saturation region, the source-drain current hardly changes with an increase in the source-drain voltage; hence, the emission luminance of the light-emitting device can be stable.

As described above, with the use of an OS transistor as a driving transistor included in the pixel circuit, it is possible to achieve "inhibition of black floating", "increase in emission luminance", "increase in gray level", "inhibition of variation in light-emitting devices", and the like. Therefore, a display apparatus including the pixel circuit can display a clear and smooth image; as a result, any one or more of the image clearness (image sharpness) and a high contrast ratio can be observed. Note that image clearness (image sharpness) sometimes refers to one or both of the state where motion blur is inhibited and the state where black blurring is inhibited. When the off state current that can flow through the driving transistor included in the pixel circuit is extremely low, black display performed by the display apparatus can be a display with as little light leakage or the like as possible (completely black display).

The transistor 500 includes a pair of conductors over the metal oxide. One of the pair of conductors functions as one of source and drain electrodes of the transistor 500, and the other of the pair of conductors functions as the other of the source and drain electrodes of the transistor 500.

The pair of conductors, the metal oxide, and the first gate insulating film are covered with an insulator 573. The insulator 573 functions as a barrier film preventing diffusion of impurities such as water and hydrogen into the metal oxide. In addition, an insulator 574 functioning as an interlayer film is provided over the insulator 573.

In a region of the insulator 574 overlapping with the first gate, an opening portion reaching the first gate insulating film is provided. In accordance with the formation of the opening portion, the pair of conductors are also formed in a self-aligned manner. A second gate insulating film is formed along the bottom and side surfaces of the opening portion. The second gate is formed over the second gate insulator to fill the opening portion. An insulator 575 is formed to be in contact with the insulator 574, the second gate insulator, and the second gate. The insulator 576 is formed such that the insulator 575 and the transistor 500 are surrounded by the insulator 514 and the insulator 576. The insulator 581 is formed over the insulator 576.

For the insulator 574, for example, silicon oxide, silicon oxynitride, silicon oxide to which fluorine is added, silicon oxide to which carbon is added, silicon oxide to which carbon and nitrogen are added, or porous silicon oxide can be used.

At least one selected from the insulator 573, the insulator 575, the insulator 576, and the insulator 581 preferably functions as a barrier insulating film that inhibits diffusion of impurities such as water and hydrogen from above the transistor 500 into the transistor 500. Thus, one or more selected from the insulator 573, the insulator 575, the insulator 576, and the insulator 581 are preferably formed using an insulating material having a function of inhibiting diffusion of impurities such as a hydrogen atom, a hydrogen molecule, a water molecule, a nitrogen atom, a nitrogen molecule, a nitrogen oxide molecule (e.g., $N_2O$, NO, or $NO_2$), or a copper atom (an insulating material through which the impurities are less likely to pass). Alternatively, it is preferable to use an insulating material having a function of inhibiting diffusion of oxygen (e.g., one or both of an oxygen atom and an oxygen molecule) (an insulating material through which the oxygen is less likely to pass).

As one or more selected from the insulator 573, the insulator 575, the insulator 576, and the insulator 581, an insulator having a function of inhibiting diffusion of oxygen and impurities such as water and hydrogen is preferably used. For example, as one or more selected from the insulator 573, the insulator 575, the insulator 576, and the insulator 581, it is preferable to use aluminum oxide, magnesium oxide, hafnium oxide, gallium oxide, indium-gallium-zinc oxide, silicon nitride, or silicon nitride oxide.

An opening portion for forming a plug or a wiring is provided in the insulator 581, the insulator 576, the insulator 575, the insulator 574, and the insulator 573, and one of the source and drain electrodes of the transistor 500. A conductor 540 functioning as a plug or a wiring is formed in the opening portion.

The insulator 581 is preferably an insulator functioning as an interlayer film and a planarization film, for example.

The insulator 224 and the insulator 226 are sequentially formed above the insulator 581 and the conductor 540. Note that for the description of the insulator 224 and an insulator, a conductor, and a circuit element that are positioned above the insulator 224, description of the display apparatus 100 in FIG. 24 is referred to.

Note that FIG. 24 illustrates a display apparatus formed by bonding the semiconductor substrate provided with the light-emitting device 150, the pixel circuit, and the like and the semiconductor substrate provided with a driver circuit and the like; FIG. 26 illustrates a display apparatus in which the light-emitting device 150, the pixel circuit, and the like are formed over a semiconductor substrate provided with a driver circuit; however, the display apparatus for the electronic device of one embodiment of the present invention is not limited to the those in FIG. 24 and FIG. 26. The display apparatus for the electronic device of one embodiment of the present invention may have a structure where transistors are formed in only one layer, not a layered structure where transistors are stacked in two or more layers.

Figure 27A:
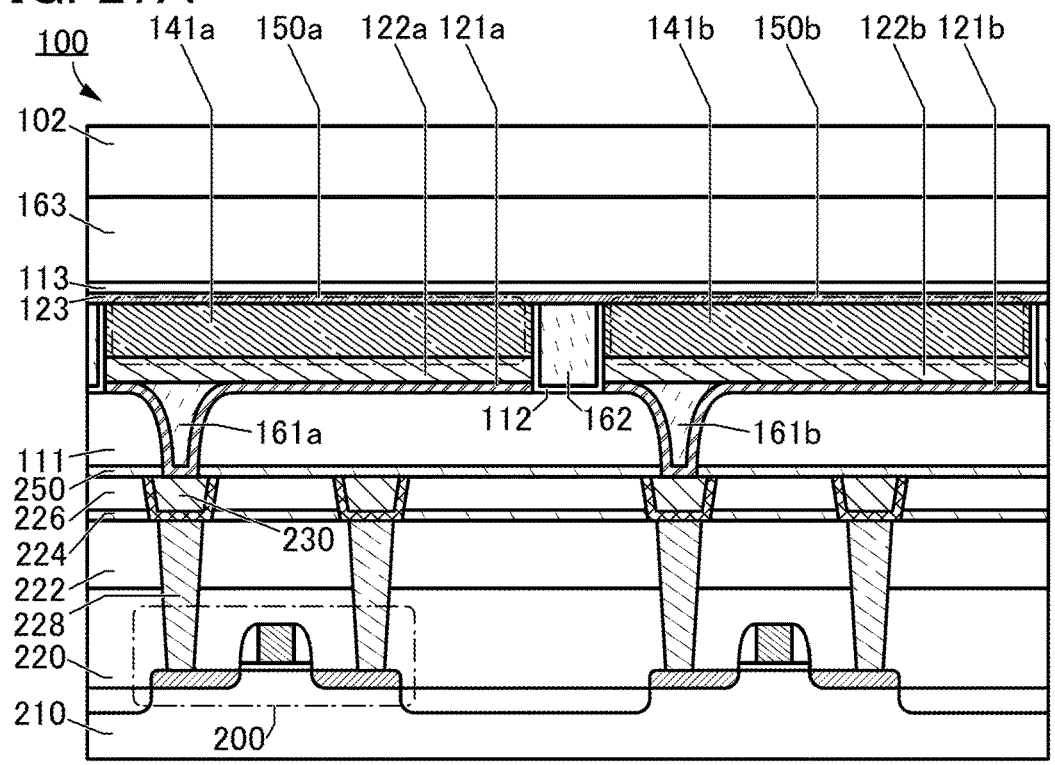
FIG. 27A and FIG. 27B are schematic cross-sectional views illustrating structure examples of a display apparatus.

Specifically, for example, the display apparatus for the electronic device of one embodiment of the present invention may include a circuit including the transistor 200 formed over the substrate 210 and the light-emitting device 150 provided above the transistor 200, as in the display apparatus 100 illustrated in FIG. 27A. For another example, a structure may be employed where the insulator 512 is formed over a substrate 501, the transistor 500 is provided over the insulator 512, and the light-emitting device 150 is provided above the transistor 500, as in the display apparatus 100 illustrated in FIG. 27B. Note that as the substrate 501, a substrate that can be used as the substrate 310 can be used, for example, and in particular, a glass substrate is preferably used.

Figure 27B:
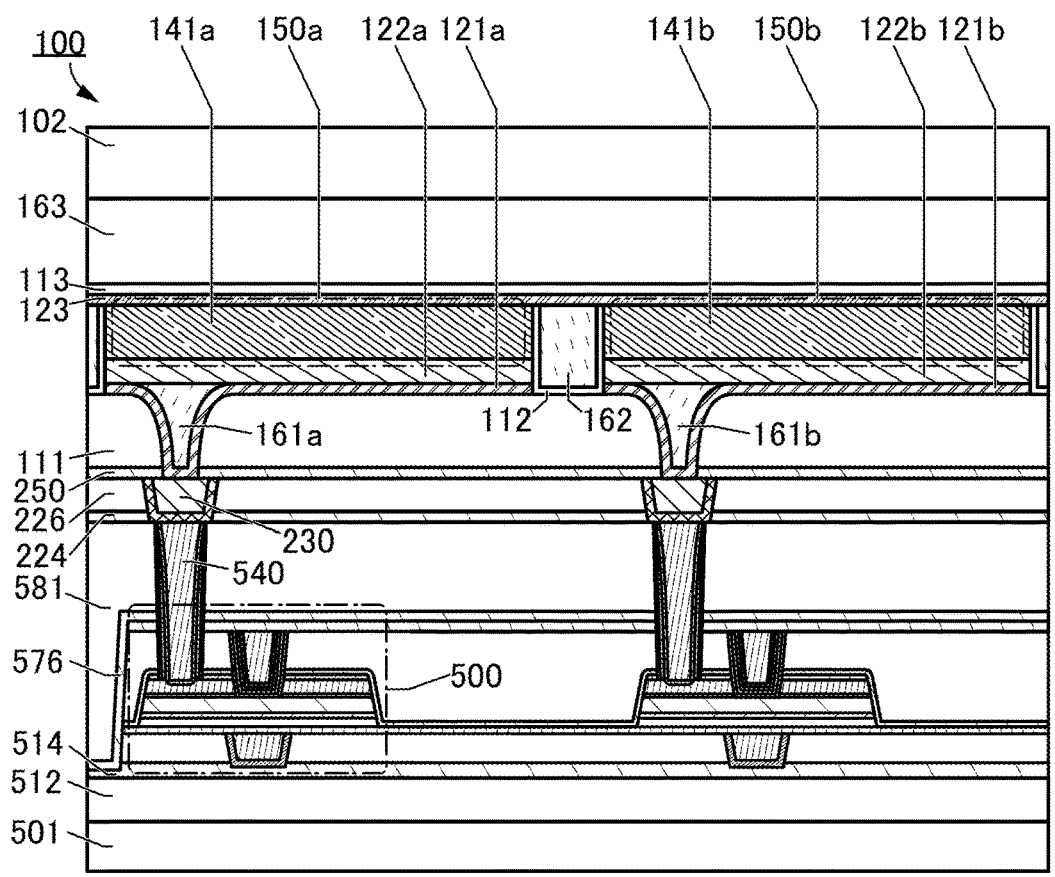

The display apparatus for the electronic device of one embodiment of the present invention may have a structure where transistors are provided in only one layer and the light-emitting device 150 is provided above the transistors, as in the display apparatus 100 illustrated in FIG. 27A or FIG. 27B. Although not illustrated, the display apparatus for the electronic device of one embodiment of the present invention may have a layered structure where transistors are formed in three or more layers.

<Sealing Structure Example of Display Apparatus>

Next, a sealing structure of the light-emitting device 150 that can be employed for the display apparatus 100 in FIG. 24 is described.

FIG. 28A is a cross-sectional view illustrating an example of a sealing structure that can be employed for the display apparatus 100 in FIG. 24. Specifically, FIG. 28A illustrates an end portion of the display apparatus 100 in FIG. 24 and components provided around the end portion. FIG. 28A selectively illustrates only part of the pixel layer PXAL of the display apparatus 100. Specifically, FIG. 28A illustrates the insulator 250, and insulators, conductors, and the light-emitting device 150a which are positioned above the insulator 250.

In a region 123CM illustrated in FIG. 28A, for example, an opening portion is provided. The conductor 123 is electrically connected to a wiring provided below the insulator 250 through the opening portion. Thus, a potential (e.g., an anode potential and a cathode potential of the light-emitting device 150a or the like) can be supplied to the conductor 123 functioning as the common electrode. Note that one or both of a conductor included in the region 123CM and a conductor around the region 123CM is referred to as a connection electrode in some cases.

In the display apparatus 100 in FIG. 28A, an adhesive layer 164 is provided at or around the end portion of the resin layer 163. Specifically, the display apparatus 100 is fabricated such that the insulator 113 and the substrate 102 are bonded to each other with the adhesive layer 164.

The adhesive layer 164 is preferably formed using, for example, a material inhibiting transmission of impurities such as air components and moisture. Using the material for the adhesive layer 164 can increase the reliability of the display apparatus 100.

A structure where the insulator 113 and the substrate 102 are bonded to each other with the resin layer 163 therebetween using the adhesive layer 164 is sometimes referred to as a solid sealing structure. In the case where the resin layer 163 in the solid sealing structure has a function of bonding the insulator 113 and the substrate 102 like the adhesive layer 164, the adhesive layer 164 is not necessarily provided.

In contrast, a structure where the insulator 113 and the substrate 102 are bonded to each other with an inert gas filled therebetween, instead of the resin layer 163, by using the adhesive layer 164 is sometimes referred to as a hollow sealing structure (not illustrated). Examples of an inert gas include nitrogen and argon.

In the sealing structure of the display apparatus 100 illustrated in FIG. 28A, two or more overlapping adhesive layers may be used. For example, as illustrated in FIG. 28B, an adhesive layer 165 may be further provided on the inner side of the adhesive layer 164 (between the adhesive layer 164 and the resin layer 163). Two or more overlapping adhesive layers can inhibit transmission of an impurity such as moisture more, further increasing the reliability of the display apparatus 100.

A desiccant may be mixed into the adhesive layer 165. In this case, the desiccant adsorbs moisture contained in the resin layer 163, insulators, conductors, and EL layers that are provided on the inner side of the adhesive layer 164 and the adhesive layer 165, increasing the reliability of the display apparatus 100.

Although the solid sealing structure is illustrated in the display apparatus 100 in FIG. 28B, a hollow sealing structure may be employed.

Furthermore, an inert liquid may be used instead of the resin layer 163 to fill the space in each of the sealing structures of the display apparatus 100 in FIG. 28A and FIG. 28B. An example of an inert liquid is a fluorine-based inert liquid.

<Variation Example of Display Apparatus>

One embodiment of the present invention is not limited to the above-described structures, and the above-described structures can be changed as appropriate in accordance with circumstances. Variation examples of the display apparatus 100 in FIG. 24 are described with reference to FIG. 29A to FIG. 30B. Note that FIG. 29A to FIG. 30B selectively illustrate only part of the pixel layer PXAL of the display apparatus 100. Specifically, each of FIG. 29A to FIG. 30B illustrates the insulator 111, and insulators, conductors, and the light-emitting device 150a and the light-emitting device 150b that are positioned above the insulator 111. In particular, each of FIG. 29A to FIG. 30B also illustrates the light-emitting device 150c, a conductor 121c, a layer 161c, a conductor 122c, and an EL layer 141c.

Note that, for example, the color of light emitted by the EL layer 141c may be different from the colors of light emitted by the EL layer 141a and the EL layer 141b. The display apparatus 100 may have a structure where the number of colors of light emitted by the light-emitting device 150a to the light-emitting device 150c is two, for example. Alternatively, the display apparatus 100 may have a structure where the number of light-emitting devices 150 is 9S increased so that the number of colors of light emitted by the light-emitting devices are four or more, for example (not illustrated).

Figure 29A:
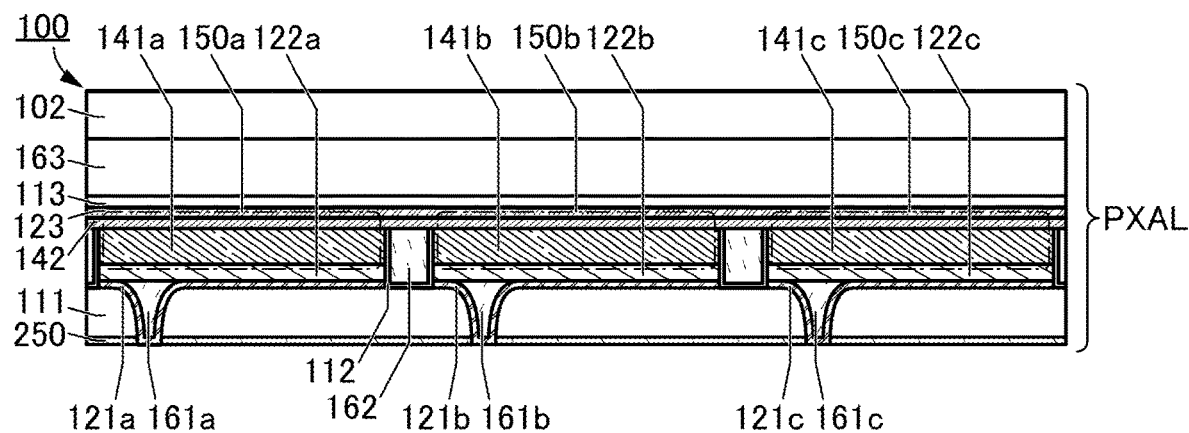
FIG. 29A and FIG. 29B are schematic cross-sectional views illustrating structure examples of a display apparatus.

The display apparatus 100 may have a structure where an EL layer 142 is formed over the EL layer 141a to the EL layer 141c, for example, as illustrated in FIG. 29A. Specifically, for example, in FIG. 25A, the EL layer 142 can include the layer 4420 when the EL layer 141a to the EL layer 141c each include the layer 4430 and the light-emitting layer 4411. In this case, the layer 4420 included in the EL layer 142 functions as a common layer shared by the light-emitting device 150a to the light-emitting device 150c. In a similar manner, for another example, in FIG. 25C, the EL layer 142 can include the layer 4420 when the EL layer 141a to the EL layer 141c each include the layer 4430, the light-emitting layer 4411, the light-emitting layer 4412, and the light-emitting layer 4413, in which case the layer 4420 included in the EL layer 142 functions as a common layer shared by the light-emitting device 150a to the light-emitting device 150c. As another example, in FIG. 25D, the EL layer 142 can include the layer 4420 of the light-emitting unit 4400b when the EL layer 141a to the EL layer 141c each include the layer 4430, the light-emitting layer 4412, and the layer 4420 that are included in the light-emitting unit 4400b, the intermediate layer 4440, and the layer 4430 and the light-emitting layer 4411 that are included in the light-emitting unit 4400a, in which case the layer 4420 of the light-emitting unit 4400a included in the EL layer 142 functions as a common layer shared by the light-emitting device 150a to the light-emitting devices 150c.

Figure 29B:
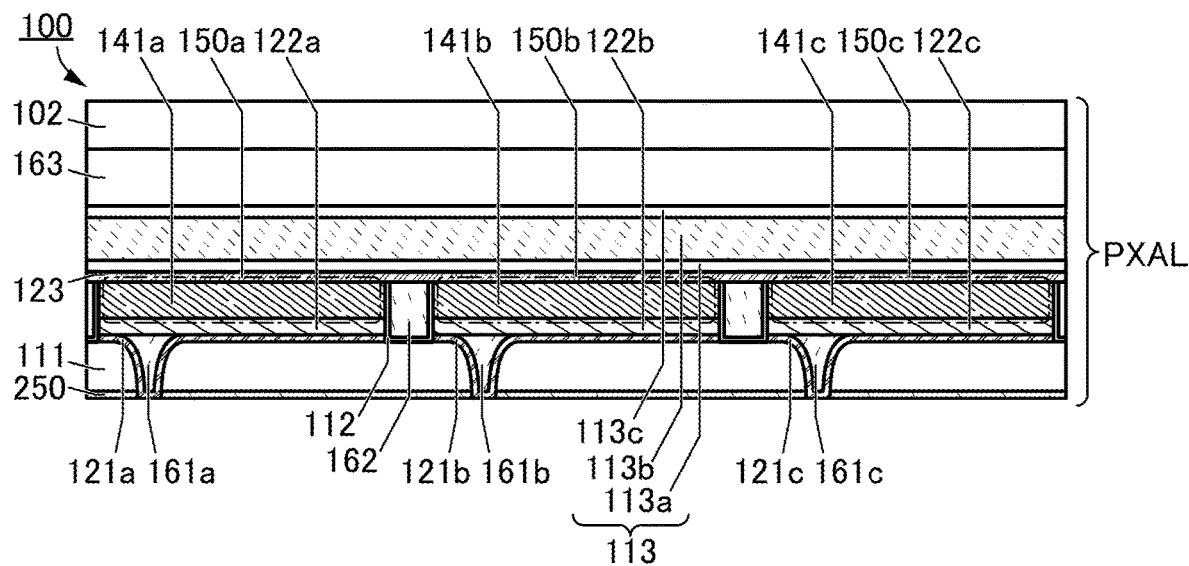

In the structure of the display apparatus 100, for example, the insulator 113 may have a stacked-layer structure of two or more layers, instead of a single layer. The insulator 113 may have a three-layer structure that includes an insulator made of an inorganic material as the first layer, an insulator made of an organic material as the second layer, and an insulator made of an inorganic material as the third layer. FIG. 29(B) illustrates a cross-sectional view of part of the display apparatus 100 in which the insulator 113 has a multilayer structure including an insulator 113a, an insulator 113b, and an insulator 111c; the insulator 113a is an insulator made of an inorganic material, the insulator 113b is an insulator made of an organic material, and the insulator 113c is an insulator made of an inorganic material.

In the structure of the display apparatus 100, for example, the EL layer 141a to the EL layer 141c may each have a microcavity structure. In the microcavity structure, for example, the conductor 122 as an upper electrode (common electrode) is formed using a light-transmitting and light-reflective conductive material, the conductor 121 as a lower electrode (pixel electrode) is formed using a light-reflective conductive material, and the distance between the bottom surface of the light-emitting layer and the top surface of the lower electrode, i.e., the thickness of the layer 4430 in FIG. 25A, is set to the thickness corresponding to the wavelength of the color of light emitted by the light-emitting layer included in the EL layer 141.

For example, light that is reflected back from the lower electrode (reflected light) considerably interferes with light that directly enters the upper electrode from the light-emitting layer (incident light); therefore, the optical path length between the lower electrode and the light-emitting layer is preferably adjusted to (2n−1)λ/4 (n is a natural number of 1 or more and λ is a wavelength of emitted light to be amplified). By adjusting the optical path length, the phases of the reflected light and the incident light each having the wavelength λ can be aligned with each other, and the light emitted from the light-emitting layer can be further amplified.

In the above structure, the EL layer may include a plurality of light-emitting layers or a single light-emitting layer. Alternatively, the above-described tandem structure of a light-emitting device and a microcavity structure may be combined, for example.

With the microcavity structure, emission intensity with a specific wavelength in the front direction can be increased, whereby power consumption can be reduced. Particularly in the case of a device for XR such as VR and AR, light emitted from the light-emitting device in the front direction often enters the eyes of the user wearing the device; thus, a display apparatus of a device for XR suitable includes a microcavity structure. Note that in the case of a display apparatus which displays images with subpixels of four colors, red, yellow, green, and blue, the display apparatus can have favorable characteristics because a microcavity structure suitable for wavelengths of the corresponding color is employed in each subpixel, in addition to the effect of an improvement in luminance owing to yellow light emission.

Figure 30A:
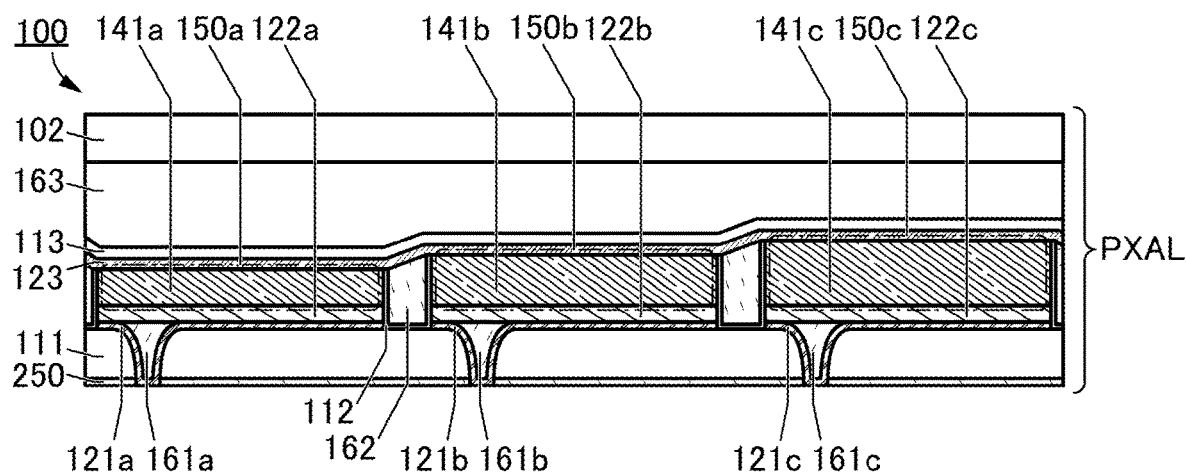
FIG. 30A and FIG. 30B are schematic cross-sectional views illustrating structure examples of a display apparatus.

As an example, FIG. 30A illustrates a cross-sectional view of part of the display apparatus 100 having a microcavity structure. In the case where the light-emitting device 150a includes a light-emitting layer emitting blue (B) light, the light-emitting device 150b includes a light-emitting layer emitting green (G) light, and the light-emitting device 150c includes a light-emitting layer emitting red (R) light, the thickness is preferably larger in the order of the EL layer 141a, the EL layer 141b and the EL layer 141c as illustrated in FIG. 30A. Specifically, the thicknesses of the layers 4430 included in the EL layer 141a, the EL layer 141b, and the EL layer 141c may be determined depending on the color of the light emitted by the corresponding light-emitting layer. In this case, the layer 4430 included in the EL layer 141a has the smallest thickness and the layer 4430 included in the EL layer 141c has the largest thickness.

Figure 30B:
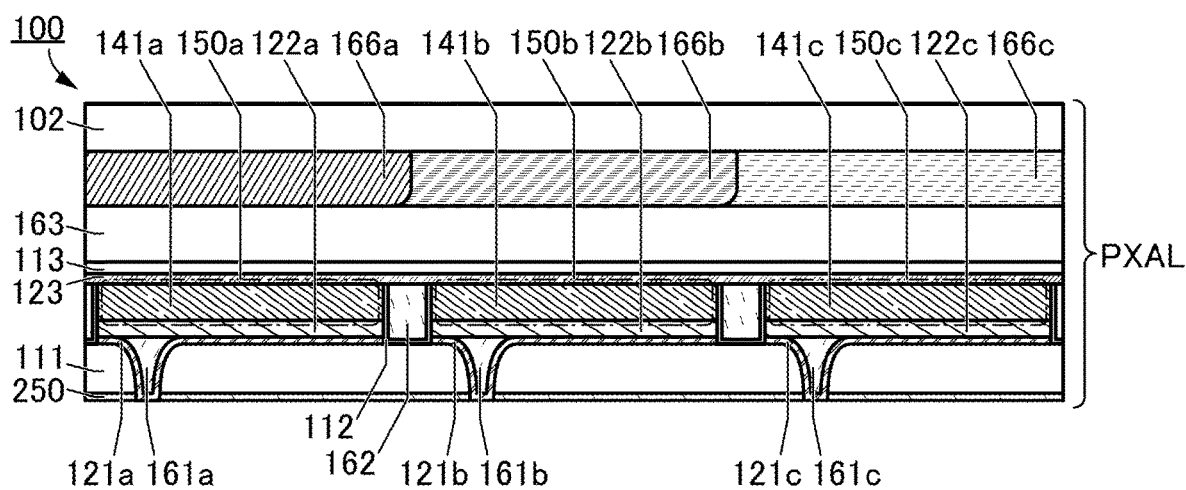

In the structure of the display apparatus 100, for example, a coloring layer (color filter) or the like may be provided. As an example, FIG. 30B illustrates a structure where a coloring layer 166a, a coloring layer 166b, and a coloring layer 166c are included between the resin layer 163 and the substrate 102. Note that the coloring layer 166a to the coloring layer 166c can be formed on the substrate 102, for example. In the case where the light-emitting device 150a includes a light-emitting layer emitting blue (B) light, the light-emitting device 150b includes a light-emitting layer emitting green (G) light, and the light-emitting device 150c includes a light-emitting layer emitting red (R) light, the coloring layer 166a is a blue coloring layer, the coloring layer 166b is a green coloring layer, and the coloring layer 166c is a red coloring layer.

The display apparatus 100 illustrated in FIG. 30B can be fabricated in such a manner that the substrate 102 provided with the coloring layer 166a to the coloring layer 166c and the substrate 310 over which components up to the light-emitting device 150a to the light-emitting device 150c are formed are bonded to each other with the resin layer 163 therebetween. At this time, the bonding is preferably performed such that the light-emitting device 150a and the coloring layer 166a overlap with each other, the light-emitting device 150b and the coloring layer 166b overlap with each other, and the light-emitting device 150c and the coloring layer 166c overlap with each other. In the display apparatus 100 provided with the coloring layer 166a to the coloring layer 166c, for example, light emitted by the light-emitting device 150b is not extracted to above the substrate 102 through the coloring layer 166a or the coloring layer 166c, but extracted to above the substrate 102 through the coloring layer 166b. That is, light emitted from the light-emitting device 150 in an oblique direction (a direction at an elevation angle with a top surface of the substrate 102 used as a horizontal plane) can be blocked in the display apparatus 100; thus, the viewing angle dependence of the display apparatus 100 can be reduced, inhibiting the display quality of an image displayed by the display apparatus 100 from decreasing when the image is viewed from an oblique direction.

The coloring layer 166a to the coloring layer 166c formed on the substrate 102 may be covered with, for example, a resin which is referred to as an overcoat layer. Specifically, the resin layer 163, the overcoat layer, the coloring layer 166a to the coloring layer 166c, and the substrate 102 may be stacked in this order in the display apparatus 100 (not illustrated). Note that examples of the resin usable for the overcoat layer include a thermosetting material having a light-transmitting property and being based on an acrylic resin or an epoxy resin.

In the structure of the display apparatus 100, for example, a black matrix may be included in addition to the coloring layers (not illustrated). The black matrix provided between the coloring layer 166a and the coloring layer 166b, between the coloring layer 166b and the coloring layer 166c, and between the coloring layer 166c and the coloring layer 166a can block more light emitted from the light-emitting device 150 in an oblique direction (a direction at an elevation angle with the top surface of the substrate 102 used as a horizontal plane) in the display apparatus 100; thus, the display quality of an image displayed by the display apparatus 100 can be more prevented from decreasing when the image is viewed from an oblique direction.

In the case where the display apparatus includes coloring layers as illustrated in FIG. 30B or the like, the light-emitting device 150a to the light-emitting device 150c of the display apparatus may each be a light-emitting device emitting white light (not illustrated). The light-emitting device can have a single structure or a tandem structure, for example.

In the above-described structure of the display apparatus 100, the conductor 121a to the conductor 121c serve as the anodes and the conductor 122 serves as a cathode; however, the display apparatus 100 may have a structure where the conductor 121a to the conductor 121c serve as cathodes and the conductor 122 serves as an anode. In other words, in the above-described fabrication process, the stacking order of the hole-injection layer, the hole-transport layer, the light-emitting layer, the electron-transport layer, and the electron-injection layer that are included in the EL layer 141a to the EL layer 141c and the EL layer 142 may be reversed.

<Structure Example of Layer 161>

Here, a cross-sectional structure of a region of the display apparatus 100, which includes the conductor 121 and the layer 161 and their vicinities is illustrated. Note that description similar to that of FIG. 31A to FIG. 31D can be applied to the light-emitting device 150a and the light-emitting device 150b.

Figure 31A:
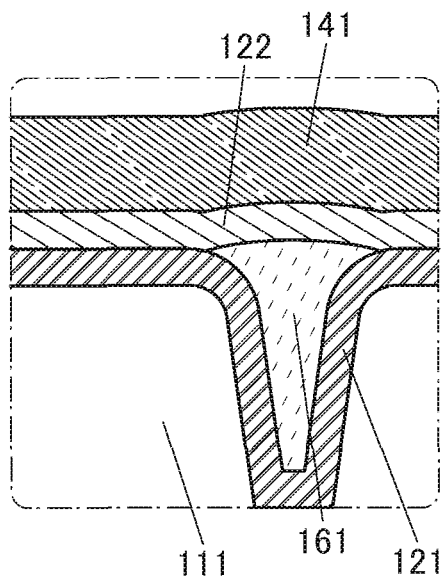
FIG. 31A to FIG. 31D are cross-sectional views illustrating examples of a display apparatus.

FIG. 24 and FIG. 26 to FIG. 30B each illustrate an example where the top surface of the layer 161 and the top surface of the conductor 121 are substantially aligned with each other; however, the present invention is not limited thereto. For example, as illustrated in FIG. 31A, the top surface of the layer 161 is at a higher level than the top surface of the conductor 121 in some cases. In this case, the top surface of the insulating layer 161 has a convex shape that is gently bulged toward the center.

Figure 31B:
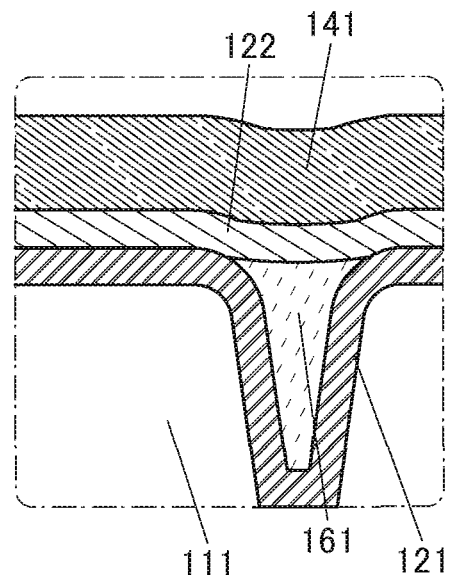

As illustrated in FIG. 31B, the top surface of the layer 161 is at a lower level than the top surface of the conductor 121 in some cases. In this case, the top surface of the insulating layer 161 has a concave shape that is gently recessed toward the center.

Figure 31C:
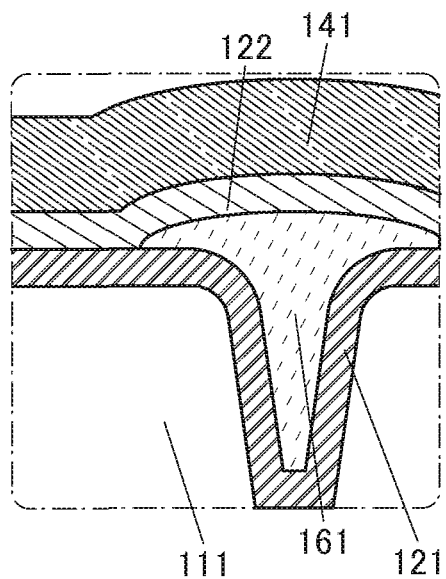

When the top surface of the layer 161 is at a higher level than the top surface of the conductor 121 as illustrated in FIG. 31C, the upper portion of the layer 161 is sometimes formed to be wider than a recessed portion formed in the conductor 121. In this case, part of the layer 161 may be formed to cover part of a substantially flat region of the conductor 121.

Figure 31D:
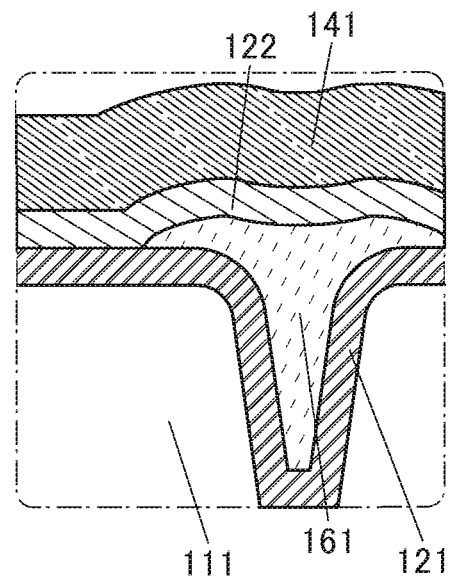

As illustrated in FIG. 31D, a depressed portion is sometimes formed in part of the top surface of layer 161 in the structure of FIG. 31C. The depressed portion has a shape that is gently recessed toward the center.

<Structure Example of Insulator 162>

Next, cross-sectional structures of a region including the insulator 162 and its periphery in the display apparatus 100 are described.

Figure 32A:
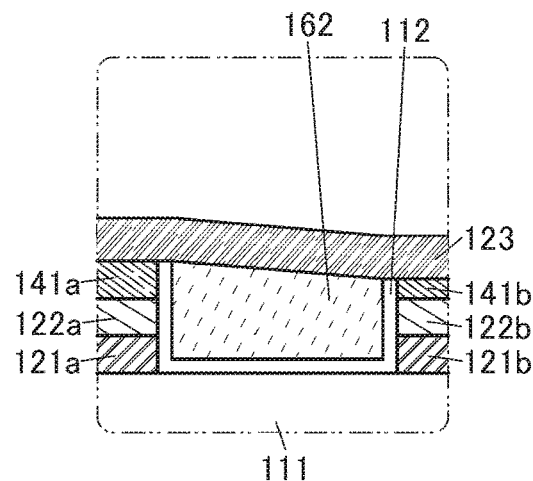
FIG. 32A to FIG. 32F are cross-sectional views illustrating examples of a method for fabricating a display apparatus.

FIG. 32A illustrates an example where the EL layer 141a and the EL layer 141b have different thicknesses. The top surface level of the insulator 112 is equal to or substantially equal to the top surface level of the EL layer 141a on the EL layer 141a side, and equal to or substantially equal to the top surface level of the EL layer 141b on the EL layer 141b side. The top surface of the insulator 112 has a gentle slope such that the side closer to the EL layer 141a is higher and the side closer to the EL layer 141b is lower. In this manner, the top surfaces of the insulator 112 and the insulator 162 are preferably level with the top surface of an adjacent EL layer. Alternatively, the top surface levels of the insulators may be equal to the top surface level of any adjacent EL layer so that their top surfaces have a flat portion.

Figure 32D:
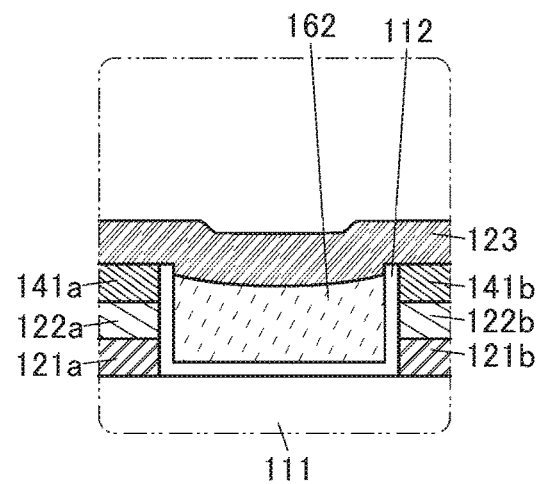
Figure 32B:
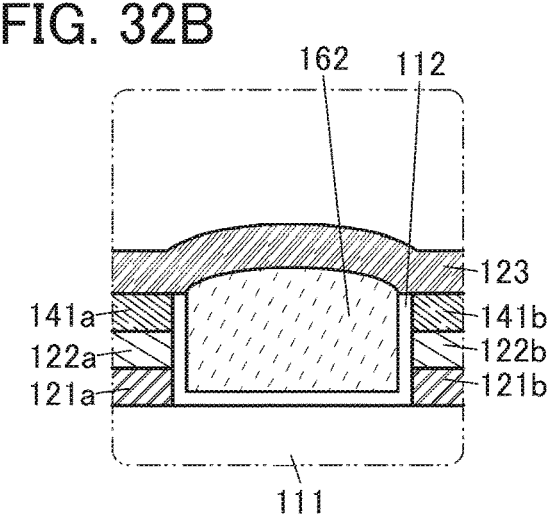

In FIG. 32B, the top surface of the insulator 162 includes a region that is at a higher level than the top surface of the EL layer 141a and the top surface of the EL layer 141b. Moreover, the top surface of the insulator 112 has a convex shape that is gently bulged toward the center.

Figure 32E:
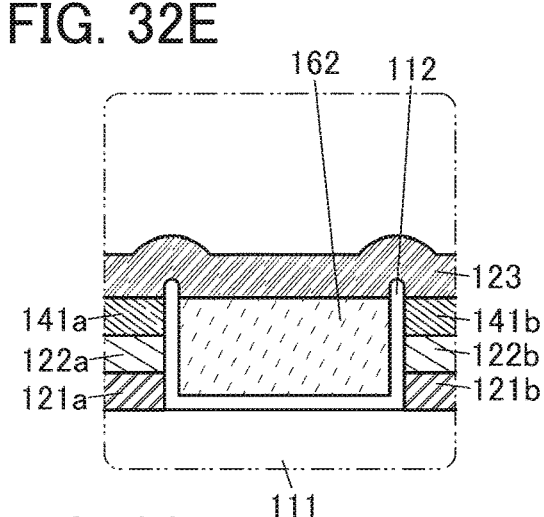
Figure 32C:
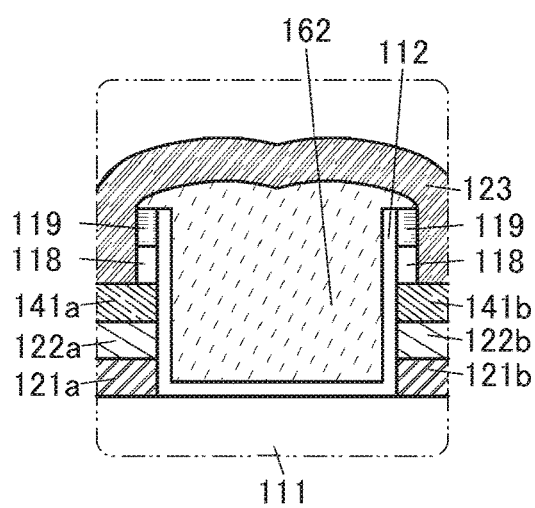

In FIG. 32C, the top surface of the insulator 112 includes a region that is at a higher level than the top surface of the EL layer 141a and the top surface of the EL layer 141b. In a region including the insulator 162 and its vicinity, the display apparatus 100 includes a first region positioned over at least one of a sacrificial layer 118 and a sacrificial layer 119. The first region is at a higher level than the top surface of the EL layer 141a and the top surface of the EL layer 141b, and part of the insulator 162 is formed in the first region. In the region including the insulator 162 and its vicinity, the display apparatus 100 includes a second region positioned over at least one of the sacrificial layer 118 and the sacrificial layer 119. The second region is at a higher level than the top surface of the EL layer 141a and the top surface of the EL layer 141b, and part of the insulator 162 is formed in the second region.

In FIG. 32D, the top surface of the insulator 162 includes a region that is at a lower level than the top surface of the EL layer 141a and the top surface of the EL layer 141b. Moreover, the top surface of the insulator 162 has a concave shape that is gently recessed toward the center.

In FIG. 32E, the top surface of the insulator 112 includes a region that is at a higher level than the top surface of the EL layer 141a and the top surface of the EL layer 141b. That is, the insulator 112 protrudes from the formation surface of the EL layer 141 and forms a projecting portion.

In formation of the insulator 112, for example, when the insulator 112 is formed to be level with or substantially level with the sacrificial layer, a shape such that the insulator 112 protrudes is sometimes formed as illustrated in FIG. 32E.

Figure 32F:
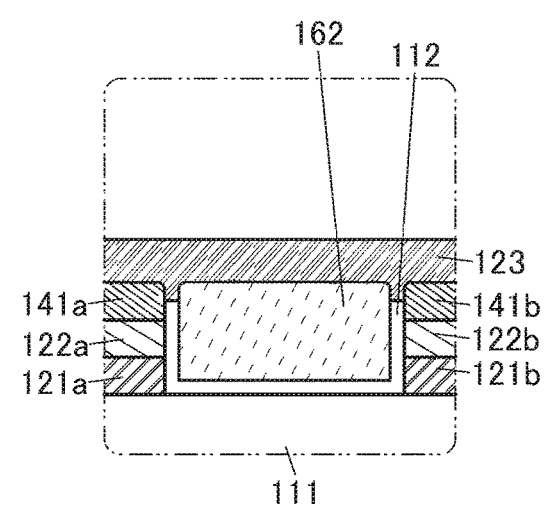

In FIG. 32F, the top surface of the insulator 112 includes a region that is at a lower level than the top surface of EL layer 141a and the top surface of the EL layer 141b. That is, the insulator 112 forms a depressed portion on the formation surface of the EL layer 141.

As described above, the insulator 112 and the insulator 162 can have a variety of shapes.

<Structure Example of Pixel Circuit>

Here, structure examples of a pixel circuit that can be included in the pixel layer PXAL are described.

Figure 33A:
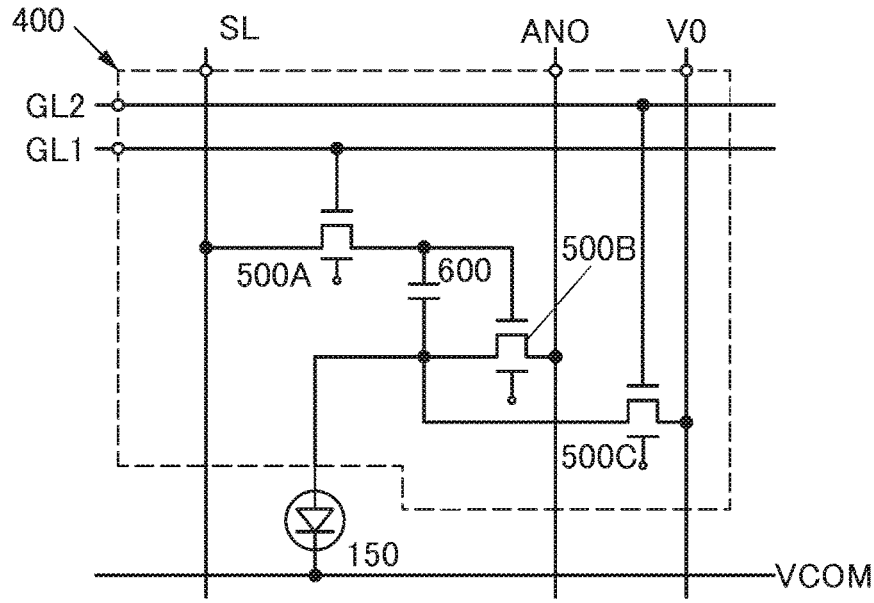
FIG. 33A is a circuit diagram illustrating a structure example of a pixel circuit included in a display apparatus.
Figure 33B:
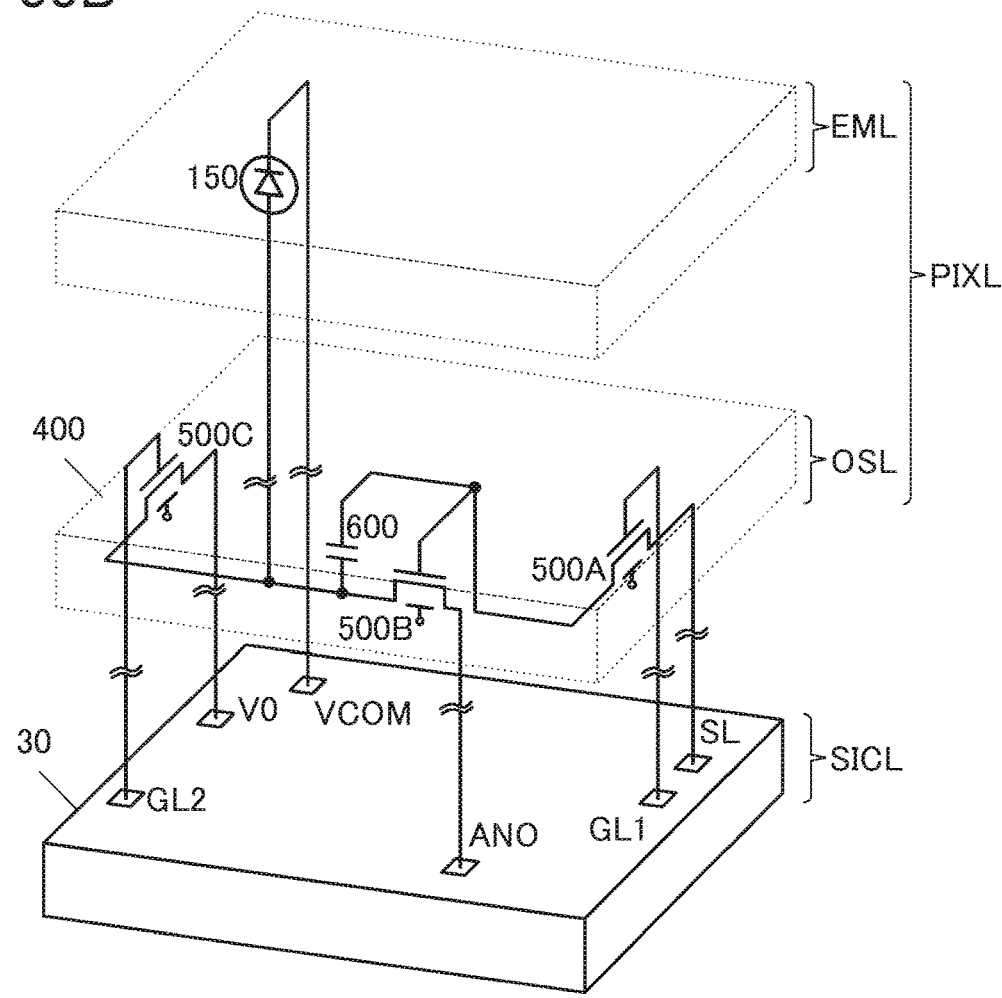
FIG. 33B is a schematic perspective view illustrating the structure example of the pixel circuit included in the display apparatus.

FIG. 33A and FIG. 33B illustrate a structure example of a pixel circuit that can be included in the pixel layer PXAL and the light-emitting device 150 connected to the pixel circuit. FIG. 33A is a diagram illustrating connection of circuit elements included in a pixel circuit 400 included in the pixel layer PXAL, and FIG. 33B is a diagram schematically illustrating the positional relation of the circuit layer SICL including a driver circuit 30 and the like, a layer OSL including a plurality of transistors of the pixel circuit, and a layer EML including the light-emitting device 150. Note that the pixel layer PXAL of the display apparatus 100 illustrated in FIG. 33B includes the layer OSL and the layer EML, for example. A transistor 500A, a transistor 500B, and a transistor 500C included in the layer OSL illustrated in FIG. 33B each correspond to the transistor 200 in FIG. 24. The light-emitting device 150 included in the layer EML illustrated in FIG. 33B corresponds to the light-emitting device 150a or the light-emitting device 150b in FIG. 24.

The pixel circuit 400 illustrated as an example in FIG. 33A and FIG. 33B includes the transistor 500A, the transistor 500B, the transistor 500C, and a capacitor 600. The transistor 500A, the transistor 500B, and the transistor 500C can be, for example, transistors usable as the transistor 200 described above as an example. That is, the transistor 500A, the transistor 500B, and the transistor 500C can be Si transistors. Alternatively, the transistor 500A, the transistor 500B, and the transistor 500C can be, for example, transistors usable as the transistor 500 described above as example. That is, the transistor 500A, the transistor 500B, and the transistor 500C can be OS transistors. In particular, in the case where the transistor 500A, the transistor 500B, and the transistor 500C are OS transistors, each of the transistor 500A, the transistor 500B, and the transistor 500C preferably includes a back gate electrode, in which case the structure where the back gate electrode is supplied with the same signals as those supplied to the gate electrode or the structure where the back gate electrode is supplied with signals different from those supplied to the gate electrode can be used. Although each of the transistor 500A, the transistor 500B, and the transistor 500C illustrated in FIG. 33A and FIG. 33B includes a back gate electrode, each of the transistor 500A, the transistor 500B, and the transistor 500C does not necessarily include a back gate electrode.

The transistor 500B includes a gate electrode electrically connected to the transistor 500A, a first electrode electrically connected to the light-emitting device 150, and a second electrode electrically connected to a wiring ANO. The wiring ANO supplies a potential for supplying a current to the light-emitting device 150.

The transistor 500A includes a first terminal electrically connected to the gate electrode of the transistor 500B, a second terminal electrically connected to a wiring SL functioning as a source line, and the gate electrode having a function of controlling the conducting state or non-conducting state on the basis of the potential of a wiring GL1 functioning as a gate line.

The transistor 500C includes a first terminal electrically connected to a wiring V0, a second terminal electrically connected to the light-emitting device 150, and the gate electrode having a function of controlling the conducting state or non-conducting state on the basis of the potential of a wiring GL2 functioning as a gate line. The wiring V0 is a wiring for supplying a reference potential and a wiring for outputting a current flowing through the pixel circuit 400 to the driver circuit 30.

The capacitor 600 includes a conductive film electrically connected to the gate electrode of the transistor 500B and a conductive film electrically connected to a second electrode of the transistor 500C.

The light-emitting device 150 includes a first electrode electrically connected to the first electrode of the transistor 500B and a second electrode electrically connected to a wiring VCOM. The wiring VCOM is a wiring for supplying a potential for supplying a current to the light-emitting device 150.

Accordingly, the intensity of light emitted by the light-emitting device 150 can be controlled in accordance with an image signal supplied to the gate electrode of the transistor 500B. Furthermore, variations in the gate-source voltage of the transistor 500B can be inhibited by the reference potential of the wiring V0 supplied through the transistor 500C.

A current amount that can be used for setting pixel parameters can be output from the wiring V0. Specifically, the wiring V0 can function as a monitor line for outputting a current flowing through the transistor 500B or a current flowing through the light-emitting device 150 to the outside. A current output to the wiring V0 is converted into a voltage by a source follower circuit or the like and output to the outside. Alternatively, a current output to the wiring V0 can be converted into a digital signal by an A-D converter or the like and output to the arithmetic circuit 1350, the arithmetic circuit MAC1, or the like described in the above embodiment.

Note that in the structure illustrated as an example in FIG. 33B, the wirings electrically connecting the pixel circuit 400 and the driver circuit 30 can be shortened, so that wiring resistance of the wirings can be reduced. Thus, data writing can be performed at high speed, leading to high-speed operation of the display apparatus 100. Therefore, even when the number of pixel circuits 400 included in the display apparatus 100 is large, a sufficiently long frame period can be ensured and thus the pixel density of the display apparatus 100 can be increased. In addition, the increased pixel density of the display apparatus 100 can increase the resolution of an image displayed by the display apparatus 100. For example, the pixel density of the display apparatus 100 can be 1000 ppi or higher, 5000 ppi or higher, or 7000 ppi or higher. Thus, the display apparatus 100 can be, for example, a display apparatus for AR or VR and can be suitably used in an electronic device with a short distance between a display portion and the user, such as an HMD.

Although FIG. 33A and FIG. 33B illustrate, as an example, the pixel circuit 400 including three transistors in total, the pixel circuit of the electronic device of one embodiment of the present invention is not limited thereto. Structure examples of a pixel circuit which can be used for the pixel circuit 400 will be described below.

Figure 34A:
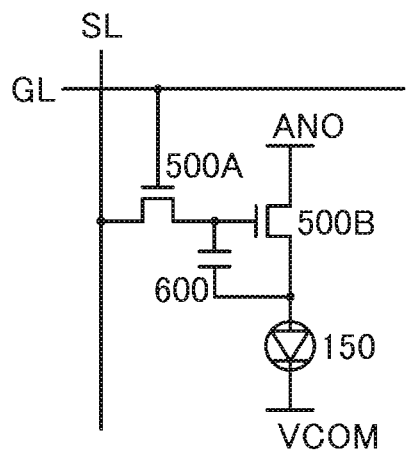
FIG. 34A to FIG. 34D are circuit diagrams illustrating structure examples of a pixel circuit included in a display apparatus.

A pixel circuit 400A illustrated in FIG. 34A includes the transistor 500A, the transistor 500B, and the capacitor 600. FIG. 34A illustrates the light-emitting device 150 connected to the pixel circuit 400A. The wiring SL, the wiring GL, the wiring ANO, and the wiring VCOM are electrically connected to the pixel circuit 400A.

A gate of the transistor 500A is electrically connected to the wiring GL, one of a source and a drain of the transistor 500A is electrically connected to the wiring SL, and the other of the source and the drain of the transistor 500A is electrically connected to a gate of the transistor 500B and one electrode of the capacitor 600. One of a source and a drain of the transistor 500B is electrically connected to the wiring ANO and the other of the source and the drain of the transistor 500B is electrically connected to an anode of the light-emitting device 150. The other electrode of the capacitor 600 is electrically connected to the anode of the light-emitting device 150. A cathode of the light-emitting device 150 is electrically connected to the wiring VCOM.

Figure 34B:
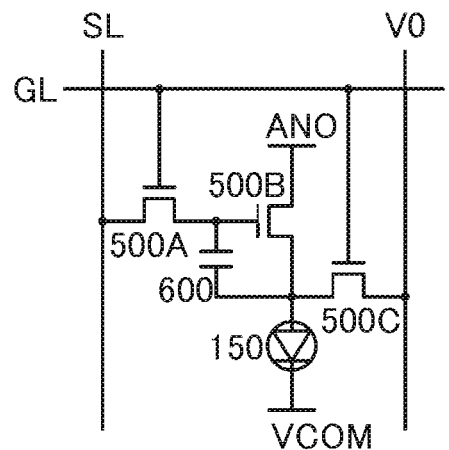

A pixel circuit 400B illustrated in FIG. 34B has a structure where the transistor 500C is added to the pixel circuit 400A. In addition, the wiring V0 is electrically connected to the pixel circuit 400B.

Figure 34C:
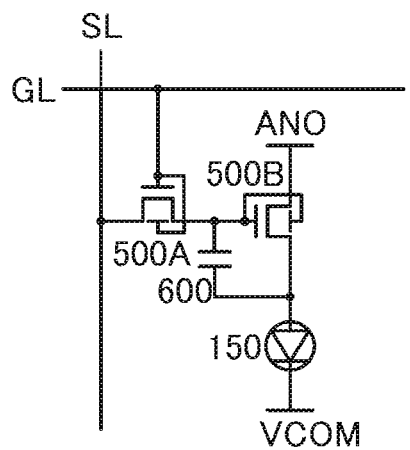
Figure 34D:
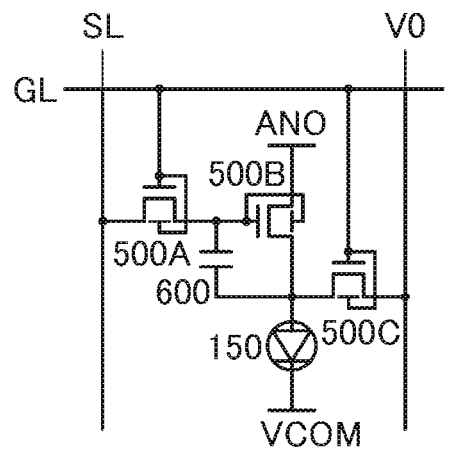

A pixel circuit 400C illustrated in FIG. 34C is an example of the case where a transistor in which a gate and a back gate are electrically connected to each other is used as each of the transistor 500A and the transistor 500B of the pixel circuit 400A. A pixel circuit 400D illustrated in FIG. 34D is an example of the case where such transistors are used in the pixel circuit 400B. Thus, a current that can flow through the transistor can be increased. Note that although a transistor in which a pair of gates are electrically connected to each other is used as all the transistors here, one embodiment of the present invention is not limited thereto. A transistor that includes a pair of gates electrically connected to different wirings may be used. For example, when a transistor in which one of the gates is electrically connected to the source is used, the reliability can be increased.

Figure 35A:
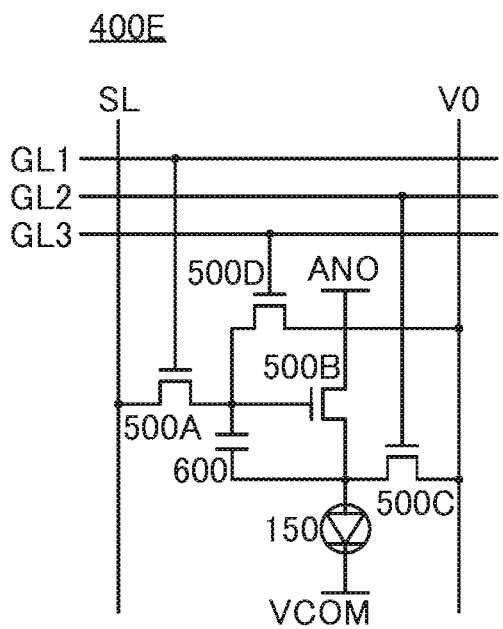
FIG. 35A to FIG. 35D are circuit diagrams illustrating structure examples of a pixel circuit included in a display apparatus.

A pixel circuit 400E illustrated in FIG. 35A has a structure where a transistor 500D is added to the pixel circuit 400B. Three wirings (the wiring GL1, the wiring GL2, and a wiring GL3) functioning as gate lines are electrically connected to the pixel circuit 400E.

A gate of the transistor 500D is electrically connected to the wiring GL3, one of a source and a drain of the transistor 500D is electrically connected to the gate of the transistor 500B, and the other of the source and the drain of the transistor 500D is electrically connected to the wiring V0. The gate of the transistor 500A is electrically connected to the wiring GL1, and the gate of the transistor 500C is electrically connected to the wiring GL2.

When the transistor 500C and the transistor 500D are brought into a conducting state at the same time, the source and the gate of the transistor 500B have the same potential, so that the transistor 500B can be brought into a non-conducting state. Thus, a current flowing through the light-emitting device 150 can be blocked forcibly. Such a pixel circuit is suitable for the case of using a display method in which a display period and a non-lighting period are alternately provided.

Figure 35B:
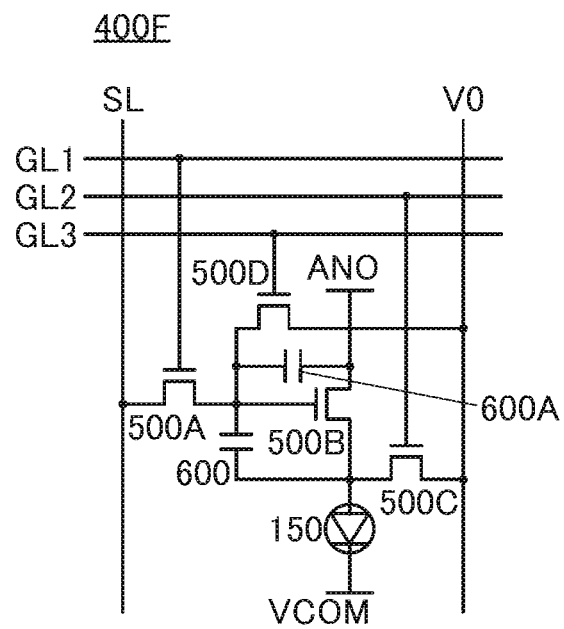

A pixel circuit 400F illustrated in FIG. 35B is an example of the case where a capacitor 600A is added to the pixel circuit 400E. The capacitor 600A functions as a storage capacitor.

Figure 35C:
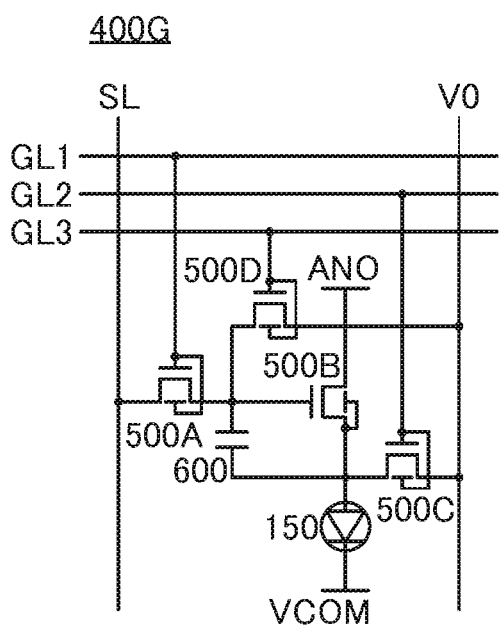
Figure 35D:
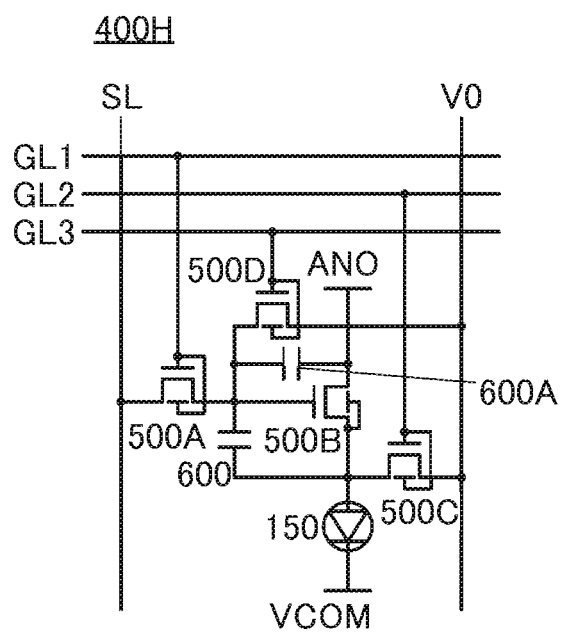

A pixel circuit 400G illustrated in FIG. 35C and a pixel circuit 400H illustrated in FIG. 35D are respectively examples of the cases where transistors each including a gate and a back gate that are electrically connected to each other are used in the pixel circuit 400E and the pixel circuit 400F. A transistor in which a gate and a back gate are electrically connected to each other is used as each of the transistor 500A, the transistor 500C, and the transistor 500D, and a transistor in which a gate is electrically connected to a source is used as the transistor 500B.

<Schematic Top View and Schematic Cross-Sectional View of Light-Emitting Device>

Figure 36A:
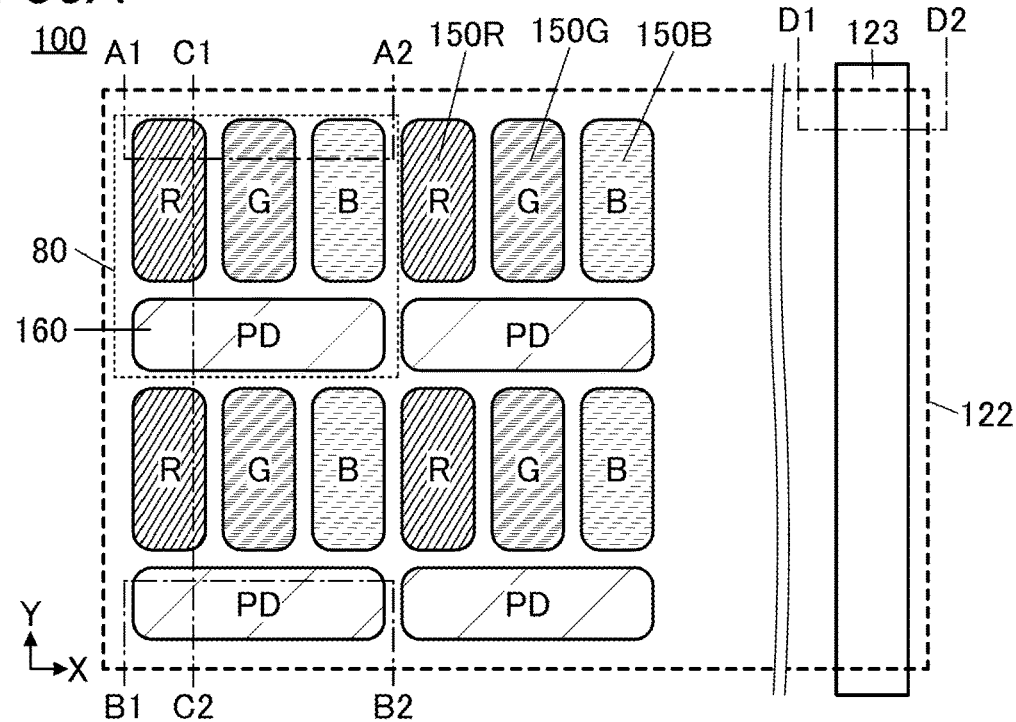
FIG. 36A and FIG. 36B are top views illustrating structure examples of light-emitting devices and light-receiving devices included in a display apparatus.

FIG. 36A is a schematic top view illustrating a structure example of the case where light-emitting devices and a light-receiving device are arranged in one pixel in the display apparatus 100 of one embodiment of the present invention. The display apparatus 100 includes a plurality of light-emitting devices 150R that emit red light, a plurality of light-emitting devices 150G that emit green light, a plurality of light-emitting devices 150B that emit blue light, and a plurality of light-receiving devices 160. In FIG. 36A, light-emitting regions of the light-emitting devices 150 are denoted by R, G, and B to easily differentiate the light-emitting devices 150. In addition, light-receiving regions of the light-receiving devices 160 are denoted by PD.

The light-emitting devices 150R, the light-emitting devices 150G, the light-emitting devices 150B, and the light-receiving devices 160 are each arranged in a matrix. FIG. 36A illustrates an example where the light-emitting devices 150R, the light-emitting devices 150G, and the light-emitting devices 150B are arranged in the X direction and the light-receiving devices 160 are arranged thereunder. FIG. 36A also illustrates a structure example where the light-emitting devices 150 that emit light of the same color are arranged in the Y direction intersecting the X direction. In the display apparatus 100 illustrated in FIG. 36A, a pixel 80 can be composed of a subpixel including the light-emitting device 150R, a subpixel including the light-emitting device 150G, and a subpixel including the light-emitting device 150B, which are arranged in the X direction, and a subpixel including the light-receiving device 160 provided under the subpixels, for example.

As each of the light-emitting device 150R, the light-emitting device 150G, and the light-emitting device 150B, an EL element such as an OLED (Organic Light Emitting Diode) or a QLED (Quantum-dot Light Emitting Diode) is preferably used. Examples of a light-emitting substance contained in the EL elements include a substance exhibiting fluorescence (a fluorescent material), a substance exhibiting phosphorescence (a phosphorescent material), an inorganic compound (e.g., a quantum dot material), and a substance exhibiting thermally activated delayed fluorescence (a thermally activated delayed fluorescent (TADF) material). Note that as a TADF material, a material in which a singlet excited state and a triplet excited state are in a thermal equilibrium state may be used. Since such a TADF material enables a short emission lifetime (excitation lifetime), an efficiency decrease of a light-emitting element in a high-luminance region can be inhibited.

For example, a pn or pin photodiode can be used as the light-receiving device 160. The light-receiving device 160 functions as a photoelectric conversion element that detects light incident on the light-receiving device 160 and generates charge. The amount of generated charge depends on the amount of incident light.

It is particularly preferable to use an organic photodiode including a layer containing an organic compound, as the light-receiving device 160. An organic photodiode, which is easily made thin, lightweight, and large in area and has a high degree of freedom for shape and design, can be used in a variety of display apparatuses.

In an electronic device of one embodiment of the present invention, an organic EL element is used as the light-emitting device 150, and an organic photodiode is used as the light-receiving device 160. The organic EL elements and the organic photodiodes can be formed over one substrate. Thus, the organic photodiodes can be incorporated in a display apparatus including the organic EL elements. A photolithography method is preferably employed to separate the organic EL elements and the organic photodiodes from each other. This can reduce the interval between the light-emitting devices, between the organic photodiodes, and between the light-emitting device and the organic photodiode, achieving a display apparatus having a higher aperture ratio than that formed using, for example, a shadow mask such as a metal mask.

FIG. 36A illustrates the conductor 122 functioning as a common electrode and the conductor 123 functioning as a connection electrode. Here, the conductor 123 is electrically connected to the conductor 122. The conductor 123 is provided outside a display portion where the light-emitting devices 150 and the light-receiving devices 160 are arranged. In FIG. 36A, the conductor 122 including a region overlapping with the light-emitting devices 150, the light-receiving devices 160, and the conductor 123 is shown by dashed lines.

The conductor 123 can be provided along the outer periphery of the display portion. For example, the conductor 123 may be provided along one side of the outer periphery of the display portion or two or more sides of the outer periphery of the display portion. That is, the top surface shape of the conductor 123 can be a band shape, an L shape, a square bracket shape, a quadrangle, or the like in the case where the top surface shape of the display portion is a rectangle.

Figure 36B:
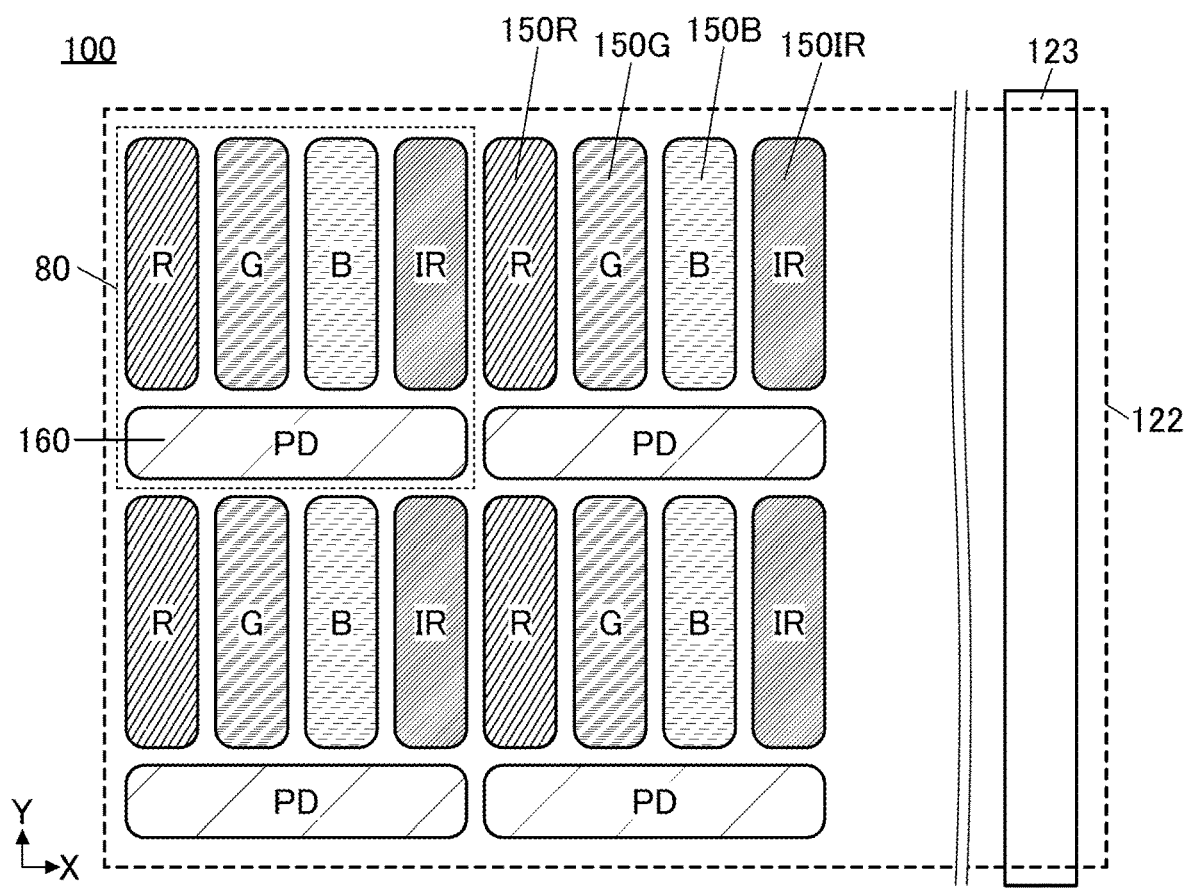

FIG. 36B is a schematic top view illustrating a structure example of the display apparatus 100 and is a variation example of the display apparatus 100 illustrated in FIG. 36A. The display apparatus 100 illustrated in FIG. 36B differs from the display apparatus 100 illustrated in FIG. 36A in that light-emitting devices 150IR that emit infrared light are included. The light-emitting devices 150IR can emit near-infrared light (light with a wavelength of greater than or equal to 750 nm and less than or equal to 1300 nm), for example.

In the example illustrated in FIG. 36B, the light-emitting devices 150IR as well as the light-emitting device 150R, the light-emitting device 150G, and the light-emitting device 150B are arranged in the X direction, and the light-receiving devices 160 are arranged thereunder. The light-receiving device 160 has a function of detecting infrared light.

Figure 37A:
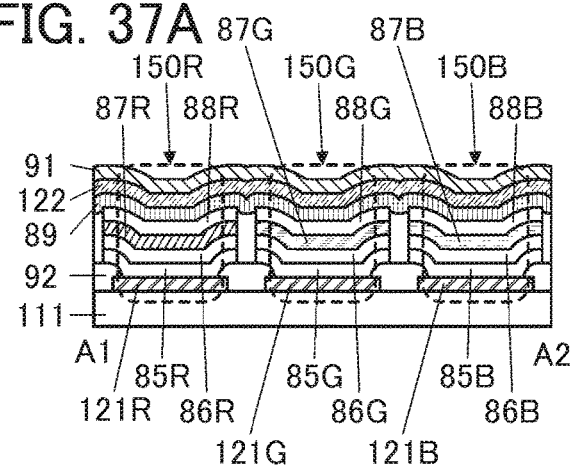
FIG. 37A to FIG. 37D are schematic cross-sectional views illustrating structure examples of light-emitting devices, a light-receiving device, and a connection electrode included in a display apparatus.
Figure 37B:
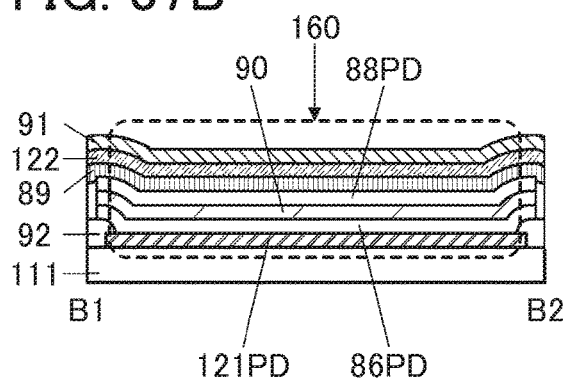
Figure 37C:
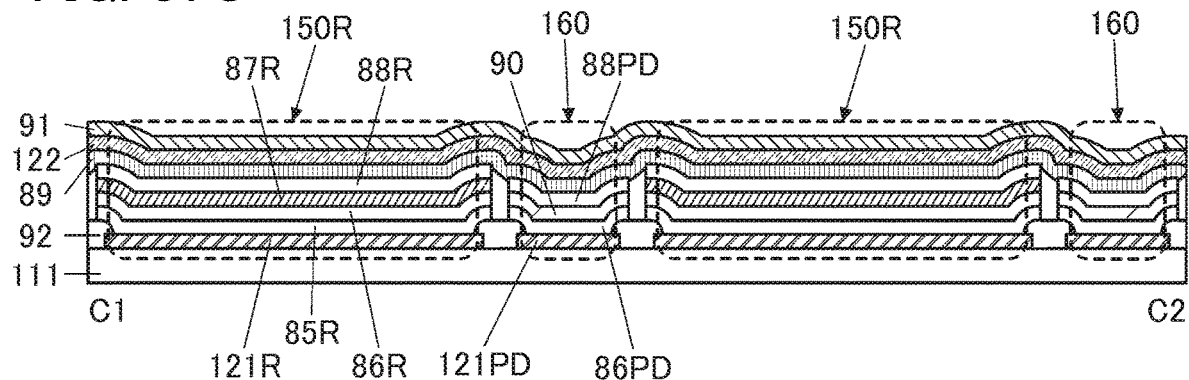
Figure 37D:
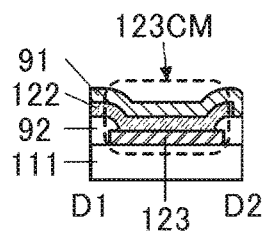

FIG. 37A is a cross-sectional view taken along dashed-dotted line A1-A2 in FIG. 36A, and FIG. 37B is a cross-sectional view taken along dashed-dotted line B1-B2 in FIG. 36A. FIG. 37C is a cross-sectional view taken along dashed-dotted line C1-C2 in FIG. 36A, and FIG. 37D is a cross-sectional view taken along dashed-dotted line D1-D2 in FIG. 36A. The light-emitting devices 150R, the light-emitting devices 150G, the light-emitting devices 150B, and the light-receiving devices 160 are provided over the insulator 111. In the case where the display apparatus 100 includes the light-emitting devices 150IR, the light-emitting devices 150IR are provided over the insulator 111.

In the case where the expression "B over A" or "B under A" is used in this specification and the like, for example, A and B do not always need to include a region where they are in contact with each other.

FIG. 37A illustrates a cross-sectional structure example of the light-emitting device 150R, the light-emitting device 150G, and the light-emitting device 150B in FIG. 36A. FIG. 37B illustrates a cross-sectional structure example of the light-receiving device 160 in FIG. 36A.

The light-emitting device 150R includes a conductor 121R functioning as a pixel electrode, a hole-injection layer 85R, a hole-transport layer 86R, a light-emitting layer 87R, an electron-transport layer 88R, a common layer 89, and the conductor 122. The light-emitting device 150G includes a conductor 121G functioning as a pixel electrode, a hole-injection layer 85G, a hole-transport layer 86G, a light-emitting layer 87G, an electron-transport layer 88G, the common layer 89, and the conductor 122. The light-emitting device 150B includes a conductor 121B functioning as a pixel electrode, a hole-injection layer 85B, a hole-transport layer 86B, a light-emitting layer 87B, an electron-transport layer 88B, the common layer 89, and the conductor 122. The light-receiving device 160 includes a conductor 121PD functioning as a pixel electrode, a hole-transport layer 86PD, a light-receiving layer 90, an electron-transport layer 88PD, the common layer 89, and the conductor 122.

As the conductor 121R, the conductor 121G, and the conductor 121B, for example, the conductor 121*a*, the conductor 121*b*, and the conductor 121*c* illustrated in FIG. 29A to FIG. 30B can be used.

The common layer 89 has a function of an electron-injection layer in the light-emitting device 150. Meanwhile, the common layer 89 has a function of an electron-transport layer in the light-receiving device 160. Therefore, the light-receiving device 160 does not necessarily include the electron-transport layer 88PD.

The hole-injection layer 85, the hole-transport layer 86, the electron-transport layer 88, and the common layer 89 can also be referred to as functional layers.

The conductor 121, the hole-injection layer 85, the hole-transport layer 86, the light-emitting layer 87, and the electron-transport layer 88 can each be separately provided for each element. The common layer 89 and the conductor 122 are provided to be shared by the light-emitting device 150R, the light-emitting device 150G, the light-emitting device 150B, and the light-receiving device 160.

The light-emitting device 150 and the light-receiving device 160 may each include a hole-blocking layer and an electron-blocking layer other than the layers illustrated in FIG. 37A. The light-emitting device 150 and the light-receiving device 160 may each include a layer containing, for example, a substance with a bipolar property (a substance with a high electron-transport property and a high hole-transport property).

An insulating layer 92 is provided to cover an end portion of the conductor 121R, an end portion of the conductor 121G, an end portion of the conductor 121B, and an end portion of the conductor 121PD. An end portion of the insulating layer 92 is preferably tapered. The insulating layer 92 is not necessarily provided when not needed.

For example, the hole-injection layer 85R, the hole-injection layer 85G, the hole-injection layer 85B, and the hole-transport layer 86PD each include a region in contact with the top surface of the conductor 121 and a region in contact with a surface of the insulating layer 92. In addition, an end portion of the hole-injection layer 85R, an end portion of the hole-injection layer 85G, an end portion of the hole-injection layer 85B, and an end portion of the hole-transport layer 86PD are positioned over the insulating layer 92.

A gap is provided between the common layer 89 and the insulating layer 92 described later. This can inhibit contact between the common layer 89 and each of a side surface of the light-emitting layer 87, a side surface of the light-receiving layer 90, a side surface of the hole-transport layer 86, and a side surface of the hole-injection layer 85. Thus, short-circuit in the light-emitting device 150 and short-circuit in the light-receiving device 160 can be inhibited.

The shorter the distance between the light-emitting layers 87 is, the more easily the gap is formed, for example. For example, when the distance is less than or equal to 1 μm, preferably less than or equal to 500 nm, further preferably less than or equal to 200 nm, less than or equal to 100 nm, less than or equal to 90 nm, less than or equal to 70 nm, less than or equal to 50 nm, less than or equal to 30 nm, less than or equal to 20 nm, less than or equal to 15 nm, or less than or equal to 10 nm, the gap can be favorably formed.

A protective layer 91 is provided over the conductor 122. The protective layer 91 has a function of preventing diffusion of impurities such as water into each light-emitting element from the above.

The protective layer 91 can have, for example, a single-layer structure or a stacked-layer structure at least including an inorganic insulating film. Examples of the inorganic insulating film include a silicon oxide film, a silicon oxynitride film, a silicon nitride oxide film, a silicon nitride film, an aluminum oxide film, an aluminum oxynitride film, and a hafnium oxide film. Alternatively, a semiconductor material such as an indium gallium oxide or an indium gallium zinc oxide may be used for the protective layer 91.

A stack of an inorganic insulating film and an organic insulating film can be used as the protective layer 91. For example, a structure where an organic insulating film is interposed between a pair of inorganic insulating films is preferable. Furthermore, the organic insulating film preferably functions as a planarization film. With this, the top surface of the organic insulating film can be flat, and accordingly, coverage with the inorganic insulating film thereover is improved, leading to an improvement in barrier property. The top surface of the protective layer 91 is flat, which is preferable because the influence of an uneven shape due to a structure below the protective layer 91 can be reduced in the case where a structure (e.g., a color filter, an electrode of a touch sensor, or a lens array) is provided above the protective layer 91.

FIG. 37A illustrates the light-emitting device 150 in which the conductor 121, the hole-injection layer 85, the hole-transport layer 86, the light-emitting layer 87, the electron-transport layer 88, the common layer 89 (electron-injection layer), and the conductor 122 are provided in this order from the bottom, and the light-receiving device 160 in which the conductor 121PD, the hole-transport layer 86PD, the light-receiving layer 90, the electron-transport layer 88PD, the common layer 89, and the conductor 122 are provided in this order from the bottom; however, the structure of the light-emitting device or the light-receiving device of an electronic device of one embodiment of the present invention is not limited to this example. For example, the light-emitting device 150 may include a conductor functioning as a pixel electrode, an electron-injection layer, an electron-transport layer, a light-emitting layer, a hole-transport layer, a hole-injection layer, and a conductor functioning as a common electrode in this order from the bottom, and the light-receiving device 160 may include a conductor functioning as a pixel electrode, an electron-transport layer, a light-receiving layer, a hole-transport layer, and a conductor functioning as a common electrode in this order from the bottom. In this case, the hole-injection layer included in the light-emitting device 150 can be a common layer, and the common layer can be provided between the hole-transport layer included in the light-receiving device 160 and the common electrode. In addition, the electron-injection layers can be separated between the light-emitting devices 150.

In the case where the sensor IS included in the electronic device HMD described in Embodiment 1 is an imaging device, the sensor IS can be the light-receiving device 160 illustrated in FIG. 36A and the like. That is, when the display portion DSP employs the arrangement structure example of the light-emitting device and the light-receiving device illustrated in FIG. 36A, the electronic device HMD described in Structure example 4 can be configured.

<Pixel Layout>

Here, a pixel layout which is different from that illustrated in FIG. 36 is described. There is no particular limitation on the arrangement of subpixels, and a variety of methods can be employed. Examples of the arrangement of subpixels include stripe arrangement, S-stripe arrangement, matrix arrangement, delta arrangement, Bayer arrangement, and pentile arrangement.

Examples of a top surface shape of the subpixel include polygons such as a triangle, a tetragon (including a rectangle and a square), and a pentagon; polygons with rounded corners; an ellipse; and a circle. Here, the top surface shape of the subpixel corresponds to the top surface shape of a light-emitting region of the light-emitting device.

Figure 38A:
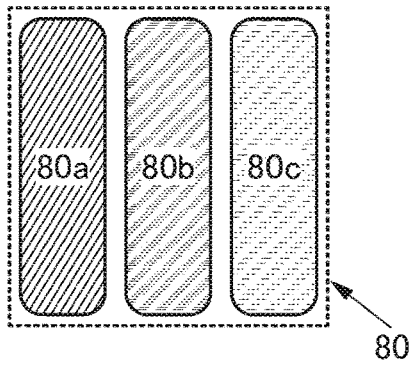
FIG. 38A to FIG. 38G are plan views illustrating examples of a pixel.
Figure 39A:
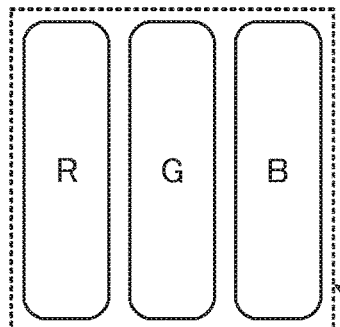
FIG. 39A to FIG. 39F are plan views illustrating examples of a pixel.

The pixel 80 illustrated in FIG. 38A employs stripe arrangement. The pixel 80 illustrated in FIG. 38A is composed of three subpixels: a subpixel 80a, a subpixel 80b, and a subpixel 80c. For example, as illustrated in FIG. 39A, the subpixel 80a may be a red subpixel R, the subpixel 80b may be a green subpixel G, and the subpixel 80c may be a blue subpixel B.

Figure 38B:
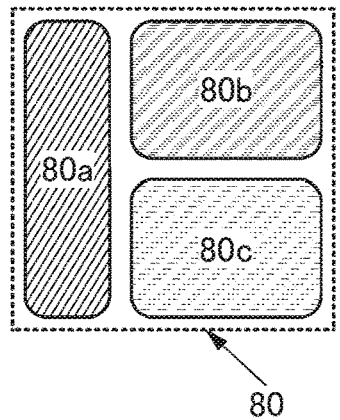
Figure 39B:
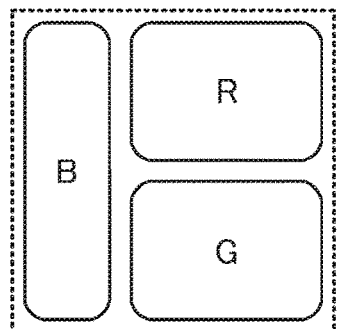

The pixel 80 illustrated in FIG. 38B employs S-stripe arrangement. The pixel 80 illustrated in FIG. 38B is composed of three subpixels: the subpixel 80*a*, the subpixel 80*b*, and the subpixel 80*c*. For example, as illustrated in FIG. 39B, the subpixel 80*a* may be the blue subpixel B, the subpixel 80*b* may be the red subpixel R, and the subpixel 80*c* may be the green subpixel G.

Figure 38C:
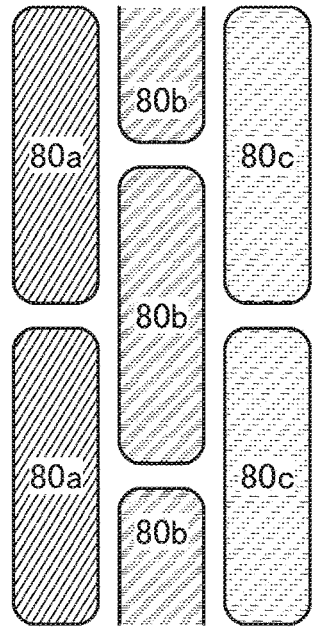
Figure 39C:
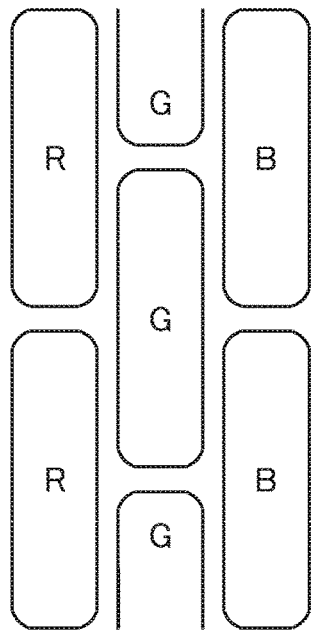

FIG. 38C illustrates an example where subpixels of different colors are arranged in a zigzag manner. Specifically, the positions of the top sides of two subpixels arranged in the column direction (e.g., the subpixel 80*a* and the subpixel 80*b* or the subpixel 80*b* and the subpixel 80*c*) are not aligned in the top view. For example, as illustrated in FIG. 39C, the subpixel 80*a* may be the red subpixel R, the subpixel 80*b* may be the green subpixel G, and the subpixel 80*c* may be the blue subpixel B.

Figure 38D:
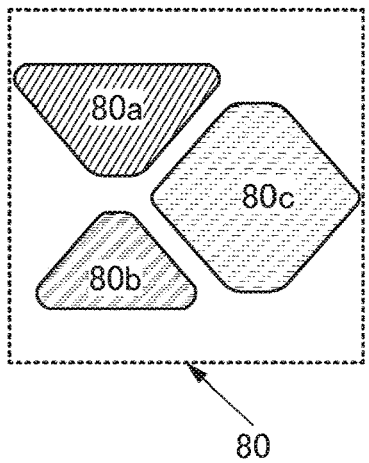
Figure 39D:
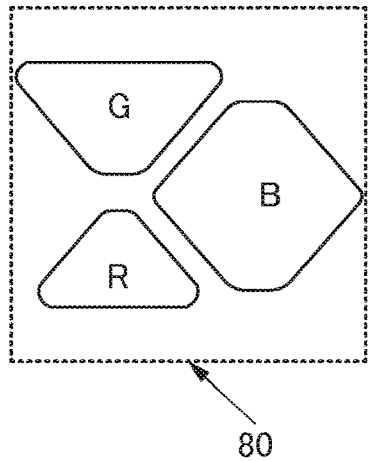

The pixel 80 illustrated in FIG. 38D includes the subpixel 80*a* whose top surface has a rough trapezoidal shape with rounded corners, the subpixel 80*b* whose top surface has a rough triangle shape with rounded corners, and the subpixel 80*c* whose top surface has a rough tetragonal or rough hexagonal shape with rounded corners. The subpixel 80*a* has a larger light-emitting area than the subpixel 80*b*. In this manner, the shapes and sizes of the subpixels can be determined independently. For example, the size of a subpixel including a light-emitting device with higher reliability can be smaller. For example, as illustrated in FIG. 39D, the subpixel 80*a* may be the green subpixel G, the subpixel 80*b* may be the red subpixel R, and the subpixel 80*c* may be the blue subpixel B.

Figure 38E:
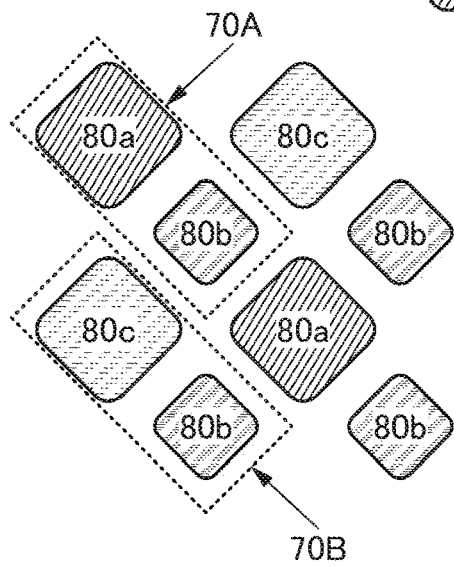
Figure 39E:
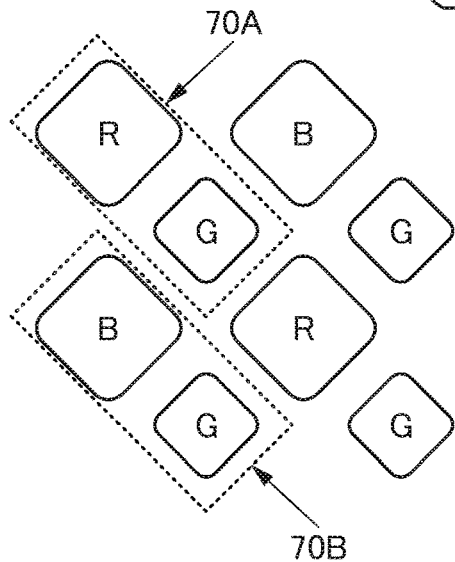

A pixel 70A and a pixel 70B illustrated in FIG. 38E employ pentile arrangement. FIG. 38E illustrates an example where the pixels 70A including the subpixel 80*a* and the subpixel 80*b* and the pixels 70B including the subpixel 80*b* and the subpixel 80*c* are alternately arranged. For example, as illustrated in FIG. 39E, the subpixel 80*a* may be the red subpixel R, the subpixel 80*b* may be the green subpixel G, and the subpixel 80*c* may be the blue subpixel B.

Figure 38F:
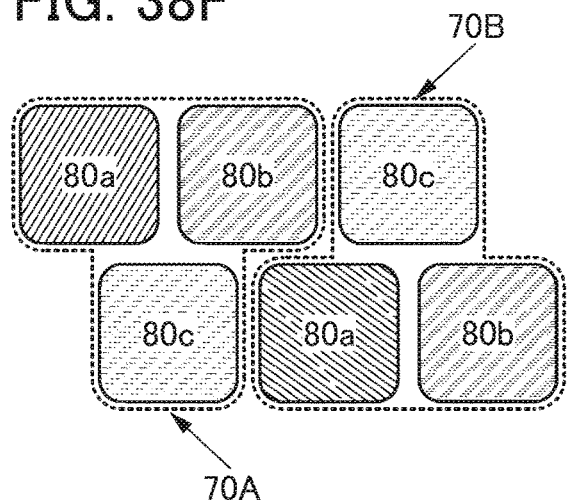
Figure 38G:
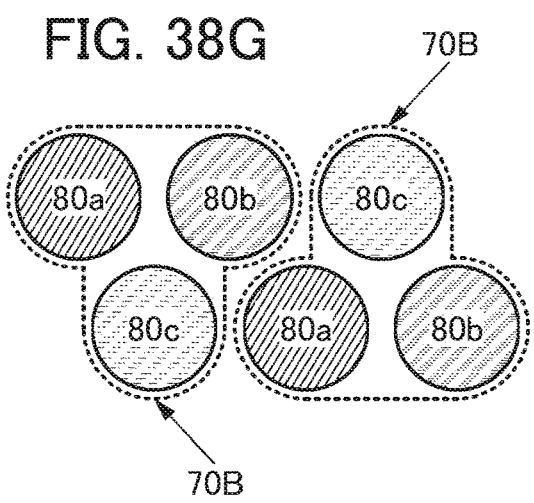
Figure 39F:
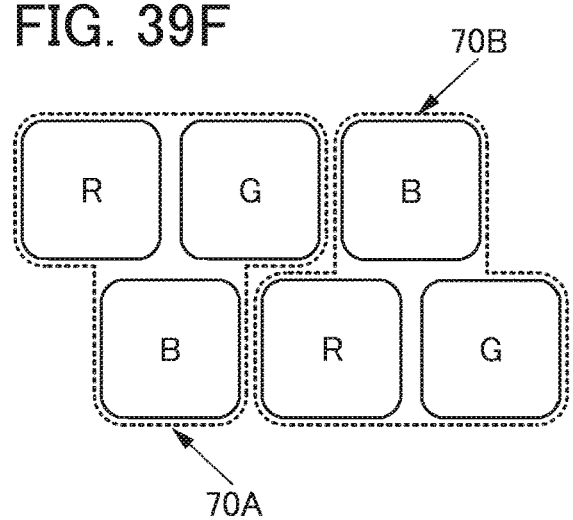

The pixel 70A and the pixel 70B illustrated in FIG. 38F and FIG. 38G employ delta arrangement. The pixel 70A includes two subpixels (the subpixel 80*a* and the subpixel 80*b*) in the upper row (first row) and one subpixel (the subpixel 80*c*) in the lower row (second row). The pixel 70B includes one subpixel (the subpixel 80*c*) in the upper row (first row) and two subpixels (the subpixel 80*a* and the subpixel 80*b*) in the lower row (second row). For example, as illustrated in FIG. 39F, the subpixel 80*a* may be the red subpixel R, the subpixel 80*b* may be the green subpixel G, and the subpixel 80*c* may be the blue subpixel B.

FIG. 38F illustrates an example where the top surface of each subpixel has a rough tetragonal shape with rounded corners, and FIG. 38G illustrates an example where the top surface of each subpixel has a circular shape.

In a photolithography method, as a pattern to be processed becomes finer, the influence of light diffraction becomes more difficult to ignore; therefore, the fidelity in transferring a photomask pattern by light exposure is degraded, and it becomes difficult to process a resist mask into a desired shape. Thus, a pattern with rounded corners is likely to be formed even with a rectangular photomask pattern.

Consequently, the top surface of a subpixel can have a polygonal shape with rounded corners, an elliptical shape, a circular shape, or the like.

Furthermore, in the method for fabricating the display apparatus of one embodiment of the present invention, the EL layer is processed into an island shape with the use of a resist mask. A resist film formed over the EL layer needs to be cured at a temperature lower than the upper temperature limit of the EL layer. Therefore, the resist film is insufficiently cured in some cases depending on the upper temperature limit of the material of the EL layer and the curing temperature of the resist material. An insufficiently cured resist film may have a shape different from a desired shape by processing. As a result, the top surface of the EL layer may have a polygonal shape with rounded corners, an elliptical shape, a circular shape, or the like. For example, when a resist mask with a square top surface is intended to be formed, a resist mask with a circular top surface may be formed, and the top surface of the EL layer may be circular.

To obtain a desired top surface shape of the EL layer, a technique of correcting a mask pattern in advance so that a transferred pattern agrees with a design pattern (an optical proximity correction (OPC) technique) may be used. Specifically, with the OPC technique, a pattern for correction is added to a corner portion or the like of a figure on a mask pattern.

Figure 40A:
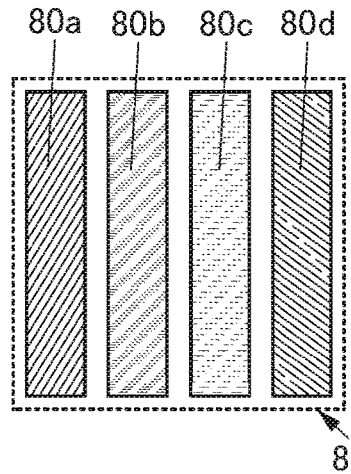
FIG. 40A to FIG. 40H are plan views illustrating examples of a pixel.
Figure 40B:
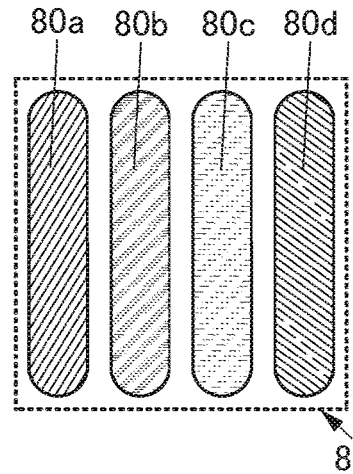
Figure 40C:
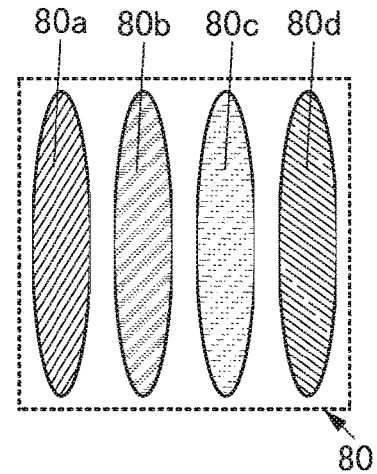

The pixels 80 illustrated in FIG. 40A to FIG. 40C employ stripe arrangement.

FIG. 40A illustrates an example where each subpixel has a rectangular top surface shape, FIG. 40B illustrates an example where each subpixel has a top surface shape formed by combining two half circles and a rectangle, and FIG. 40C illustrates an example where each subpixel has an elliptical top surface shape.

Figure 40D:
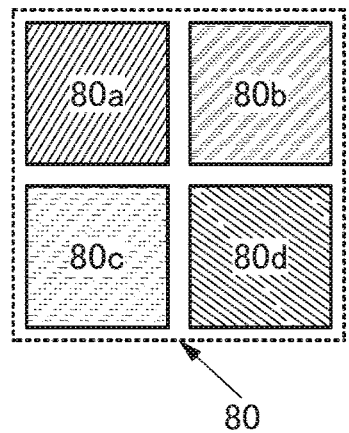
Figure 40E:
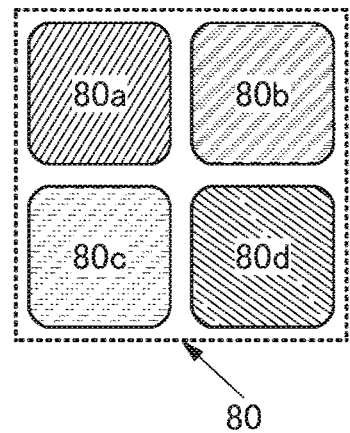
Figure 40F:
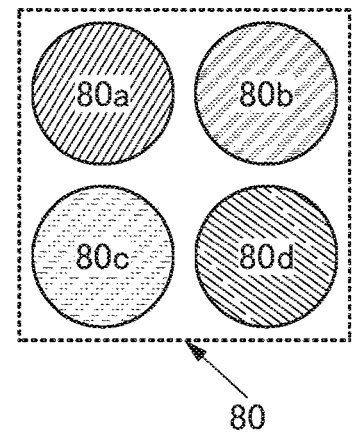

The pixels 80 illustrated in FIG. 40D to FIG. 40F employ matrix arrangement.

FIG. 40D illustrates an example where each subpixel has a square top surface shape, FIG. 40E illustrates an example where each subpixel has a substantially square top surface shape with rounded corners, and FIG. 40F illustrates an example where each subpixel has a circular top surface shape.

Figure 41A:
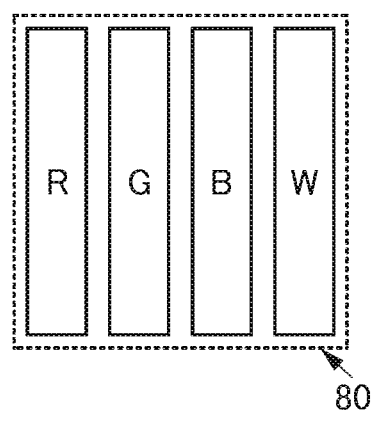
FIG. 41A to FIG. 41D are plan views illustrating examples of a pixel.
Figure 41B:
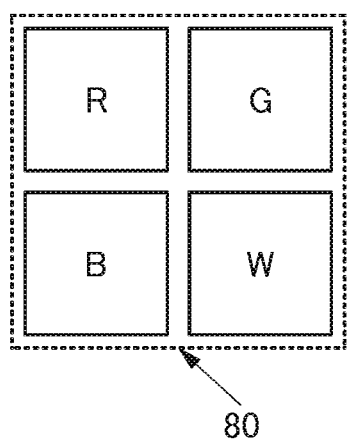

The pixels 80 illustrated in FIG. 40A to FIG. 40F are each composed of four subpixels: the subpixel 80*a*, the subpixel 80*b*, the subpixel 80*c*, and a subpixel 80*d*. The subpixel 80*a*, the subpixel 80*b*, the subpixel 80*c*, and the subpixel 80*d* emit light of different colors. For example, the subpixel 80*a*, the subpixel 80*b*, the subpixel 80*c*, and the subpixel 80*d* can be red, green, blue, and white subpixels, respectively, as illustrated in FIG. 41A and FIG. 41B. Alternatively, the subpixel 80*a*, the subpixel 80*b*, the subpixel 80*c*, and the subpixel 80*d* can be red, green, blue, and infrared-light subpixels, respectively.

The subpixel 80*d* includes a light-emitting device. The light-emitting device includes, for example, a pixel electrode, an EL layer, and the conductor 123 functioning as a common electrode. For the pixel electrode, a material similar to that of the conductor 121*a*, the conductor 121*b*, the conductor 121*c*, the conductor 122*a*, the conductor 122*b*, or the conductor 122*c* can be used. For the EL layer, a material similar to that of the EL layer 141*a*, the EL layer 141*b*, or the EL layer 141*c* can be used, for example.

Figure 40G:
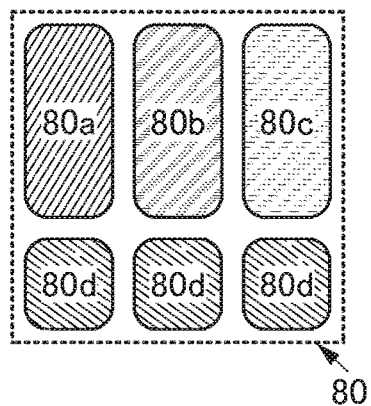

FIG. 40G illustrates an example where one pixel 80 is composed of two rows and three columns. The pixel 80 includes three subpixels (the subpixel 80*a*, the subpixel 80*b*, and the subpixel 80*c*) in the upper row (first row) and three subpixels 80*d* in the lower row (second row). In other words, the pixel 80 includes the subpixel 80*a* and the subpixel 80*d* in the left column (first column), the subpixel 80*b* and another subpixel 80*d* in the center column (second column), and the subpixel 80*c* and another subpixel 80*d* in the right column (third column). Matching the positions of the subpixels in the upper row and the lower row as illustrated in FIG. 40G enables dust and the like that would be produced in the manufacturing process to be removed efficiently. Thus, a display apparatus with high display quality can be provided.

Figure 40H:
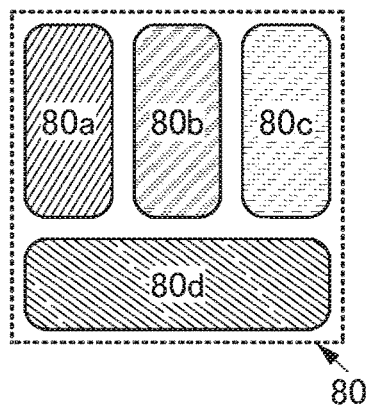

FIG. 40H illustrates an example where one pixel 80 is composed of two rows and three columns. The pixel 80 includes three subpixels (the subpixel 80a, the subpixel 80b, and the subpixel 80c) in the upper row (first row) and one subpixel (the subpixel 80d) in the lower row (second row). In other words, the pixel 80 includes the subpixel 80a in the left column (first column), the subpixel 80b in the center column (second column), the subpixel 80c in the right column (third column), and the subpixel 80d across these three columns.

Figure 41C:
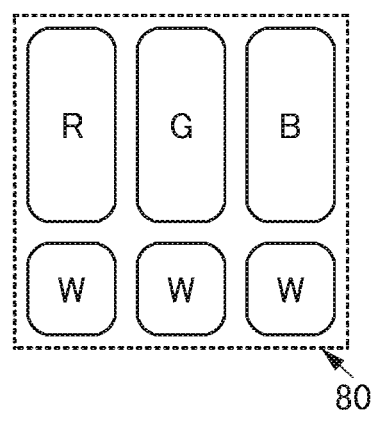
Figure 41D:
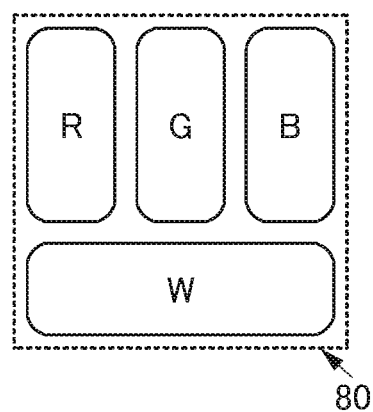

In the pixel 80 illustrated in each of FIG. 40G and FIG. 40H, for example, the subpixel 80a can be the red subpixel R, the subpixel 80b can be the green subpixel G, the subpixel 80c can be the blue subpixel B, and the subpixel 80d can be a white subpixel W, as illustrated in FIG. 41C and FIG. 41D.

The display apparatus of one embodiment of the present invention may include a light-receiving device in the pixel.

Three of the four subpixels included in the pixel 80 in FIG. 40G may include a light-emitting device and the other one may include a light-receiving device.

For example, a pn or pin photodiode can be used as the light-receiving device. The light-receiving devices function as photoelectric conversion devices (also referred to as photoelectric conversion elements) that detect light entering the light-receiving devices and generate charge. The amount of charge generated from the light-receiving devices depends on the amount of light entering the light-receiving devices.

It is particularly preferable to use an organic photodiode including a layer containing an organic compound, as the light-receiving device. An organic photodiode, which is easily made thin, lightweight, and large in area and has a high degree of freedom for shape and design, can be used in a variety of display apparatuses.

In one embodiment of the present invention, organic EL devices are used as the light-emitting devices, and organic photodiodes are used as the light-receiving devices. The organic EL device and the organic photodiode can be formed over the same substrate. Thus, the organic photodiode can be incorporated in the display apparatus including the organic EL device.

The light-receiving device includes at least an active layer that functions as a photoelectric conversion layer between a pair of electrodes. In this specification and the like, one of the pair of electrodes may be referred to as a pixel electrode and the other may be referred to as a common electrode.

For example, the subpixel 80a, the subpixel 80b, and the subpixel 80c may be subpixels for three colors of R, G, and B, and the subpixel 80d may be a subpixel including the light-receiving device. In this case, the fourth layer includes at least an active layer.

One of the pair of electrodes of the light-receiving device functions as an anode, and the other electrode functions as a cathode. Hereinafter, the case where the pixel electrode functions as an anode and the common electrode functions as a cathode is described as an example. When the light-receiving device is driven by application of reverse bias between the pixel electrode and the common electrode, light entering the light-receiving device can be detected and charge can be generated and extracted as current. Alternatively, the pixel electrode may function as a cathode and the common electrode may function as an anode.

A fabrication method similar to that of the light-emitting device can be employed for the light-receiving device. An island-shaped active layer (also referred to as a photoelectric conversion layer) included in the light-receiving device is formed by processing a film that is to be the active layer and formed on the entire surface, not by using a pattern of a metal mask; thus, the island-shaped active layer with a uniform thickness can be formed. In addition, a sacrifice layer provided over the active layer can reduce damage to the active layer in the fabrication process of the display apparatus, increasing the reliability of the light-receiving device.

Here, a layer shared by the light-receiving device and the light-emitting device might have different functions in the light-emitting device and the light-receiving device. In this specification, the name of a component is based on its function in the light-emitting device in some cases. For example, a hole-injection layer functions as a hole-injection layer in the light-emitting device and functions as a hole-transport layer in the light-receiving device. Similarly, an electron-injection layer functions as an electron-injection layer in the light-emitting device and functions as an electron-transport layer in the light-receiving device. A layer shared by the light-receiving device and the light-emitting device might have the same function in both the light-emitting device and the light-receiving device. The hole-transport layer functions as a hole-transport layer in both the light-emitting device and the light-receiving device, and the electron-transport layer functions as an electron-transport layer in both the light-emitting device and the light-receiving device.

The active layer included in the light-receiving device includes a semiconductor. Examples of the semiconductor include an inorganic semiconductor such as silicon and an organic semiconductor including an organic compound. This embodiment shows an example where an organic semiconductor is used as the semiconductor included in the active layer. The use of an organic semiconductor is preferable because the light-emitting layer and the active layer can be formed by the same method (e.g., a vacuum evaporation method) and thus the same manufacturing apparatus can be used.

Examples of an n-type semiconductor material contained in the active layer include electron-accepting organic semiconductor materials such as fullerene (e.g., $C_{60}$ and $C_{70}$) and fullerene derivatives. Fullerene has a soccer ball-like shape, which is energetically stable. Both the HOMO level and the LUMO level of fullerene are deep (low). Having a deep LUMO level, fullerene has an extremely high electron-accepting property (acceptor property). In general, when π-electron conjugation (resonance) spreads in a plane as in benzene, an electron-donating property (donor property) becomes high; however, since fullerene has a spherical shape, fullerene has a high electron-accepting property even when π-electrons widely spread. The high electron-accepting property efficiently causes rapid charge separation and is useful for the light-receiving element. Both $C_{60}$ and $C_{70}$ have a wide absorption band in the visible light region, and $C_{70}$ is especially preferable because of having a larger π-electron conjugation system and a wider absorption band in the long wavelength region than $C_{60}$. Other examples of fullerene derivatives include [6,6]-phenyl-$C_{71}$-butyric acid methyl ester (abbreviation: $PC_{70}BM$), [6,6]-phenyl-$C_{61}$-butyric acid methyl ester (abbreviation: $PC_{60}BM$), and 1',1", 4',4"-tetrahydro-di[1,4]methanonaphthaleno[1,2:2',3',56,60: 2",3"][5,6]fullerene-$C_{60}$ (abbreviation: ICBA).

Other examples of an n-type semiconductor material include a metal complex having a quinoline skeleton, a metal complex having a benzoquinoline skeleton, a metal complex having a oxazole skeleton, a metal complex having a thiazole skeleton, an oxadiazole derivative, a triazole derivative, an imidazole derivative, an oxazole derivative, a thiazole derivative, a phenanthroline derivative, a quinoline derivative, a benzoquinoline derivative, a quinoxaline derivative, a dibenzoquinoxaline derivative, a pyridine derivative, a bipyridine derivative, a pyrimidine derivative, a naphthalene derivative, an anthracene derivative, a coumarin derivative, a rhodamine derivative, a triazine derivative, and a quinone derivative.

Examples of a p-type semiconductor material contained in the active layer include electron-donating organic semiconductor materials such as copper(II) phthalocyanine (CuPc), tetraphenyldibenzoperiflanthene (DBP), zinc phthalocyanine (ZnPc), tin phthalocyanine (SnPc), and quinacridone.

Other examples of the p-type semiconductor material include a carbazole derivative, a thiophene derivative, a furan derivative, and a compound having an aromatic amine skeleton. Other examples of the p-type semiconductor material include a naphthalene derivative, an anthracene derivative, a pyrene derivative, a triphenylene derivative, a fluorene derivative, a pyrrole derivative, a benzofuran derivative, a benzothiophene derivative, an indole derivative, a dibenzofuran derivative, a dibenzothiophene derivative, an indolocarbazole derivative, a porphyrin derivative, a phthalocyanine derivative, a naphthalocyanine derivative, a quinacridone derivative, a polyphenylene vinylene derivative, a polyparaphenylene derivative, a polyfluorene derivative, a polyvinylcarbazole derivative, and a polythiophene derivative.

The HOMO level of the electron-donating organic semiconductor material is preferably shallower (higher) than the HOMO level of the electron-accepting organic semiconductor material. The LUMO level of the electron-donating organic semiconductor material is preferably shallower (higher) than the LUMO level of the electron-accepting organic semiconductor material.

Fullerene having a spherical shape is preferably used as the electron-accepting organic semiconductor material, and an organic semiconductor material having a substantially planar shape is preferably used as the electron-donating organic semiconductor material. Molecules of similar shapes tend to aggregate, and aggregated molecules of similar kinds, which have molecular orbital energy levels close to each other, can increase the carrier-transport property.

For example, the active layer is preferably formed by co-evaporation of an n-type semiconductor and a p-type semiconductor. Alternatively, the active layer may be formed by stacking an n-type semiconductor and a p-type semiconductor.

In addition to the active layer, the light-receiving device may further include a layer containing any of a substance with a high hole-transport property, a substance with a high electron-transport property, a substance with a bipolar property (a substance with a high electron-transport property and a high hole-transport property), and the like. Without limitation to the above, a layer containing one or more selected from a substance with a high hole-injection property, a hole-blocking material, a material with a high electron-injection property, and an electron-blocking material may be further included.

Either a low molecular compound or a high molecular compound can be used in the light-receiving device, and an inorganic compound may also be included. Each layer included in the light-receiving device can be formed by an evaporation method (including a vacuum evaporation method), a transfer method, a printing method, an inkjet method, a coating method, or the like.

As the hole-transport material, a high molecular compound such as poly(3,4-ethylenedioxythiophene)/poly(styrenesulfonic acid) (PEDOT/PSS), or an inorganic compound such as a molybdenum oxide or copper iodide (CuI) can be used, for example. As the electron-transport material, an inorganic compound such as zinc oxide (ZnO) can be used.

For the active layer, a high molecular compound such as poly[[4,8-bis[5-(2-ethylhexyl)-2-thienyl]benzo[1,2-b:4,5-b']dithiophene-2,6-diyl]-2,5-thiophenediyl[5,7-bis(2-ethylhexyl)-4,8-dioxo-4H,8H-benzo[1,2-c:4,5-c']dithiophene-1,3-diyl]] polymer (abbreviation: PBDB-T) or a PBDB-T derivative, which functions as a donor, can be used. For example, a method in which an acceptor material is dispersed to PBDB-T or a PBDB-T derivative can be used.

The active layer may contain a mixture of three or more kinds of materials. For example, a third material may be mixed with an n-type semiconductor material and a p-type semiconductor material in order to extend the wavelength range. The third material may be a low molecular compound or a high molecular compound.

In the display apparatus including the light-emitting device and the light-receiving device in the pixel, the pixel has a light-receiving function, which enables detection of a touch or approach of an object while an image is displayed. For example, all the subpixels included in the display apparatus can display an image; alternatively, some of the subpixels can emit light as a light source and the other subpixels can display an image.

In the display apparatus of one embodiment of the present invention, the light-emitting devices are arranged in a matrix in a display portion, and an image can be displayed on the display portion. Furthermore, the light-receiving devices are arranged in a matrix in the display portion, and the display portion has one or both of an image capturing function and a sensing function in addition to an image displaying function. The display portion can be used as an image sensor or a touch sensor. That is, by detecting light with the display portion, an image can be captured or an approach or touch of an object (e.g., a finger, a hand, or a pen) can be detected. Furthermore, in the display apparatus of one embodiment of the present invention, the light-emitting devices can be used as a light source of the sensor. Accordingly, a light-receiving portion and a light source do not need to be provided separately from the display apparatus; hence, the number of components of an electronic device can be reduced.

In the display apparatus of one embodiment of the present invention, when an object reflects (or scatters) light emitted from the light-emitting device included in the display portion, the light-receiving device can detect reflected light (or scattered light); thus, image capturing or touch detection is possible even in a dark place.

In the case where the light-receiving devices are used as the image sensor, the display apparatus can capture an image with the use of the light-receiving devices. For example, the display apparatus of this embodiment can be used as a scanner.

For example, data on biological information such as a fingerprint or a palm print can be obtained with the use of the image sensor. That is, a biometric authentication sensor can be incorporated in the display apparatus. When the display apparatus incorporates a biometric authentication sensor, the number of components of an electronic device can be reduced as compared to the case where a biometric authentication sensor is provided separately from the display apparatus; thus, the size and weight of the electronic device can be reduced.

In the case where the light-receiving devices are used as the touch sensor, the display apparatus can detect an approach or touch of an object with the use of the light-receiving devices.

Pixels illustrated in FIG. 42A to FIG. 42D each include the subpixel G, the subpixel B, the subpixel R, and a subpixel PS.

Figure 42A:
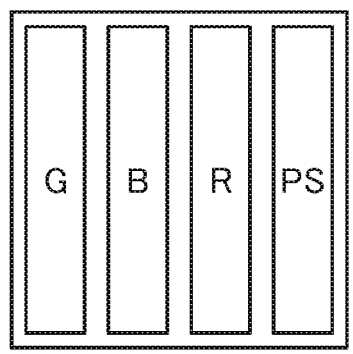
FIG. 42A to FIG. 42D are plan views illustrating examples of a pixel.
Figure 42B:
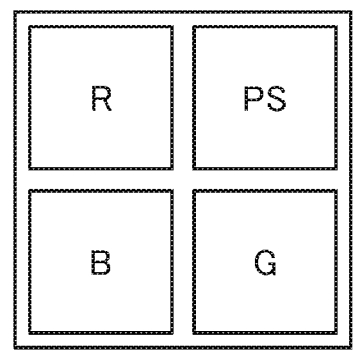

The pixel illustrated in FIG. 42A employs stripe arrangement. The pixel illustrated in FIG. 42B employs matrix arrangement.

Figure 42C:
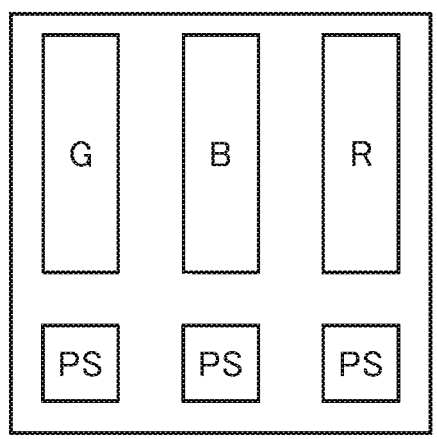
Figure 42D:
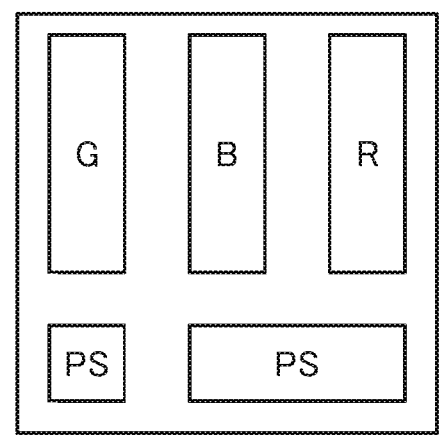

FIG. 42C and FIG. 42D illustrate an example where one pixel is provided in two rows and three columns. Three subpixels (the subpixel G, the subpixel B, and the subpixel R) are provided in the upper row (first row). In FIG. 42C, three subpixels PS are provided in the lower row (second row). In FIG. 42D, two subpixels PS are provided in the lower row (second row). Aligning the positions of the subpixels in the upper row and the lower row as illustrated in FIG. 42C enables dust and the like that would be produced in the manufacturing process to be removed efficiently. Thus, a display apparatus with high display quality can be provided. Note that the layout of the subpixels is not limited to the structures illustrated in FIG. 42A to FIG. 42D.

Each of the subpixel R, the subpixel G, and the subpixel B includes a light-emitting device that emits white light. In each of the subpixel R, the subpixel G, and the subpixel B, the corresponding coloring layer is provided to overlap with the light-emitting device.

The subpixel PS includes the light-receiving device. There is no particular limitation on the wavelength of light detected by the subpixel PS.

The light-receiving device included in the subpixel PS preferably detects visible light, and preferably detects one or more of blue light, violet light, bluish violet light, green light, yellowish green light, yellow light, orange light, and red light, for example. The light-receiving device included in the subpixel PS may detect infrared light.

Figure 42E:
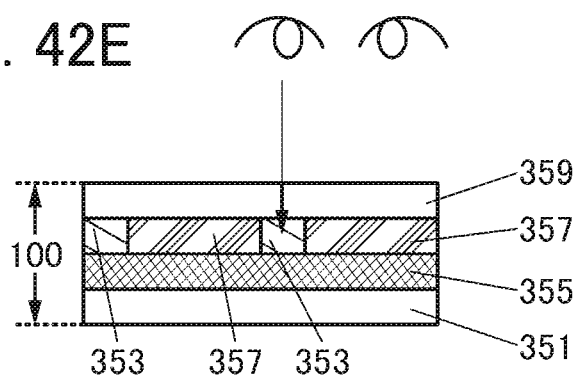
FIG. 42E is a cross-sectional view illustrating an example of a display apparatus.

The display apparatus 100 illustrated in FIG. 42E includes a layer 353 including a light-receiving device, a functional layer 355, and a layer 357 including a light-emitting device, between a substrate 351 and a substrate 359.

The functional layer 355 includes a circuit for driving a light-receiving device and a circuit for driving a light-emitting device. For example, a switch, a transistor, a capacitor, a resistor, a wiring, a terminal, and the like can be provided in the functional layer 355. Note that in the case where the light-emitting device and the light-receiving device are driven by a passive-matrix method, a structure not provided with a switch and a transistor may be employed.

For example, after light emitted from the light-emitting device in the layer 357 including light-emitting devices is reflected by a human eye and its surroundings as illustrated in FIG. 42E, the light-receiving device in the layer 353 including light-receiving devices detects the reflected light. Accordingly, information of the surroundings, surface, or inside of the human eye (e.g., the number of blinks, the movement of an eyeball, and the movement of an eyelid) can be detected.

Note that the insulators, the conductors, the semiconductors, and the like disclosed in this specification and the like can be formed by a PVD (Physical Vapor Deposition) method or a CVD (Chemical Vapor Deposition) method. Examples of a PVD method include a sputtering method, a resistance heating evaporation method, an electron beam evaporation method, and a PLD (Pulsed Laser Deposition) method. Examples of the CVD method include a plasma CVD method and a thermal CVD method. In particular, examples of a thermal CVD method include a MOCVD (Metal Organic Chemical Vapor Deposition) method and an ALD (Atomic Layer Deposition) method.

A thermal CVD method, which is a deposition method not using plasma, has an advantage that no defect due to plasma damage is generated.

Deposition by a thermal CVD method may be performed in such a manner that a source gas and an oxidizer are supplied into a chamber at a time, the pressure in the chamber is set to an atmospheric pressure or a reduced pressure, and they are made to react with each other in the vicinity of the substrate or over the substrate to be deposited over the substrate.

Deposition by an ALD method may be performed in such a manner that pressure in a chamber is set to an atmospheric pressure or a reduced pressure, source gases for reaction are sequentially introduced into the chamber, and then the sequence of the gas introduction is repeated. For example, two or more kinds of source gases are sequentially supplied to the chamber by switching respective switching valves (also referred to as high-speed valves); in order to avoid mixing of the plurality of kinds of source gases, an inert gas (e.g., argon or nitrogen) or the like is introduced at the same time as or after introduction of a first source gas and then a second source gas is introduced. Note that in the case where the first source gas and the inert gas are introduced at a time, the inert gas serves as a carrier gas, and the inert gas may also be introduced at the same time as the introduction of the second source gas. Alternatively, the second source gas may be introduced after the first source gas is exhausted by vacuum evacuation instead of the introduction of the inert gas. The first source gas is adsorbed on the surface of the substrate to form a first thin layer; then the second source gas is introduced to react with the first thin layer; as a result, a second thin layer is stacked over the first thin layer, so that a thin film is formed. The sequence of the gas introduction is controlled and repeated a plurality of times until a desired thickness is obtained, so that a thin film with excellent step coverage can be formed. The thickness of the thin film can be adjusted by the number of repetition times of the sequence of the gas introduction; therefore, an ALD method makes it possible to accurately adjust the thickness and is thus suitable for fabricating a minute FET.

A variety of films such as the metal film, the semiconductor film, and the inorganic insulating film disclosed in the above-described embodiments can be formed by a thermal CVD method such as an MOCVD method and an ALD method; for example, in the case of forming an In—Ga—Zn—O film, trimethylindium ($In(CH_3)_3$), trimethylgallium ($Ga(CH_3)_3$), and dimethylzinc ($Zn(CH_3)_2$) are used. Without limitation to the above combination, triethylgallium ($Ga(C_2H_5)_3$) can also be used instead of trimethylgallium, and diethylzinc ($Zn(C_2H_5)_2$) can also be used instead of dimethylzinc.

For example, in the case where a hafnium oxide film is formed with a deposition apparatus using ALD method, two kinds of gases, ozone ($O_3$) as an oxidizer and a source gas which is obtained by vaporizing liquid containing a solvent and a hafnium precursor compound (e.g., hafnium alkoxide and hafnium amide such as tetrakis(dimethylamide)hafnium (TDMAH, $Hf[N(CH_3)_2]_4$)), are used. Examples of another material include tetrakis(ethylmethylamide)hafnium.

For example, in the case where an aluminum oxide film is formed with a deposition apparatus using an ALD method, two kinds of gases, $H_2O$ as an oxidizer and a source gas which is obtained by vaporizing liquid containing a solvent and an aluminum precursor compound (e.g., trimethylaluminum (TMA, $Al(CH_3)_3$)) are used. Examples of another material include tris(dimethylamide)aluminum, triisobutylaluminum, and aluminum tris(2,2,6,6-tetramethyl-3,5-heptanedionate).

For example, in the case where a silicon oxide film is formed by a deposition apparatus utilizing ALD, hexachlorodisilane is adsorbed on a surface on which a film is to be formed, and radicals of an oxidizing gas ($O_2$ or dinitrogen monoxide) are supplied to react with the adsorbate.

For example, in the case where a tungsten film is formed by a deposition apparatus utilizing ALD, a $WF_6$ gas and a $B_2H_6$ gas are sequentially and repeatedly introduced to form an initial tungsten film, and then a $WF_6$ gas and an $H_2$ gas are sequentially and repeatedly introduced to form a tungsten film. Note that an $SiH_4$ gas may be used instead of a $B_2H_6$ gas.

In the case where an In—Ga—Zn—O film is formed as an oxide semiconductor film with a deposition apparatus using an ALD method, a precursor (generally referred to as a metal precursor or the like in some cases) and an oxidizer (generally referred to as a reactant, a non-metal precursor, or the like in some cases) are sequentially and repetitively introduced. Specifically, for example, an $In(CH_3)_3$ gas as a precursor and an $O_3$ gas) as an oxidizer are introduced to form an In—O layer; a $Ga(CH_3)_3$ gas as a precursor and an $O_3$ gas) as an oxidizer are introduced to form a GaO layer; and then, a $Zn(CH_3)_2$ gas as a precursor and an $O_3$ gas) as an oxidizer are introduced to form a ZnO layer. Note that the order of these layers is not limited to this example. A mixed oxide layer such as an In—Ga—O layer, an In—Zn—O layer, or a Ga—Zn—O layer may be formed with the use of these gases. Note that although an $H_2O$ gas which is obtained by bubbling water with an inert gas such as Ar may be used instead of an $O_3$ gas), it is preferable to use an $O_3$ gas) which does not contain H. Furthermore, instead of an $In(CH_3)_3$ gas, an $In(C_2H_5)_3$ gas may be used. Furthermore, instead of a $Ga(CH_3)_3$ gas, a $Ga(C_2H_5)_3$ gas may be used. Furthermore, a $Zn(CH_3)_2$ gas may be used.

There is no particular limitation on the screen ratio (aspect ratio) of the display portion of the electronic device of one embodiment of the present invention. For example, the display portion is compatible with a variety of screen ratios such as 1:1 (a square), 4:3, 16:9, and 16:10.

There is no particular limitation on the shape of the display portion of the electronic device of one embodiment of the present invention. The display portion can have any of various shapes such as a rectangular shape, a polygonal shape (e.g., octagon), a circular shape, and an elliptical shape.

Note that this embodiment can be combined with any of the other embodiments described in this specification as appropriate.

Embodiment 4

In this embodiment, a display module that can be used for the electronic device of one embodiment of the present invention is described.
<Structure Example of Display Module>
First, a display module including the display apparatus which can be used for the electronic device of one embodiment of the present invention is described.

Figure 43A:
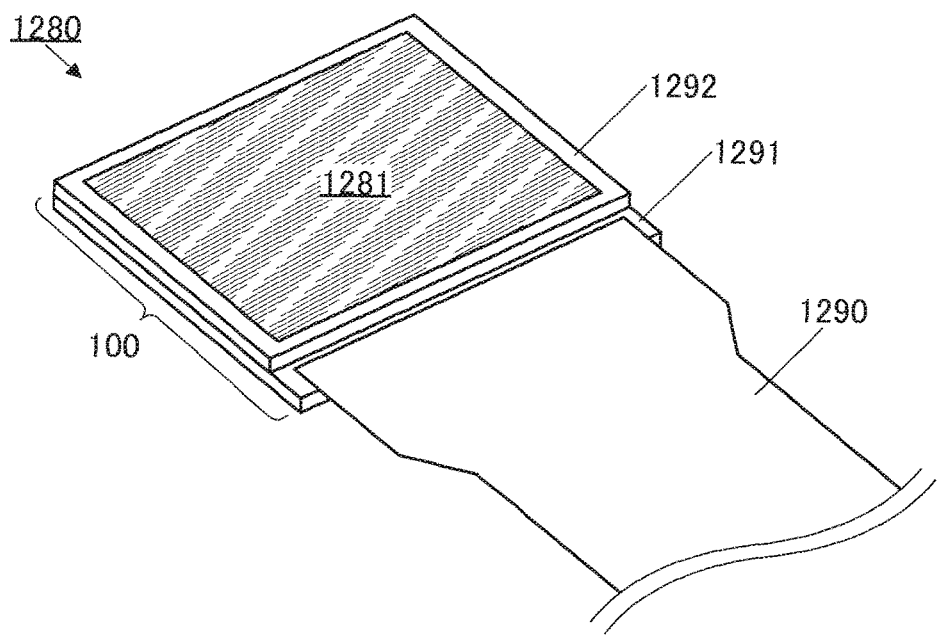
FIG. 43A and FIG. 43B are diagrams illustrating a structure example of a display module.

FIG. 43A is a perspective view of a display module 1280. The display module 1280 includes the display apparatus 100 and an FPC 1290.

The display module 1280 includes a substrate 1291 and a substrate 1292. The display module 1280 includes a display portion 1281. The display portion 1281 is a region of the display module 1280 where an image is displayed, and is a region where light emitted from pixels provided in a pixel portion 1284 described later can be seen.

Figure 43B:
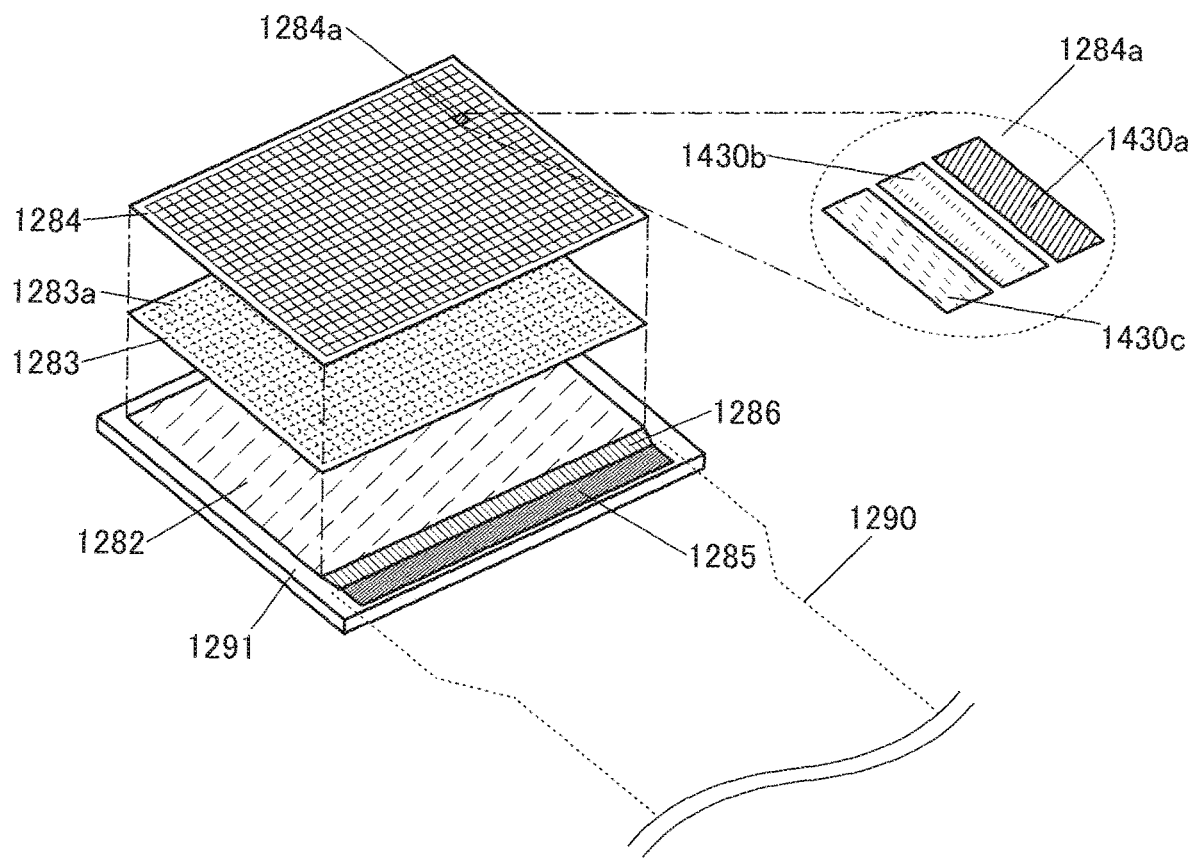

FIG. 43B is a perspective view schematically illustrating a structure on the substrate 1291 side. A circuit portion 1282, a pixel circuit portion 1283 over the circuit portion 1282, and the pixel portion 1284 over the pixel circuit portion 1283 are stacked over the substrate 1291. In addition, a terminal portion 1285 for connection to the FPC 1290 is provided in a portion not overlapping with the pixel portion 1284 over the substrate 1291. The terminal portion 1285 and the circuit portion 1282 are electrically connected to each other through a wiring portion 1286 formed of a plurality of wirings.

Note that the pixel portion 1284 and the pixel circuit portion 1283 correspond to the pixel layer PXAL described above, for example. The circuit portion 1282 corresponds to the circuit layer SICL described above, for example.

The pixel portion 1284 includes a plurality of pixels 1284a arranged periodically. An enlarged view of one pixel 1284a is shown on the right side in FIG. 43B. The pixel 1284a includes a light-emitting device 1430a, a light-emitting device 1430b, and a light-emitting device 1430c that emit light of different colors. Note that the light-emitting device 1430a, the light-emitting device 1430b, and the light-emitting device 1430c (e.g., the plurality of light-emitting devices corresponding to the light-emitting device 150a, the light-emitting device 150b, and the light-emitting device 150c described above) may be arranged in a stripe pattern as illustrated in FIG. 43B. Alternatively, a variety of arrangement methods, such as delta arrangement and pentile arrangement, can be employed.

The pixel circuit portion 1283 includes a plurality of pixel circuits 1283a arranged periodically.

One pixel circuit 1283a is a circuit that controls light emission of three light-emitting devices included in one pixel 1284a. One pixel circuit 1283a may be provided with three circuits each of which controls light emission of one light-emitting device. For example, the pixel circuit 1283a can include one or more selected from one selection transistor, one current control transistor (driving transistor), and a capacitor for one light-emitting device. In this case, a gate signal is input to a gate of the selection transistor, and a source signal is input to one of a source and a drain of the selection transistor. Thus, an active-matrix display apparatus is achieved.

The circuit portion 1282 includes a circuit for driving the pixel circuits 1283a in the pixel circuit portion 1283. For example, one or both of a gate line driver circuit and a source line driver circuit are preferably included. In addition, one or more selected from an arithmetic circuit, a memory circuit, a power supply circuit, and the like may be included.

The FPC 1290 functions as a wiring for supplying a video signal, a power supply potential, or the like to the circuit portion 1282 from the outside. In addition, an IC may be mounted on the FPC 1290.

The display module 1280 can have a structure where one or both of the pixel circuit portion 1283 and the circuit portion 1282 are stacked below the pixel portion 1284; thus, the aperture ratio (the effective display area ratio) of the display portion 1281 can be significantly high. For example, the aperture ratio of the display portion 1281 can be higher than or equal to 40% and lower than 100%, preferably higher than or equal to 50% and lower than or equal to 95%, further preferably higher than or equal to 60% and lower than or equal to 95%. Furthermore, the pixels 1284a can be arranged extremely densely and thus the display portion 1281 can have an extremely high resolution. For example, the pixels 1284a are preferably arranged in the display portion 1281 with a resolution higher than or equal to 2000 ppi, preferably higher than or equal to 3000 ppi, further preferably higher than or equal to 5000 ppi, still further preferably higher than or equal to 6000 ppi, and lower than or equal to 20000 ppi or lower than or equal to 30000 ppi.

Such the display module 1280 has an extremely high resolution, and thus can be suitably used for a VR device such as a head mounted display or a glasses-type AR device. For example, even with a structure where the display portion of the display module 1280 is seen through a lens, pixels of the extremely-high-resolution display portion 1281 included in the display module 1280 are prevented from being perceived when the display portion is enlarged by the lens, so that display providing a high sense of immersion can be performed. Without being limited thereto, the display module 1280 can be suitably used for electronic devices including a relatively small display portion. For example, the display module 1280 can be suitably used in a display portion of a wearable electronic device such as a wrist watch.

Note that this embodiment can be combined with any of the other embodiments described in this specification as appropriate.

Embodiment 5

In this embodiment, electronic devices each including a display apparatus are described as examples of an electronic device of one embodiment of the present invention.

Figure 44A:
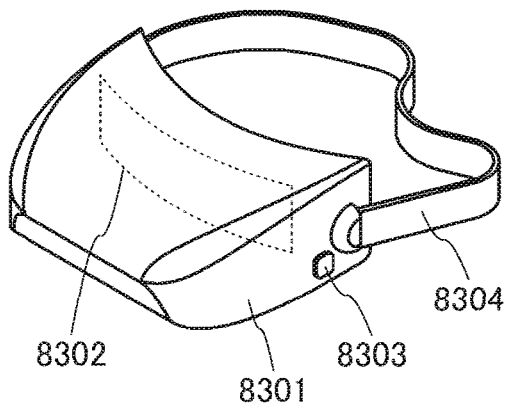
FIG. 44A to FIG. 44F are diagrams illustrating structure examples of an electronic device.
Figure 44B:
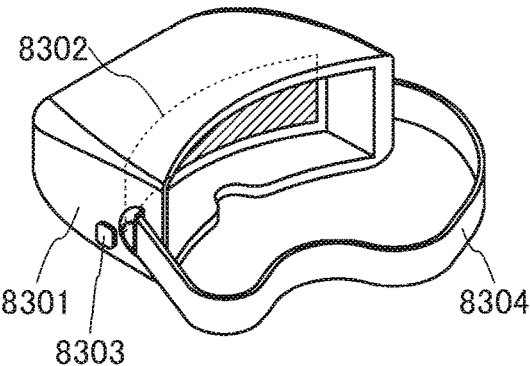

FIG. 44A and FIG. 44B each illustrate an appearance of an electronic device 8300 that is a head-mounted display.

The electronic device 8300 includes a housing 8301, a display portion 8302, an operation button 8303, and a band-shaped fixing unit 8304.

The operation button 8303 has a function of a power button or the like. The electronic device 8300 may include a button other than the operation button 8303.

Figure 44C:
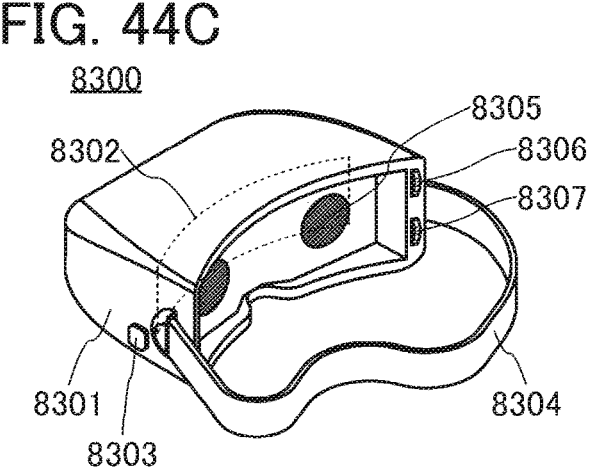

As illustrated in FIG. 44C, lenses 8305 may be included between the display portion 8302 and the positions of the user's eyes. The user can see magnified images on the display portion 8302 through the lenses 8305, leading to a higher realistic sensation. In this case, as illustrated in FIG. 44C, a dial 8306 for changing the positions of the lenses and adjusting visibility may be included.

For the display portion 8302, a display apparatus with an extremely high resolution is preferably used, for example. When a high-resolution display apparatus is used for the display portion 8302, it is possible to display a more realistic image that does not allow the user to perceive pixels even when the image is magnified using the lenses 8305 as illustrated in FIG. 44C.

FIG. 44A to FIG. 44C illustrate an example where one display portion 8302 is provided. Such a structure can reduce the number of components.

The display portion 8302 can display an image for the right eye and an image for the left eye side by side on a right region and a left region, respectively. Thus, a three-dimensional image using binocular disparity can be displayed.

One image which can be seen by both eyes may be displayed on the entire display portion 8302. A panorama image can thus be displayed from end to end of the field of view, which can provide a higher sense of reality.

Here, the electronic device 8300 preferably has, for example, a mechanism for changing the curvature of the display portion 8302 to an optimal value in accordance with or more selected from the size of the user's head, the position of the user's eyes, and the like. For example, the user himself or herself may adjust the curvature of the display portion 8302 by operating a dial 8307 for adjusting the curvature of the display portion 8302. Alternatively, a sensor for detecting the size of the user's head, the position of the user's eyes, or the like (e.g., a camera, a contact sensor, and a noncontact sensor) may be provided on the housing 8301, and a mechanism for adjusting the curvature of the display portion 8302 on the basis of detection data obtained by the sensor may be provided.

In the case where the lenses 8305 are used, a mechanism for adjusting the position and angle of the lenses 8305 in synchronization with the curvature of the display portion 8302 is preferably provided. Alternatively, the dial 8306 may have a function of adjusting the angle of the lenses.

Figure 44D:
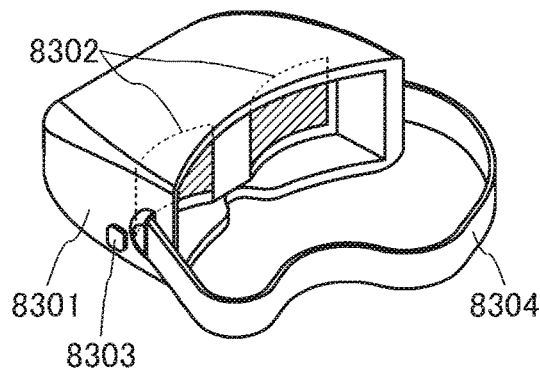
Figure 44E:
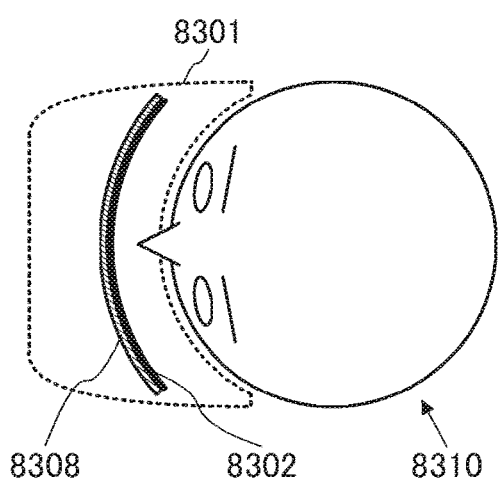
Figure 44F:
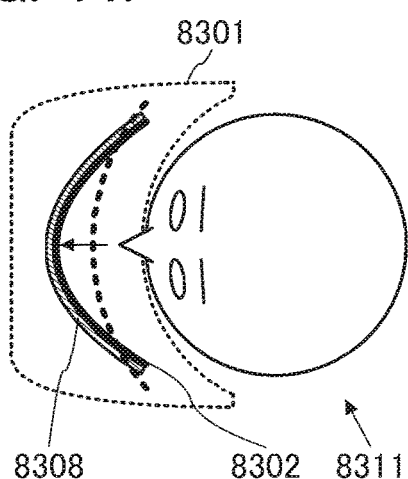

FIG. 44E and FIG. 44F illustrate an example where a driver portion 8308 controlling the curvature of the display portion 8302 is provided. The driver portion 8308 is fixed to at least a part of the display portion 8302. The driver portion 8308 has a function of changing the shape of the display portion 8302 when the part that is fixed to the display portion 8302 changes in shape or moves.

FIG. 44E is a schematic diagram illustrating the case where a user 8310 having a relatively large head wears the housing 8301. In this case, the driver portion 8308 adjusts the shape of the display portion 8302 so that the curvature is relatively small (the radius of curvature is large).

In contrast, FIG. 44F illustrates the case where a user 8311 having a smaller head than the user 8310 wears the housing 8301. The user 8311 has a shorter distance between the eyes than the user 8310. In this case, the driver portion 8308 adjusts the shape of the display portion 8302 so that the curvature of the display portion 8302 is large (the radius of curvature is small). 1?9 In FIG. 44F, the position and shape of the display portion 8302 in FIG. 44E are denoted by a dashed line.

When the electronic device 8300 has such a mechanism for adjusting the curvature of the display portion 8302, an optimal display can be offered to a variety of users of all ages and genders.

When the curvature of the display portion 8302 is changed in accordance with contents displayed on the display portion 8302, the user can have a more realistic sensation. For example, shaking can be expressed by fluctuating the curvature of the display portion 8302. In this way, it is possible to produce various effects in depending on the scene in contents, and provide the user with new experiences. A further realistic display can be provided when the display portion 8302 operates in conjunction with a vibration module provided in the housing 8301.

Note that the electronic device 8300 may include two display portions 8302 as illustrated in FIG. 44D.

Since the two display portions 8302 are included, the user's eyes can see their respective display portions. This allows a high-definition image to be displayed even when three-dimensional display using parallax is performed. In addition, the display portion 8302 is curved around an arc with the user's eye as an approximate center. This allows a uniform distance between the user's eye and display surface of the display portion; thus, the user can see a more natural image. Even when the luminance or chromaticity of light from the display portion is changed depending on the angle at which the user see it, since the user's eye is positioned in a normal direction of the display surface of the display portion, the influence of the change can be substantially ignorable and thus a more realistic image can be displayed.

Figure 45A:
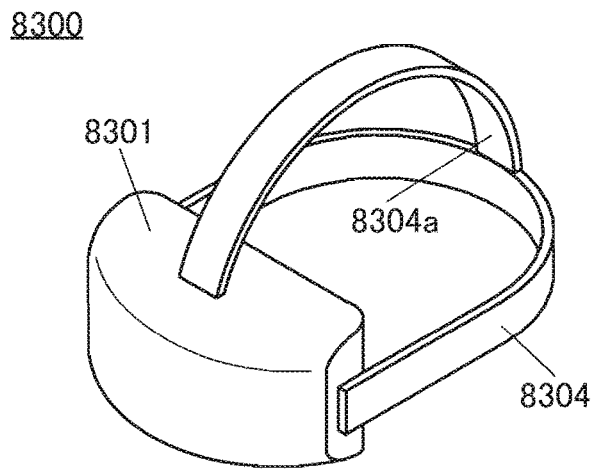
FIG. 45A to FIG. 45D are diagrams illustrating structure examples of electronic devices.
Figure 45B:
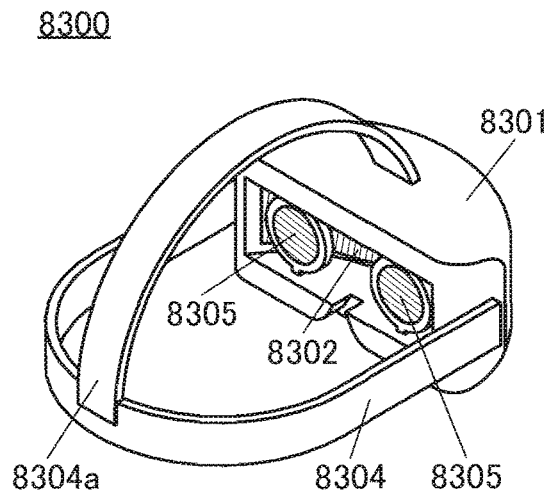
Figure 45C:
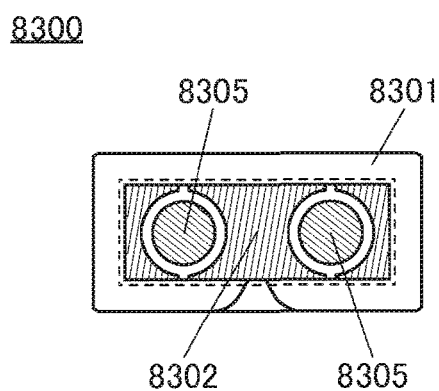

FIG. 45A to FIG. 45C are diagrams illustrating an appearance of another electronic device 8300, which is different from the electronic devices 8300 illustrated in FIG. 44A to FIG. 44D. Specifically, FIG. 45A to FIG. 45C are different from FIG. 44A to FIG. 44D in including a fixing means 8304*a* worn on a head and a pair of lenses 8305, for example.

A user can see display on the display portion 8302 through the lenses 8305. The display portion 8302 is preferably curved so that the user can feel high realistic sensation. Another image displayed on another region of the display portion 8302 is seen through the lenses 8305, so that three-dimensional display using parallax can be performed. Note that the structure is not limited to the structure where one display portion 8302 is provided; two display portions 8302 may be provided and one display portion may be provided per eye of the user.

For the display portion 8302, a display apparatus with a high resolution is preferably used, for example. When a high-resolution display apparatus is used for the display portion 8302, it is possible to display a more realistic image that does not allow the user to perceive pixels even when the image is magnified using the lenses 8305 as illustrated in FIG. 45C.

Figure 45D:
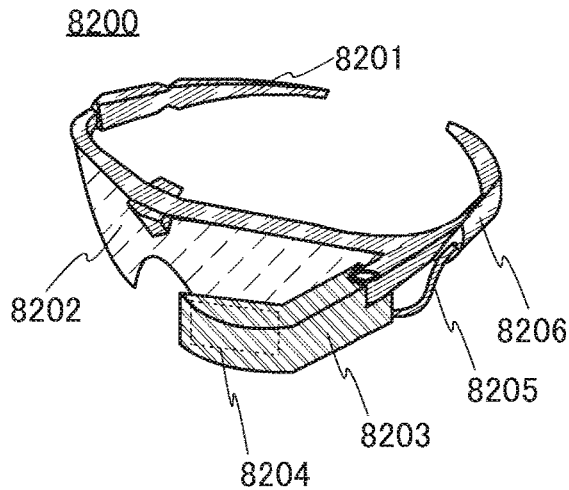

The head-mounted display, which is an electronic device of one embodiment of the present invention, may be an electronic device 8200 illustrated in FIG. 45D, which is a glasses-type head-mounted display.

The electronic device 8200 includes a mounting portion 8201, a lens 8202, a main body 8203, a display portion 8204, a cable 8205, and the like. A battery 8206 is incorporated in the mounting portion 8201.

The cable 8205 supplies power from the battery 8206 to the main body 8203. The main body 8203 includes a wireless receiver and can display received video information on the display portion 8204. The main body 8203 includes a camera, and information on the movement of the eyeballs or the eyelids of the user can be used as an input means.

The mounting portion 8201 may include a plurality of electrodes capable of sensing current flowing accompanying with the movement of the user's eyeballs at a position in contact with the user to recognize his or her gaze. The mounting portion 8201 may also have a function of monitoring the user's pulse with use of current flowing through the electrodes. The mounting portion 8201 may include a variety of sensors such as a temperature sensor, a pressure sensor, and an acceleration sensor to have a function of displaying the user's biological information on the display portion 8204, a function of changing a video displayed on the display portion 8204 in accordance with the movement of the user's head, and the like.

Figure 46A:
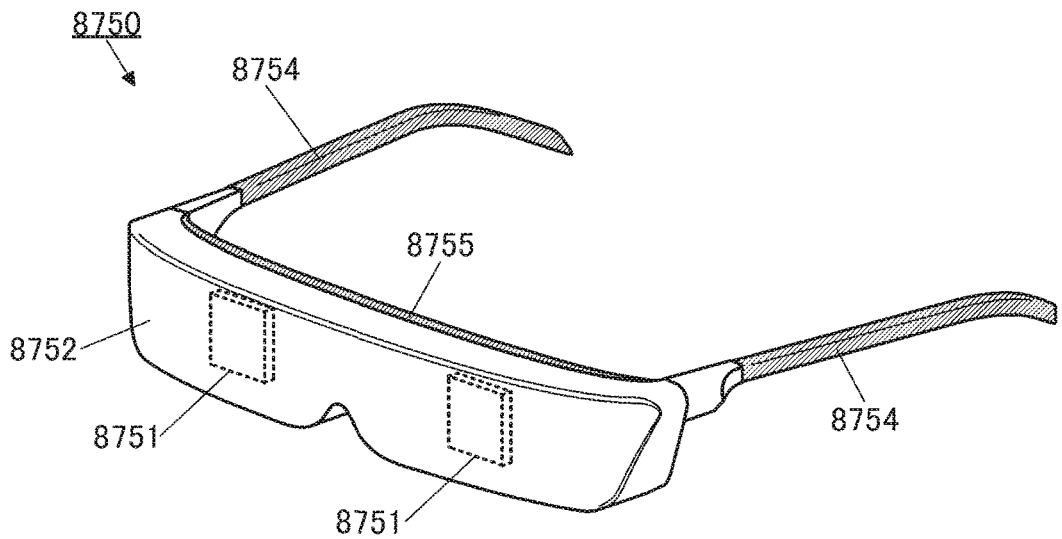
FIG. 46A to FIG. 46C are diagrams illustrating structure examples of an electronic device.
Figure 46B:
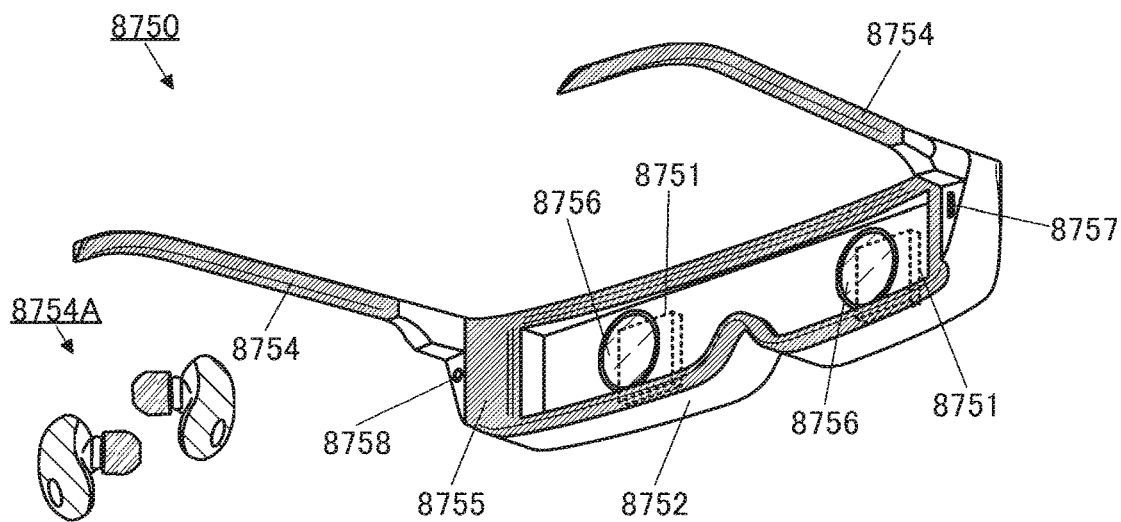
Figure 46C:
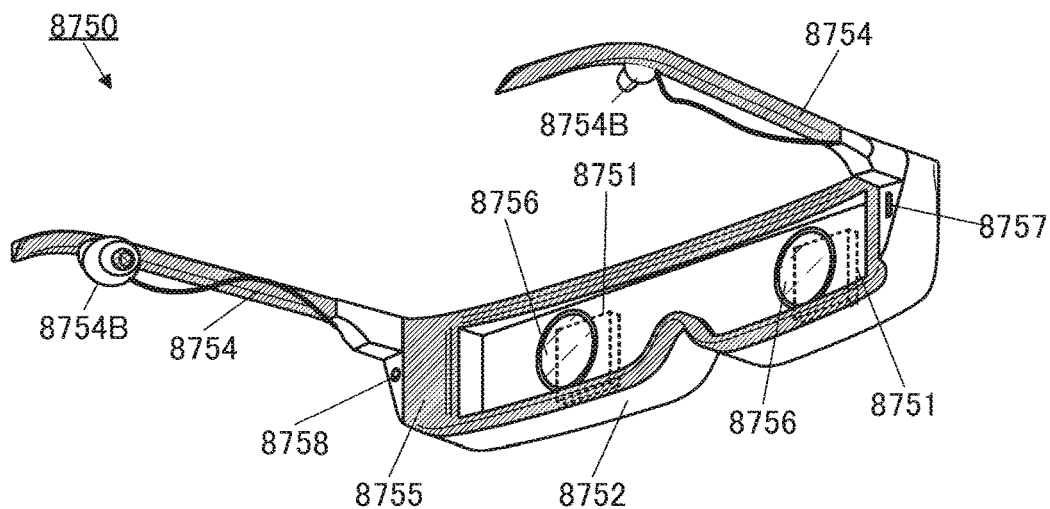

FIG. 46A to FIG. 46C are diagrams illustrating appearances of an electronic device 8750, which is different from the electronic devices 8300 illustrated in FIG. 44A to FIG. 44D and FIG. 45A to FIG. 45C and the electronic device 8200 illustrated in FIG. 45D.

FIG. 46A is a perspective view illustrating the front surface, the top surface, and the left side surface of the electronic device 8750, and FIG. 46B and FIG. 46C are each a perspective view illustrating the back surface, the bottom surface, and the right side surface of the electronic device 8750.

The electronic device 8750 includes a pair of display apparatuses 8751, a housing 8752, a pair of wearing portions 8754, a cushion 8755, a pair of lenses 8756, and the like. The pair of display apparatuses 8751 is positioned to be seen through the lenses 8756 inside the housing 8752.

Here, one of the pair of display apparatuses 8751 corresponds to the display portion DSP illustrated in FIG. 1A. Although not illustrated, the electronic device 8750 illustrated in FIG. 46A to FIG. 46C includes an electronic component including the processing unit described in the above embodiment (e.g., the peripheral circuit PH illustrated in FIG. 6). Although not illustrated, the electronic device 8750 illustrated in FIG. 46A to FIG. 46C includes a camera (e.g., the sensor IS in FIG. 7 described in the above embodiment). The camera can take an image of the user's eye and its periphery. Although not illustrated, in the housing 8752 of the electronic device 8750 illustrated in FIG. 46A to FIG. 46C, a motion detection portion, an audio, a control portion, a communication portion, and a battery are provided.

The electronic device 8750 is an electronic device for VR. A user wearing the electronic device 8750 can see an image displayed on the display apparatus 8751 through the lens 8756. Furthermore, the pair of display apparatuses 8751 may display different images, whereby three-dimensional display using parallax can be performed.

An input terminal 8757 and an output terminal 8758 are provided on the back side of the housing 8752. To the input terminal 8757, a cable for supplying a video signal from a video output device or the like, power for charging a battery provided in the housing 8752, or the like can be connected. The output terminal 8758 can function as, for example, an audio output terminal to which earphones, headphones, or the like can be connected.

The housing 8752 preferably includes a mechanism by which the left and right positions of the lens 8756 and the display apparatus 8751 can be adjusted to the optimal positions in accordance with the position of the user's eye. In addition, the housing 8752 preferably includes a mechanism for adjusting focus by changing the distance between the lens 8756 and the display apparatus 8751.

With use of the camera, the display apparatus 8751, and the above electronic component, the electronic device 8750 can estimate the state of a user of the electronic device 8750 and can display information on the estimated user's state on the display apparatus 8751. Alternatively, information on a user of an electronic device connected to the electronic device 8750 through a network can be displayed on the display apparatus 8751.

The cushion 8755 is a portion in contact with the user's face (e.g., forehead and cheek). The cushion 8755 is in close contact with the user's face, so that light leakage can be prevented, which increases the sense of immersion. A soft material is preferably used for the cushion 8755 so that the cushion 8755 is in close contact with the face of the user wearing the electronic device 8750. For example, any of a variety of materials such as rubber, silicone rubber, urethane, and sponge can be used. Furthermore, when a sponge whose surface is covered with cloth or leather (natural leather or synthetic leather) is used, a gap is unlikely to be generated between the user's face and the cushion 8755, whereby light leakage can be suitably prevented. Furthermore, using such a material is preferable because it has a soft texture and the user does not feel cold when wearing the device in a cold season, for example. The member in contact with user's skin, such as the cushion 8755 or the wearing portion 8754, is preferably detachable because cleaning or replacement can be easily performed.

The electronic device in this embodiment may further include earphones 8754A. The earphones 8754A include a communication portion (not illustrated) and have a wireless communication function. The earphones 8754A can output audio data with the wireless communication function. Note that the earphones 8754A may include a vibration mechanism to function as bone-conduction earphones.

Like earphones 8754B illustrated in FIG. 46C, the earphones 8754A can be connected to the wearing portion 8754 directly or by wiring. The earphones 8754B and the wearing portion 8754 may each have a magnet. This is preferable because the earphones 8754B can be fixed to the wearing portion 8754 with magnetic force and thus can be easily housed.

The earphones 8754A may include a sensor portion. With use of the sensor portion, the state of the user of the electronic device can be estimated.

The electronic device of one embodiment of the present invention may include one or more of an antenna, a battery, a camera, a speaker, a microphone, a touch sensor, and an operation button, in addition to any one of the above components.

The electronic device of one embodiment of the present invention may include a secondary battery, and it is preferable that the secondary battery be capable of being charged by contactless power transmission.

Examples of the secondary battery include a lithium ion secondary battery such as a lithium polymer battery using a gel electrolyte (lithium ion polymer battery), a nickel-hydride battery, a nickel-cadmium battery, an organic radical battery, a lead-acid battery, an air secondary battery, a nickel-zinc battery, and a silver-zinc battery.

The electronic device of one embodiment of the present invention may include an antenna. When a signal is received by the antenna, the electronic device can display a video, information, or the like on a display portion. When the electronic device includes an antenna and a secondary battery, the antenna may be used for contactless power transmission.

A display portion in an electronic device of one embodiment of the present invention can display a video with a definition of, for example, full high definition, 4K2K, 8K4K, 16K8K, or higher.

Note that this embodiment can be combined with any of the other embodiments described in this specification as appropriate.

REFERENCE NUMERALS

HMD: electronic device, KYT: housing, DSP: display portion, TRM: sending portion, OSC: oscillator, UPCMX: mixer, USC: ultrasonic wave transmission circuit, RCV: receiving portion, OSCr: oscillator, DNCMX: mixer, FNC: functional circuit, TM: temple, SNO: sound output portion, PH: peripheral circuit, CTRL: control circuit, VWC: voltage waveform generation circuit, DRV: driver circuit, SNBD: sound processing circuit, USS: ultrasonic wave sensor, IS: sensor, NVS: sensor, NVSa: sensor, NVSb: sensor, GPC: sensor control circuit, NVC: sensor control circuit, DEV: display apparatus, IF: interface, EXPC: external terminal, HE: wearing portion, HP: wearing portion, USR: user, OBS: observer, ME: eye, ER: ear, SK: skin, KM: cornea, SST: crystalline lens, MM: retina, GT: vitreous humor, SSK: optic nerve, MKN: retina blood vessel, KN: blood vessel, BC: blood cell, USW: ultrasonic wave, USWr: ultrasonic wave, PIC1: image, PIC2: image, VM: sound, TME: information, BS: substrate, SICL: circuit layer, LINL: wiring layer, PXAL: pixel layer, OPA: region, DSPPX: region, DSPa: region, DSPb: region, SKWa: wall, SKWb: wall, OSL: layer, EML: layer, ANO: wiring, V0: wiring, VCOM: wiring, SL: wiring, GL: wiring, GL1: wiring, GL2: wiring, GL3: wiring, ACTF: circuit, AFP: circuit, ALP: array portion, ANN: neural network, CA: cell array, C1: capacitor, C1r: capacitor, C5: capacitor, C5m: capacitor, F1: transistor, F1m: transistor, F2: transistor, F2m: transistor, F3: transistor, F4: transistor, HC: holding portion, ILD: circuit, IM: cell, IMref: cell, ITRZ: converter circuit, MAC1: arithmetic circuit, MC: circuit, MCr: circuit, MP: circuit, M1: transistor, M1r: transistor, M2: transistor, M3: transistor, M3r: transistor, NN: node, NNref: node, n1: node, OL: wiring, OLB: wiring, PS: subpixel, SWL1: wiring, SWL2: wiring, SWS1: circuit, SWS2: circuit, TW: circuit, VE: wiring, VEr: wiring, WCL: wiring, WCS: circuit, WL: wiring, WLD: circuit, WSD: circuit, WSL: wiring, WX1L: wiring, w1: data, XCL: wiring, XCS: circuit, XLD: circuit, 30: driver circuit, 70A: pixel, 70B: pixel, 80: pixel, 80a: subpixel, 80b: subpixel, 80c: subpixel, 80d: subpixel, 85R: hole-injection layer, 85G: hole-injection layer, 85B: hole-injection layer, 86R: hole-transport layer, 86G: hole-transport layer, 86B: hole-transport layer, 86PD: hole-transport layer, 87R: light-emitting layer, 87G: light-emitting layer, 87B: light-emitting layer, 88R: electron-transport layer, 88G: electron-transport layer, 88B: electron-transport layer, 88PD: electron-transport layer, 89: common layer, 90: light-receiving layer, 91: protective layer, 92: insulating layer, 100: display apparatus, 102: substrate, 111: insulator, 112: insulator, 113: insulator, 113a: insulator, 113b: insulator, 113c: insulator, 118: sacrificial layer, 119: sacrificial layer, 121a: conductor, 121b: conductor, 121c: conductor, 121B: conductor, 121G: conductor, 121R: conductor, 121PD: conductor, 122a: conductor, 122b: conductor, 122c: conductor, 123: conductor, 123CM: region, 141a: EL layer, 141b: EL layer, 141c: EL layer, 142: EL layer, 150a: light-emitting device, 150b: light-emitting device, 150c: light-emitting device, 150B: light-emitting device, 150G: light-emitting device, 150R: light-emitting device, 150IR: light-emitting device, 160: light-receiving device, 161a: layer, 161b: layer, 162: insulator, 163: resin layer, 164: adhesive layer, 165: adhesive layer, 166a: coloring layer, 166b: coloring layer, 166c: coloring layer, 200: transistor, 202: insulator, 210: substrate, 214: insulator, 216: conductor, 220: insulator, 222: insulator, 224: insulator, 226: insulator, 228: conductor, 230: conductor, 250: insulator, 300: transistor, 310: substrate, 312: element isolation layer, 313: semiconductor region, 314a: low-resistance region, 314b: low-resistance region, 315: insulator, 316: conductor, 317: insulator, 320: insulator, 322: insulator, 324: insulator, 326: insulator, 328: conductor, 330: conductor, 350: insulator, 351: substrate, 352: insulator, 353: layer, 354: insulator, 355: functional layer, 356: conductor, 357: layer, 359: substrate, 360: insulator, 362: insulator, 364: insulator, 366: conductor, 370: insulator, 372: insulator, 376: conductor, 380: insulator, 400: pixel circuit, 400A: pixel circuit, 400B: pixel circuit, 400C: pixel circuit, 400D: pixel circuit, 400E: pixel circuit, 400F: pixel circuit, 400G: pixel circuit, 400H: pixel circuit, 500: transistor, 500A: transistor, 500B: transistor, 500C: transistor, 500D: transistor, 501: substrate, 512: insulator, 514: insulator, 540: conductor, 573: insulator, 574: insulator, 575: insulator, 576: insulator, 581: insulator, 600: capacitor, 600A: capacitor, 700: electronic device, 710: endoscope apparatus, 711: monitor device, 712: doctor, 713: doctor, 714: doctor, 715: patient, 800: semiconductor device, 810: n-plus layer, 820: p-minus layer, 830: p-plus layer, 840*a*: electrode, 840*b*: electrode, 850: sensor portion, 900: measurement apparatus, 910: laser light source, 920: beam splitter, 930: objective lens, 940: slide glass, 950: power source, 960: microwave source, 970: detection device, 980: control device, 1010*a*: electronic device, 1010*b*: electronic device, 1011: display apparatus, 1012: display portion, 1013*a*: region, 1013*b*: region, 1015*a*: student, 1015*b*: student, 1016*a*1: image, 1016*a*2: image, 1016*a*3: image, 1016*b*1: image, 1016*b*2: image, 1016*b*3: image, 1016*c*: image, 1020: electronic device, 1021: electronic device, 1022: camera, 1023: display portion, 1025: teacher, 1026: image data, 1027: display portion, 1030: network, 1280: display module, 1281: display portion, 1290: FPC, 1283: pixel circuit portion, 1283*a*: pixel circuit, 1284: pixel portion, 1284*a*: pixel, 1285: terminal portion, 1286: wiring portion, 1291: substrate, 1292: substrate, 1350: arithmetic circuit, 1430*a*: light-emitting device, 1430*b*: light-emitting device, 1430*c*: light-emitting device, 1960: eyebrow, 1961: eyelash, 1962: pupil, 1963: cornea, 1965: sclera, 1966: upper eyelid, 1967: lower eyelid, 4400*a*: light-emitting unit, 4400*b*: light-emitting unit, 4411: light-emitting layer, 4412: light-emitting layer, 4413: light-emitting layer, 4420: layer, 4420-1: layer, 4420-2: layer, 4430: layer, 4430-1: layer, 4430-2: layer, 4440: intermediate layer, 8200: electronic device, 8201: wearing portion, 8202: lens, 8203: main body, 8204: display portion, 8205: cable, 8206: battery, 8300: electronic device, 8301: housing, 8302: display portion, 8303: operation button, 8304: fixing means, 8304*a*: fixing means, 8305: lens, 8306: dial, 8307: dial, 8308: driver portion, 8310: user, 8311: user, 8750: electronic device, 8751: display apparatus, 8752: housing, 8754: wearing portion, 8754A: earphones, 8754B: earphones, 8756: lens, 8757: input terminal, 8758: output terminal

The invention claimed is:

1. An electronic device comprising:
   a display portion comprising a first region and a second region; and
   a sensor portion over the display portion,
   wherein the first region comprises a first light-emitting device,
   wherein the second region comprises a second light-emitting device and a light-receiving device,
   wherein the sensor portion comprises a diamond layer,
   wherein the sensor portion and the second region overlap each other,
   wherein the electronic device further comprises a wall between the first light-emitting device and the second light-emitting device,
   wherein, when first light from the second light-emitting device enters the sensor portion, second light from the sensor portion enters to the light-receiving device, and
   wherein the electronic device is configured to measure a temperature from an intensity of the second light.

2. The electronic device according to claim 1, wherein the diamond layer comprises an NV center.

3. The electronic device according to claim 1, wherein the sensor portion and the first region do not overlap each other.

4. The electronic device according to claim 1, wherein the sensor portion and an eye of a user do not overlap each other.

5. The electronic device according to claim 1, wherein the first light-emitting device comprises a laser light source.

6. The electronic device according to claim 1, wherein the wall is configured to prevent entry of light between the first region and the second region.

7. The electronic device according to claim 1, further comprising an objective lens between the second region and the sensor portion.

* * * * *